(12) United States Patent
Dodge et al.

US007125840B2

(10) Patent No.: US 7,125,840 B2
(45) Date of Patent: Oct. 24, 2006

(54) SUBSTITUTED DIPEPTIDES AS GROWTH HORMONE SECRETAGOGUES

(75) Inventors: Jeffrey Alan Dodge, Indianapolis, IN (US); Britta Evers, Hamburg (DE); Louis Nickolaus Jungheim, Indianapolis, IN (US); Brian Stephen Muehl, Greenwood, IN (US); Gerd Ruehter, Hamburg (DE); Kenneth Jeff Thrasher, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 346 days.

(21) Appl. No.: 10/380,867

(22) PCT Filed: Oct. 9, 2001

(86) PCT No.: PCT/US01/27756

§ 371 (c)(1),
(2), (4) Date: Mar. 14, 2003

(87) PCT Pub. No.: WO02/32888

PCT Pub. Date: Apr. 25, 2002

(65) Prior Publication Data

US 2004/0058971 A1    Mar. 25, 2004

(51) Int. Cl.
*A01N 37/18* (2006.01)
(52) U.S. Cl. ......................................................... 514/2
(58) Field of Classification Search ..................... None
See application file for complete search history.

(56) References Cited

U.S. PATENT DOCUMENTS

| | | | |
|---|---|---|---|
| 3,711,495 A | 1/1973 | Kulsa et al. ................. 260/307 |
| 3,984,426 A | 10/1976 | Winkelmann et al. .. 260/302 H |
| 5,242,903 A | 9/1993 | Bender et al. ................. 514/18 |
| 5,380,866 A | 1/1995 | Barnett et al. ........... 548/330.1 |
| 5,401,851 A | 3/1995 | Boyd et al. .................. 548/112 |
| 5,459,156 A | 10/1995 | Muller-Gliemann et al. ............................. 514/397 |
| 5,492,916 A | 2/1996 | Marriello et al. ........... 514/318 |
| 5,492,920 A | 2/1996 | Chen et al. .................. 514/323 |
| 5,494,919 A | 2/1996 | Marriello et al. ........... 514/323 |
| 5,559,128 A | 9/1996 | Chakravarty et al. ....... 514/323 |
| 5,574,167 A | 11/1996 | Jaber ........................ 548/327.1 |
| 5,578,593 A | 11/1996 | Chen et al. .................. 514/212 |
| 5,583,130 A | 12/1996 | Bochis et al. ............... 514/183 |
| 5,652,235 A | 7/1997 | Chen et al. .................. 514/215 |
| 5,661,161 A | 8/1997 | Anthony et al. ............ 514/326 |
| 5,663,146 A | 9/1997 | Bowers et al. ................. 514/16 |
| 5,663,171 A | 9/1997 | Chen et al. .................... 514/19 |
| 5,700,827 A | 12/1997 | Schnorrenberg et al. .... 514/414 |
| 5,721,250 A | 2/1998 | Morriello et al. ........... 514/318 |
| 5,756,528 A | 5/1998 | Anthony et al. ............ 514/399 |
| 5,773,441 A | 6/1998 | Hipskind et al. ............ 514/253 |
| 5,798,337 A | 8/1998 | Somers et al. ................. 514/19 |
| 5,830,855 A | 11/1998 | Takemoto ..................... 514/11 |
| 6,046,333 A | 4/2000 | Dorziotis et al. ............. 546/18 |

FOREIGN PATENT DOCUMENTS

| | | |
|---|---|---|
| EP | 0 662 481 B1 | 8/1993 |
| EP | 0 615977 A1 | 9/1994 |
| EP | 0 761219 A1 | 8/1996 |
| EP | 0 761 219 A | 12/1997 |
| EP | 0 761 220 A | 12/1997 |
| WO | WO 94/13696 A1 | 6/1994 |
| WO | WO 95/11029 A1 | 4/1995 |
| WO | WO 96/15148 A1 | 5/1996 |
| WO | WO 96/35713 A1 | 11/1996 |
| WO | WO 96/38471 A1 | 12/1996 |
| WO | WO 97/15573 A1 | 5/1997 |
| WO | WO 97/24369 A1 | 7/1997 |
| WO | WO 97/34604 A1 | 9/1997 |
| WO | WO 97/41878 A1 | 11/1997 |
| WO | WO 98/16527 A1 | 4/1998 |
| WO | WO 98/18815 | 5/1998 |
| WO | WO 98/58948 A1 | 12/1998 |
| WO | WO 99 08697 A1 | 2/1999 |
| WO | WO 99/08699 A1 | 2/1999 |
| WO | WO 00/12047 A2 | 3/2000 |
| WO | WO 00/49037 A1 | 8/2000 |

OTHER PUBLICATIONS

Peschke, et al., Eur. J. Med. Chem., 2000, 35, 599-618.*
Vippagunta, et al., Advanced Drug Delivery Review, 2001, 48, 3-26.*
*Synthesis of 4-Nitroimidazoles with I-Substituents Containing Acid, Ester or Phenol Functions, and Radiosensitizing Efficiency of Some of These Compounds*, Suwinski, et al., Arch. Pharm., vol. 325, pp. 317-324 (1992).
*Synthetic Approaches to the 'Azole' Peptide Mimetics*: Gordon, et al., Tetrahedron Letters, vol. 34, No. 12, pp. 1901-1904 (1993).
Chem. Abst. No. 130:209977, Kaufffman, et al.: *Treatment of Congestive Heart Failure with Growth Hormone Secretagogues*, Kauffman, et al. application of WO 99/08697, Aug. 19, 1998.
Chem. Abst. No. 130:182769, Dodge, et al.: *Preparation of Heterocyclic Peptide Derivatives as Growth Hormone Secretagogues*, application of WO 9908699, Aug. 19, 1998.

(Continued)

*Primary Examiner*—Bruce R. Campell
*Assistant Examiner*—Satyanarayana R. Gudibande
(74) *Attorney, Agent, or Firm*—James B. Myers

(57) ABSTRACT

This invention relates to novel compounds which are useful in the modulation of endogenous growth hormone levels in a mammal. The invention further relates to novel intermediates for use in the synthesis of said compounds, as well as novel processes employed in these syntheses. Also included are methods of treating a mammal which include the administration of said compounds.

44 Claims, No Drawings

OTHER PUBLICATIONS

*New Highly Potent Dipeptidic Growth Hormone Secretagogues with Low Molecular* Weight: Eur. J. Med. Chem. 35, pp. 599-618 (2000).

*Growth Hormone Secretagogues Derived form NN703 with Hydrazides as C-terminal*: Eur. J. Med. Chem. 35, pp. 487-497 (2000).

Chem. Abst. No. 119:261758: Uzunov, D., et al., *Some Aspects of the Enantiorecongition of Derivatized Primary Amines on a Pirkle-type Chiral Stationary Phase Utilizing Tocainide and Mexiletine as Model Compounds*, Institute of Organic Chemistry with Centre of Phytochemistry, Bulgarian Academy of Sciences, Sofia, 1113, Bulg. J. Chromatogr., (1993), 645(2), 233-9.

* cited by examiner

SUBSTITUTED DIPEPTIDES AS GROWTH HORMONE SECRETAGOGUES

Growth hormone, which is secreted by the pituitary gland, has wide-ranging developmental effects on the organism. Artificial manipulation of growth hormone levels has been demonstrated to have significant therapeutic utility. Human growth hormone supplementation has been shown to be an effective treatment for growth hormone deficiencies and their related disease states in humans. Apart from this application, studies have uncovered new and significant properties of growth hormone which lend further importance to the ability to control growth hormone levels. For example, clinical studies have indicated that growth hormone supplementation may be useful in combating the maladies of aging in humans. Elevated growth hormone levels in animals have been shown to result in increased lean muscle mass. One application of this latter observation could result in higher production of leaner meat products or in the production of larger and/or stronger animals.

While growth hormone is naturally produced by the pituitary gland, the secretion of growth hormone into the bloodstream is controlled by a second protein, Growth Hormone Releasing Factor (GRF). This hormone is also commonly known in the art as somatocrinin, Growth Hormone Releasing Hormone (GHRH), and Growth Releasing Hormone (GRH).

There are two ways to approach the problem of increasing circulating levels of growth hormone: (1) increase the level of human growth hormone in the organism directly or (2) increase the organism's natural tendency to produce growth hormone. The latter strategy may be achieved via supplementation with GRF. GRF has been demonstrated to increase the circulatory levels of growth hormone in vivo. (Rivier, et al., Nature (London), 300:276 (1982). The effect of GRF, including structural analogs thereof, on growth hormone production has been widely studied. A primary obstacle to the use of GRF as a direct supplement is its short lifespan in vivo. L. A. Frohman, et al., Journal of Clinical Investigation, 78:906 (1986). More potent and/or longer lasting GRF molecules are therefore desirable for the development of effective human therapeutic or animal husbandry agents.

The structure of GRF has been modified in numerous ways resulting in longer lasting and/or more potent GRF analogs. It has been demonstrated that the first 29 amino acids from the N-terminus are sufficient to retain full GRF activity. Speiss, et al., Biochemistry, 21:6037 (1982). One strategy has been the incorporation of novel D-amino acid residues in various regions of the GRF molecule. V. A. Lance, et al., Biochemical and Biophysical Research Communications, 119:265 (1984); D. H. Coy, et al., Peptides, 8(suppl. 1):49 (1986). Another strategy has modified the peptide backbone of GRF by the incorporation of peptide bond isosteres in the N-terminal region. D. Tourwe, Janssen. Chim. Acta, 3:3 (1985); S. J. Hocart, et al., Journal of Medicinal Chemistry, 33:1954–58 (1990). A series of very active analogs of GHRH is described in European Patent Publication 511,003, published Oct. 28, 1992.

In addition to the actions of GHRH there are various ways known to release growth hormone. For example, chemicals such as arginine, L-3,4-dihydroxyphenylalanine (L-DOPA), glucagon, vasopressin, and insulin-induced hypoglycemia, as well as activities such as sleep and exercise, indirectly cause growth hormone to be released from the pituitary by acting in some fashion on the hypothalamus, perhaps either to decrease somatostatin secretion or to increase the secretion of GHRH.

In cases where increased levels of growth hormone are desired, the problem has generally been solved by providing exogenous growth hormone or by administering GHRH, or a related peptidyl compound which stimulates growth hormone production or release. In either instance the peptidyl nature of the compound has necessitated that it be administered by injection.

Other compounds have been developed which stimulate the release of endogenous growth hormone, such as analogous peptidyl compounds related to GHRH. These peptides, while considerably smaller than growth hormones are still susceptible to metabolic instability.

Administration of the hexapeptide growth hormone releasing peptide-6 (GHRP-6) results in the secretion of growth hormone in many species, including humans. This peptide is one of a series of synthetic peptides, the structures of which were based on the pentapeptide Metenkephalin. It has been shown that GHRP binds specifically to the pituitary, although the binding does not involve the opioid, GHRH, or the somatostatin receptors.

In recent years significant efforts have been taken to develop nonpeptidyl analogs of this series of compounds. Such compounds, termed growth hormone secretagogues, should be orally bioavailable, induce the production or release of growth hormone, and act in concert, or synergistically with GHRH. These compounds are non-peptidyl in nature and are, therefore, more metabolically stable than growth hormone, growth hormone releasing hormone, or analogs of either of these proteins.

The compounds of this invention are especially desired due to the enhanced in vivo pharmaceutical activity of the compounds.

The present invention relates to compounds of Formula I

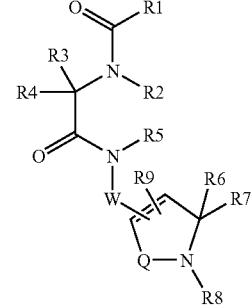

Formula I wherein:

R1 is NHR10 or $C_1$–$C_6$alkylNHR10;

R10 selected from the group consisting of hydrogen, $C_1$–$C_6$alkyl, $C_1$–$C_6$alkyl(OH), $C_1$–$C_6$alkylidenyl(OH)R11, and an amino protecting group;

R11 is selected from the group consisting of $C_1$–$C_6$alkyl, $C_1$–$C_6$alkenyl, $C_1$–$C_6$alkyl(O)$C_1$–$C_6$alkyl, C(O)O—$C_1$–$C_6$alkyl, aryl, and $C_1$–$C_6$alkylaryl;

R2 is selected from hydrogen, $C_1$–$C_6$alkyl, aryl, and $C_1$–$C_6$alkylaryl;

R3 is selected from the group consisting of optionally substituted aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl) $C_3$–$C_8$ cycloalkyl, indolyl, indolinyl, ($C_1$–$C_6$ alkyl) indolyl;

R4 is hydrogen, $C_1$–$C_6$alkyl, aryl, $C_1$–$C_6$alkylaryl, $C_1$–$C_6$alkenyl;

R5 is selected from hydrogen, $C_1$–$C_6$alkyl, aryl, and $C_1$–$C_6$alkylaryl;

W is —$CH_2C_6H_4$— or —$(CH_2)_m$, where m is a number selected from 1 to 4;

R6 and R7 are independently selected from the group consisting of hydrogen, $C_1$–$C_6$alkyl, $C_1$–$C_6$alkenyl, or R6 and R7 together with the carbon atom to which they are attached may form a carbocyclic ring of up to 8 atoms which is optionally partly unsaturated;

R8 is selected from the group consisting of hydrogen, $C_1$–$C_6$alkyl, aryl, and $C_1$–$C_6$alkylaryl;

R9 is selected from the group consisting of hydrogen, $C_1$–$C_6$alkyl, $C_1$–$C_6$alkenyl, $C_1$–$C_6$alkynyl, $C_3$–$C_8$cycloalkyl, $C_3$–$C_8$cycloalkenyl, cyano, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), —S-aryl-aryl(K1)(K2), —O—$C_1$–$C_6$alkyl, and $C_1$–$C_6$alkylaryl, wherein K1 is halo or —$CF_3$, and K2 is hydrogen, halo or —$CF_3$; and Q is —$S(O)_2$— or —$C(O)$—;

or a pharmaceutically acceptable salt or solvate thereof.

The present invention further relates to pharmaceutical formulations containing compounds of formula I, alone or in combination with other growth hormone secretagogue compounds, and/or in combination with suitable bone-antiresorptive agents, and the use of said compounds and/or formulations at least for the increase in endogenous levels of growth hormone in a mammal.

The present invention yet further relates to methods for the treatment or prevention of a physiological condition which may be modulated by an increase in endogenous growth hormone, which method comprises administering to an animal in need of said treatment an effective amount of a compound of formula I.

An alternate embodiment of the invention is a compound of Formula I wherein R3 is selected from the group consisting of aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl) $C_3$–$C_8$ cycloalkyl, indolyl, indolinyl, ($C_1$–$C_6$ alkyl) indolyl; and R9 is selected from the group consisting of hydrogen, $C_1$–$C_6$alkyl, $C_1$–$C_6$alkenyl, $C_1$–$C_6$alkynyl, $C_3$–$C_8$cycloalkyl, $C_3$–$C_8$cycloalkenyl, optionally substituted aryl, optionally substituted —O-aryl, optionally substituted —N-aryl, optionally substituted —S-aryl, —O—$C_1$–$C_6$alkyl, and $C_1$–$C_6$alkylaryl; or a pharmaceutically acceptable salt or solvate thereof.

A preferred embodiment of the invention is a compound of Formula II

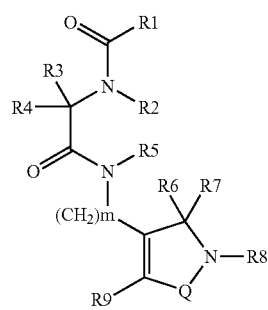

Formula II wherein
R1 is NHR10 or $C_1$–$C_6$alkylNHR10;

R10 selected from the group consisting of hydrogen, $C_1$–$C_6$alkyl, $C_1$–$C_6$alkyl(OH), $C_1$–$C_6$alkylidenyl(OH)R11, and an amino protecting group;

R11 is selected from the group consisting of $C_1$–$C_6$alkyl, $C_1$–$C_6$alkenyl, $C_1$–$C_6$alkyl(O)$C_1$–$C_6$alkyl, $C(O)O$—$C_1$–$C_6$alkyl, aryl, and $C_1$–$C_6$alkylaryl;

R2 is selected from hydrogen, $C_1$–$C_6$alkyl, aryl, and $C_3$–$C_6$alkylaryl;

R3 is selected from the group consisting of aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl) $C_3$–$C_8$ cycloalkyl, indolyl, indolinyl, ($C_1$–$C_6$ alkyl) indolyl;

R4 is hydrogen, $C_1$–$C_6$alkyl, aryl, $C_1$–$C_6$alkylaryl, $C_1$–$C_6$alkenyl;

R5 is selected from hydrogen, $C_1$–$C_6$alkyl, aryl, and $C_1$–$C_6$alkylaryl;

R6 and R7 are independently selected from the group consisting of hydrogen, $C_1$–$C_6$alkyl, $C_1$–$C_6$alkenyl, or R6 and R7 together with the carbon atom to which they are attached may form a carbocyclic ring of up to 8 atoms which is optionally partly unsaturated;

R8 is selected from the group consisting of hydrogen, $C_1$–$C_6$alkyl, aryl, and $C_1$–$C_6$alkylaryl;

R9 is selected from the group consisting of hydrogen, $C_1$–$C_6$alkyl, $C_1$–$C_6$alkenyl, $C_1$–$C_6$alkynyl, $C_3$–$C_8$cycloalkyl, $C_3$–$C_8$cycloalkenyl, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), —S-aryl-aryl(K1)(K2), —O—$C_1$–$C_6$alkyl, and $C_1$–$C_6$alkylaryl, wherein K1 is halo or —$CF_3$ and K2 is hydrogen, halo or —$CF_3$; and Q is —$S(O)_2$— or —$C(O)$—; and m is a number selected from 1 to 2;

or a pharmaceutically acceptable salt or solvate thereof.

A further preferred embodiment of the invention is a compound of Formula III

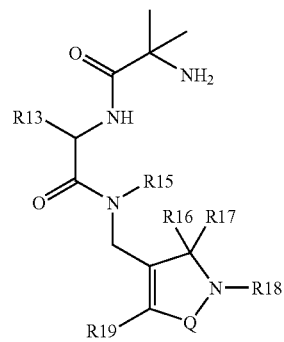

Formula III or a pharmaceutically acceptable salt or solvate thereof, wherein:

R13 is 3-phenylpropyl, phenylmethoxymethyl, 3-indolylmethyl, or cyclohexylmethyl;

R15 is hydrogen, methyl, ethyl, or n-propyl;

R16 and R17 both are methyl or ethyl, or together with the carbon atom to which they are attached form a cyclopentane or cyclohexane ring;

R18 is selected from hydrogen, methyl or ethyl;

R19 is thienyl, naphthyl, thiazolyl, oxazolyl, pyridinyl, O-phenyl, or phenyl, which is optionally substituted with one or more substituents independently selected from the group consisting of $C_1-C_6$ alkyl, $C_1-C_6$ alkoxy, $CONH_2$, $CONH(C_1-C_6$ alkyl), $NHCO(C_1-C_6$ alkyl), $SO_2NH_2$, $SO_2NH(C_1-C_6$ alkyl), $NHSO_2(C_1-C_6$ alkyl), COOH, COO($C_1-C_6$ alkyl), hydroxy, nitro, halo, $SO_2(C_{1-6}$ alkyl), and cyano; and Q is —$S(O)_2$— or —C(O)—.

The present invention additionally relates to compounds of formula IV in which R13 to R19 have the same definition as in Formula III:

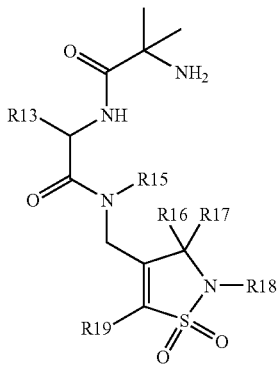

Formula IV

The present invention further relates to compounds of formula IVA which correspond to compounds of formula IV except that R16 and R17 together with the carbon atom to which they are attached form a cyclopentane or cyclohexane ring.

The present invention still further relates to compounds of formula V in which R13 to R19 have the same definition as in Formula III:

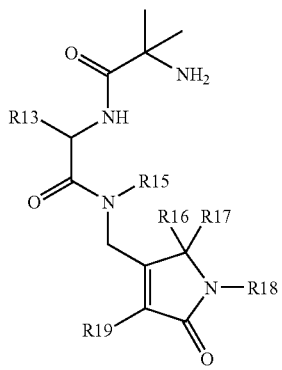

Formula V

The present invention further relates to compounds of formula VA which correspond to compounds of formula V except that R16 and R17 together with the carbon atom to which they are attached form a cyclopentane or cyclohexane ring.

The present invention still further relates to processes for the preparation of compounds of formula I.

The terms and abbreviations used in the instant examples have their normal meanings unless otherwise designated. For example "° C." refers to degrees Celsius; "N" refers to normal or normality; "mmol" refers to millimole or millimoles; "g" refers to gram or grams; "mL" means milliliter or milliliters; "M" refers to molar or molarity; "MS" refers to mass spectrometry; "FDMS" refers to field desorption mass spectrometry; "IS" refers to ion spray ionisation; "EI" refers to electron impact ionisation; "UV" refers to ultraviolet spectroscopy; "IR" refers to infrared spectroscopy; and "NMR" refers to nuclear magnetic resonance spectroscopy.

As used herein, the term "$C_1-C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1-C_6$ alkyl" includes within its definition the term "$C_1-C_4$ alkyl".

As used herein, the term "cycloalkyl" refers to cyclized chains of 3 to 6 carbon atoms and includes, but is not limited to, cyclopropyl, cyclobutyl, cyclopentyl, and cyclohexyl.

The term "halo" means chloro, fluoro, bromo or iodo. Halo may most preferably be chloro or bromo.

"$C_1-C_6$ alkoxy" represents a straight or branched alkyl chain having from one to six carbon atoms attached to an oxygen atom. Typical $C_1-C_6$ alkoxy groups include methoxy, ethoxy, propoxy, isopropoxy, butoxy, t-butoxy, pentoxy and the like. The term "$C_1-C_6$ alkoxy" includes within its definition the term "$C_1-C_4$ alkoxy".

"$C_2-C_6$ alkanoyl" represents a straight or branched alkyl chain having from one to five carbon atoms attached through a carbonyl moiety. Typical $C_2-C_6$ alkanoyl groups include ethanoyl (also referred to as acetyl), propanoyl, isopropanoyl, butanoyl, t-butanoyl, pentanoyl, hexanoyl, and the like.

"$C_1-C_6$ alkylidenyl" refers to a straight or branched, divalent, saturated aliphatic chain of one to six carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like.

The term "aryl" represents an aromatic ring or rings and aromatic residues of 5 to 7-membered mono- or bicyclic rings with 1 to 4 heteroatoms (a "heteroaryl") including but not limited to such groups as phenyl, napthyl, biphenyl, thiophenyl, benzothiophenyl, furanyl, benzofuranyl, and the like. The term "carbocyclic aryl" means that the aryl ring does not contain any heteroatoms (the ring is not heteroaryl).

The term "optionally substituted aryl", "optionally substituted N-aryl", and "optionally substituted S-aryl" means that each of the respective aryl groups (which aryl group may contain heteroatoms as described above), is optionally substituted with from one to four substituents, independently selected from the group consisting of $C_1-C_6$ alkyl, —$OC_1-C_6$ alkyl, —$OCF_3$, amide, aryl, aryloxy, $SO_2(C_{1-6}$ alkyl), NHamide, carboxamide, sulfonamide, NHsulfonamide, imide, hydroxy, carboxy, nitro, halo, tri(chloro or fluoro)methyl, and cyano. The aromatic ring may be attached at any carbon atom or heteroatom which affords a stable structure. The group, 3,4-methylenedioxyphenyl is embraced by this definition.

The term "—O-aryl" means an aryloxy substituent which is bonded to the parent molecule through the O group. The term "optionally substituted —O-aryl" means that the aryl group of the —O-aryl substituent is optionally substituted with from one to four substituents independently selected from the group consisting of $C_1-C_6$ alkyl, —$OC_1-C_6$ alkyl, —$OCF_3$, amide, aryl, aryloxy, $SO_2(C_{1-6}$ alkyl), NHamide, carboxamide, sulfonamide, NHsulfonamide, imide, hydroxy, carboxy, nitro, halo, tri(chloro or fluoro)methyl, and cyano.

The term "-aryl-aryl(K1)(K2)" refers to an aryl group substituted with an additional aryl group said additional aryl group being disubstituted with K1 and K2. K1 is defined to include halo and —CF$_3$, and K2 is defined to include hydrogen, halo, and —CF$_3$. Similarly, the terms "—O-aryl-aryl(K1)(K2)", "—N-aryl-aryl(K1)(K2)", and "—S-aryl-aryl(K1)(K2)" are likewise defined. For example, the term "—O-aryl-aryl(K1)(K2)" means an aryloxy substituent as defined above which is substituted with an additional aryl group, said additional aryl group being disubstituted with K1 and K2. K1 and K2 are as defined immediately above.

The term "carboxy-protecting group" as used herein refers to substituents of the carboxy group commonly employed to block or protect the carboxy functionality while reacting other functional groups on the compound. Examples of such protecting groups include methyl, ethyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4,'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and the like. A preferred carboxy-protecting group for the practice of the present invention is methyl or ethyl. Further examples of these groups may be found in E. Haslam, supra, at Chapter 5, and T. W. Greene, et al., supra, at Chapter 5.

The term "amino-protecting group" as used herein refers to substituents of the amino group commonly employed to block or protect the amino functionality while reacting other functional groups on the compound. Examples of such amino-protecting groups can be found at T. W. Greene, et al., supra.

Examples of such amino-protecting groups include, but are not limited to, formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, n-butoxycarbonyl, (NBoc) t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxy-carbonyl (FMOC), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; benzoylmethylsulfonyl group, 2-nitrophenylsulfenyl, diphenylphosphine oxide and like amino-protecting groups.

The amino-protecting group employed is usually not critical so long as the derivatized amino group is stable to the condition of subsequent reactions on other positions of the intermediate molecule, and may be selectively removed at the appropriate point without disrupting the remainder of the molecule including any other amino-protecting groups. A preferred amino-protecting group for the practice of the present invention is t-butoxycarbonyl (NBoc). Further examples of groups referred to by the above terms are described by E. Haslam, Protective Groups in Organic Chemistry, (J. G. W. McOmie, ed., 1973), at Chapter 2; and T. W. Greene and P. G. M. Wuts, Protective Groups in Organic Synthesis (1991), at Chapter 7.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, azido, or —O—CO—(C$_4$–C$_7$ alkyl).

The term "heterocycle" represents a stable 5- to 7-membered monocyclic or 7- to 10-membered bicyclic heterocyclic ring which is saturated or unsaturated and which consists of carbon atoms and from 1 to 4 heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure, and may be optionally substituted with one or more substituents selected from the group consisting of C$_1$–C$_6$ alkyl, —OC$_1$–C$_6$ alkyl, hydroxy, nitro, halo, and tri(halo)methyl.

The compounds of the present invention may be prepared by a number of routes, many of which are known to those of skill in the art. The particular order of steps to be employed in the synthesis of compounds of formula I is dependent upon the compound to be synthesized, the starting material employed, and the relative lability of the various substituted moieties.

During any of the following synthetic sequences it may be necessary or desirable to protect sensitive or reactive groups on any of the molecules concerned. This may be achieved by employing conventional protecting groups as described, supra.

The compounds used in the method of the present invention may have one or more asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in Nomenclature of Organic Compounds: Principles and Practice, (J. H. Fletcher, et al., eds., 1974) at pages 103–120.

In addition to the (R)-(S) system, the older D-L system is also used in this document to denote absolute configuration, especially with reference to amino acids. In this system, a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, a number of routes are available. As an example, a mixture of enantiomers may be prepared, and then the two enantiomers may be separated. A commonly employed method for the resolution of the racemic mixture (or mixture of enantiomers) into the individual enantiomers is to first convert the enantiomers to diastereomers by way of forming a salt with an optically active acid or base. These diastereomers may then be separated using differential solubility, fractional crystallization, chromatography, or the like. Further details regarding resolution of enantiomeric mixtures may be found in J. Jacques, et al., Enantiomers, Racemates, and Resolutions, (1991).

Representative starting material for this synthesis is a compound of formula VIa, which may be coupled with an ethinylcyclohexylamine of formula VII using activating agents for N-acylation reactions known in the art, like HOBT, DCC, EDC, oxalyl chloride, TBTU or other coupling reagents known to the skilled artisan, to result in a compound of formula VIIIa. Preferred for the practice of the present invention is TBTU. Intermediates of formula VIa and VII are commercially available or can be prepared by methods known in the art. Alternatively, a compound of formula VIa' may be reacted with a compound of formula VII by methods known in the art to yield a compound of formula VIIIa. Intermediates of formula VIa' may be prepared from commercial compounds by standard methods as described in Tetrahedron Lett. 25 (1984), 4553–4556.

A compound of formula VIIIa may be hydrated by standard methods to yield a compound of formula VIIIb and subsequently cyclized by treatment with a deprotonating agent, such as sodium hydride, optionally in the presence of an alkylating agent to yield a compound of formula VIIIc. Treatment of the resulting compound with a bromination reagent, such as N-bromosuccinimide, results in a compound of formula VIII. Reaction with an amine, generates compounds of formula IX in which m=1. Representative reactions are provided in Scheme A below. An example of formula VIIIc where Q is $SO_2$, R8 is hydrogen and R9 is 4-chlorophenyl is described in Pestic. Sci. 39 (1993), 185–192.

Compounds of formula IX in which the starting material VII is the commercial 1,1-diethylpropargylamine or 1,1-dimethylpropargylamine may also be prepared by the route described in Scheme A.

SCHEME A

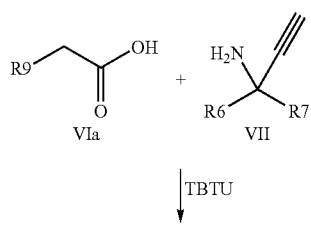

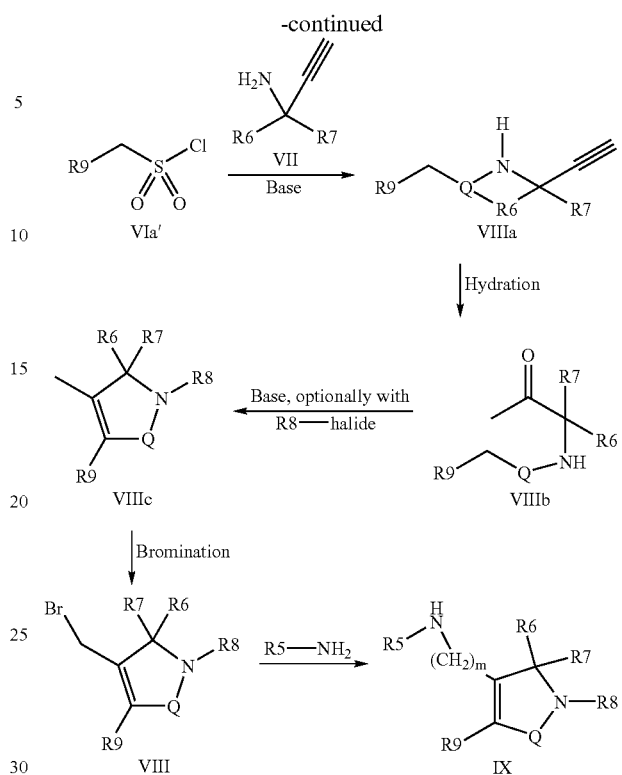

Scheme A' shows an alternative synthesis for acetyl intermediates of Formula VIIIb:

Scheme A'

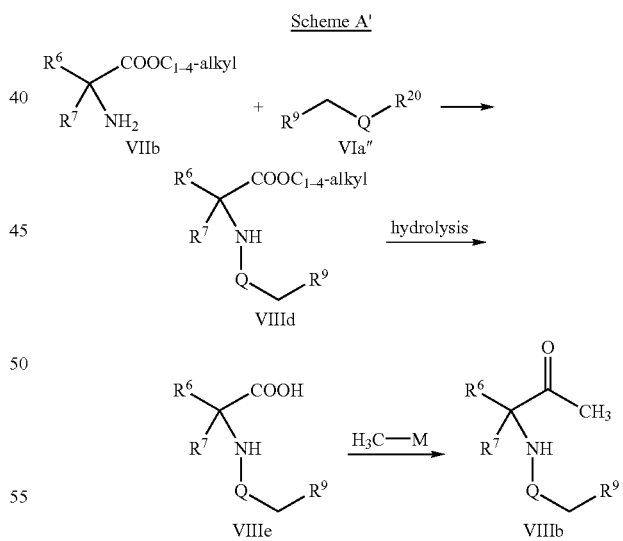

Esters of aminoacids of Formula VIIb, preferably methyl or ethyl esters, are coupled with derivatives of carboxylic acids or sulfonic acids of Formula VIa" by methods described in Scheme A to give intermediates of Formula VIIId. The esters are hydrolized by standard methods to give carboxylic acids of Formula VIIIe. These are treated with organometallic methyl compounds to prepare the acetyl intermediates of Formula VIIIb. Preferred organometallic reagents are methyl Grignard reagents (M=MgCl, MgBr, or MgI) or methyl lithium (M=Li), more preferred methyl lithium. Examples for this reaction are known from the literature, e.g. J. Org. Chem. 58 (1993), 4758; J. Org. Chem. 62 (1997), 6862; Tetrahedron Lett. 35 (1994), 3745. In a preferred method a solution of the carboxylic acid in a solvent like THF or DME is treated with an excess of methyl lithium in diethylether at a temperature below −60° C. followed by warming to room temperature.

Compounds of Formula I in which W=—$CH_2CH_2$— may be prepared as shown in Scheme B below.

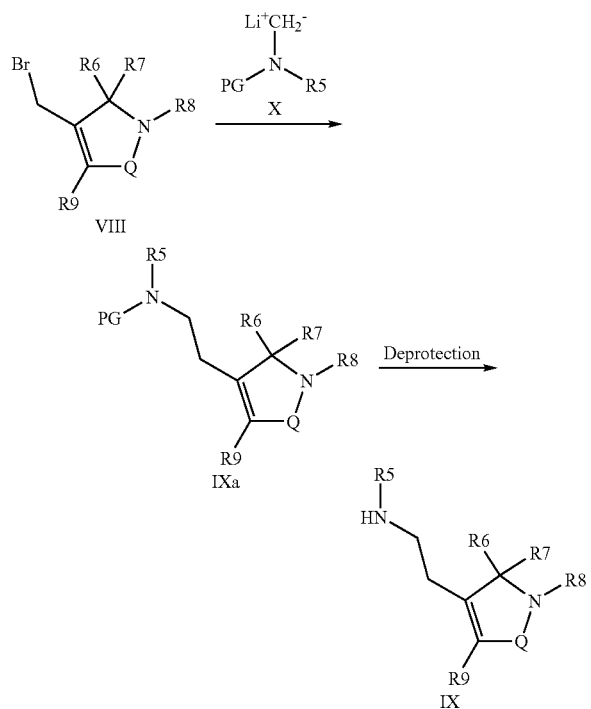

SCHEME B

A compound of formula X is obtained by treatment of a protected methylamine with a deprotonating agent like butyllithium as described for example in Tetrahedron Lett. 35(24), 1994, 4067–70. As used in Scheme B, the substituent "PG" means a protecting group, which is known to the artisan, and all other substituents are as defined by Formula I, herein. One preferred protecting group is the BOC group or another N-protecting group known in the art and stable under the reaction conditions. A compound of formula VIII is treated with a compound of formula X to yield a compound of formula IXa.

It is to be understood that the bromine group on the compound of formula VIII may in fact be any suitable leaving group, as defined herein.

The term "leaving group" refers to a group of atoms that is displaced from a carbon atom by the attack of a nucleophile in a nucleophilic substitution reaction. Suitable leaving groups include bromo, chloro, and iodo, benzenesulfonyloxy, methanesulfonyloxy, and toluenesulfonyloxy. The term "leaving group" includes activating groups.

A second portion of the overall synthesis of compounds of formula I is provided in Scheme C below.

Representative starting material for this synthesis is a compound of formula XIa, which is a chemically-protected form of the amino acid O-serine. By chemically-protected it is meant that both the amino- and carboxy-functional groups have been suitably protected in order to facilitate further reactions with this molecule. Such protection reactions are known to those of skill in the art, and may be applied to other suitable starting materials. Intermediates of formula XIa are commercially available, or may be prepared by standard syntheses of amino acids. Such syntheses are well known to persons of ordinary skill in the art and are described, for example, in Chemistry and Biochemistry of Amino Acids, (G. C. Chapman ed., 1985). The protected amino group may be specifically deprotected using trifluoroacetic acid and methylene chloride to allow for further reactions with this amino functional group. This deprotection reaction results in a compound of formula XIb.

A compound of formula XIb may then be N-acylated with an amino-protected compound of formula XII to produce a compound of formula XIc. Suitable activating agents for this N-acylation reaction are known in the art and include DCC, HOBT, EDC, and oxalyl chloride. Preferred for the practice of the present invention is HOBT. Compounds of formula XII are commercially available, or are readily prepared from suitable available starting materials. The protected carboxy group on the compound of formula XIc is then selectively deprotected, typically using lithium hydroxide, to generate a compound of formula XI. Compounds of formula XI in which the starting material XIa is 2-Nboc-amino-5-phenyl-pentanoic acid methyl ester or 2-Nboc-amino-3-(3-indolyl)-propionic acid methyl ester may also be prepared by the route described in Scheme C.

A compound of formula XI is then coupled with a compound of formula IX and subsequently deprotected to generate a compound of formula Ia. Again, typical reagents for this N-acylation are known in the art, and include DCC and HOBT, which is the preferred method of coupling employed in the practice of the present invention. Compounds of formula Ia are encompassed by formula I, and are pharmaceutically active.

The preferred reaction temperature range employed in these reactions is between −40 and 150° C., and the most preferred range is between 10 and 40° C. These reactions may be conveniently carried out in situ, without isolation of the particular compound after its preparation.

Representative reactions are provided below in Scheme C.

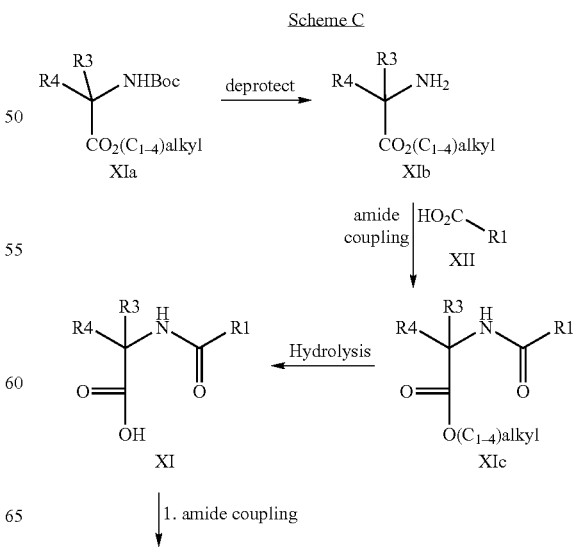

Scheme C

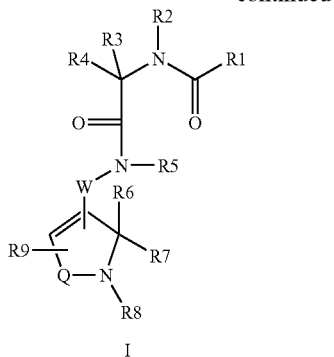

I

The compounds of the present invention can be useful for modulating growth hormone secretion and as research tools. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of Formula I are:

a) $R_3$ is

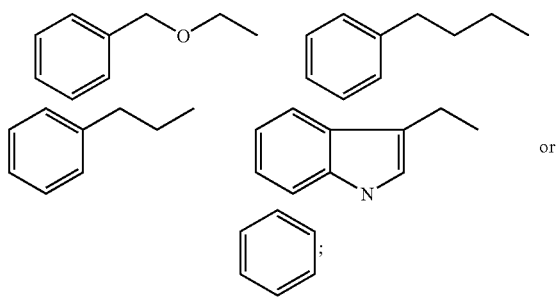

b) $R_1$ is

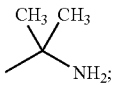

c) Q is $S(O)_2$;
d) Q is C(O);
e) R6 and R7 form a carbocyclic ring;
f) R6 and R7 form a 5 or 6 membered carbocyclic ring;
g) R6 and R7 are each C1–3 alkyl;
h) R6 and R7 are each independently selected from the group consisting of methyl and ethyl;
i) W is $(CH_2)_m$;
j) R2 is hydrogen;
k) R4 is hydrogen;
l) R3 is phenylmethoxymethyl or 3-phenylpropyl;
m) R5 is hydrogen, methyl, ethyl, or n-propyl;
n) R6 and R7 are both each methyl or ethyl;
o) R9 is thienyl, naphthyl, O-phenyl or phenyl, which is optionally substituted with one or more substituents independently selected from the group consisting of $C_1$–$C_6$ alkyl, —$C_1$–$C_6$ alkoxy, halo($C_1$–$C_6$ alkyl), halo ($C_1$–$C_6$ alkoxy), O-aryl, $CONH_2$, $CONH(C_1$–$C_6$ alkyl), $NHCO(C_1$–$C_6$ alkyl), $SO_2NH_2$, $SO_2NH(C_1$–$C_6$ alkyl), $NHSO_2(C_1$–$C_6$ alkyl), COOH, $COO(C_1$–$C_6$ alkyl), hydroxy, nitro, halo, $SO_2(C_{1-6}$ alkyl), and cyano;
p) R9 is thienyl, naphthyl, O-phenyl or phenyl;
q) R8 is hydrogen, methyl or ethyl;
r) W is $CH_2$;
s) R9 is carbocyclic aryl;
t) R9 is thienyl;
u) R6 and R7 together form a cyclopentyl ring;
v) R6 and R7 together form a cyclohexyl ring; and
w) The compound of Formula I is a pharmaceutically acceptable salt.

Specific compounds of the invention include: 2-(R)-2-(2-Amino-2-methylpropionylamino)-3-phenylmethoxy propionic acid N-(3-(4-chlorophenyl)-2,2-dioxo-1-methyl-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)-N-methylamide, 2-(R)-2-(2-Amino-2-methylpropionylamino)-3-(3-indolyl) propionic acid N-(3-(4-chlorophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-(3-(4-chlorophenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-tert-butylphenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-chloro-phenyl)-2,2-dioxo-2-thia-1-azaspiro[4.5]dec-3-ene-4-ylmethyl)-N-propylamide, 2-(R)-2-(2-Amino-2-methylpropionylamino)-5-phenyl-pentanoic acid N-(3-(4-chlorophenyl)-2,2-dioxo-2-thia-1-azaspiro[4.5]dec-3-ene-4-ylmethyl)-N-methylamide, 2-(R)-2-(2-Amino-2-methylpropionylamino)-3-phenylmethoxy-propionic acid N-ethyl-N-(1-methyl-2,2-dioxo-3-phenyl-2-thia-1-azaspiro[4.5]dec-3-ene-4-ylmethyl)amide, 2-(R)-2-(2-Amino-2-methylpropionylamino)-3-phenylmethoxy-propionic acid N-(3-(3-chlorophenyl)-1-methyl-2,2-dioxo-2-thia-1-azaspiro[4.5]dec-3-ene-4-ylmethyl)-N-ethylamide, 2-(R)-2-(2-Amino-2-methylpropionylamino)-3-phenyl-methoxy-propionic acid N-(3-(2-chlorophenyl)-1-methyl-2,2-dioxo-2-thia-1-azaspiro[4.5]dec-3-ene-4-ylmethyl)-N-ethylamide, 2-(R)-2-(2-Amino-2-methylpropionylamino)-3-phenyl-methoxypropionic acid N-ethyl-N-1-methyl-2,2-dioxo-3-(4-trifluoromethylphenyl)-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(1-methyl-3-(4-nitrophenyl)-2,2-dioxo-2-thia-1-azaspiro[4.5]dec-3-ene-4-ylmethyl)amide, 2-(R)-2-(2-Amino-2-methylpropionylamino)-3-phenylmethoxy-propionic acid N-(3-(4-bromophenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-ethyl-N-(2,2-dioxo-3-(4-methylphenyl)-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(1-ethyl-2,2-dioxo-3-phenyl-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(2,2-dioxo-3-(3-phenoxyphenyl)-2-thia-1-azaspiro[4.5]dec-3-ene-4-ylmethyl)-N-ethylamide, 2-(R)-2-(2-Amino-2-methylpropionylamino)-3-phenyl-methoxy-propionic acid N-(3-(3-bromophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-ethyl-N-(2,2-dioxo-3-phenyl-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(3-(4-fluorophenyl)-2,2-dioxo-2-thia-1-azaspiro[4.5]dec-3-ene-4-ylmethyl)amide, 2-(R)-2-(2-Amino-2-methylpropionylamino)-5-phenyl-pentanoic acid N-ethyl-N-(3-(4-fluorophenyl)-2,2-dioxo-2-thia-1-azaspiro[4.5]dec-3-ene-4-ylmethyl)amide, 2-(R)-2-(2-Amino-2-methylpropionylamino)-3-phenylmethoxy-propionic acid N-(3-(2-bromophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-(3-(2-bromophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-(3-(2-bromophenyl)-2,2-dioxo-2-thia-1-azaspiro[4.5]dec-3-ene-4-ylmethyl)-N-ethylamide, 2-Amino-N-{2-benzyloxy-1-[(3,3-dimethyl-1,1-dioxo-5-phenyl-2,3-dihydro-1H-1$\gamma^6$-isothiazol-4-yl-methyl)-ethyl-carbamoyl]-ethyl}-2-methyl-propionamide, 2-(2-Amino-2-methyl-propionylamino)-5-phenyl-pentanoic acid (3,3-dimethyl-1,1-dioxo-5-phenyl-2,3-dihydro-1H-1$\gamma^6$-isothiazol-4-ylmethyl)-ethyl-amide, 2-Amino-N-{2-benzyloxy-1-[2,2-dioxo-3-phenyl-2$\lambda^6$-thia-1-aza-spiro[4.4]non-3-en-4-ylmethyl)-ethyl-carbamoyl]-ethyl}-2-methyl-propionamide, 2-(2-Amino-2-methyl-propionylamino)-5-phenyl-pentanoic acid [5-(4-chloro-phenyl)-3,3-dimethyl-1,1-dioxo-2,3-dihydro-1H-1$\gamma^6$-isothiazol-4-ylmethyl]-ethylamide, 2-(2-Amino-2-methyl-propionylamino)-5-phenyl-pentanoic acid (2,2-dioxo-3-phenyl-2$\lambda^6$-thia-1-aza-spiro[4.4]non-3-en-4-ylmethyl)-ethylamide, 2-Amino-N-(2-benzyloxy-1-{[3-(4-chloro-phenyl)-2,2-dioxo-2$\lambda^6$-thia-1-aza-spiro[4.4]non-3-en-4-yl methyl]-ethyl-carbamoyl}-ethyl)-2-methyl-propionamide, and 2-(R)-2-(2-Amino-2-methylpropionylamino)-3-phenyl-methoxypropionic acid N-ethyl-N-(2,2-dioxo-3-phenyl-2-thia-1-azaspiro[4.5]dec-3-ene-4-ylmethyl)amide; or pharmaceutically acceptable salts thereof.

Compounds of formula I may be conveniently screened for growth hormone secretagogue activity. A typical assay may employ pituitary cells established in culture, followed by a challenge with the various compounds of formula I, and the levels of growth hormone determined accordingly. Growth hormone levels may be calculated using various radioimmunoassay techniques known to those of skill in the art. Screening of compounds for growth hormone secretagogue activity may conveniently be scaled up for high throughput screening.

The invention further encompasses methods employing the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, $\gamma$-hydroxybutyrate, glycollate, tartrate, methanesulfonate, propanesulfonate, naphthalene-1-sulfonate, naphthalene-2-sulfonate, mandelate, mesylate, and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further encompasses methods employing pharmaceutically acceptable solvates of the compounds of Formula I. Many of the formula I compounds can combine with solvents such as water, methanol, and ethanol to form pharmaceutically acceptable solvates such as the corresponding hydrate, methanolate, and ethanolate.

This invention also encompasses methods employing the pharmaceutically acceptable prodrugs of the compounds of formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:
1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra.

Conventional procedures for the selection and preparation of suitable prodrug derivatives are described, for example, in H, Bundgaard, Design of Prodrugs, (1985).

As used herein, the term "effective amount" means an amount of compound of the instant invention which is capable of inhibiting, alleviating, ameliorating, treating, or preventing further symptoms in mammals, including humans, which may be due to decreased levels of endogenous growth hormone.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound required to treat, inhibit, or prevent the symptoms and/or disease of congestive heart failure in a mammal, including humans, according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy.

In addition, the growth hormone secretagogue compounds as disclosed herein may be administered to a patient in need of treatment in combination with other growth hormone secretagogues known in the art, and/or with a suitable bone anti-resorptive agent or agents for the prevention or treatment of osteoporosis and/or loss of muscle strength. Said suitable bone anti-resorptive agents include selective estrogen receptor modulators, bisphophonates, calcitonin, and hormone replacement therapeutic agents. Additionally, PTH may be administered in combination with said growth hormone secretagogues. Said combination therapy may be administered concomitantly or sequentially.

The compositions are preferably formulated in a unit dosage form, each dosage containing from about 0.01 to about 500 mg, more usually about 0.5 to about 200 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.01 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 mg compound per $cm^2$ of an affected tissue. Preferably, the applied amount of compound will range from about 30 to about 300 $mg/cm^2$, more preferably, from about 50 to about 200 $mg/cm^2$, and, most preferably, from about 60 to about 100 $mg/cm^2$.

Suitable dosing ranges of compounds of formula I include 0.01 mg/kg/day to 60 mg/kg/day. Representative pharmaceutical formulations containing compounds of formula I–IV are provided below.

The formulations which follow are given for purposes of illustration and are not intended to be limiting in any way. The total active ingredients in such formulations comprises from 0.1% to 99.9% by weight of the formulation. The term "active ingredient" means a compound of formula I, including but not limited to compounds of formulas II, III, IV and V.

Formulation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation 9

An intravenous formulation may be prepared as follows:

| Ingredient | Quantity |
| --- | --- |
| Active Ingredient | 250.0 mg |
| Isotonic saline | 1000 mL |

Formulation 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another formulation employed in the methods of the present invention employs transdermal delivery devices or patches. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, the disclosure of which is herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, the disclosure of which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The following Examples and Preparations are illustrative of the processes employed in the synthesis of the compounds of the present invention. As would be understood by persons skilled in the art, other synthetic schemes may be employed to prepare the compounds of the instant invention.

EXAMPLE 1

2-(R)-2-(2-Amino-2-methylpropionylamino)-3-phenylmethoxy propionic acid N-(3-(4-chlorophenyl)-2,2-dioxo-1-methyl-2-thia-1-azaspiro[4.5]dec-3-ene-4-ylmethyl)-N-ethylamide trifluoroacetate

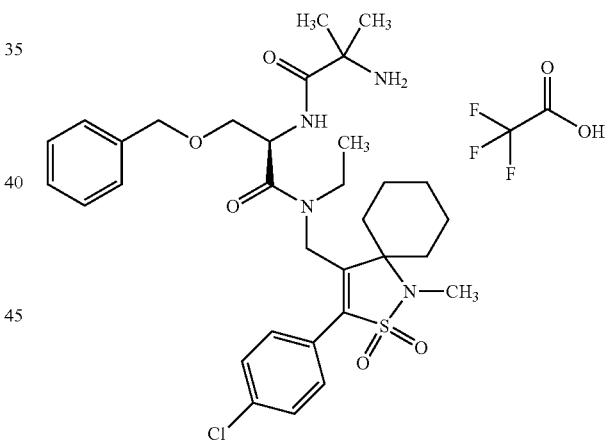

The title compound, as shown above, was prepared as follows.

4-Chlorobenzylchloride (30 g, 0.186 mol) and $Na_2SO_3$ (47 g, 2 eq.) were refluxed for several hours in 150 mL water. A phase transfer agent like trioctylmethylammonium chloride may be added as described in Tetrahedron Lett. 1984, 25(40), 4553–6. After cooling to room temperature, the solution was extracted with ethyl acetate, the water layer was evaporated and the residue suspended in ethanol. The mixture was filtered, the filtrate was concentrated and the solid was dried at 50° C. under vacuum. 4-Chlorophenyl-methanesulfonate (23.5 g, 55%; MS (EI): 205 [M]$^{+}$ was obtained. $POCl_3$ (20 mL) was cooled to 0° C., 4-chlorophenyl-methanesulfonate (15.9 g, 69.5 mmol) and $PCl_5$ (20.3 g, 1.4 eq.) were added. The mixture was stirred overnight at room temperature and evaporated under vacuum. The residue was suspended in ethyl acetate and filtered. After concentration of the filtrate, 12 g (75%) of the crystalline 4-chlorophenylmethanesulfonyl chloride, shown below, were obtained. MS (EI): 125 [ClC$_6$H$_4$CH$_2$]$^{·+}$, 224 [M]$^{·+}$

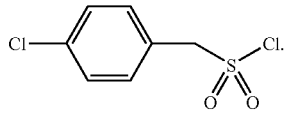

The preparation of N-(1-acetylcyclohexyl)-4-chlorophenyl-methanesulfonamide, shown below, was performed as described in Pestic. Sci. 1993, 39, 185–192. 4-chloro-phenylmethanesulfonyl chloride (1.37 g, 6 mmol) and ethynyl-cyclohexylamine (0.73 g, 6 mmol) were stirred in tetrahydrofuran (10 mL) with triethylamine (0.9 mL, 6.6 mmol) for several hours at room temperature. The mixture was diluted with ethyl acetate, washed with water, dried (Na$_2$SO$_4$) and evaporated. Recrystallisation from ethanol yielded 4-chlorophenyl-N-(1-ethynylcyclohexyl)methane-sulfonamide (1.5 g, 80%) as a solid.

This compound was suspended in ethylene glycol (25 mL). 2 mL water, 100 mg HgO, and 5 drops conc. sulfuric acid were added and the mixture was heated at 175° C. for 1 hour, cooled to room temperature, diluted with dichloromethane, washed with water, dried (Na$_2$SO$_4$) and evaporated to yield N-(1-acetylcyclohexyl)-4-chloro-phenylmethanesulfonamide as a solid (1.5 g, 95%). MS (IS): 330 [MH]$^+$

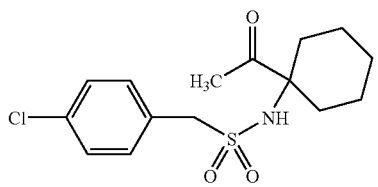

N-(1-Acetylcyclohexyl)-4-chlorophenylmethane sulfonamide (1.02 g, 3.1 mmol) was dissolved in dry DMF (10 mL) under Ar. NaH (60%, 2.2 eq.) and iodomethane (2 eq.) were added and the mixture was stirred overnight at 120° C. After dilution with water the solution was extracted with ethyl acetate. The organic layer was washed with NaCl solution and water, dried (Na$_2$SO$_4$) and concentrated to yield 696 mg (69%) of the 3-(4-chlorophenyl)-1,4-dimethyl-2-thia-1-azaspiro[4.5]dec-3-ene 2,2-dioxide, shown below as a solid. MS (IS): 326 [MH]$^+$.

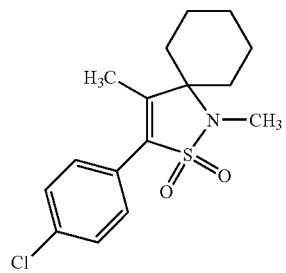

3-(4-Chlorophenyl)-1,4-dimethyl-2-thia-1-azaspiro[4.5] dec-3-ene 2,2-dioxide (0.63 g, 1.93 mmol) and N-bromo succinimide (1 eq.) were stirred in 60 mL CCl$_4$ with a catalytic amount of benzoyl peroxide for 3 hours at 85° C. After cooling to room temperature the mixture was diluted with CH$_2$Cl$_2$, washed with water, dried (Na$_2$SO$_4$) and evaporated to yield 4-bromomethyl-3-(4-chloro-phenyl)-2-methyl-2-thia-1-azaspiro[4.5]dec-3-ene 2,2-dioxide as a syrup. Without further purification the product was dissolved in ethanol (100 mL), ethylamine (70% solution in water, 20 mL) was added and the mixture was stirred overnight at room temperature. After concentration the residue was dissolved in CH$_2$Cl$_2$, washed with water and extracted with 0.5 M HCl. After addition of NaOH and extraction with CH$_2$Cl$_2$ the organic layer was dried (Na$_2$SO$_4$) and evaporated to yield 3-(4-chlorophenyl)-4-ethylamino methyl-1-methyl-2-thia-1-azaspiro[4.5]dec-3-ene 2,2-dioxide, shown below, as a solid. Yield: 306 mg (43%) MS (IS): 369 [MH]$^+$

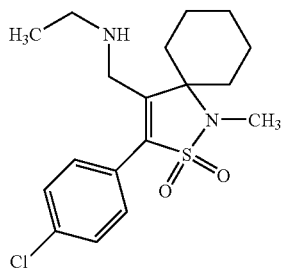

2-(R)-2-(2-(N-tert-Butoxycarbonylamino)-2-methyl propionylamino)-3-phenylmethoxypropionic acid (1.2 eq.) in CH$_2$Cl$_2$ (15 mL) was stirred for 15 min with dicyclohexylcarbodiimide (1.1 eq.) and 1-hydroxy-7-azabenzotriazole (1.1 eq.), 3-(4-chlorophenyl)-4-ethyl aminomethyl-1-methyl-2-thia-1-azaspiro[4.5]dec-3-ene 2,2-dioxide (306 mg, 0.83 mmol) in CH$_2$Cl$_2$ (8 mL) was added and the mixture was stirred overnight at room temperature. After filtration the filtrate was diluted with ethyl acetate, washed with 0.1 M citric acid, saturated NaHCO$_3$ and the organic layer was dried (Na$_2$SO$_4$) and evaporated to yield 2-(R)-2-(2-(N-tert-Butoxycarbonylamino)-2-methyl propionylamino)-3-phenylmethoxypropionic acid N-(3-(4-chlorphenyl)-1-methyl-2,2-dioxo-2-thia-1-azaspiro[4.5]dec-3-ene-4-y (methyl)-N-ethyl amide, shown below (593 mg, 98%) as a colorless oil. MS (IS): 732 [MH]$^+$.

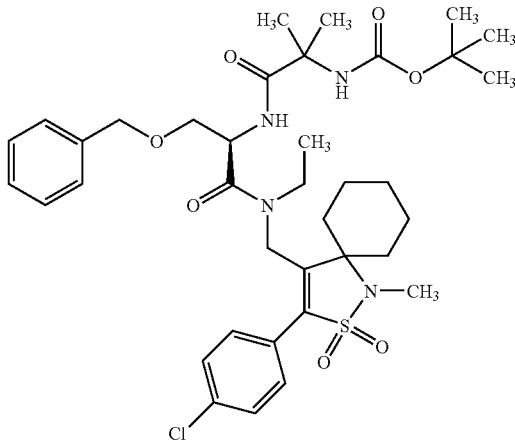

2-(R)-2-(2-(N-tert-Butoxycarbonylamino)-2-methyl propionylamino)-3-phenylmethoxy-propionic acid N-(3-(4-chlorphenyl)-1-methyl-2,2-dioxo-2-thia-1-azaspiro[4.5] dec-3-ene-4-ylmethyl)-N-ethylamide (593 mg, 0.81 mmol) was dissolved in dichloromethane (5 mL) and trifluoroacetic acid (5 mL) and stirred overnight. The mixture was poured into dry ethyl ether (200 mL). The precipitate was filtered off and dried at 50° C. under vacuum to yield the title compound (520 mg, 86%) as a solid. MS (IS): 631 [MH]$^+$; m.p. 95–120° C.

EXAMPLE 2

2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)-N-ethylamide trifluoroacetate

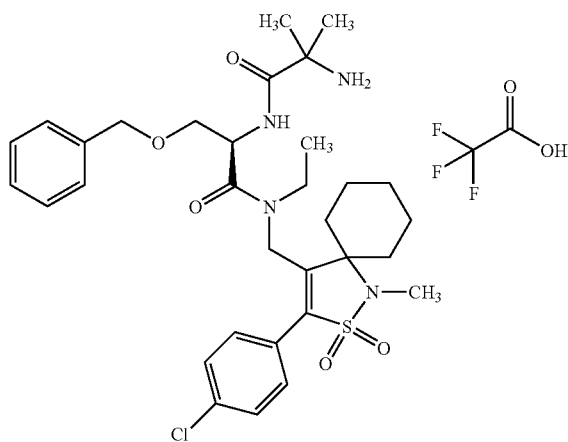

The title compound, as shown above, was prepared as follows.

To N-(1-acetylcyclohexyl)-(4-chlorophenyl)methane-sulfonamide (612 mg, 1.86 mmol), from Example 1, in dry DMF (6 mL) was added NaH (60%, 2.2 eq.) under Ar. The mixture was stirred overnight at 120° C., water was added and the solution was extracted with ethyl acetate. The organic layer was washed with NaCl solution and water, dried (Na$_2$SO$_4$) and concentrated. Recrystallization from ethyl acetate yielded 0.37 g (64%) of 3-(4-chlorophenyl)-4-methyl-2-thia-1-azaspiro[4.5]dec-3-ene, 2,2-dioxide, shown below as a solid. MS (IS): 312 [MH]$^+$

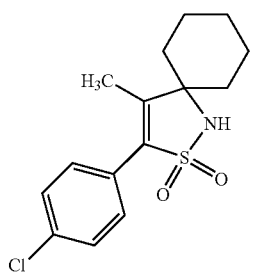

3-(4-Chlorophenyl)-4-methyl-2-thia-1-azaspiro[4.5]dec-3-ene 2,2-dioxide was brominated to yield 4-bromomethyl-3-(4-chloro-phenyl)-2-thia-1-azaspiro[4.5]dec-3-ene 2,2-dioxide and treated with ethylamine according to the methods described in Example 1. 3-(4-chlorophenyl)-4-ethylaminomethyl-2-thia-1-azaspiro[4.5]dec-3-ene 2,2-dioxide, shown below, was obtained in a yield of 558 mg (74%). MS (IS): 355 [MH]$^+$

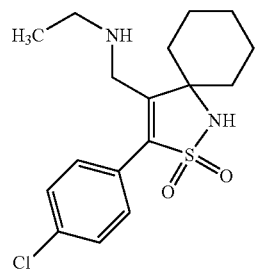

The title compound was prepared and deprotected according to the methods described in Example 1. Yield: 930 mg, 83% MS (IS): 617 [MH]$^+$; m.p. 125–135° C.

EXAMPLE 3

2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)-N-methylamide trifluoroacetate

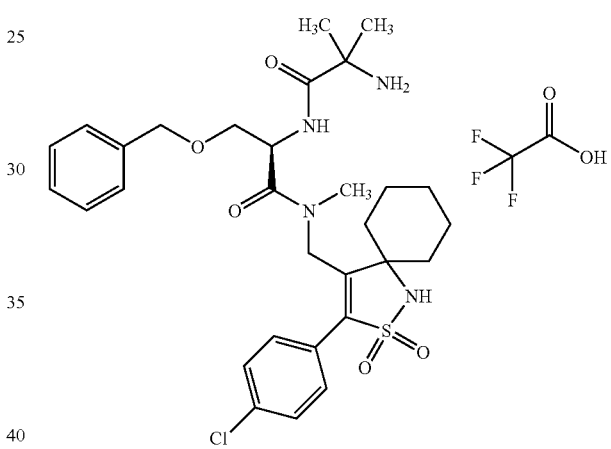

The title compound, as shown above, was prepared as follows.

4-Bromomethyl-3-(4-chlorophenyl)-2-thia-1-azaspiro[4.5]dec-3-ene 2,2-dioxide, made as described in Example 2, (270 mg, 0.69 mmol) was dissolved in ethanol (30 mL). Methylamine (70% solution in water, 8 mL) was added and the mixture was stirred overnight at room temperature and concentrated. The residue was dissolved in CH$_2$Cl$_2$, washed with water and extracted with 0.5 M HCl. After addition of NaOH and extraction with CH$_2$Cl$_2$ the organic layer was dried (Na$_2$SO$_4$) and evaporated to yield 80 mg (34%) of 3-(4-Chlorophenyl)-4-methylaminomethyl-2-thia-1-azaspiro[4.5]dec-3-ene 2,2-dioxide as a solid. MS (IS): 341 [MH]$^+$

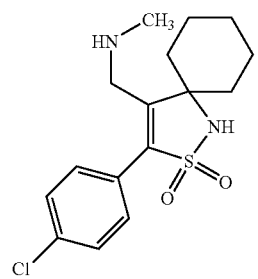

The title compound was prepared and deprotected according to the methods described in Example 1. Yield: 120 mg, 91%; MS (IS): 603 [MH]+; m.p. 143–145° C.

EXAMPLE 4

2-(R)-2-(2-Amino-2-methylpropionylamino)-3-(3-indolyl) propionic acid N-(3-(4-chlorophenyl)-2,2-dioxo-2-thia-1-azaspiro[4.5]dec-3-ene-4-ylmethyl)-N-ethylamide trifluoroacetate

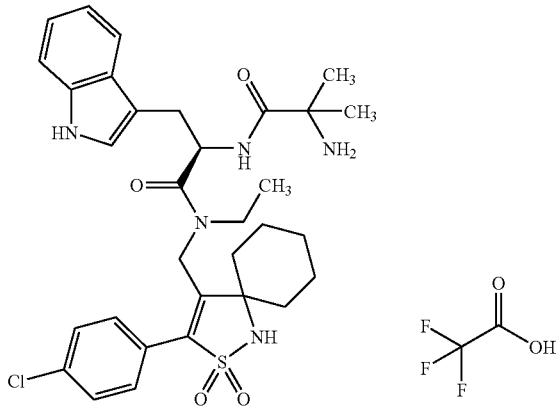

The title compound, shown above, was prepared by coupling 2-(R)-2-(2-(N-tert-butoxycarbonylamino)-2-methylpropionylamino)-3-(3-indolyl)propionic acid (1.2 eq.) with 3-(4-chlorophenyl)-4-ethylaminomethyl-2-thia-1-azaspiro[4.5]dec-3-ene 2,2-dioxide, as described in Example 2, and subsequent deprotection according to the methods described in Example 1. Yield: 68 mg, 60%; MS (IS): 626 [MH]+; m.p. 170–175° C.

EXAMPLE 5

2-(R)-2-(2-Amino-2-methylpropionylamino)-5-phenyl-pentanoic acid N-(3-(4-chlorophenyl)-2,2-dioxo-2-thia-1-azaspiro[4.5]dec-3-ene-4-ylmethyl)-N-ethylamide trifluoroacetate

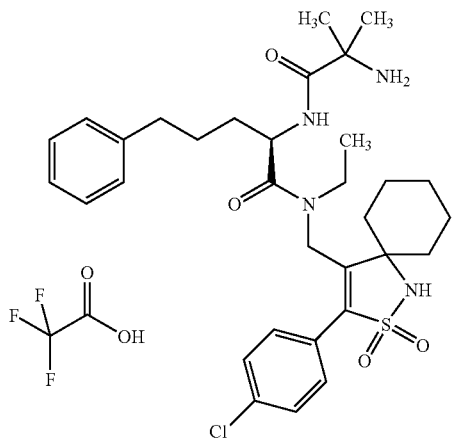

The title compound, shown above, was prepared by coupling 2-(R)-2-(2-(N-tert-butoxycarbonylamino)-2-methylpropionylamino)-5-phenylpentanoic acid (1.2 eq.) with 3-(4-chlorophenyl)-4-ethylaminomethyl-2-thia-1-azaspiro[4.5]dec-3-ene 2,2-dioxide, as described in Example 2, and subsequent deprotection according to the methods described in Example 1. Yield: 78 mg, 70%; MS (IS): 615 [MH]+; m.p. 130–140° C.

EXAMPLE 6

2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)amide trifluoroacetate

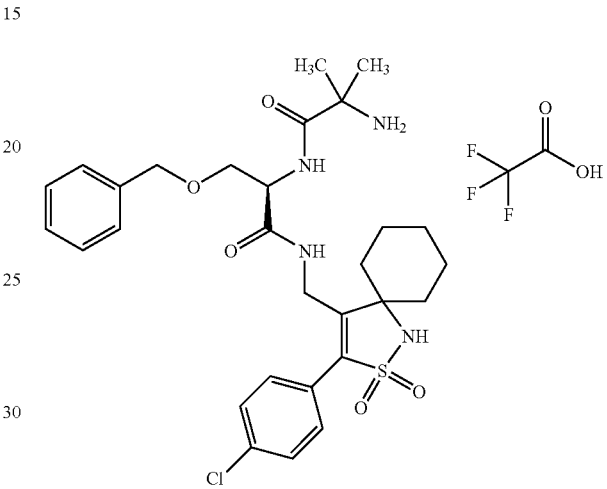

The title compound, as shown, above, was prepared as follows.

A solution of 4-bromomethyl-3-(4-chlorophenyl)-2-thia-1-azaspiro[4.5]dec-3-ene 2,2-dioxide, synthesized as described in Example 2, (154 mg, 0.40 mmol) and potassium phthalimide (2 eq.) in DMF (15 mL) was stirred at 80° C. for 17 h, after cooling to room temperature diluted with CH$_2$Cl$_2$ and washed with water and NaHCO$_3$ solution. The organic layer was dried (Na$_2$SO$_4$) and evaporated to yield 180 mg (100%) of 3-(4-Chlorophenyl)-4-(N-phthalimido) methyl-2-thia-1-azaspiro[4.5]dec-3-ene 2,2-dioxide, as shown below, as a white solid. MS (IS): 457 [MH]+.

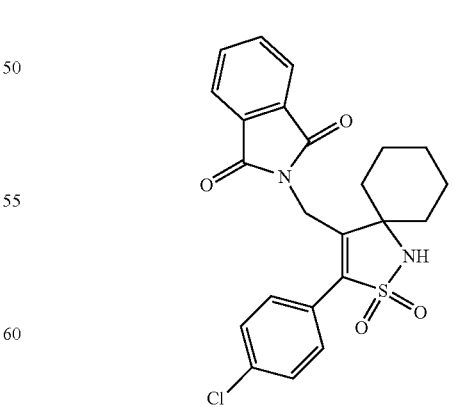

3-(4-Chlorophenyl)-4-(N-phthalimido)methyl-2-thia-1-azaspiro[4.5]dec-3-ene 2,2-dioxide (159 mg, 0.35 mmol) and ethylenediamine (4.5 mL) were dissolved in dry n-butanol (25 mL) and stirred overnight at 90° C. The mixture was then diluted with ethyl acetate, washed with NaCl solution and water and extracted with 0.5 M HCl. After addition of NAOH and extraction with ethyl acetate the organic layer was dried (Na$_2$SO$_4$) and evaporated to yield 77 mg (68%) of 4-Aminomethyl-3-(4-chlorophenyl)-2-thia-1-azaspiro[4.5]dec-3-ene 2,2-dioxide, shown below, as a solid MS (IS): 327 [MH]$^+$

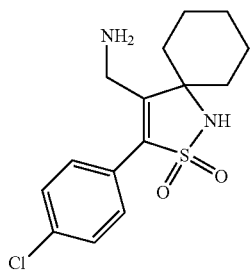

The title compound was prepared and deprotected according to the methods described in Example 1. Yield: 66 mg, 61%; MS (IS): 589 [MH]$^+$; m.p. >110° C. (decomp.)

EXAMPLE 7

2-(R)-2-(2-Amino-2-methylpropionylamino)-3-phenylmethoxy-propionic acid N-(5-(4-chlorophenyl)-3,3-diethyl-2-methyl-1,1-dioxo-2,3-dihydroisothiazol-4-ylmethyl)-N-ethylamide hydrochloride

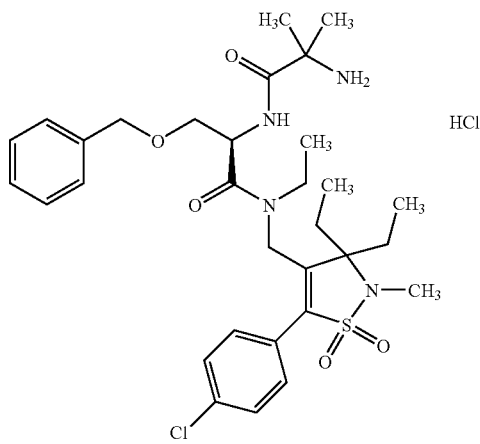

The title compound, as shown above, was prepared as follows.

4-Chlorophenyl-N-(1,1-diethyl-2-oxo-propyl)methanesulfonamide, shown below, was prepared from 4-chlorophenylmethanesulfonyl chloride and 1,1-diethylpropargylamine according to the methods described in Example 1. Yield: 1.2 g, 69%; MS (IS): 318 [MH]$^+$

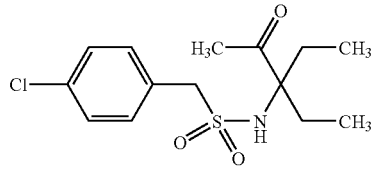

5-(4-Chlorophenyl)-3,3-diethyl-2,4-dimethyl-2,3-dihydroisothiazol 1,1-dioxide, shown below, was prepared according to the methods described in Example 1. Yield: 580 mg, 100%; MS (IS): 336 [MNa]$^+$, 314 [MH]$^+$

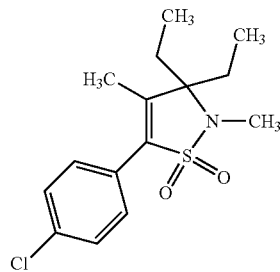

5-(4-chlorophenyl)-4-ethylaminomethyl-3,3-diethyl-2-methyl-2,3-dihydroisothiazol 1,1-dioxide, shown below, was prepared according to the methods described in Example 1. Yield: 257 mg, 39%; MS (IS): 357 [MH]$^+$.

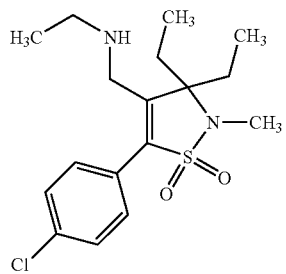

2-(R)-2-(2-(N-tert-Butoxycarbonylamino)-2-methylpropionyl -amino)-3-phenyl-methoxypropionic acid N-(5-(4-chloro-phenyl)-3,3-diethyl-2-methyl-1,1-dioxo-2,3-dihydro-isothiazol-4-ylmethyl)-N-ethylamide, shown below, was prepared according to the methods described in Example 1. Yield: 258 mg, 50%; MS (IS): 719 [MH]$^+$

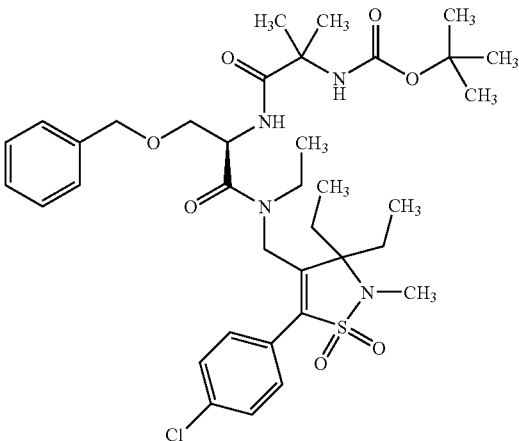

2-(R)-2-(2-(N-tert-Butoxycarbonylamino)-2-methyl-propionylamino)-3-phenylmethoxypropionic acid N-(5-(4-chlorophenyl)-3,3-diethyl-2-methyl-1,1-dioxo-2,3-dihydro-isothiazol-4-ylmethyl)-N-ethylamide (258 mg, 0.36 mmol) was dissolved in ethanol saturated with HCl (15 mL) and stirred overnight at room temperature. The solution was concentrated to a volume of 3 mL and poured into dry diethylether (100 mL). The title compound, as a precipitate, was filtered off and dried at 50° C. under vacuum. Yield: 95 mg, 43%; MS (IS): 619 [MH]+; m.p. 111–118° C.

EXAMPLE 8

2-(R)-2-(2-Amino-2-methylpropionylamino)-3-phenylmethoxypropionic acid N-(5-(4-chlorophenyl)-3,3-dimethyl-1,1-dioxo-2,3-dihydroisothiazol-4-ylmethyl)-N-ethylamide hydrochloride

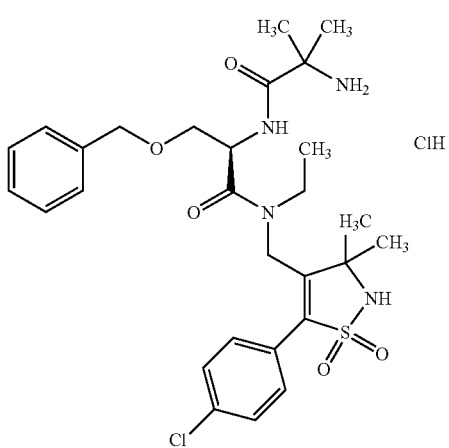

The title compound, shown above, was prepared as follows.

4-Chlorophenyl-N-(1,1-dimethyl-2-oxopropyl) methanesulfonamide, shown below, was prepared from 4-chlorophenyl-methanesulfonyl chloride and 1,1-dimethyl-propargylamine according to the methods described in Example 1. Yield: 1.58 g, 30%; MS (ES): 290 [MH]+

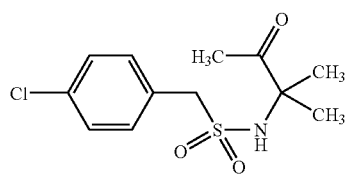

5-(4-chlorophenyl)-3,3,4-trimethyl-2,3-dihydro-isothiazol 1,1-dioxide shown below, was prepared according to the methods described in Example 2. Yield: 1.78 g, 94%; MS (ES): 272 [MH]+.

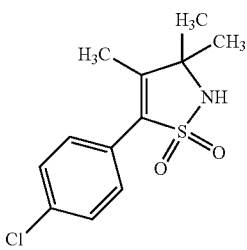

5-(4-Chlorophenyl)-4-ethylaminomethyl-3,3-dimethyl-2,3-dihydroisothiazol 1,1-dioxide, shown below, was prepared according to the methods described in Example 1. Yield: 670 mg, 53%; MS (ES): 315 [MH]+.

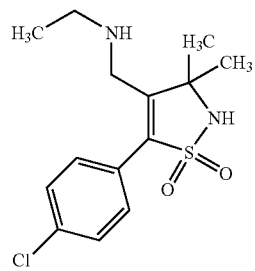

2-(R)-2-(2-(N-tert-Butoxycarbonylamino)-2-methyl-propionylamino)-3-phenylmethoxypropionic acid N-(5-(4-chlorophenyl)-3,3-dimethyl-1,1-dioxo-2,3-dihydro-isothiazol-4-ylmethyl)-N-ethylamide, shown below, was prepared according to the methods described in Example 1. Yield: 1.0 g, 92%; MS (ES): 677 [MH]+.

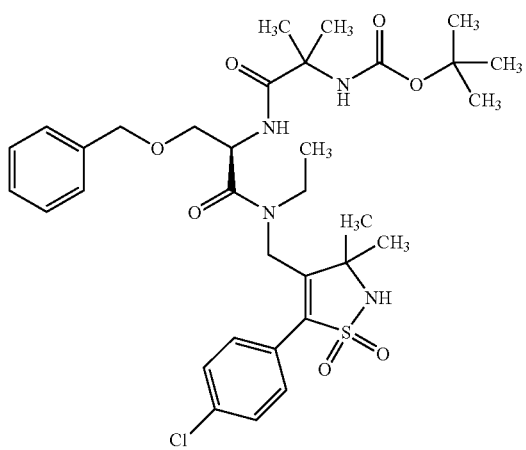

The title compound was prepared according to the methods described in Example 7. Yield: 370 mg, 41%; MS (ES): 579 [MH]+; m.p. 107–113° C.

EXAMPLE 9

2-(R)-2-(2-Amino-2-methylpropionylamino)-3-phenylmethoxy-propionic acid N-(2-(3-(4-chlorophenyl)-2,2-dioxo-2-thia-1-azaspiro[4.5]dec-3-ene-4-yl)ethyl)-N-ethylamide trifluoroacetate

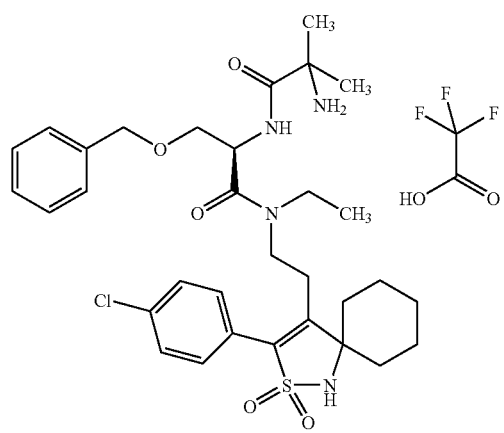

The title compound, shown above, was prepared as follows.

To a solution of tetramethylethylenediamine (5 eq.) in THF (60 mL) under Ar were added at −75° C. sec-butyllithium (5 eq., in hexane) and N-tert-butoxycarbonyl-ethylmethylamine (5.eq.). The mixture was stirred for 7 h at −75° C., 4-bromomethyl-3-(4-chloro-phenyl)-2-thia-1-azaspiro[4.5]dec-3-ene 2,2-dioxide (870 mg, 2.23 mmol) in THF (15 mL) was added and the mixture was stirred overnight at room temperature. After addition of acetic acid and saturated NaHCO$_3$ the solution was extracted with ethyl acetate. The organic layer was dried (Na$_2$SO$_4$) and evaporated. The residue was dissolved in CH$_2$Cl$_2$ (3 mL) and trifluoroacetic acid (3 mL), stirred for 2 h and after neutralization with NaHCO$_3$ was extracted with ethyl acetate. The organic layer was dried (Na$_2$SO$_4$) and concentrated. After addition of diethylether, 3-(4-chlorophenyl)-4-(2-ethylamino)ethyl-2-thia-1-azaspiro[4.5]dec-3-ene 2,2-dioxide, shown below, was obtained as white crystals. Yield: 52 mg, 6.3%; MS (IS): 369 [MH]$^+$.

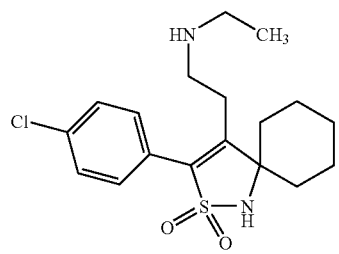

The title compound was prepared and deprotected according to the methods described in Example 1. Yield: 70 mg, 69%; S (IS): 631 [MH]$^+$; m.p. >90° C. (decomp.)

EXAMPLE 10

2-(R)-2-(2-Amino-2-methylpropionylamino)-3-phenylmethoxy-propionic acid N-(3-(4-tert-butylphenyl)-2,2-dioxo-2-thia-1-azaspiro[4.5]dec-3-ene-4-ylmethyl)-N-ethylamide trifluoroacetate

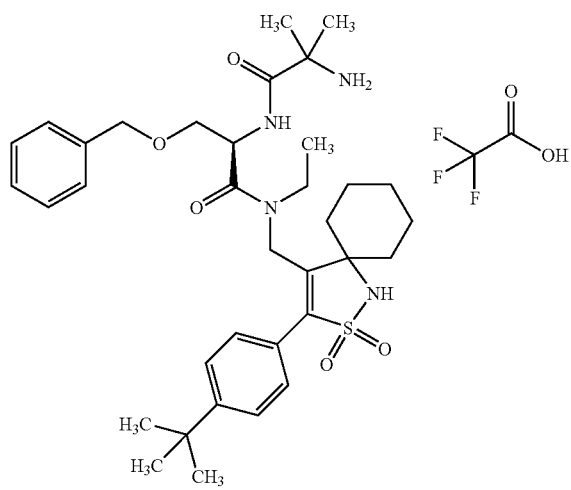

The title compound, as shown above, was prepared as follows.
3-(4-tert-Butylphenyl)-4-methyl-2-thia-1-azaspiro[4.5]dec-3-ene 2,2-dioxide, shown below, was prepared from 4-tert-butyl-benzylchloride and 1-ethynyl-1-cyclohexylamine according to the methods described in Examples 1 and 2. Yield: 1.23 g, 37%; MS (IS): 334 [MH]$^+$.

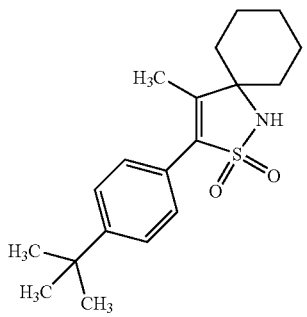

3-(4-tert-Butylphenyl)-4-ethylaminomethyl-2-thia-1-azaspiro[4.5]dec-3-ene 2,2-dioxide, shown below, was prepared according to the methods described in Example 1. Yield: 318 mg, 39%; MS (IS): 377 [MH]$^+$.

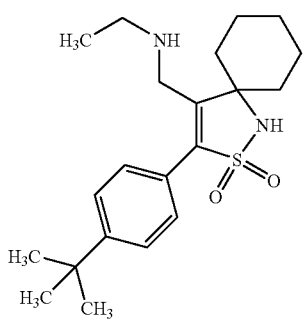

2-(R)-2-(2-(N-tert-Butoxycarbonylamino)-2-methyl-propionylamino)-3-phenyl-methoxypropionic acid N-(3-(4-tert-butylphenyl)-2,2-dioxo-2-thia-1-azaspiro[4.5]dec-3-ene-4-ylmethyl)-N-ethylamide, shown below, was prepared according to the method described in Example 1. Yield: 523 mg, 83%; MS (IS): 740 [MH]$^+$.

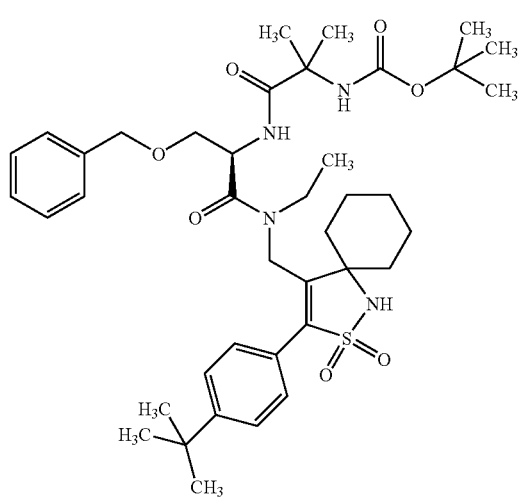

The title compound was prepared according to the method described in Example 1. Yield: 291 mg, 55%; MS (IS): 639 [MH]+; m.p. 234° C.

EXAMPLE 11

2-(R)-2-(2-Amino-2-methylpropionylamino)-3-phenylmethoxy-propionic acid N-(3-(4-chloro-phenyl)-2,2-dioxo-2-thia-1-azaspiro[4.5]dec-3-ene-4-ylmethyl)-N-propylamide trifluoroacetate

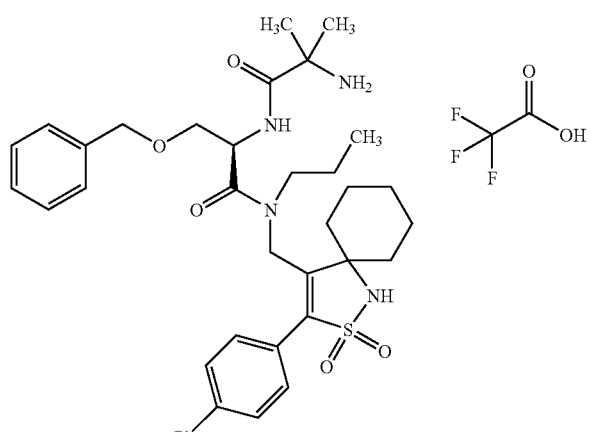

The title compound, as shown above, was prepared as follows.

3-(4-Chlorophenyl)-4-propylaminomethyl-2-thia-1-azaspiro[4.5]dec-3-ene 2,2-dioxide was prepared according to the methods described in Example 3 using propylamine instead of methylamine. Yield: 72 mg, 57%; MS (IS): 369 [MH]+.

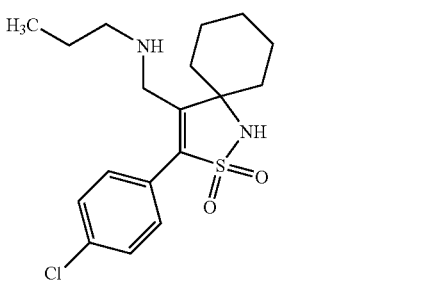

The title compound was prepared and deprotected according to the methods described in Example 1. Yield: 80 mg, 70%; MS (IS): 631 [MH]+; m.p. 136–138° C.

EXAMPLE 12

2-(R)-2-(2-Amino-2-methylpropionylamino)-3-phenylmethoxy-propionic acid N-butyl-N-(3-(4-chlorophenyl)-2,2-dioxo-2-thia-1-azaspiro[4.5]dec-3-ene-4-ylmethyl)amide trifluoroacetate

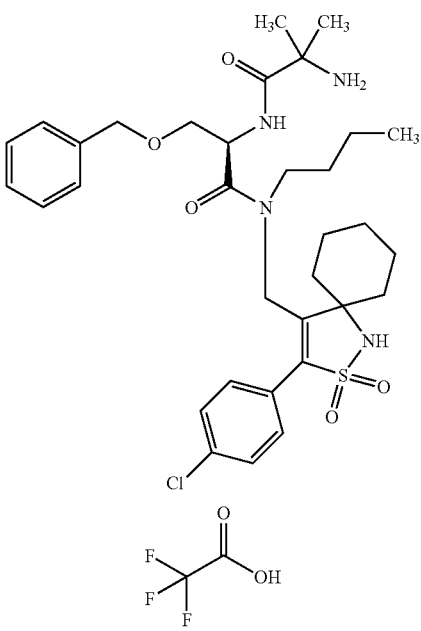

The title compound, as shown above, was prepared as follows.

4-Butylaminomethyl-3-(4-chlorophenyl)-2-thia-1-azaspiro[4.5]dec-3-ene 2,2-dioxide was prepared according to the methods described in Example 3 using butylamine instead of methylamine. Yield: 76 mg, 51%; MS (IS): 383 [MH]+.

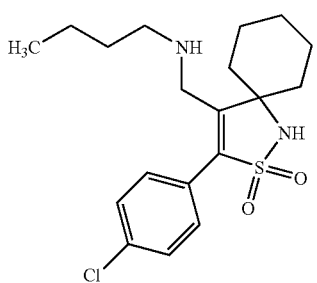

The title compound was prepared and deprotected according to the methods described in Example 1. Yield: 65 mg, 56%; MS (IS): 645 [MH]+; m.p. 145–147° C.

EXAMPLE 13

2-(R)-2-(2-Amino-2-methylpropionylamino)-3-phenylmethoxy-propionic acid N-benzyl-N-(3-(4-chlorophenyl)-2,2-dioxo-2-thia-1-azaspiro[4.5]dec-3-ene-4-ylmethyl)amide trifluoroacetate

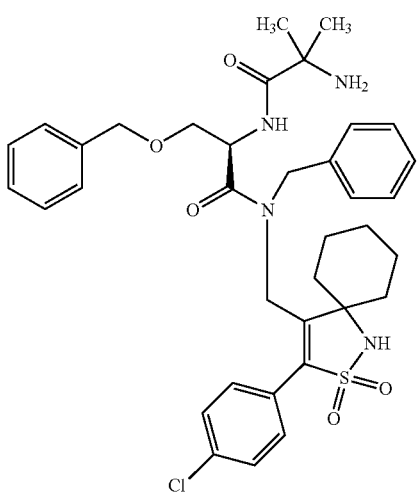

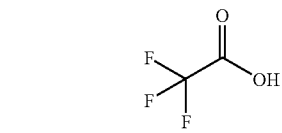

The title compound, as shown above, was prepared as follows.

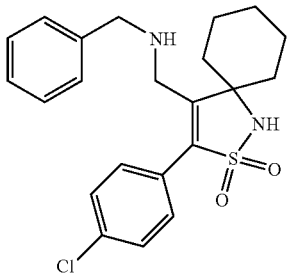

4-Benzylaminomethyl-3-(4-chlorophenyl)-2-thia-1-azaspiro[4.5]dec-3-ene 2,2-dioxide, shown above, was prepared according to the methods described in Example 3 using benzylamine instead of methylamine. Yield: 86 mg, 53%; MS (IS): 467 [MH]+.

The title compound was prepared and deprotected according to the methods described in Example 1. Yield: 23 mg, 20%; MS (IS): 679 [MH]+; m.p. 124–128° C.

EXAMPLE 14

2-(R)-2-(2-Amino-2-methylpropionylamino)-5-phenyl-pentanoic acid N-(3-(4-chlorophenyl)-2,2-dioxo-2-thia-1-azaspiro[4.5]dec-3-ene-4-ylmethyl)-N-methylamide trifluoroacetate

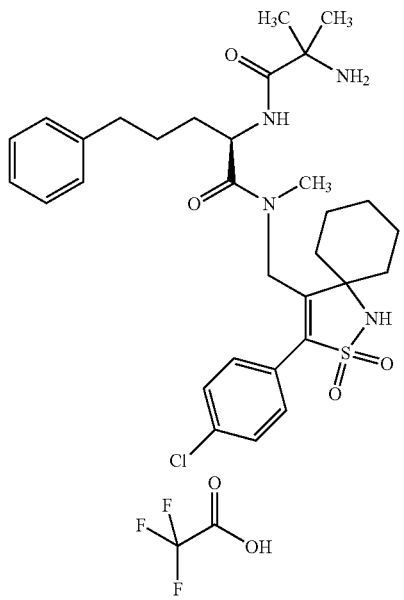

The title compound was prepared by coupling 2-(R)-2-(2-(N-tert-butoxycarbonylamino)-2-methylpropionylamino)-5-phenylpentanoic acid (1.2 eq.) with 3-(4-chlorophenyl)-4-methylaminomethyl-2-thia-1-azaspiro[4.5]dec-3-ene 2,2-dioxide (Example 3) and subsequent deprotection according to the methods described in Example 1. Yield: 100 mg, 91%; MS (IS): 601 [MH]+; m.p. 120–123° C.

EXAMPLE 15

2-(R)-2-(2-Amino-2-methylpropionylamino)-3-phenylmethoxy-propionic acid N-ethyl-N-(1-methyl-2,2-dioxo-3-phenyl-2-thia-1-azaspiro[4.5]dec-3-ene-4-ylmethyl)amide hydrochloride

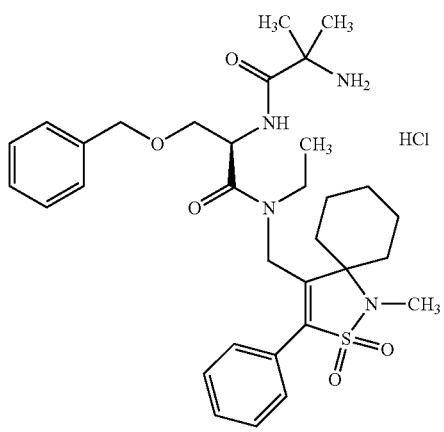

The title compound, as shown above, was prepared as follows.

N-(1-Acetylcyclohexyl)phenylmethanesulfonamide was prepared from phenylmethane-sulfonylchloride and 1-ethynylcyclohexylamine according to the methods described in Example 1. Yield: 6 g, 73%; MS (IS): 296 [MH]⁺.

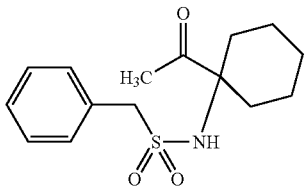

1,4-Dimethyl-3-phenyl-2-thia-1-azaspiro[4.5]dec-3-ene 2,2-dioxide, shown below, was prepared according to the methods described in Example 1. Yield: 2.08 g, 99%; MS (IS): 292 [MH]⁺.

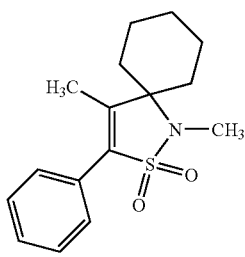

4-Ethylaminomethyl-1-methyl-3-phenyl-2-thia-1-azaspiro[4.5]dec-3-ene 2,2-dioxide, shown below, was prepared according to the methods described in Example 1. Yield: 1.2 g, 50%; MS (IS): 335 [MH]⁺.

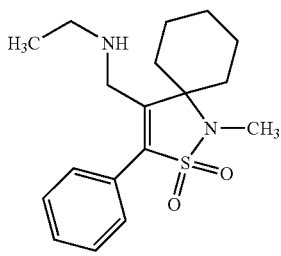

2-(R)-2-(2-(N-tert-Butoxycarbonylamino)-2-methyl-propionylamino)-3-phenylmethoxy-propionic acid N-ethyl-N-(1-methyl-2,2-dioxo-3-phenyl-2-thia-1-azaspiro[4.5]dec-3-ene-4-ylmethyl)amide, shown below, was prepared according to the methods described in Example 1. Yield: 640 mg, 98%; MS (IS): 697 [MH]⁺.

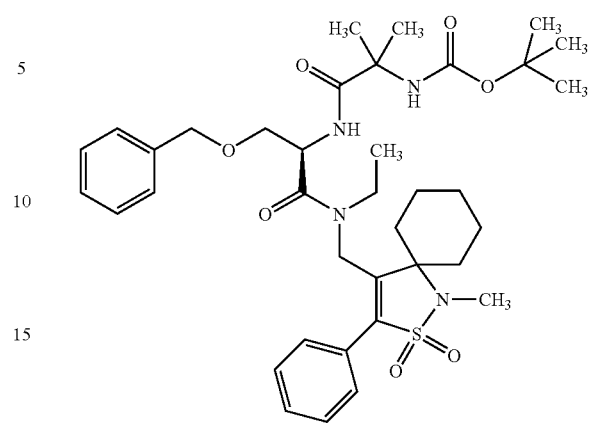

The title compound was prepared according to the methods described in Example 7. Yield: 1.2 g, 50%; MS (IS): 597 [MH]⁺; m.p. >106° C. (decomp.)

EXAMPLE 16

2-(R)-2-(2-Amino-2-methylpropionylamino)-3-phenyl-methoxypropionic acid N-ethyl-N-(2,2-dioxo-3-phenyl-2-thia-1-azaspiro[4.5]dec-3-ene-4-ylmethyl) amide hydrochloride

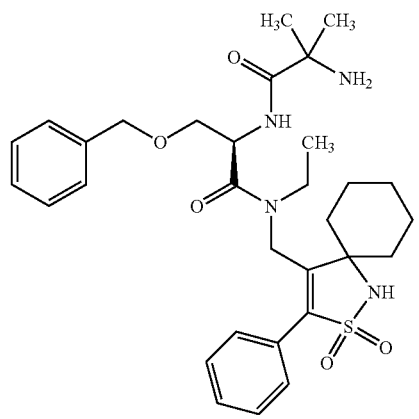

The title compound, as shown above, was prepared as follows.

4-Methyl-3-phenyl-2-thia-1-azaspiro[4.5]dec-3-ene 2,2-dioxide, shown below, was prepared from N-(1-acetylcyclohexyl)-phenylmethanesulfonamide, prepared in Example 15, according to the methods described in Example 2. Yield: 1.7 g, 70%; MS (IS): 278 [MH]⁺.

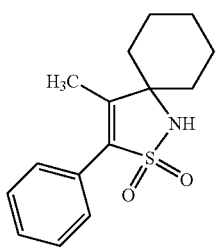

4-Ethylaminomethyl-3-phenyl-2-thia-1-azaspiro[4.5]dec-3-ene 2,2-dioxide, shown below, was prepared according to the methods described in Example 1. Yield: 440 mg, 22%; MS (IS): 321 [MH]+.

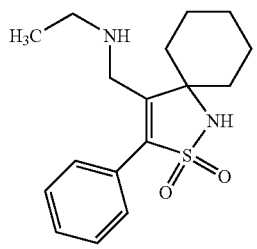

2-(R)-2-(2-(N-tert-Butoxycarbonylamino)-2-methyl-propionylamino)-3-phenylmethoxy-propionic acid N-ethyl-N-(2,2-dioxo-3-phenyl-2-thia-1-azaspiro[4.5]dec-3-ene-4-ylmethyl)amide, shown below, was prepared according to the methods described in Example 1. Yield: 900 mg, 96%; MS (IS): 683 [MH]+.

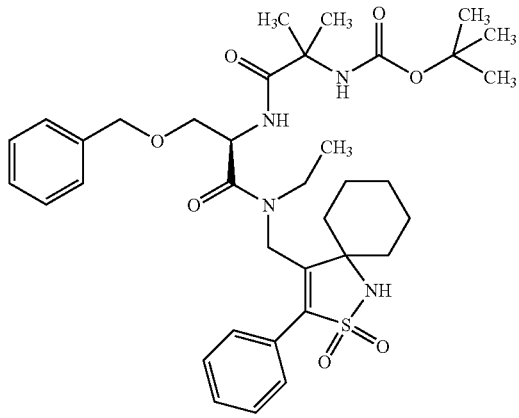

The title compound was prepared according to the methods described in Example 7. Yield: 450 mg, 55%; MS (IS): 583 [MH]+; m.p. >94° C. (decomp.)

EXAMPLE 17

2-(R)-2-(2-Amino-2-methylpropionylamino)-3-phenylmethoxy-propionic acid N-(3-(3-chlorophenyl)-1-methyl-2,2-dioxo-2-thia-1-azaspiro[4.5]dec-3-ene-4-ylmethyl)-N-ethylamide hydrochloride

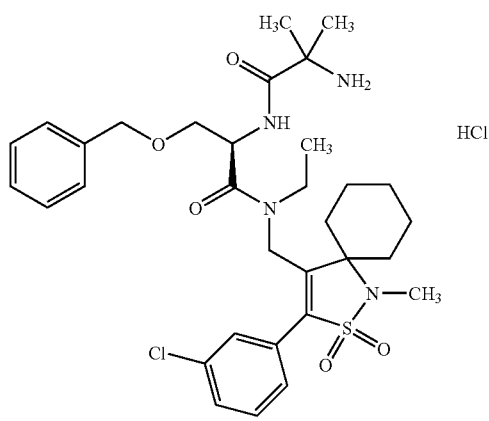

The title compound, as shown above, was prepared as follows.

N-(1-Acetylcyclohexyl)-3-chlorophenylmethane-sulfonamide, shown below, was prepared from 3-chlorobenzyl-chloride and 1-ethynylcyclohexylamine according to the methods described in Example 1. Yield: 0.77 g, 35%; MS (IS): 330 [MH]+.

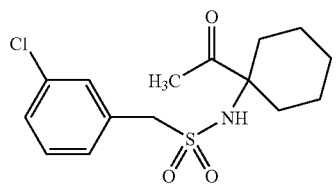

3-(3-Chlorophenyl)-1,4-dimethyl-2-thia-1-azaspiro[4.5]dec-3-ene 2,2-dioxide, shown below, was prepared according to the methods described in Example 1. Yield: 0.7 g, 94%; MS (IS): 326 [MH]+.

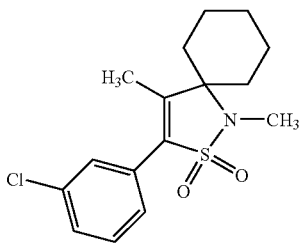

3-(3-Chlorophenyl)-4-ethylaminomethyl-1-methyl-2-thia-1-azaspiro[4.5]dec-3-ene 2,2-dioxide, shown below, was prepared according to the methods described in Example 1. Yield: 230 mg, 31%; MS (IS): 369 [MH]+.

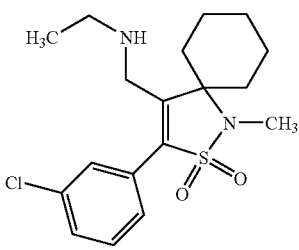

2-(R)-2-(2-(N-tert-Butoxycarbonylamino)-2-methyl-propionylamino)-3-phenylmethoxypropionic acid N-(3-(3-chlorophenyl)-1-methyl-2,2-dioxo-2-thia-1-azaspiro[4.5]dec-3-ene-4-ylmethyl)-N-ethylamide was prepared according to the methods described in Example 1. Yield: 430 mg, 98%; MS (IS): 731 [MH]⁺.

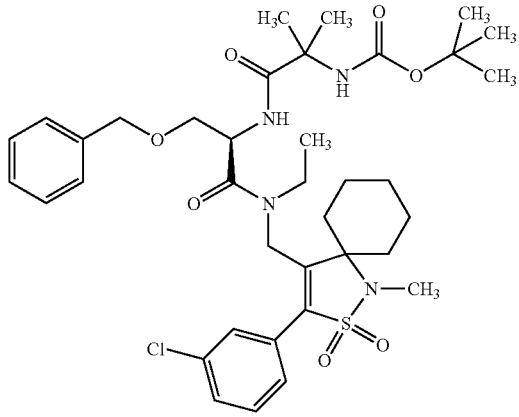

The title compound was prepared according to the methods described in Example 7. Yield: 340 mg, 89%; MS (IS): 631 [MH]⁺; m.p. >128° C. (decomp.)

EXAMPLE 18

2-(R)-2-(2-Amino-2-methylpropionylamino)-3-phenylmethoxy-propionic acid N-(3-(2-chlorophenyl)-1-methyl-2,2-dioxo-2-thia-1-azaspiro[4.5]dec-3-ene-4-ylmethyl)-N-ethylamide hydrochloride

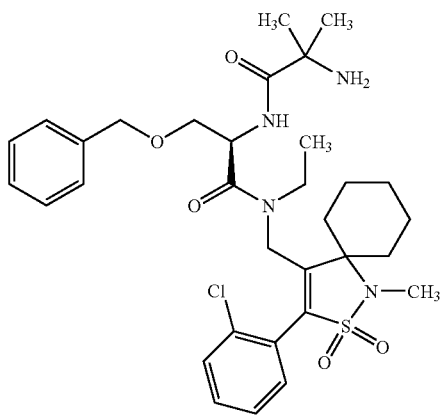

The title compound, as shown above, was prepared as follows.

N-(1-Acetylcyclohexyl)-2-chlorophenylmethane-sulfonamide, shown below, was prepared from 2-chlorobenzylchloride and 1-ethynylcyclohexylamine according to the methods described in Example 1. Yield: 1.67 g, 35%; MS (IS): 330 [MH]⁺.

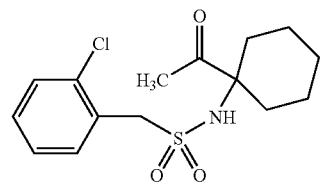

3-(2-Chlorophenyl)-1,4-dimethyl-2-thia-1-azaspiro[4.5]dec-3-ene 2,2-dioxide, shown below, was prepared according to the methods described in Example 1. Yield: 630 mg, 39%; MS (IS): 326 [MH]⁺.

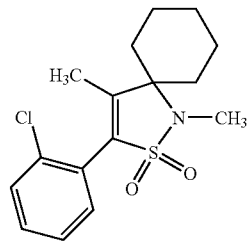

3-(2-Chlorophenyl)-4-ethylaminomethyl-1-methyl-2-thia-1-azaspiro[4.5]dec-3-ene 2,2-dioxide, shown below, was prepared according to the methods described in Example 1. Yield: 230 mg, 30%; MS (IS): 369 [MH]⁺.

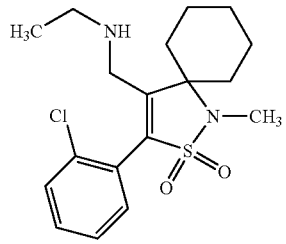

2-(R)-2-(2-(N-tert-Butoxycarbonylamino)-2-methyl-propionylamino)-3-phenylmethoxy-propionic acid N-(3-(2-chlorophenyl)-1-methyl-2,2-dioxo-2-thia-1-azaspiro[4.5]dec-3-ene-4-ylmethyl)-N-ethylamide was prepared according to the methods described in Example 1. Yield: 430 mg, 98%; MS (IS): 731 [MH]⁺.

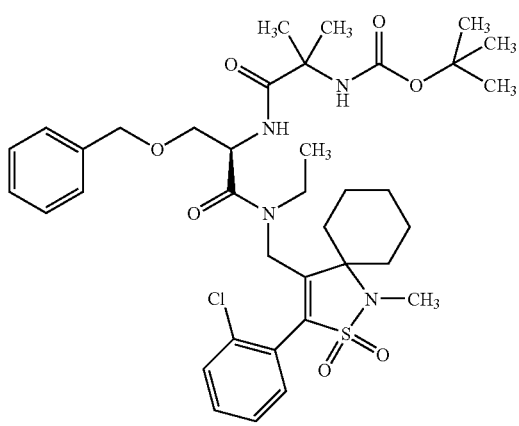

The title compound was prepared according to the methods described in Example 7. Yield: 310 mg, 81%; MS (IS): 631 [MH]+; m.p. >130° C. (decomp.)

EXAMPLE 19

2-(R)-2-(2-Amino-2-methylpropionylamino)-3-phenyl-methoxypropionic acid N-ethyl-N-1-methyl-2,2-dioxo-3-(4-trifluoromethylphenyl)-2-thia-1-azaspiro[4.5]dec-3-ene-4-ylmethyl)amide hydrochloride

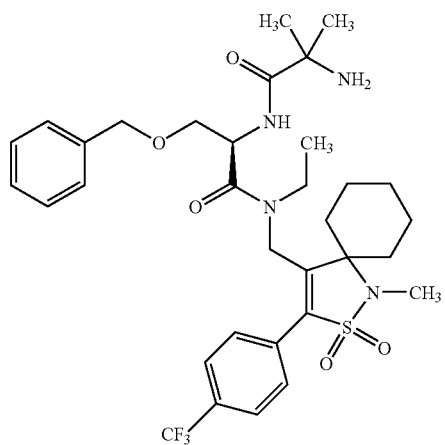

The title compound, as shown above, was prepared as follows.

N-(1-Acetylcyclohexyl)-(4-trifluoromethylphenyl) methanesulfonamide was prepared from 4-trifluoromethyl-benzylchloride and 1-ethynylcyclohexylamine according to the methods described in Example 1. Yield: 1.38 g, 33%; MS (IS): 364 [MH]+.

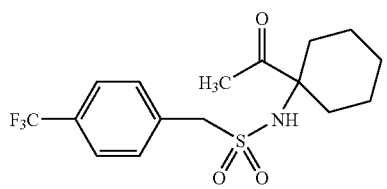

1,4-Dimethyl-3-(4-trifluoromethylphenyl)-2-thia-1-azaspiro[4.5]dec-3-ene 2,2-dioxide, shown below, was prepared according to the methods described in Example 1. Yield: 1.3 g, 97%; MS (IS): 360 [MH]+.

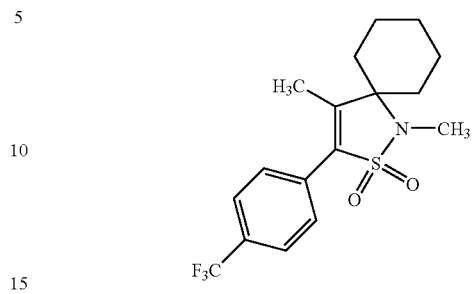

4-Ethylaminomethyl-1-methyl-3-(4-trifluoromethyl-phenyl)-2-thia-1-azaspiro[4.5]dec-3-ene 2,2-dioxide was prepared according to the methods described in Example 1. Yield: 630 mg, 42%; MS (IS): 403 [MH]+.

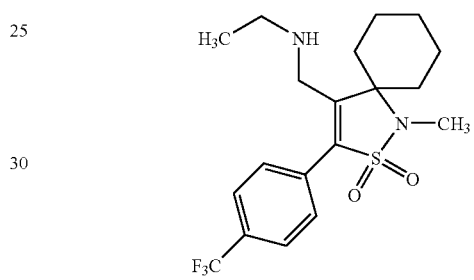

2-(R)-2-(2-(N-tert-Butoxycarbonylamino)-2-methyl-propionylamino)-3-phenylmethoxy-propionic acid N-ethyl-N-(1-methyl-2,2-dioxo-3-(4-trifluoromethylphenyl)-2-thia-1-azaspiro[4.5]dec-3-ene-4-ylmethyl)amide, shown below, was prepared according to the methods described in Example 1. Yield: 330 mg, 96%; MS (IS): 765 [MH]+.

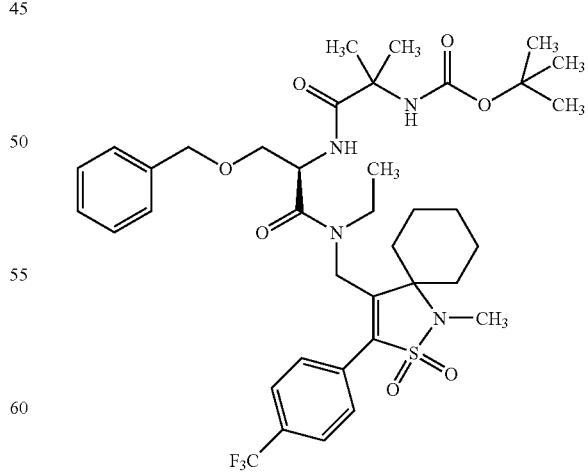

The title compound was prepared according to the methods described in Example 7. Yield: 160 mg, 56%; MS (IS): 665 [MH]+; m.p. >110° C. (decomp.)

EXAMPLE 20

2-(R)-2-(2-Amino-2-methylpropionylamino)-3-phenylmethoxy-propionic acid N-ethyl-N-(1-methyl-3-(4-nitrophenyl)-2,2-dioxo-2-thia-1-azaspiro[4.5]dec-3-ene-4-ylmethyl)amide hydrochloride

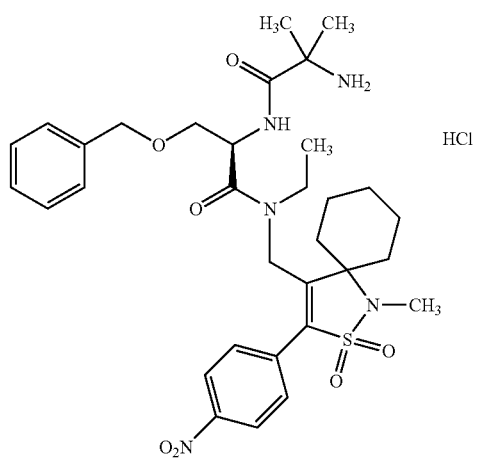

The title compound, as shown above, was prepared as follows.

N-(1-acetylcyclohexyl)-(4-nitrophenyl) methane-sulfonamide was prepared from 4-nitrobenzyl-chloride and 1-ethynylcyclohexylamine according to the methods described in Example 1. Yield: 1.8 g, 52%; MS (IS): 341 [MH]+.

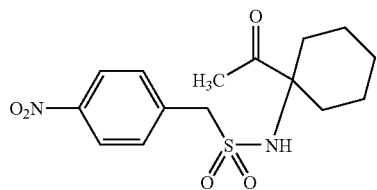

1,4-Dimethyl-3-(4-nitrophenyl)-2-thia-1-azaspiro[4.5]dec-3-ene 2,2-dioxide, shown below, was prepared according to the methods described in Example 1. Yield: 750 mg, 50%; MS (IS): 337 [MH]+.

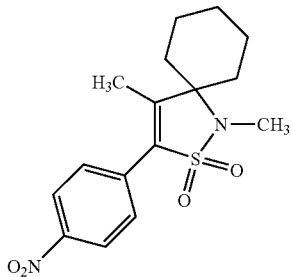

4-Ethylaminomethyl-1-methyl-3-(4-nitrophenyl)-2-thia-1-azaspiro[4.5]dec-3-ene 2,2-dioxide, shown below, was prepared according to the methods described in Example 1. Yield: 300 mg, 36%; MS (IS): 380 [MH]+.

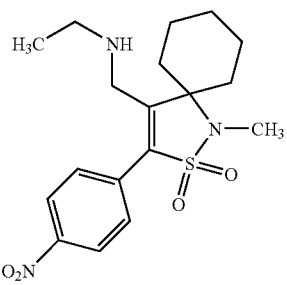

2-(R)-2-(2-(N-tert-Butoxycarbonylamino)-2-methyl-propionylamino)-3-phenyl-methoxypropionic acid N-ethyl-N-(1-methyl-3-(4-nitrophenyl)-2,2-dioxo-2-thia-1-azaspiro[4.5]dec-3-ene-4-ylmethyl)amide was prepared according to the methods described in Example 1. Yield: 230 mg, 41%; MS (IS): 742 [MH]+.

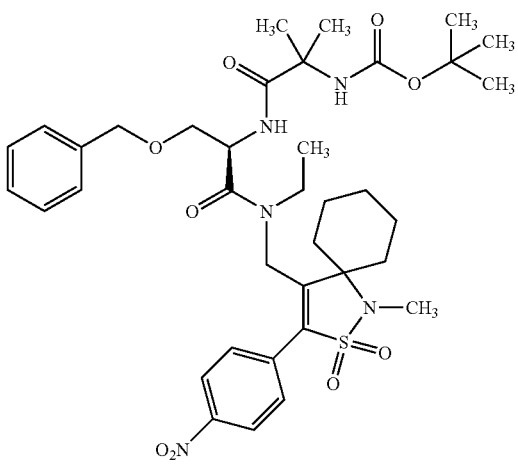

The title compound was prepared according to the methods described in Example 7. Yield: 160 mg, 76%; MS (IS): 642 [MH]+; m.p. 131–135° C.

EXAMPLE 21

2-(R)-2-(2-Amino-2-methylpropionylamino)-3-phenylmethoxy-propionic acid N-(3-(4-bromophenyl)-2,2-dioxo-2-thia-1-azaspiro[4.5]dec-3-ene-4-ylmethyl)-N-ethylamide hydrochloride

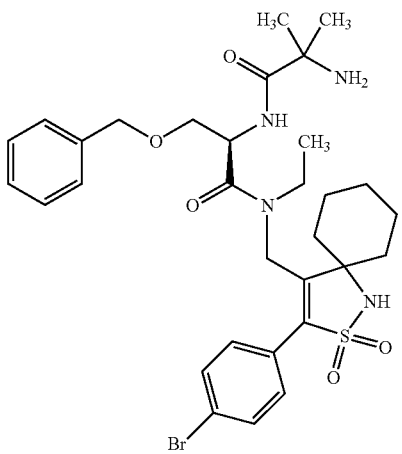

The title compound, as shown above, was prepared as follows.

4-Bromomethyl-3-(4-bromophenyl)-2-thia-1-azaspiro[4.5]dec-3-ene 2,2-dioxide, shown below, was prepared from 4-bromobenzylchloride and 1-ethynylcyclohexylamine according to the methods described in Examples 1 and 2. Yield: 232 mg, 48%; MS (IS): 434 [MH]⁺.

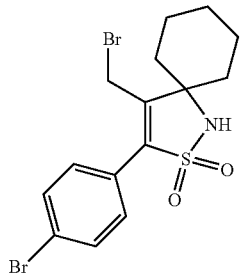

3-(4-Bromophenyl)-4-ethylaminomethyl-2-thia-1-azaspiro[4.5]dec-3-ene 2,2-dioxide, shown below, was prepared according to the methods described in Example 1. Yield: 125 mg, 59%; MS (IS): 399 [MH]⁺.

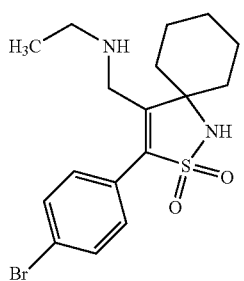

The title compound was prepared and deprotected according to the methods described in Examples 1 and 7. Yield: 140 mg, 72%; MS (IS): 661 [MH]⁺; m.p. >140° C. (decomp.)

EXAMPLE 22

2-(R)-2-(2-Amino-2-methylpropionylamino)-3-phenylmethoxy-propionic acid N-ethyl-N-2,2-dioxo-3-(3-trifluoromethyl-phenyl)-2-thia-1-azaspiro[4.5]dec-3-ene-4-ylmethyl)amide trifluoroacetate

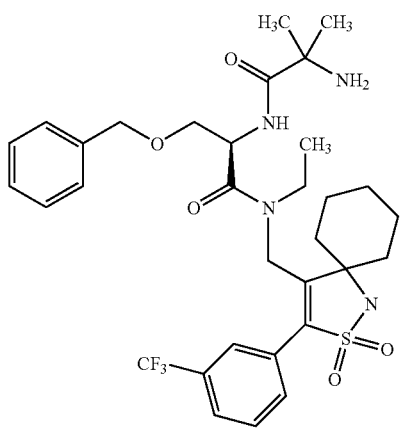

-continued

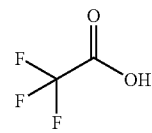

The title compound, as shown above, was prepared as follows.

4-Bromomethyl-3-(3-trifluoromethylphenyl)-2-thia-1-azaspiro[4.5]dec-3-ene 2,2-dioxide, shown below, was prepared from 3-trifluoromethylbenzyl-chloride and 1-ethynyl-cyclohexylamine according to the methods described in Examples 1 and 2. Yield: 1.59 g, 47%; MS (IS): 424 [MH]⁺.

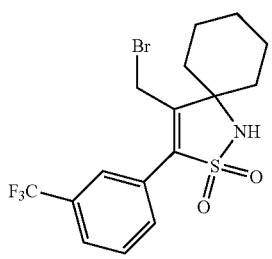

4-Ethylaminomethyl-3-3-trifluoromethylphenyl)-2-thia-1-azaspiro[4.5]dec-3-ene 2,2-dioxide, shown below, was prepared according to the methods described in Example 1. Yield: 389 mg, 27%; MS (IS): 389 [MH]⁺.

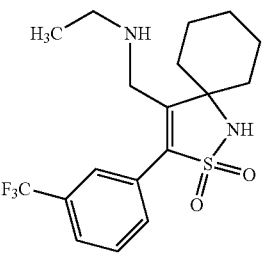

The title compound was prepared and deprotected according to the methods described in Example 1. Yield: 400 mg, 63%; MS (IS): 651 [MH]⁺; m.p. >105° C. (decomp.)

EXAMPLE 23

2-(R)-2-(2-Amino-2-methylpropionylamino)-3-phenylmethoxy-propionic acid N-ethyl-N-(2,2-dioxo-3-(4-methylphenyl)-2-thia-1-azaspiro[4.5]dec-3-ene-4-ylmethyl)amide trifluoroacetate

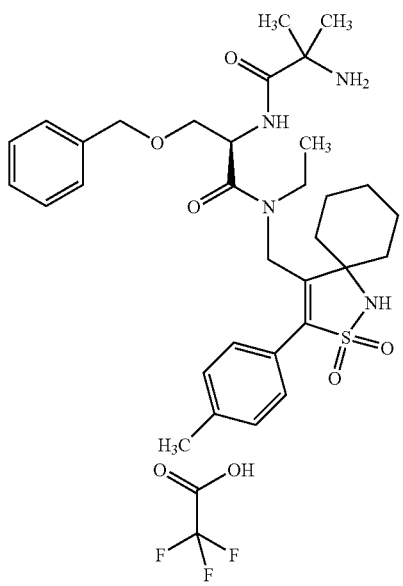

The title compound, as shown above, was prepared as follows.

4-Ethylaminomethyl-3-(4-methylphenyl)-2-thia-1-azaspiro[4.5]dec-3-ene 2,2-dioxide, shown below, was prepared according to the methods described in Examples 1 and 2. Bromination with N-bromosuccinimide afforded a mixture of 4-bromomethyl-3-4-methylphenyl)-2-thia-1-azaspiro[4.5]dec-3-ene 2,2-dioxide and 3-(4-bromomethyl-phenyl)-4-methyl-2-thia-1-azaspiro[4.5]dec-3-ene 2,2-dioxide. The raw mixture (400 mg) was dissolved in ethanol (10 mL) and ethylamine (70% in water, 5 mL) was added. The solution was stirred overnight at room temperature, concentrated and the residue was dissolved in $CH_2Cl_2$, washed with water and extracted with 0.5 M HCl. After addition of NaOH and extraction with $CH_2Cl_2$ the organic layer was dried ($Na_2SO_4$) and evaporated. The two products were separated by column chromatography ($CH_2Cl_2$/acetone 9:1) and the title compound compound [4-Ethylaminomethyl-3-(4-methylphenyl)-2-thia-1-azaspiro[4.5]dec-3-ene 2,2-dioxide] was isolated as white crystals. Yield: 80 mg, 24%; MS (IS): 334 [MH]$^+$.

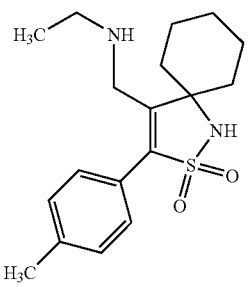

The title compound was prepared according to the methods described in Example 1. Yield: 70 mg, 41%; MS (IS): 597 [MH]$^+$; m.p. >90° C. (decomp.)

EXAMPLE 24

2-(R)-2-(2-Amino-2-methylpropionylamino)-3-phenylmethoxy-propionic acid N-ethyl-N-(4-(4-methyl-2,2-dioxo-2-thia-1-azaspiro[4.5]dec-3-ene-3-yl)phenylmethyl)amide trifluoroacetate

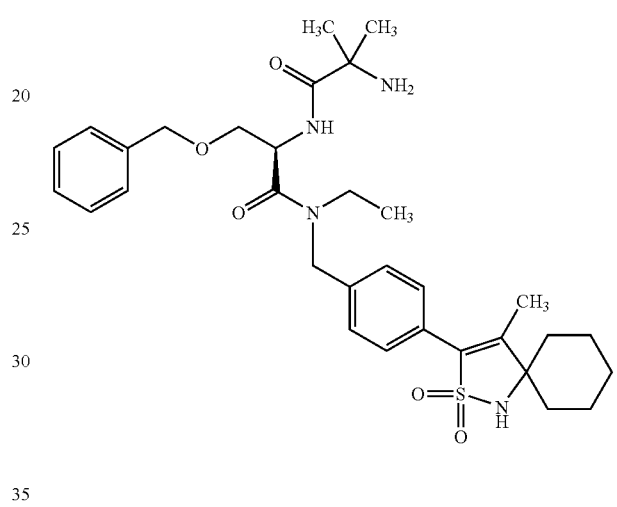

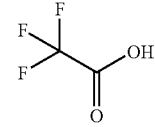

The title compound, as shown above, was prepared as follows.

3-(4-Ethylaminomethylphenyl)-4-methyl-2-thia-1-azaspiro[4.5]dec-3-ene 2,2-dioxide, shown below, was isolated as a second fraction from column chromatography in -the experiment described in Example 23. Yield: 80 mg, 24%; MS (IS): 334 [MH]$^+$.

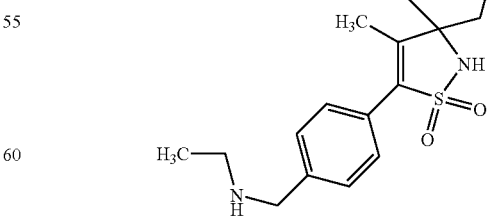

The title compound was prepared and deprotected according to the methods described in Examples 1 and 7. Yield: 90 mg, 53%; MS (IS): 597 [MH]$^+$; m.p. 90–100° C. (decomp.)

EXAMPLE 25

2-(R)-2-(2-Amino-2-methylpropionylamino)-3-phenylmethoxy-propionic acid N-ethyl-N-(1-ethyl-2,2-dioxo-3-phenyl-2-thia-1-azaspiro[4.5]dec-3-ene-4-ylmethyl)amide trifluoroacetate

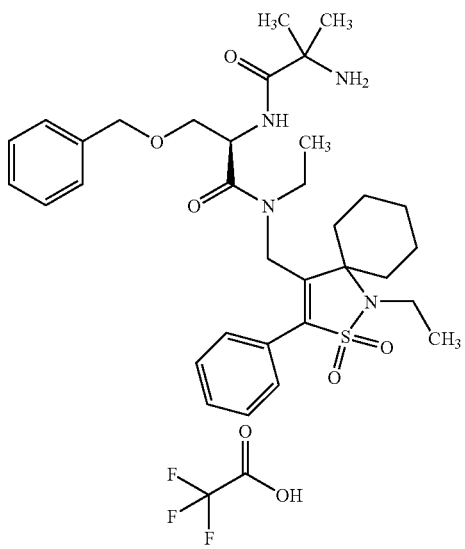

The title compound, as shown above, was prepared as follows.

1-Ethyl-4-methyl-3-phenyl-2-thia-1-azaspiro[4.5]dec-3-ene 2,2-dioxide, shown below, was prepared from N-(1-acetylcyclohexyl)-phenylmethanesulfonamide (Example 15) according to the methods described in Example 1 using iodoethane instead of iodomethane. Yield: 1.56 g, 75%; MS (IS): 306 [MH]+.

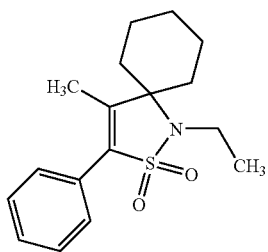

1-Ethyl-4-ethylaminomethyl-3-phenyl-2-thia-1-azaspiro[4.5]dec-3-ene 2,2-dioxide was prepared according to the methods described in Example 1. Yield: 150 mg, 6%; MS (IS): 349 [MH]+.

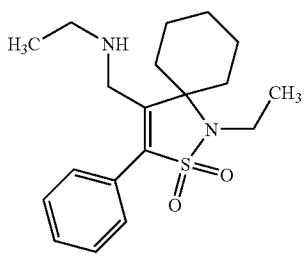

The title compound was prepared and deprotected according to the methods described in Example 1. Yield: 150 mg, 52%; MS (IS): 611 [MH]+; m.p. >90° C. (decomp.)

EXAMPLE 26

2-(R)-2-(2-Amino-2-methylpropionylamino)-3-phenylmethoxy-propionic acid N-ethyl-N-(2,2-dioxo-3-(3-phenoxyphenyl)-2-thia-1-azaspiro[4.5]dec-3-ene-4-ylmethyl)-N-ethylamide trifluoroacetate

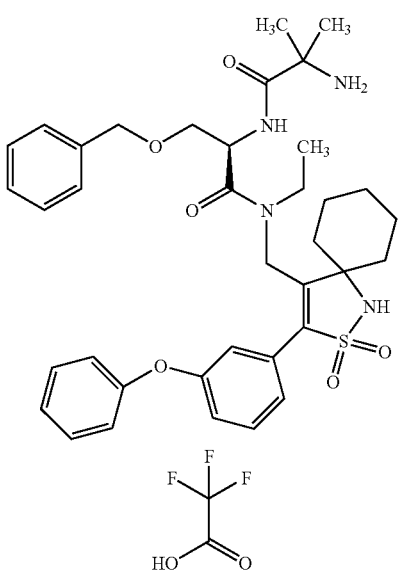

The title compound, as shown above, was prepared as follows.

N-(1-Acetylcyclohexyl)-3-phenoxyphenylmethane-sulfonamide, shown below, was prepared from 3-phenoxybenzylchloride and 1-ethynylcyclohexylamine according to the methods described in Example 1. Yield: 1.57 g, 18%; MS (IS): 388 [MH]+.

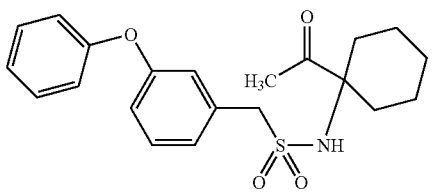

4-Methyl-3-(3-phenoxyphenyl)-2-thia-1-azaspiro[4.5]dec-3-ene 2,2-dioxide was prepared according to the methods described in Example 2. Yield: 0.35 g, 37%; MS (IS): 370 [MH]+.

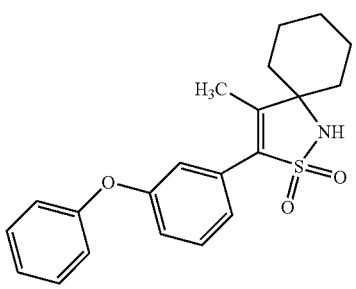

4-Ethylaminomethyl-3-(3-phenoxyphenyl)-2-thia-1-azaspiro[4.5]dec-3-ene 2,2-dioxide, shown below, was prepared according to the methods described in Example 1. Yield: 120 mg, 30%; MS (IS): 413 [MH]$^+$.

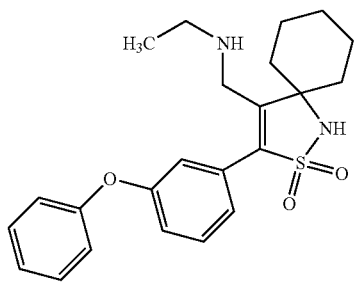

The title compound was prepared and deprotected according to the methods described in Example 1. Yield: 15 mg, 7%; MS (IS): 675 [MH]$^+$; m.p. 79° C.

EXAMPLE 27

2-(R)-2-(2-Amino-2-methylpropionylamino)-3-phenylmethoxy-propionic acid N-(3-(3-bromophenyl)-2,2-dioxo-2-thia-1-azaspiro[4.5]dec-3-ene-4-ylmethyl)-N-ethylamide trifluoroacetate

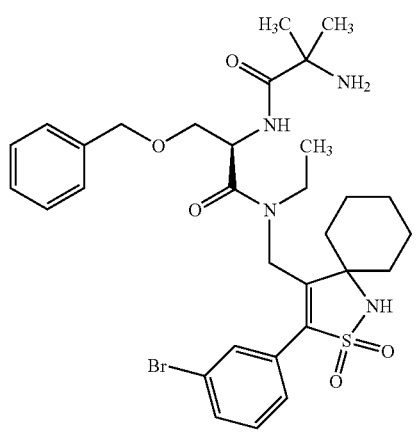

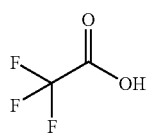

The title compound, as shown above, was prepared as follows.

3-(3-Bromophenyl)-4-methyl-2-thia-1-azaspiro[4.5]dec-3-ene 2,2-dioxide was prepared from 3-bromobenzyl-bromide and 1-ethynyl-1-cyclohexylamine according to the methods described in Examples 1 and 2. Yield: 680 mg, 72%; MS (IS): 357 [MH]$^+$.

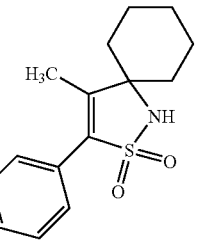

3-(3-Bromophenyl)-4-ethylaminomethyl-2-thia-1-azaspiro[4.5]dec-3-ene 2,2-dioxide was prepared according to the methods described in Example 1. Yield: 95 mg, 13%; MS (IS): 399 [MH]$^+$.

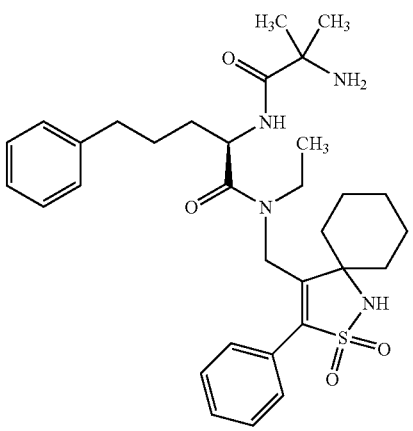

The title compound was prepared and deprotected according to the methods described in Example 1. Yield: 150 mg, 81%; MS (IS): 663 [MH]$^+$; m.p. 140–147° C.

EXAMPLE 28

2-(R)-2-(2-Amino-2-methylpropionylamino)-5-phenyl-pentanoic acid N-ethyl-N-(2,2-dioxo-3-phenyl-2-thia-1-azaspiro[4.5]dec-3-ene-4-ylmethyl)amide trifluoroacetate

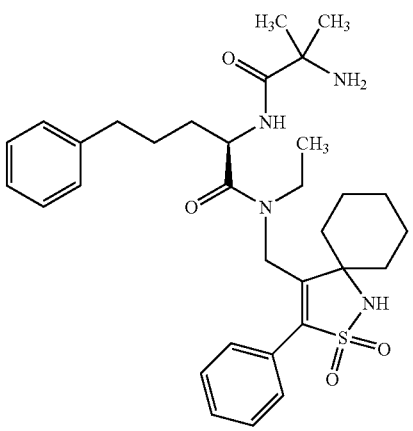

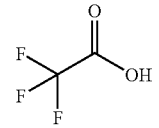

The title compound, shown above, was prepared as follows.

The title compound was prepared from 4-ethylaminomethyl-3-phenyl-2-thia-1-azaspiro[4.5]dec-3-ene 2,2-dioxide (Example 16) and deprotected according to the methods described in Example 5. Yield: 670 mg, 90%; MS (IS): 582 [MH]+; m.p. 95–110° C.

EXAMPLE 29

2-(R)-2-(2-Amino-2-methylpropionylamino)-3-phenylmethoxy-propionic acid N-ethyl-N-(3-(4-fluorophenyl)-2,2-dioxo-2-thia-1-azaspiro[4.5]dec-3-ene-4-ylmethyl)amide trifluoroacetate

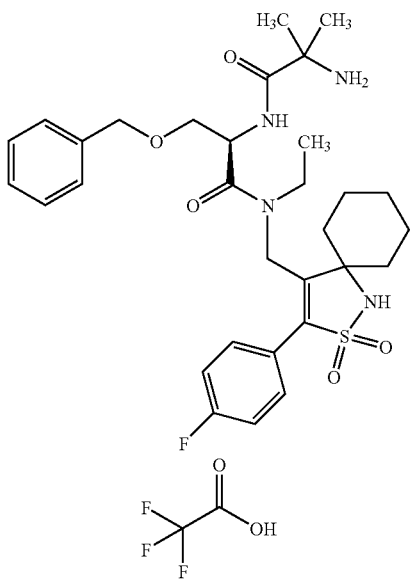

The title compound, as shown above, was prepared as follows.

3-(4-Fluorophenyl)-4-methyl-2-thia-1-azaspiro[4.5]dec-3-ene 2,2-dioxide, shown below, was prepared from 4-fluorobenzyl-chloride and 1-ethynyl-1-cyclohexylamine according to the methods described in Examples 1 and 2. Yield: 2.0 g, 76%; MS (IS): 296 [MH]+.

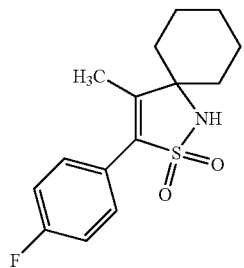

4-Ethylaminomethyl-3-(4-fluorophenyl)-2-thia-1-azaspiro[4.5]dec-3-ene 2,2-dioxide, shown below, was prepared according to the methods described in Example 1. Yield: 670 mg, 30%; MS (IS): 339 [MH]+.

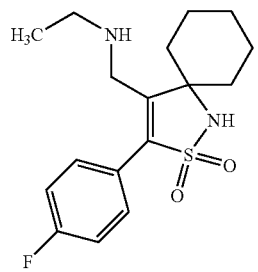

2-(R)-2-(2-(N-tert-Butoxycarbonylamino)-2-methyl-propionylamino)-3-phenyl-methoxypropionic acid N-ethyl-N-(3-(4-fluorophenyl)-2,2-dioxo-2-thia-1-azaspiro[4.5]dec-3-ene-4-ylmethyl)amide was prepared according to the methods described in Example 1. Yield: 510 mg, 71%; MS (IS): 701 [MH]+.

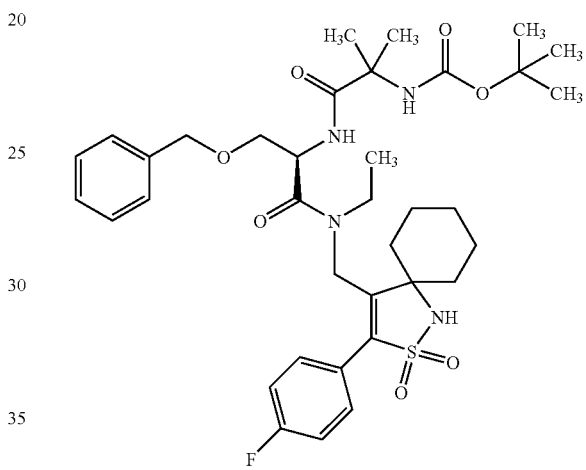

The title compound was prepared according to the methods described in Example 1. Yield: 400 mg, 79%; MS (IS): 601 [MH]+.

EXAMPLE 30

2-(R)-2-(2-Amino-2-methylpropionylamino)-5-phenyl-pentanoic acid N-ethyl-N-(3-(4-fluorophenyl)-2,2-dioxo-2-thia-1-azaspiro[4.5]dec-3-ene-4-ylmethyl)amide trifluoroacetate

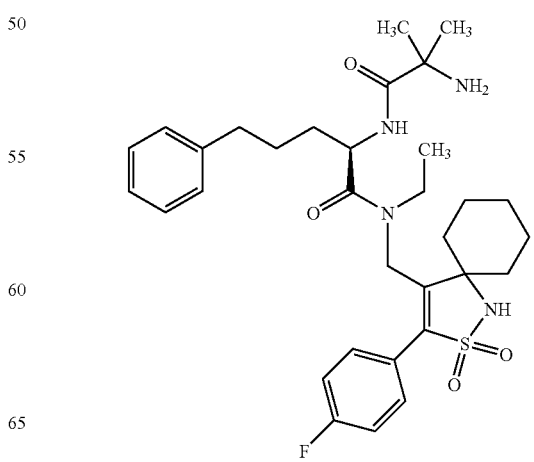

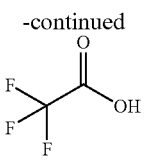

The title compound was prepared from 4-ethylaminomethyl-3-(4-fluorophenyl)-2-thia-1-azaspiro[4.5]dec-3-ene 2,2-dioxide and 2-(R)-2-(2-(N-tert-butoxycarbonyl-amino)-2-methyl-propionylamino)-5-phenylpentanoic acid and deprotected according to the methods described in Example 1. Yield: 340 mg, 53%; MS (IS): 599 [MH]⁺.

EXAMPLE 31

2-(R)-2-(2-Amino-2-methylpropionylamino)-3-phenylmethoxy-propionic acid N-(3-(2-chlorophenyl)-2,2-dioxo-2-thia-1-azaspiro[4.5]dec-3-ene-4-ylmethyl)-N-ethylamide trifluoroacetate

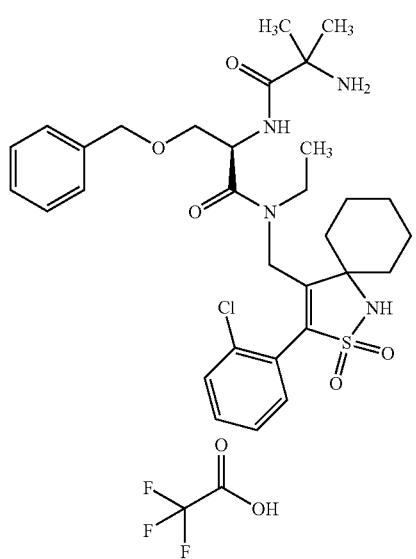

The title compound, shown above, was prepared as follows.

3-(2-Chlorophenyl)-4-methyl-2-thia-1-azaspiro[4.5]dec-3-ene 2,2-dioxide, shown below, was prepared from 2-chlorobenzyl-chloride and 1-ethynyl-1-cyclohexylamine according to the methods described in Examples 1 and 2. Yield: 710 mg, 24%; MS (IS): 312 [MH]⁺.

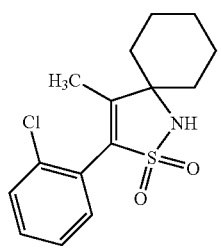

3-(2-Chlorophenyl)-4-ethylaminomethyl-2-thia-1-azaspiro[4.5]dec-3-ene 2,2-dioxide, shown below, was prepared according to the methods described in Example 1. Yield: 390 mg, 51%; MS (IS): 341 [MH]⁺.

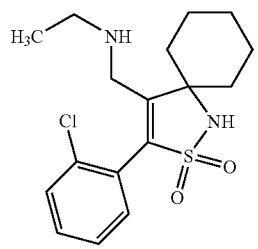

2-(R)-2-(2-(N-tert-Butoxycarbonylamino)-2-methyl-propionylamino)-3-phenyl-methoxypropionic acid N-(3-(2-chlorophenyl)-2,2-dioxo-2-thia-1-azaspiro[4.5]dec-3-ene-4-ylmethyl)-N-ethylamide, shown below, was prepared according to the methods described in Example 1. Yield: 700 mg, 88%; MS (IS): 717 [MH]⁺.

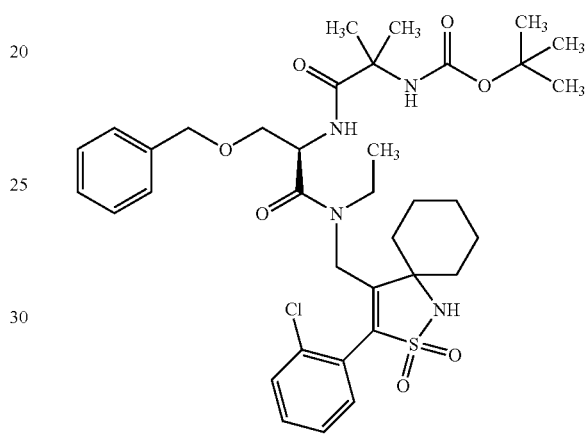

The title compound was prepared according to the method described in Example 1. Yield: 460 mg, 66%; MS (IS): 617 [MH]⁺.

EXAMPLE 32

2-(R)-2-(2-Amino-2-methylpropionylamino)-3-phenylmethoxy-propionic acid N-(3-(4-biphenyl)-2,2-dioxo-2-thia-1-azaspiro[4.5]dec-3-ene-4-ylmethyl)-N-ethylamide trifluoroacetate

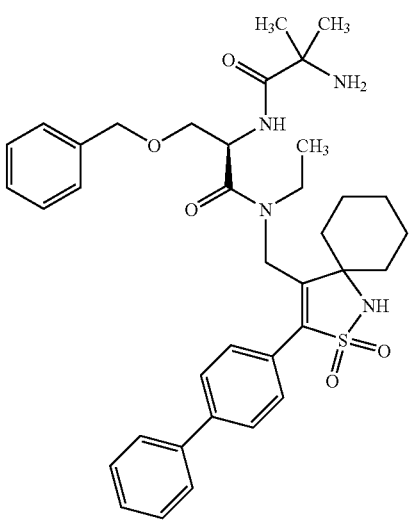

-continued

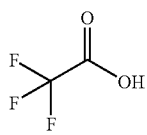

The title compound, as shown above, was prepared as follows.

3-(4-Biphenyl)-4-methyl-2-thia-1-azaspiro[4.5]dec-3-ene 2,2-dioxide, shown below, was prepared from 4-biphenylmethylchloride and 1-ethynylcyclohexylamine according to the methods described in Examples 1 and 2. Yield: 450 mg, 4%; MS (IS): 354 [MH]+.

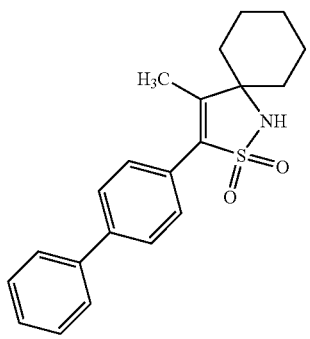

3-(4-Biphenyl)-4-ethylaminomethyl-2-thia-1-azaspiro[4.5]dec-3-ene 2,2-dioxide, shown below, was prepared according to the methods described in Example 1. Yield: 180 mg, 37%; MS (IS): 397 [MH]+.

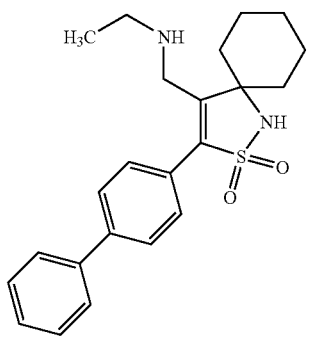

The title compound was prepared and deprotected according to the methods described in Example 1. Yield: 133 mg, 52%; MS (IS): 659 [MH]+.

EXAMPLE 33

2-(R)-2-(2-Amino-2-methylpropionylamino)-3-phenylmethoxy-propionic acid N-(3-(2-bromophenyl)-2,2-dioxo-2-thia-1-azaspiro[4.5]dec-3-ene-4-ylmethyl)-N-ethylamide trifluoroacetate

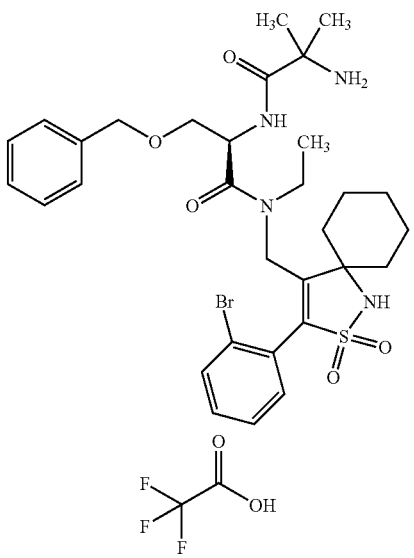

The title compound, shown above, was prepared as follows.

3-(2-Bromophenyl)-4-methyl-2-thia-1-azaspiro[4.5]dec-3-ene 2,2-dioxide, shown below, was prepared from 2-bromobenzylchloride and 1-ethynyl-1-cyclohexylamine according to the methods described in Examples 1 and 2. The cyclization was performed in the presence of 1 eq. of 3,4-dimethoxybenzylbromide. The dimethoxybenzyl residue was cleaved by stirring overnight with 2 eq. DDQ (2,3-dichloro-5,6-dicyano-1,4-benzoquinone) in CH$_2$Cl$_2$/H$_2$O 20:1. The mixture was filtered, the filtrate evaporated and purified on a silica column (toluene). Recrystallization from ethanol/hexane yielded the desired compound. Yield: 1.04 g, 15%; MS (IS): 356 [MH]+.

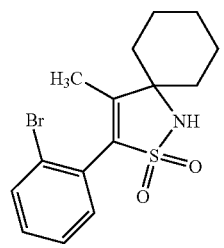

3-(2-Bromophenyl)-4-ethylaminomethyl-2-thia-1-azaspiro[4.5]dec-3-ene 2,2-dioxide was prepared according to the methods described in Example 1. Yield: 870 mg, 79%; MS (IS): 399 [MH]+.

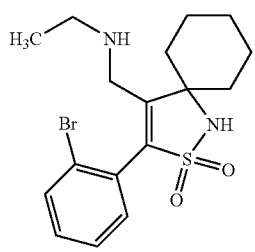

The title compound was prepared according to the method described in Example 1. Yield: 620 mg, 80%; MS (IS): 663 [MH]+; m.p. 145–150° C.

EXAMPLE 34

2-(R)-2-(2-Amino-2-methylpropionylamino)-5-phenyl-pentanoic acid N-(3-(2-bromophenyl)-2,2-dioxo-2-thia-1-azaspiro[4.5]dec-3-ene-4-ylmethyl)-N-ethylamide trifluoroacetate

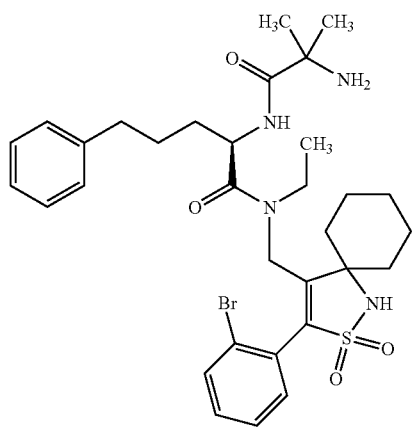

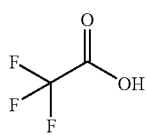

The title compound was prepared from 3-(2-bromo-phenyl)-4-ethylaminomethyl-2-thia-1-azaspiro[4.5]dec-3-ene 2,2-dioxide and 2-(R)-2-(2-(N-tert-butoxycarbonyl-amino)-2-methyl-propionylamino)-5-phenylpentanoic acid and deprotected according to the methods described in Example 1. Yield: 615 mg, 80%; MS (IS): 661 [MH]+; m.p. 135–140° C.

EXAMPLE 35

2-(R)-2-(2-Amino-2-methylpropionylamino)-3-phenylmethoxy-propionic acid N-(3-(4-cyano-phenyl)-2,2-dioxo-2-thia-1-azaspiro[4.5]dec-3-ene-4-ylmethyl)-N-ethylamide trifluoroacetate

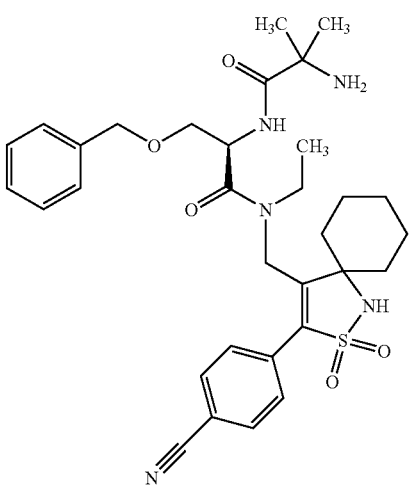

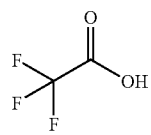

The title compound, as shown above, was prepared as follows.

3-(4-Cyanophenyl)-4-methyl-2-thia-1-azaspiro[4.5]dec-3-ene 2,2-dioxide, shown below, was prepared from 4-cyanobenzylchloride and 1-ethynyl-1-cyclohexyl-amine according to the methods described in Examples 1 and 2. Yield: 1.74 g, 44%; MS (IS): 303 [MH]+.

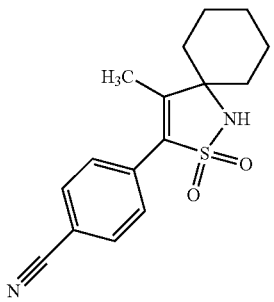

3-(4-Cyanophenyl)-4-ethylaminomethyl-2-thia-1-azaspiro[4.5]dec-3-ene 2,2-dioxide, shown below, was prepared according to the methods described in Example 1. Yield: 330 mg, 19%; MS (IS): 346 [MH]⁺.

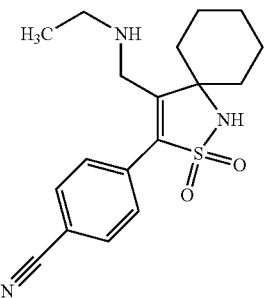

The title compound was prepared and deprotected according to the methods described in Example 1. Yield: 109 mg, 47%; MS (IS): 609 [MH]⁺.

EXAMPLE 36

2-(R)-2-(2-Amino-2-methylpropionylamino)-3-phenylmethoxy-propionic acid N-(3-(4-carbamoylphenyl)-2,2-dioxo-2-thia-1-azaspiro[4.5]dec-3-ene-4-ylmethyl)-N-ethylamide trifluoroacetate

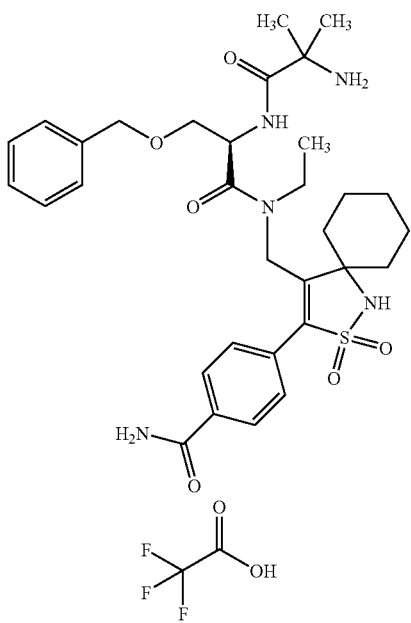

The title compound was prepared by coupling 3-(4-cyanophenyl)-4-ethylaminomethyl-2-thia-1-azaspiro[4.5]dec-3-ene 2,2-dioxide with 2-(R)-2-(2-(N-tert-butoxy-carbonyl-amino)-2-methyl-propionylamino)-5-phenyl-pentanoic acid according to the method described in Example 1 and subsequent treatment with trifluoroacetic acid in dichloromethane (1:1) as described in Example 1. The product was purified by chromatography on silica gel (CH₂Cl₂/acetone 95:5) and by HPLC (ODS, acetonitrile/water-gradient). Yield: 3.9 mg, 1.7%; S (IS): 627 [MH]⁺.

EXAMPLE 37

2-Amino-N-{2-benzyloxy-1-[(3,3-dimethyl-1,1-dioxo-5-phenyl-2,3-dihydro-1H-1γ⁶-isothiazol-4-yl-methyl)-ethyl-carbamoyl]-ethyl}-2-methyl-propionamide hydrochloride

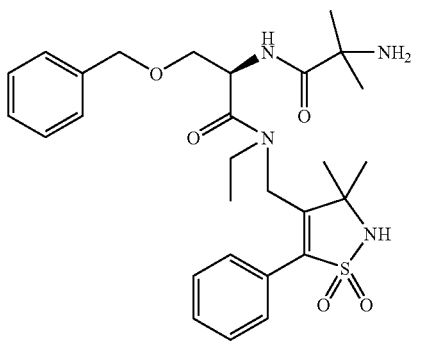

The title compound, as shown above, was prepared as follows.

To a solution of methyl-n-amylethynylcarbinyl amine, 4.0 g (48.0 mmol, as described in JACS, 75, 1653 (1954)) in 120 mL of dichloromethane at 0° C. was added 8.0 mL (52.8 mmol) of 1,8-diazabicyclo(5.4.0)undec-7-ene. After stirring for 10 min, 9.2 g (48.0 mmol) of alpha-toluenesulfonyl chloride was added. The reaction mixture was stirred for 2 h at 0° C. and was concentrated to dryness and partitioned between ethyl acetate and water. The mixture was acidified to pH=2.0 with 1 N HCl and extracted with ethyl acetate. The combined organics were washed with brine, dried over sodium sulfate, filtered and concentrated to dryness to yield 9.32 g (80%) of the desired product, shown below, as a clear oil which solidifies upon standing. ¹H-NMR is consistent with structure; MS (ion spray) 236 (M−1); Anal. Calc'd for C₁₂H₁₅NO₂S: C, 60.73; H, 6.37; N, 5.90. Found: C, 60.46; H, 6.15; N, 6.02.

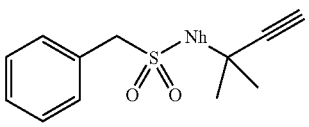

To a solution of N-(1,1-dimethyl-prop-2-ynyl)-C-phenyl-methanesulfonamide, 1.0 g (4.2 mmol) in 15 mL of ethylene glycol was added 0.1 g of mercury oxide (yellow), 1 mL of water and 5 drops concentrated sulfuric acid. The mixture was heated at 170° C. for 1 h then was cooled to ambient temperature, poured into water and extracted with ethyl acetate. The combined organics were washed with brine, dried over sodium sulfate, filtered and concentrated to dryness. The resulting residue was chromatographed on silica gel using 5% methanol/chloroform as eluant to yield 0.9 g (84%) of the desired product, shown below, as a white solid. ¹H-NMR is consistent with structure; MS (ion spray) 256.2 (M+1); Anal. Calc'd for C₁₂H₁₇NO₃S.0.3H₂O: C, 55.28; H, 6.80; N, 5.37. Found: C, 55.20; H, 6.52; N, 5.55.

N-(1,1-dimethyl-2-oxo-propyl)-C-phenyl-methane-sulfonamide.

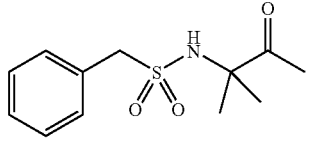

To a solution of N-(1,1-dimethyl-2-oxo-propyl)-C-phenyl-methanesulfonamide, 6.72 g (26.0 mmol) in 100 mL of dimethylformamide was added 2.2 g (54.6 mmol) of sodium hydride. The reaction mixture was heated at 90° C. for 24 H, then cooled to ambient temperature and concentrated to dryness. The residue was partitioned between ethyl acetate and water and was acidified to pH=3.0 with 1 N HCl. The mixture was extracted with ethyl acetate. The combined organics were washed with brine, dried over sodium sulfate, filtered and concentrated to dryness. The residue was chromatographed on silica using chloroform as eluant to yield 5.0 g (81%) of the desired product, shown below, as a tan solid. $^1$H-NMR is consistent with structure; MS (ion spray) 238.0 (M+1); Anal. Calc'd for $C_{12}H_{15}NO_2S \cdot 0.03CHCl_3$: C, 59.98; H, 6.29; N, 5.81. Found: C, 60.13; H, 6.36; N, 5.72.

3,3,4-trimethyl-5-phenyl-2,3-dihydro-isothiazole 1,1-dioxide.

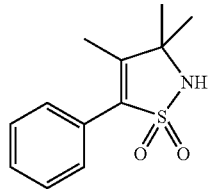

To a solution of 3,3,4-trimethyl-5-phenyl-2,3-dihydro-isothiazole 1,1-dioxide, 1.3 g (5.5 mmol) in 130 mL of carbon tetrachloride was added 1.46 g (8.25 mmol) of N-bromosuccinimide and 0.1 g of 2,2'-azobis(2-methylpropionitrile). The mixture was heated to reflux for 4 h then cooled to ambient temperature. Chloroform was added and the solution was washed with water, washed with brine, dried over sodium sulfate, filtered and concentrated to dryness. To a solution of the residue in 60 mL of absolute ethanol was added 3.6 mL (55.0 mmol) of ethylamine (70% solution in water). The reaction mixture was stirred 24 h at ambient temperature then concentrated to dryness. The residue was purified by chromatography on silica gel with methanol/chloroform as eluant to yield 0.59 g (38%) of the desired product, shown below, as a tan oil. $^1$H-NMR is consistent with structure; MS (ion spray) 281.1 (M+1).

(3,3-dimethyl-1,1-dioxo-5-phenyl-2,3-dihydro-1H-1$\gamma^6$-isothiazol-4-ylmethyl-)-ethyl-amine.

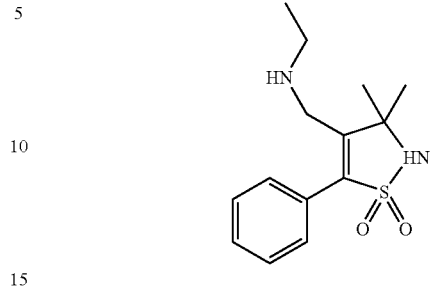

To a solution of (3,3-dimethyl-1,1-dioxo-5-phenyl-2,3-dihydro-1H-1$\gamma^6$-isothiazol-4-ylmethyl)-ethyl-amine, 0.3 g (0.79 mmol) in 8 mL of tetrahydrofuran was added 0.22 g (0.79 mmol) of 368979, 0.12 g (0.87 mmol) of 1-hydroxy-benzotriazole hydrate and 0.18 g (0.87 mmol) of 1,3-dicyclohexyl-carbodiimide. After stirring 24 h, the reaction mixture was concentrated to dryness. The residue was slurried in ethyl acetate and water was added. The mixture was extracted with ethyl acetate. The combined organics were washed with brine, dried over sodium sulfate, filtered and concentrated to dryness. The residue was chromatographed on silica gel using 3% methanol/chloroform as eluant to yield 0.36 g (72%) of the desired product, shown below, as a tan foam. $^1$H-NMR is consistent with structure; MS (ion spray) 641.3 (M−1); Anal. Calc'd for $C_{33}H_{46}N_4O_7S$: C, 61.66; H, 7.21; N, 8.72. Found: C, 61.38; H, 7.17; N, 8.89.

(1-{2-benzyloxy-1-[(3,3-dimethyl-1,1-dioxo-5-phenyl-2,3-dihydro-1H-1$\gamma^6$-isothiazol-4-ylmethyl)-ethyl-carbamoyl]-ethylcarbamoyl}-1-methyl-ethyl)-carbamic acid tert-butyl ester.

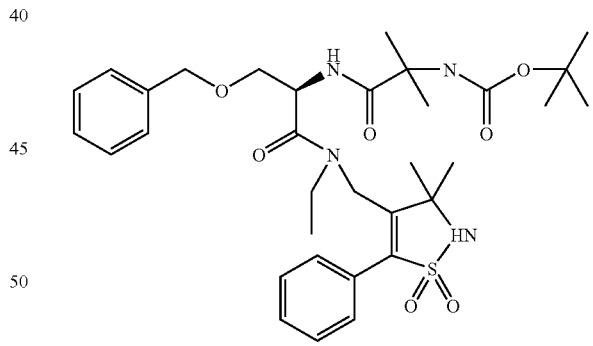

A solution of 0.3 g (0.47 mmol) of (1-{2-benzyloxy-1-[(3,3-dimethyl-1,1-dioxo-5-phenyl-2,3-dihydro-1H-1$\gamma^6$-isothiazol-4-ylmethyl)-ethyl-carbamoyl]-ethylcarbamoyl}-1-methyl-ethyl)-carbamic acid tert-butyl ester in 10 mL of acetic acid saturated with HCl gas was stirred at ambient temperature for 4 h, then concentrated to dryness. The residue was dissolved in toluene and concentrated to dryness three times to azeotrope off the acetic acid. The residue was slurried in ether and filtered to yield 0.2 g (69%) of the desired product as a white solid. $^1$H-NMR is consistent with structure; MS (ion spray) 543.3 (M+1); Anal. Calc'd for $C_{28}H_{38}N_4O_5S \cdot 1.4HCl$: C, 56.64; H, 6.69; N, 9.44. Found: C, 56.40; H, 6.74; N, 9.36.

EXAMPLE 38

2-(2-Amino-2-methyl-propionylamino)-5-phenyl-pentanoic acid (3,3-dimethyl-1,1-dioxo-5-phenyl-2,3-dihydro-1H-1$\gamma^6$-isothiazol-4-ylmethyl)-ethyl-amide hydrochloride

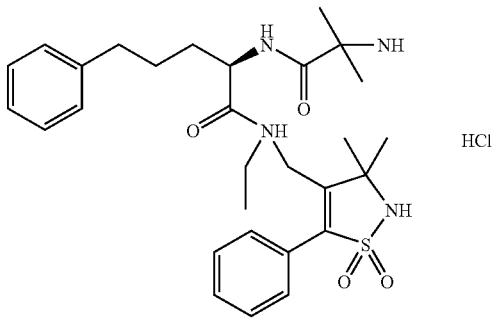

To a solution of (3,3-dimethyl-1,1-dioxo-5-phenyl-2,3-dihydro-1H-1$\gamma^6$-isothiazol-4-ylmethyl)-ethyl-amine, 0.55 g (2.0 mmol) as described in Example 37 in 10 ml of tetrahydrofuran was combined with 0.74 g (2.0 mmol) of 2-(2-tert-Butoxycarbonylamino-2-methyl-propionylamino)-5-phenyl-pentanoic acid, 0.46 g (2.2 mmol) of 1,3-dicyclohexylcarbodiimide. After stirring 24 h, the reaction mixture was concentrated to dryness. The residue was slurried in ethyl acetate and water was added. The mixture was extracted with ethyl acetate. The combined organics were washed with brine, dried over sodium sulfate, filtered and concentrated to dryness. The residue was chromatographed on silica gel using 4% methanol/chloroform as eluant to yield 1.05 g (82%) of the desired product, shown below, as a tan foam. $^1$H-NMR is consistent with structure; MS (ion spray) 639.2 (M−1); Anal. Calc'd for $C_{34}H_{48}N_4O_6S$: C, 63.72; H, 7.55; N, 8.74. Found: C, 63.38; H, 7.51; N, 8.92.

(1-{1-[(3,3-dimethyl-1,1-dioxo-5-phenyl-2,3-dihydro-1H-1$\gamma^6$-isothiazol-4-ylmethyl)-ethyl-carbamoyl]-4-phenyl-butylcarbamoyl}-1-methyl-ethyl)-carbamic acid tert-butyl ester.

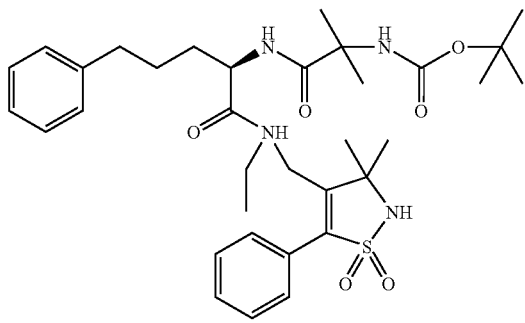

A solution of (1-{1-[(3,3-dimethyl-1,1-dioxo-5-phenyl-2,3-dihydro-1H-1$\gamma^6$-isothiazol-4-ylmethyl)-ethyl-carbamoyl]-4-phenyl-butylcarbamoyl}-1-methyl-ethyl)-carbamic acid tert-butyl ester, 1.02 g (1.6 mmol) in 10 mL of acetic acid saturated with HCl gas was stirred at ambient temperature for 4 h, then concentrated to dryness. The residue was dissolved in toluene and concentrated to dryness three times to azeotrope off the acetic acid. The residue was slurried in ether and filtered to yield 0.47 g (52%) of the title product as a white solid. $^1$H-NMR is consistent with structure; MS (ion spray) 541.5 (M+1); Anal. Calc'd for $C_{29}H_{40}N_4O_4S.1.2HCl$: C, 59.59; H, 7.10; N, 9.59. Found: C, 59.93; H, 7.03; N, 9.23.

EXAMPLE 39

2-(2-Amino-2-methyl-propionylamino)-5-phenyl-pentanoic acid [5-(4-chloro-phenyl)-3,3-dimethyl-1,1-dioxo-2,3-dihydro-1H-1$\gamma^6$-isothiazol-4-ylmethyl]-ethyl-amide hydrochloride

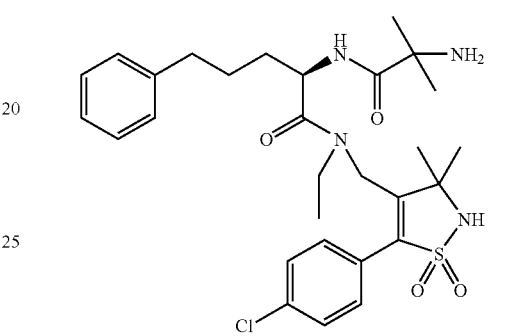

To a solution of sodium (p-chloro-O-toluene)sulfonic acid sodium salt (prepared as described herein), 8.9 g (39.0 mmol) in 20 mL of phosphorus oxychloride at 0° C., was added 11.6 g of phosphorus pentachloride. The reaction mixture was slowly warmed to ambient temperature, stirred 48 h and concentrated to dryness.

To a solution of methyl-n-amylethynylcarbinyl amine, 3.23 g (39.0 mmol, as described in JACS, 75, 1653 (1954)) in 50 mL of dichloromethane at 0° C. was added 6.41 mL (42.9 mmol) of 1,8-diazabicyclo(5.4.0)undec-7-ene. After stirring for 10 min, 8.8 g (39.0 mmol) of the above residue in 70 mL of dichloromethane was added. The reaction mixture was stirred for 2 h at 0° C. and was concentrated to dryness and partitioned between ethyl acetate and water. The mixture was acidified to pH=2.0 with 1 N HCl and was extracted with ethyl acetate. The combined organics were washed with brine, dried over sodium sulfate, filtered and concentrated to dryness. The resulting residue was chromatographed over silica gel using 5% methanol/chloroform as eluant to yield 6.15 g (58%) of the desired product, shown below, as a white solid. $^1$H-NMR is consistent with structure; MS (ion spray) 270.3 (M−1); Anal. Calc'd for $C_{12}H_{14}ClNO_2S$: C, 53.04; H, 5.19; N, 5.15. Found: C, 52.54; H, 5.19; N, 4.93.

C-(4-Chloro-phenyl)-N-(1,1-dimethyl-prop-2-ynyl)-methanesulfonamide.

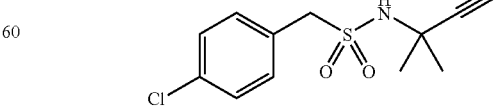

To a solution of C-(4-chloro-phenyl)-N-(1,1-dimethyl-prop-2-ynyl)-methanesulfonamide, 5.88 g (22.0 mmol) in 40 mL of ethylene glycol was added 0.3 g of mercury oxide (yellow), 4 mL of water and 6 drops concentrated sulfuric acid. The mixture was heated at 170° C. for 80 min then was cooled to ambient temperature, poured into water and extracted with ethyl acetate. The combined organics were washed with brine, dried over sodium sulfate, filtered and concentrated to dryness. The resulting residue was chromatographed on silica gel using chloroform as eluant to yield 4.31 g (68%) of the desired product, shown below, as a tan solid. $^1$H-NMR is consistent with structure; MS (ion spray) 288.0 (M−1); Anal. Calc'd for $C_{12}H_{16}ClNO_3S$: C, 49.74; H, 5.56; N, 4.83. Found: C, 49.59; H, 5.50; N, 4.73. C-(4-Chloro-phenyl)-N-(1,1-dimethyl-2-oxo-propyl)-methanesulfonamide.

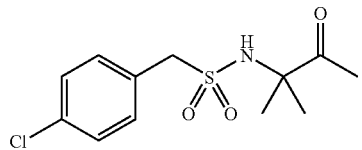

To a solution-of C-(4-Chloro-phenyl)-N-(1,1-dimethyl-2-oxo-propyl)-methanesulfonamide, 4.2 g (15.0 mmol) in 60 mL of dimethylformamide was added 1.3 g (31.5 mmol) of sodium hydride. The reaction mixture was heated at 90° C. for 24 H, then cooled to ambient temperature and concentrated to dryness. The residue was partitioned between ethyl acetate and water and was acidified to pH=3.0 with 1 N HCl. The mixture was extracted with ethyl acetate. The combined organics were washed with brine, dried over sodium sulfate, filtered and concentrated to dryness. The residue was chromatographed over silica using chloroform as eluant to yield 3.27 g (80%) of the desired product, shown below, as a tan solid. $^1$H-NMR is consistent with structure; MS (ion spray) 270.3 (M−1); Anal. Calc'd for $C_{12}H_{14}ClNO_2S$: C, 53.04; H, 5.19; N, 5.15. Found: C, 52.72; H, 5.18; N, 4.98. 5-(4-Chloro-phenyl)-3,3,4-trimethyl-2,3-dihydro-isothiazole 1,1-dioxide.

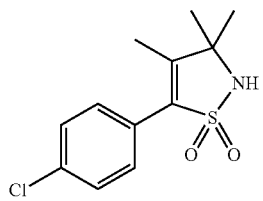

To a solution of 5-(4-Chloro-phenyl)-3,3,4-trimethyl-2,3-dihydro-isothiazole 1,1-dioxide, 1.5 g (5.5 mmol) in 150 mL of carbon tetrachloride was added 1.5 g (8.25 mmol) of N-bromosuccinimide and 0.13 g of 2,2'-azobis(2-methylpropionitrile). The mixture was heated to reflux for 4 h then cooled to ambient temperature. Chloroform was added and the solution was washed with water, washed with brine, dried over sodium sulfate, filtered and concentrated to dryness. To a solution of the residue in 75 mL of absolute ethanol was added 3.6 mL (55.0 mmol) of ethylamine (70% solution in water). The reaction mixture was stirred 24 h at ambient temperature then concentrated to dryness. The residue was purified by chromatography on silica gel with methanol/chloroform as eluant to yield 0.21 g (12%) of the desired product, shown below, as a tan oil. $^1$H-NMR is consistent with structure; MS (ion spray) 313.0 (M−1); Anal.

Calc'd for $C_{14}H_{19}ClN_2O_2S \cdot 0.1CHCl_3$: C, 51.83; H, 5.89; N, 8.57. Found: C, 51.58; H, 6.38; N, 8.04.

[5-(4-Chloro-phenyl)-3,3-dimethyl-1,1-dioxo-2,3-dihydro-1H-1$\gamma^6$-isothiazol-4-ylmethy]-ethyl-amine

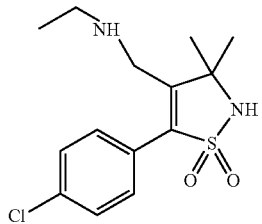

To a solution of [5-(4-chloro-phenyl)-3,3-dimethyl-1,1-dioxo-2,3-dihydro-1H-1$\gamma^6$-isothiazol-4-ylmethyl]-ethyl-amine, 0.2 g (0.63 mmol) in 10 mL of tetrahydrofuran was added 0.24 g (0.63 mmol) of 368979, 0.1 g (0.69 mmol) of 1-hydroxybenzotriazole hydrate and 0.14 g (0.69 mmol) of 1,3-dicyclohexylcarbodiimide. After stirring 24 h, the reaction mixture was concentrated to dryness. The residue was slurried in ethyl acetate and water was added. The mixture was extracted with ethyl acetate. The combined organics were washed with brine, dried over sodium sulfate, filtered and concentrated to dryness. The residue was chromatographed on silica gel using 2% methanol/chloroform as eluant to yield 0.3 g (70%) of the desired product as a tan foam. $^1$H-NMR is consistent with structure; MS (ion spray) 675.7 (M+1). [1-(1-{[5-(4-Chloro-phenyl)-3,3-dimethyl-1,1-dioxo-2,3-dihydro-1H-1$\gamma^6$-isothiazol-4-ylmethyl]-ethyl-carbamoyl}-4-phenyl-butylcarbamoyl)-1-methyl-ethyl]-carbamic acid tert-butyl ester.

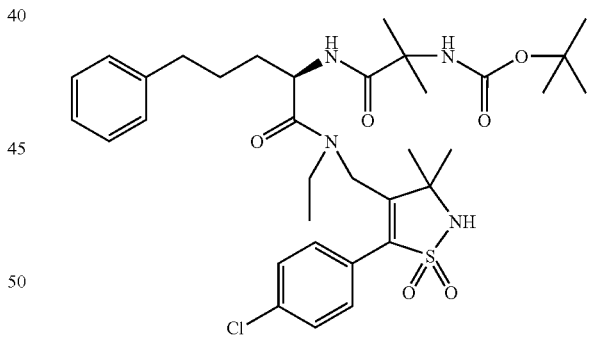

A solution of 0.3 g (0.45 mmol) of [1-(1-{[5-(4-Chloro-phenyl)-3,3-dimethyl-1,1-dioxo-2,3-dihydro-1H-1$\gamma^6$-isothiazol-4-ylmethyl]-ethyl-carbamoyl}-4-phenyl-butyl-carbamoyl)-1-methyl-ethyl]-carbamic acid tert-butyl ester in 10 mL of acetic acid saturated with HCl gas was stirred at ambient temperature for 4 h, then concentrated to dryness. The residue was dissolved in toluene and concentrated to dryness three times to azeotrope off the acetic acid. The residue was slurried in ether and filtered to yield 0.24 g (89%) of the title product as a white solid. $^1$H-NMR is consistent with structure; MS (ion spray) 573.3 (M−1); Anal. Calc'd for $C_{29}H_{39}N_4O_4S \cdot 1.6HCl$: C, 54.98; H, 6.46; N, 8.84. Found: C, 54.82; H, 6.21; N, 8.66.

EXAMPLE 39B

2-Amino-N-(2-benzyloxy-1-{[5-(4-chloro-phenyl)-3,3-dimethyl-1,1-dioxo-2,3-dihydro-1H-1λ⁶-isothiazol-4-ylmethyl]-ethyl-carbamoyl}-ethyl)-2-methyl-propionamide hydrochloride

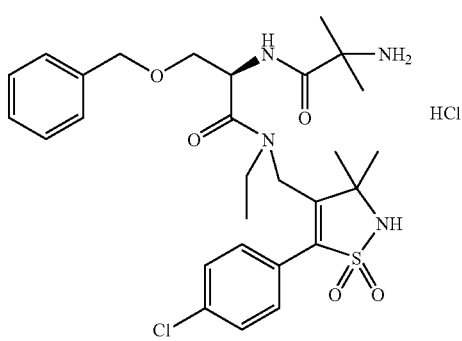

The title compound was prepared as follows:

The intermediate, [5-(4-Chloro-phenyl)-3,3-dimethyl-1,1-dioxo-2,3-dihydro-1H-1λ⁶-isothiazol-4-ylmethyl]-ethyl-amine (0.55 g, 1.6 mmol), was combined with 1-hydroxybenzotriazole hydrate (0.22 g, 1.6 mmol), 1,3-dicyclohexylcarbodiimide (0.33 g, 1.6 mmol), and 3-benzyloxy-2-(2-tert-butoxycarbonylamino-2-methyl-propionylamino)-propionic acid (0.61 g, 1.6 mmol) in tetrahydrofuran and the resulting mixture stirred overnight at room temperature. The mixture was concentrated and the residue was taken up in ethyl acetate and the mixture filtered. Concentration of the filtrate and chromatography of the residue over silica (methanol/chloroform) allowed for recovery of 1.0 g (92%) of reasonably pure product as an off white solid. MS(ES): (M+1)⁺ 677.4 m/z.

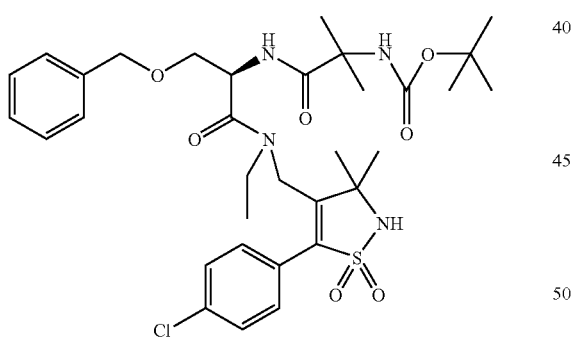

The compound from above, [1-(2-benzyloxy-1-{[5-(4-chloro-phenyl)-3,3-dimethyl-1,1-dioxo-2,3-dihydro-1H-1λ⁶-isothiazol-4-ylmethyl]-ethyl-carbamoyl}-ethylcarbamoyl)-1-methyl-ethyl]-carbamic acid tert-butyl ester (1.00 g, 1.48 mmol) was dissolved in dichloromethane (30 mL) and trifluoroacetic acid added (5 mL) and the mixture stirred for 2 hours at room temperature. The mixture was concentrated in vacuo and the residue treated with saturated aqueous sodium bicarbonate followed by extraction with ethyl acetate. The combined extracts were dried over sodium sulfate. Concentration left a residue which was chromatographed over silica (methanol/chloroform) to give the amine. This amine was dissolved in minimal ethyl acetate and treated with excess ether/hydrochloric acid. Concentration and drying netted 0.37 g (41%) of the desired hydrochloride salt as a white solid. Anal. Calc'd for C₂₈H₃ClN₄O₅S.1.1HCl: C, 54.49; H, 6.22; N, 9.38. Found: C, 54.17; H, 6.16; N, 9.38. m.p. 107–113° C. MS(ES): (M+1)⁺ 579.4 m/z.

EXAMPLES 40 AND 41

2-Amino-N-{2-benzyloxy-1-[2,2-dioxo-3-phenyl-2λ⁶-thia-1-aza-spiro[4.4]non-3-en-4-ylmethyl)-ethyl-carbamoyl]-ethyl}-2-methyl-propionamide hydrochloride

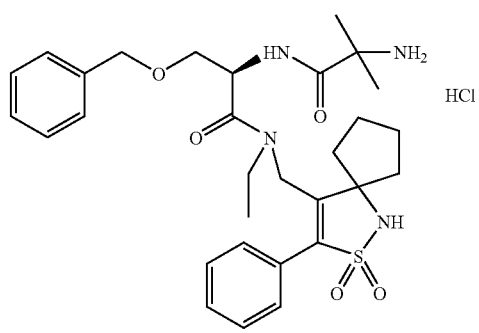

and 2-(2-Amino-2-methyl-propionylamino)-5-phenyl-pentanoic acid (2,2-dioxo-3-phenyl-2λ⁶-thia-1-aza-spiro[4.4]non-3-en-4-ylmethyl)-ethyl-amide hydrochloride

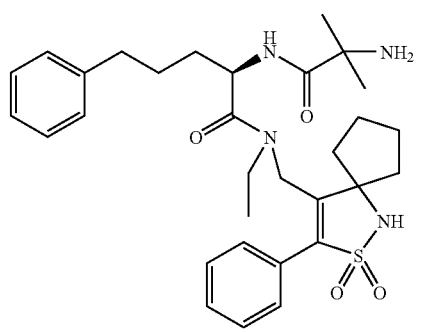

The title compounds, as shown above, were prepared as follows:

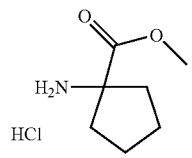

1-Amino-1-cyclopentane-carboxylic acid (5.00 g, 38.8 mmol), was dissolved in methanol (100 mL) and then thionyl chloride (9.25 g, 77.7 mmol) was added dropwise with stirring. The resulting mixture was stirred overnight at room temperature and then concentrated in vacuo which left a white solid. The solid was tritruated in ethyl ether, filtered, and dried to give 6.78 g (97%) of the amino-ester hydrochloride as a white solid. $^1$H NMR was consistent with product. ESMS (M+1) 144.2

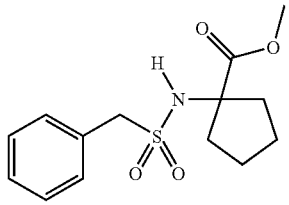

The amino-ester hydrochloride (2.00 g, 11.2 mmol) was combined with triethylamine (3.90 mL, 28.0 mmol), and 4-dimethylaminopyridine (cat. 20 mg), in dichloromethane (25 mL) at room temperature. Then α-toluenesulfonylchloride (2.12 g, 11.2 mmol) was added and the resulting mixture stirred over the weekend at room temperature. Aqueous 1N hydrochloric acid (25 mL) was then added and the aqueous phase extracted with 3×25 mL of dichloromethane. The combined extracts were dried over sodium sulfate and concentrated in vacuo to give a residue which was chromatographed over silica (chloroform/methanol) to give 2.40 g (72%) of the desired product as an off white solid. $^1$H NMR was consistent with product. ESMS: (M+1)$^+$ 298.4. Anal. Calcd. for $C_{14}H_{19}NO_4S$: C, 56.55; H, 6.44; N, 4.71. Found: C, 56.28; H, 6.46; N, 4.69.

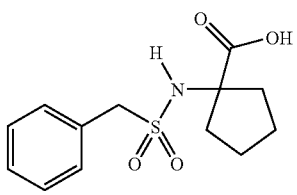

The ester from above (5.50 g, 18.5 mmol) was combined with 2 N aqueous sodium hydroxide (60 mL), tetrahydrofuran (5 mL), and ethanol (5 mL) and the mixture stirred at room temperature until hydrolysis was complete. Aqueous hydrochloric acid (5 N) was added until the aqueous mixture reached pH 2.0–2.5 and the aqueous phase was then extracted with ethyl acetate. Concentration of the extracts and drying of the resulting solid netted 4.90 g (94%) of the desired acid. An analytical sample was obtained by chromatography over silica (5–10% methanol/chloroform). ESMS: (M−1)$^-$ 282.2. $^1$H NMR was consistent with product. Anal. Calcd. for $C_{13}H_{17}NO_4S$: C, 55.11; H, 6.05; N, 4.94. Found: C, 55.00; H, 6.00; N, 4.92.

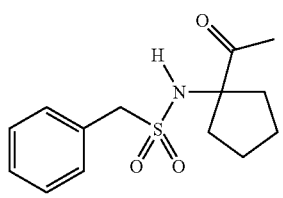

The acid from above (2.00 g, 7.0 mmol) was dissolved in anhydrous tetrahydrofuran (75 mL) and the mixture cooled to −70° C. (dry ice/acetone bath) under nitrogen. Then methyl lithium (25.24 mL, 1.4 M in ethyl ether) was added via syringe and the resulting mixture stirred for 5 hours while slowly warming to near room temperature. The reaction was then quenched into a stirred mixture of ice/1N aqueous hydrochloric acid and the aqueous mixture extracted with ethyl acetate. The combined extracts were concentrated and the resulting residue chromatographed over silica (chloroform/methanol) which allowed for isolation of 1.30 g (65%) of the desired ketone as a white solid. $^1$H NMR was consistent with product. ESMS: (M+1)$^+$ 282.2. Anal. Calcd. for $C_{14}H_{19}NO_3S$: C, 59.76; H, 6.81; N, 4.98. Found: C, 59.56; H, 6.62; N, 4.79.

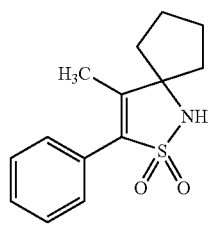

The ketone (1.50 g, 5.3 mmol) was dissolved in N,N-dimethyl-formamide (25 mL) and then sodium hydride (60%, 0.53 g, 13.25 mmol) added and the resulting mixture heated at 90° C. overnight. The solvent was then removed in vacuo and the resulting residue taken up in dilute aqueous hydrochloric acid. The aqueous mixture was extracted with ethyl acetate and the combined extracts were concentrated to leave a residue. This residue was chromatographed over silica (chloroform/methanol) which allowed for isolation of the desired product 1.15 g (82%) as a white solid. ESMS: (M+1)$^+$ 264.2. $^1$H NMR was consistent with product.

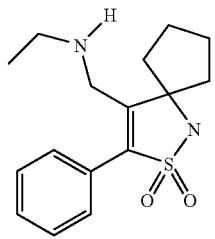

The product from above (1.00 g, 3.8 mmol) was slurried in carbon tetrachloride (40 mL) and N-bromosuccinimide (1.01 g, 5.7 mmol) and 2,2'-azobis(2-methyl)-propionitrile (0.05 g, cat.) were added. This mixture was heated at reflux for 2 hours after which time the reaction was cooled to ambient temperature and diluted with dichloromethane. The organic mixture was washed with water (2×40 mL) and dried over sodium sulfate. Concentration left a residue which was taken up in ethanol (30 mL) followed by the addition of ethylamine (70%, 2.5 mL) and this mixture allowed to stir overnight at room temperature. The mixture was then concentrated and the residue chromatographed over silica (chloroform/methanol) which allowed for isolation of 0.75 g (64%) of the desired product as a yellow solid. ESMS: (M+1)$^+$ 307.2. $^1$H NMR was consistent with product.

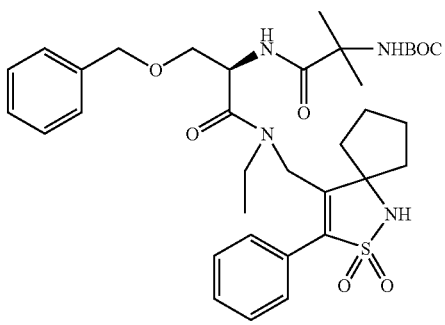

The amine from above (0.70 g, 2.29 mmol) was combined with

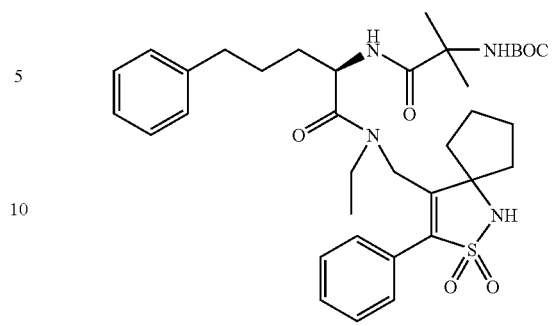

The amine from above (0.30 g, 0.98 mmol) was combined with

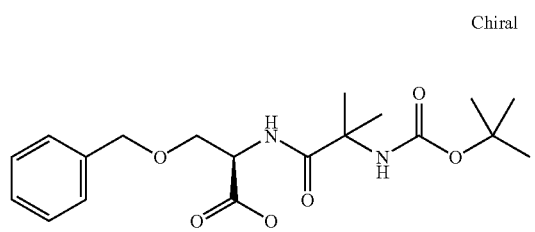

(0.87 g, 2.29 mmol), 1-hydroxybenzotriazole hydrate (0.31 g, 2.29 mmol), and 1,3-dicyclohexyl-carbodiimide (0.47 g, 2.29 mmol) in tetrahydrofuran (30 mL) and the mixture stirred overnight at ambient temperature. The reaction was then concentrated and the residue taken up in ethyl acetate and filtered. The filtrate was concentrated and this residue chromatographed over silica (chloroform/methanol) which allowed for isolation of the desired product 1.40 g (91%) as an off white foam. ESMS: (M+1)$^+$ 669.4. $^1$H NMR was consistent with product. Anal. Calcd. for $C_{35}H_{48}N_4O_7S$: C, 62.85; H, 7.23; N, 8.38. Found: C, 62.58; H, 7.23; N, 8.67.

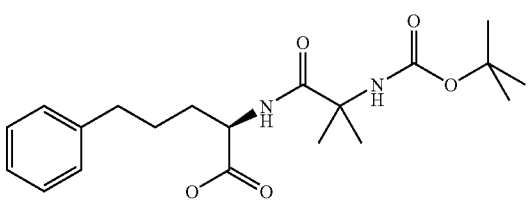

(0.37 g, 0.98 mmol), 1-hydroxy-benzotriazole hydrate (0.13 g, 0.98 mmol), and 1,3-dicyclohexyl-carbodiimide (0.20 g, 0.98 mmol) in tetrahydrofuran (20 mL) and the mixture stirred over the weekend at ambient temperature. The reaction was then concentrated and the residue taken up in ethyl acetate and filtered. The filtrate was concentrated and this residue chromatographed over silica (chloroform/methanol) which allowed for isolation of the desired product 0.12 g (65%). $^1$H NMR was consistent with product. ESMS: (M+1)$^+$ 667.4.

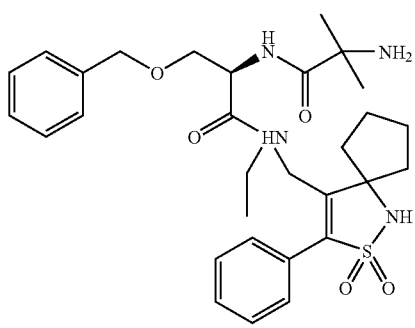

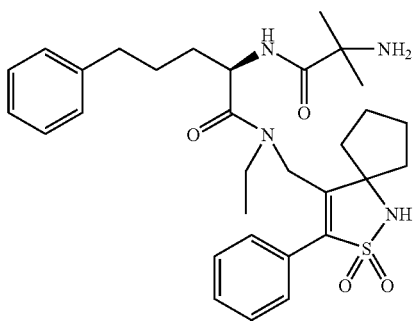

The BOC protected derivative from above (0.80 g, 1.20 mmol) was added to a solution of acetic acid saturated with HCl gas (10 mL). The mixture was stirred for 4 hours at room temperature after which time the mixture was concentrated in vacuo. The residue was concentrated twice from toluene and the resulting light solid was slurried in diethyl ether, filtered, and dried to net 0.57 g (78%) of the HCl salt as an off white solid. $^1$H NMR was consistent with product. ESMS: (M+1)$^+$ 569.4, 570.5. Anal. Calcd. for $C_{30}H_{41}N_4O_5SCl$: C, 59.54; H, 6.83; N, 9.26. Found: C, 59.26; H, 6.85; N, 9.25.

The BOC protected derivative from above (0.12 g, 0.18 mmol) was added to a solution of acetic acid saturated with HCl gas (2.0 mL). The mixture was stirred for 4 hours at room temperature after which time the mixture was concentrated in vacuo. The residue was concentrated twice from toluene and the resulting light solid was slurried in diethyl ether, filtered, and dried to net 0.07 g (67%) of the HCl salt as a tan solid. $^1$H NMR was consistent with product. ESMS: (M+1)$^+$ 567.5, 568.5. Anal. Calcd. for $C_{31}H_{41}N_4O_4S \cdot 2.5HCl$: C, 56.59; H, 6.82; N, 8.52. Found: C, 56.76; H, 6.63; N, 9.65.

EXAMPLE 42

2-Amino-N-(2-benzyloxy-1-{[3-(4-chloro-phenyl)-2, 2-dioxo-2λ⁶-thia-1-aza-spiro[4.4]non-3-en-4-yl methyl]-ethyl-carbamoyl}-ethyl)-2-methyl-propionamide hydrochloride

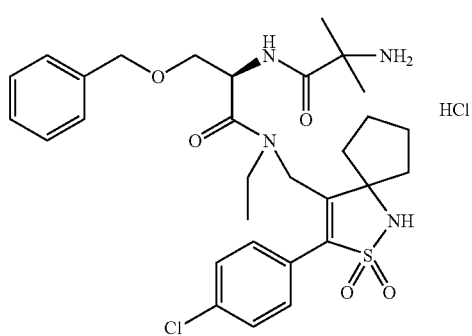

The title compound, as shown above, was prepared as follows:

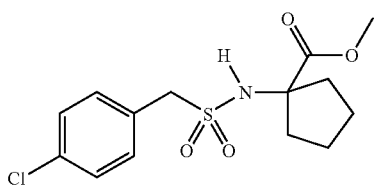

The amino-ester hydrochloride (2.50 g, 14.0 mmol) (as previously described) was combined with triethylamine (9.0 mL, 64.7 mmol), and 4-dimethylaminopyridine (cat. 50 mg), in dichloromethane (75 mL) at room temperature. Then 4-chloro-α-toluene-sulfonylchloride (as previously described) (3.00 g, 13.4 mmol) was added and the resulting mixture stirred overnight at room temperature. Water was then added and the pH of the aqueous phase adjusted to 2.5 with aqueous hydrochloric acid. The mixture was then extracted with dichloromethane and the combined extracts were dried over sodium sulfate and concentrated in vacuo. The resulting residue was chromatographed over silica (chloroform/methanol) to give 2.00 g (45%) of the desired product as a light yellow solid. ¹H NMR was consistent with product. ESMS: (M−1)⁻ 330.1, 331.2. Anal. Calcd. for $C_{14}H_{18}NO_4SCl$: C, 50.68; H, 5.47; N, 4.22. Found: C, 50.14; H, 5.50; N, 4.21.

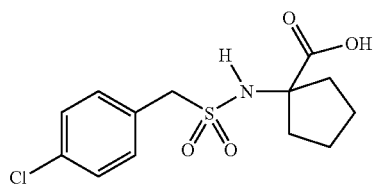

The ester from above (1.90 g, 5.74 mmol) was combined with 2 N aqueous sodium hydroxide (40 mL), tetrahydrofuran (5 mL), and ethanol (5 mL) and the mixture stirred at room temperature until hydrolysis was complete. Aqueous hydrochloric acid (5 N) was added until the aqueous mixture reached pH 2.0 and the aqueous phase was then extracted with ethyl acetate. The combined extracts were dried over sodium sulfate and the solution concentrated in vacuo. The resulting solid was triturated in diethyl ether, filtered and dried to give 1.75 g (97%) of the desired acid as a white solid. ¹H NMR was consistent with product. ESMS: (M+1)⁺ 316.0, 317.1. Anal. Calcd. for $C_{13}H_{16}NO_4SCl$: C, 49.13; H, 5.08; N, 4.41. Found: C, 49.16; H, 5.01; N, 4.20.

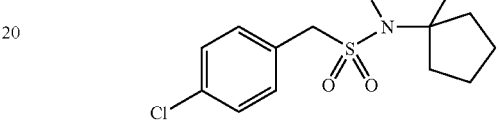

The acid from above (2.90 g, 9.2 mmol) was dissolved in anhydrous dimethoxyethane (75 mL) and the mixture cooled to −60° C. (dry ice/acetone bath) under nitrogen. Then methyl lithium (32.7 mL, 1.4 M in ethyl ether) was added via syringe and the resulting mixture stirred for 4.5 hours while slowly warming to near 0° C. The reaction was then quenched into a stirred mixture of ice/1N aqueous hydrochloric acid and the aqueous mixture extracted with ethyl acetate. The combined extracts were concentrated and the resulting residue chromatographed over silica (chloroform/methanol) which allowed for isolation of 2.30 g (79%) of the desired ketone as a white solid. ¹H NMR was consistent with product. ESMS: (M+1)⁺ 316.1. Anal. Calcd. for $C_{14}H_{18}NO_3SCl$: C, 53.24; H. 5.74; N, 4.43. Found: C, 52.50; H, 5.48; N, 4.29.

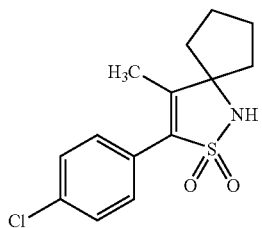

The ketone (2.50 g, 7.94 mmol) was dissolved in N,N-dimethylformamide (40 mL) and then sodium hydride (60%, 0.70 g, 17.4 mmol) was added and the resulting mixture heated at 100° C. overnight. The solvent was then removed in vacuo and the resulting residue taken up in dilute aqueous hydrochloric acid. The aqueous mixture was extracted with ethyl acetate and the combined extracts were concentrated to leave a residue. This residue was chromatographed over silica (chloroform/methanol) which allowed for isolation of the desired product 2.00 g (84%) as a white solid. ESMS: (M+1)⁺ 298.4. ¹H NMR was consistent with product. Anal. Calcd. for $C_{14}H_{16}NO_2SCl$: C, 56.46; H, 5.41; N, 4.70. Found: C, 56.17; H, 5.32; N, 4.69.

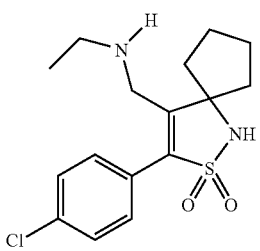

The product from above (1.80 g, 6.1 mmol) was slurried in carbon tetrachloride (50 mL) and N-bromosuccinimide (1.62 g, 9.1 mmol) and 2,2'-azobis(2-methyl)-propionitrile (0.05 g, cat.) were added. This mixture was heated at reflux for 4 hours after which time the reaction was cooled to ambient temperature and diluted with dichloromethane. The organic mixture was washed with water (2×40 mL) and dried over sodium sulfate. Concentration left a residue which was taken up in ethanol (40 mL) followed by the addition of ethylamine (70%, 4.0 mL) and this mixture allowed to stir overnight at room temperature. The mixture was then concentrated and the residue chromatographed over silica (chloroform/methanol) which allowed for isolation of 0.36 g (17%) of the desired product. ESMS: (M+1)+ 341.1, 343.0.

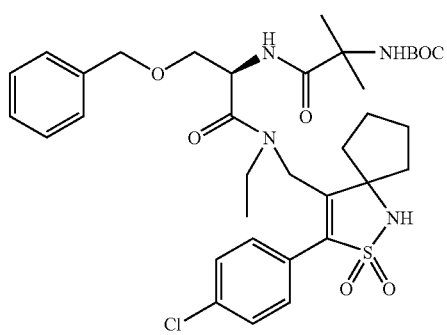

The amine from above (0.35 g, 1.03 mmol) was combined with

Chiral

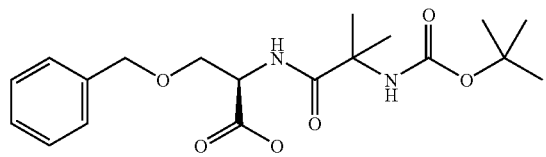

(0.39 g, 1.03 mmol), 1-hydroxybenzotriazole hydrate (0.14 g, 1.03 mmol), and 1,3-dicyclohexyl-carbodiimide (0.21 g, 1.03 mmol) in tetrahydrofuran (25 mL) and the mixture stirred overnight at ambient temperature. The reaction was then concentrated and the residue taken up in ethyl acetate and filtered. The filtrate was concentrated and this residue chromatographed over silica (chloroform/methanol) which allowed for isolation of the desired product 0.21 g (29%). ESMS: (M+1)+ 703.5. $^1$H NMR was consistent with product.

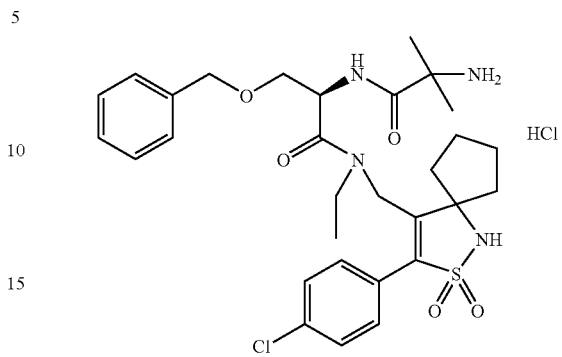

The BOC protected derivative from above (0.20 g, 0.28 mmol) was added to a solution of acetic acid saturated with HCl gas (5 mL). The mixture was stirred for 3 hours at room temperature after which time the mixture was concentrated in vacuo. The residue was concentrated twice from toluene and the resulting light solid was slurried in diethyl ether, filtered, and dried to net 0.08 g (45%) of the HCl salt as a tan solid. $^1$H NMR was consistent with product. ESMS: (M+1)+ 603.2, 604.4. Anal. Calcd. for $C_{30}H_{40}N_4O_5SCl_2$: C, 56.33; H, 6.30; N, 8.76. Found: C, 53.55; H, 6.03; N, 8.85.

EXAMPLE 43

2-(R)-2-(2-Amino-2-methylpropionylamino)-3-phenylmethoxy-propionic acid N-ethyl-N-(3-(4-methoxyphenyl)-2-oxo-1-azaspiro[4.5]dec-3-ene-4-ylmethyl)amide trifluoroacetate

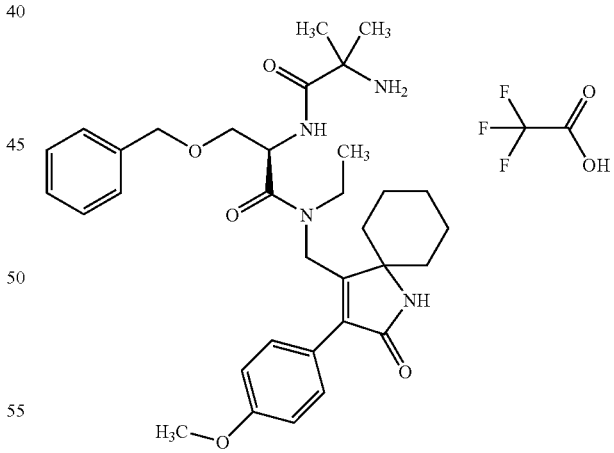

The title compound, as shown above, was prepared as follows.

4-Methoxyphenylacetic acid (739 mg, 4.44 mmol) was dissolved in THF (18 mL), triethylamine (0.9 mL) and tetramethylbenzotriazolyl urea (1.42 g, 4.42 mmol) were added. After stirring for 10 min, 1-ethynyl-1-cyclo-hexylamine (300 μl, 2.22 mmol) was added and the mixture was stirred for 90 min at room temperature, diluted with $CH_2Cl_2$ and washed with water, diluted HCl and saturated $NaHCO_3$.

The organic layer was dried (Na₂SO₄) and evaporated. The product was recrystallized from EtOH to yield 485 mg (81%) of white solid N-(1-ethynylcyclo-hexyl)-4-methoxyphenylacetamide, shown below. MS (IS): 272 [MH]⁺.

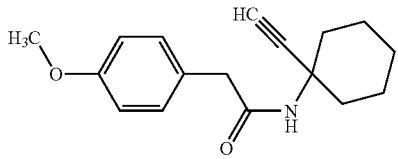

N-(1-Acetylcyclohexyl)-4-methoxyphenylacetamide was prepared according to the method described in Pestic. Sci. 1993, 39, 185–192. Yield: 477 mg, 92%; MS (IS): 290 [MH]⁺.

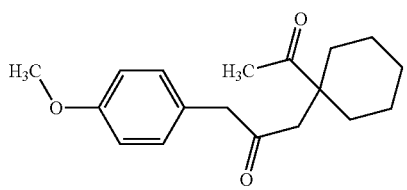

N-(1-Acetylcyclohexyl)-4-methoxyphenylacetamide (460 mg, 1.59 mmol) was dissolved in acetonitrile (60 mL) and dichloromethane (10 mL) under argon and NaH (60%, 2.4 eq.) was added in portions. The mixture was stirred overnight at room temperature, water was added and the solvent evaporated. The residue was dissolved in dichloromethane, washed with water and the organic layer was dried (Na₂SO₄) and concentrated.

Recrystallization from EtOH yielded the product (397 mg, 92%) as white solid. 3-(4-methoxyphenyl)-4-methyl-1-azaspiro[4.5]dec-3-ene-2-one, shown below. MS (IS): 272 [MH]⁺.

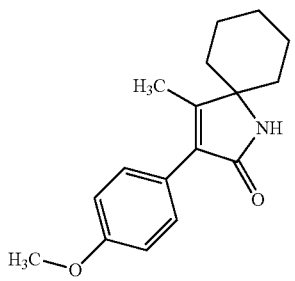

3-(4-Methoxyphenyl)-4-methyl-1-azaspiro[4.5]dec-3-ene-2-one (200 mg, 0.76 mmol) and N-bromosuccinimide (1 eq.) were stirred in 20 mL CCl₄ with a catalytic amount of benzoyl peroxide for 3 h at 85° C. After cooling to room temperature the mixture was diluted with CH₂Cl₂, washed with water, dried (Na₂SO₄) and evaporated. Recrystallization from ethanol yielded the product (250 mg, 97%) as white solid 4-bromomethyl-3-(4-methoxy-phenyl)-1-azaspiro[4.5]dec-3-ene-2-one, shown below. MS (IS): 350 [MH]⁺.

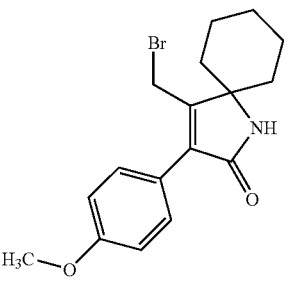

4-Bromomethyl-3-(4-methoxyphenyl)-1-azaspiro[4.5]dec-3-ene-2-one (250 mg, 0.71 mmol) was dissolved in ethanol (15 mL) and ethylamine (70% solution in water, 2 mL), the mixture was stirred overnight at room temperature and concentrated. The residue was dissolved in CH₂Cl₂, washed with water and extracted with 0.5 M HCl. After addition of NaOH and extraction with CH₂Cl₂ the organic layer was dried (Na₂SO₄) and evaporated to yield 0.22 g (98%)of 4-ethylaminomethyl-3-(4-methoxyphenyl)-1-azaspiro[4.5]dec-3-ene-2-one, shown below, as a solid. MS (IS): 315 [MH]⁺.

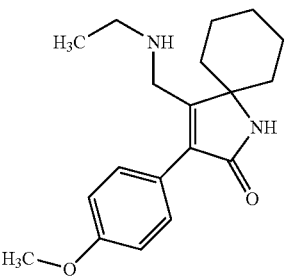

2-(R)-2-(2-(N-tert-Butoxycarbonylamino)-2-methyl-propionylamino)-3-phenylmethoxypropionic acid N-ethyl-N-(3-(4-methoxyphenyl)-2-oxo-1-azaspiro[4.5]dec-3-ene-4-ylmethyl)amide was prepared according to the methods described in Example 1. Yield: 127 mg, 60% MS (IS): 677 [MH]⁺.

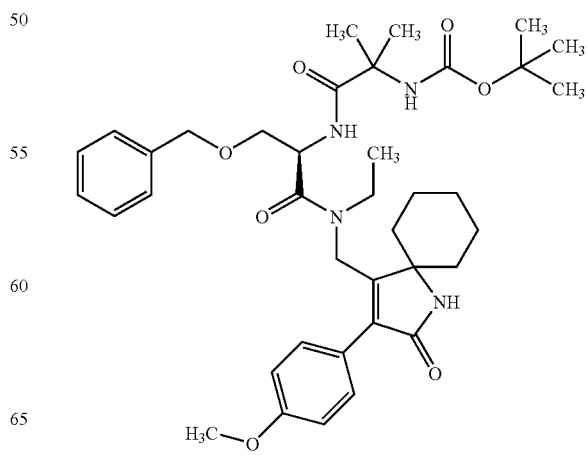

The title compound was prepared according to the methods described in Example 1. Yield: 87 mg, 80%; MS (IS): 599 [MNa]+, 577 [MH]+; m.p. 132° C.

EXAMPLE 44

2-(R)-2-(2-Amino-2-methylpropionylamino)-3-phenylmethoxy-propionic acid N-ethyl-N-(3-(4-methoxyphenyl)-1-methyl-2-oxo-1-azaspiro[4.5]dec-3-ene-4-ylmethyl)amide hydrochloride

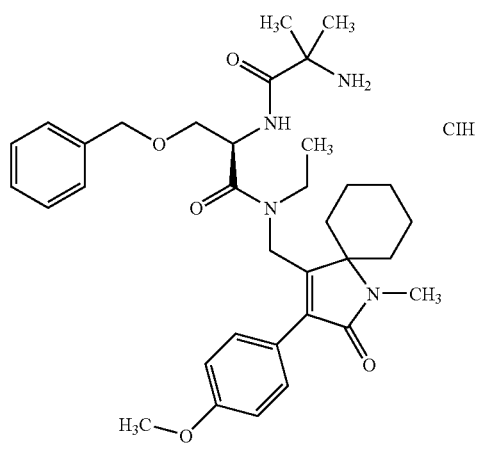

The title compound, shown above, was prepared as follows:

N-(1-Acetylcyclohexyl)-4-methoxyphenylacetamide (from Example 10) (1.66 g, 6.10 mmol) was dissolved in acetonitrile (200 mL) and dichloromethane (30 mL) under argon, NaH (60%, 2.4 eq.) and iodomethane (1.3 eq.) were added in portions. The mixture was stirred overnight at room temperature, water was added and the solvent evaporated. The residue was dissolved in dichloromethane, washed with water and the organic layer was dried (Na$_2$SO$_4$) and concentrated.

Recrystallization from EtOH yielded 3-(4-methoxyphenyl)-1,4-dimethyl-1-azaspiro[4.5]dec-3-ene-2-one (1.08 g, 62%), shown below, as a white solid. MS (IS): 286 [MH]+.

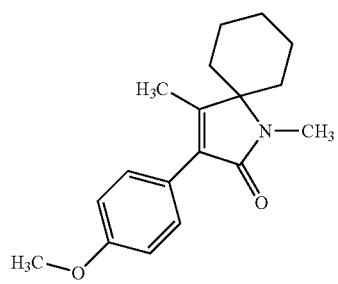

3-(4-Methoxyphenyl)-1,4-dimethyl-1-azaspiro[4.5]dec-3-ene-2-one (881 mg, 3.09 mmol) and N-bromosuccinimide (1.2 eq.) were stirred in 40 mL CCl$_4$ with a catalytic amount of benzoyl peroxide for 3 h at 85° C. After cooling to room temperature the mixture was diluted with CH$_2$Cl$_2$, washed with water, dried (Na$_2$SO$_4$) and evaporated. The 4-bromomethyl-3-(4-methoxyphenyl)-1-methyl-1-azaspiro[4.5]dec-3-ene-2-one thus obtained was dissolved in ethanol (100 mL), CH$_2$Cl$_2$ (20 mL), and ethylamine (70% solution in water, 2 mL), the mixture was stirred overnight at room temperature and concentrated. The residue was dissolved in CH$_2$Cl$_2$, washed with water and extracted with 0.5 M HCl.

After addition of NaOH and extraction with CH$_2$Cl$_2$ the organic layer was dried (Na$_2$SO$_4$) and evaporated to yield 646 mg (64%) of 4-ethylamino-methyl-3-(4-methoxyphenyl)-1-methyl-1-azaspiro[4.5]dec-3-ene-2-one product, shown below, as a solid. MS (IS): 329 [MH]+.

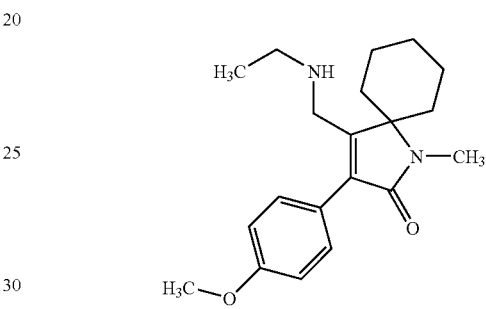

2-(R)-2-(2-(N-tert-Butoxycarbonylamino)-2-methylpropionylamino)-3-phenylmethoxypropionic acid N-ethyl-N-(3-(4-methoxyphenyl)-1-methyl-2-oxo-1-azaspiro[4.5]dec-3-ene-4-ylmethyl)amide was prepared according to the methods described in Example 1. Yield: 1.209 g, 87%; MS (IS): 713 [MNa]+, 691 [MH]+.

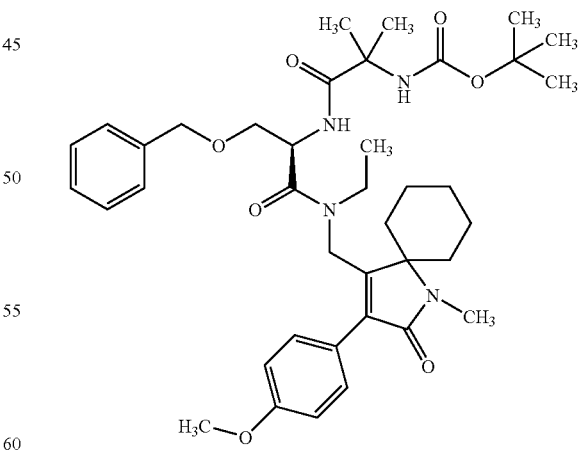

The title compound was prepared according to the methods described in Example 7. Yield: 564 mg, 51%; MS (IS): 613 [MNa]+, 591 [MH]+; m.p. 137° C.

EXAMPLE 45

2-(R)-2-(2-Amino-2-methylpropionylamino)-3-phenylmethoxy-propionic acid N-(3-(4-methoxyphenyl)-2-oxo-1-azaspiro[4.5]dec-3-ene-4-ylmethyl) amide trifluoroacetate

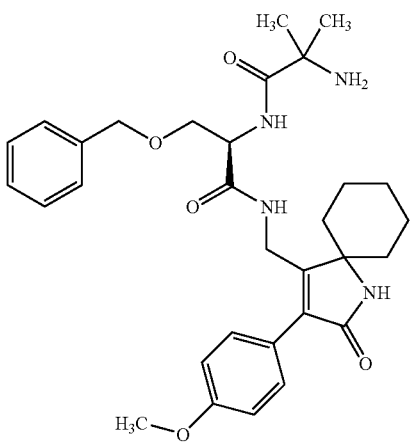

The title compound, shown above, was prepared as follows.

A solution of 4-bromomethyl-3-(4-methoxyphenyl)-1-azaspiro[4.5]dec-3-ene-2-one (from Example 43), (123 mg, 0.35 mmol) and potassium phthalimide (2 eq.) in DMF (15 mL) was stirred at 80° C. for 17 h, after cooling to room temperature diluted with CH$_2$Cl$_2$ and washed with water and NaHCO$_3$ solution.

The organic layer was dried (Na$_2$SO$_4$) and evaporated to yield 146 mg (100%) of 3-(4-methoxyphenyl)-4-(N-phthalimido)methyl-1-azaspiro[4.5]dec-3-ene-2-one, shown below, as a white solid. MS (IS): 439 [MNa]$^+$, 417 [MH]$^+$.

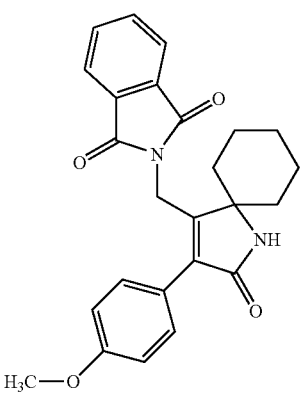

3-(4-Methoxyphenyl)-4-(N-phthalimido)methyl-1-azaspiro[4.5]dec-3-ene-2-one (146 mg, 0.35 mmol) and ethylenediamine (4.5 mL) were dissolved in dry n-butanol (25 mL) and stirred overnight at 90° C. The mixture was then diluted with ethyl acetate, washed with NaCl solution and water and extracted with 0.5 M HCl. After addition of NaOH and extraction with ethyl acetate the organic layer was dried (Na$_2$SO$_4$) and evaporated to yield 86 mg (86%) of 4-aminomethyl-3-(4-methoxyphenyl)-1-azaspiro[4.5]dec-3-ene-2-one, shown below, as a solid. MS (IS): 287 [MH]$^+$.

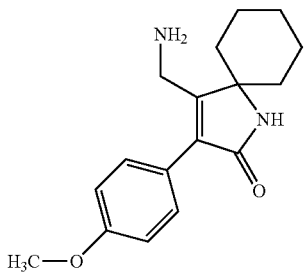

2-(R)-2-(2-(N-tert-Butoxycarbonylamino-2-methyl-propionylamino)-3-phenylmethoxypropionic acid N-(3-(4-methoxyphenyl)-2-oxo-1-azaspiro[4.5]dec-3-ene-4-yl-methyl)amide, shown below, was prepared according to the methods described in Example 1. Yield: 97 mg, 50%; MS (IS): 650 [MH]$^+$.

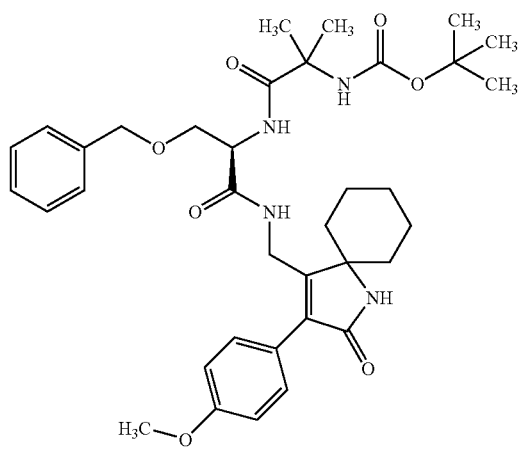

The title compound was prepared according to the methods described in Example 1. Yield: 27 mg, 33%; MS (IS): 550 [MH]$^+$; m.p. 122–128° C. (decomp.)

EXAMPLE 46

2-(R)-2-(2-Amino-2-methylpropionylamino)-3-phenylmethoxy-propionic acid N-(4-(4-chlorophenyl)-2,2-diethyl-5-oxo-3-pyrrolin-3-ylmethyl)-N-ethylamide trifluoroacetate

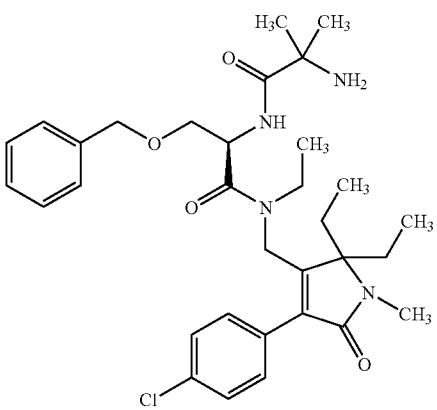

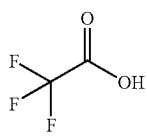

The title compound, shown above, was prepared as follows.

4-Chlorophenyl-N-(1,1-diethyl-2-oxopropyl)acetamide, shown below, was prepared from 4-chlorophenylacetic acid and 1,1-diethylpropargylamine according to the methods described in Example 43. Yield: 950 mg, 57%; MS (IS): 282 [MH]$^+$.

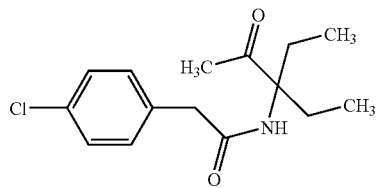

3-(4-Chlorophenyl)-5,5-diethyl-4-methyl-3-pyrrolin-2-one, shown below, was prepared according to the methods described in Example 43. Yield: 900 mg, 99%; MS (IS): 264 [MH]$^+$.

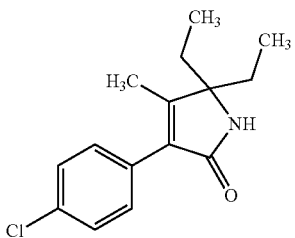

4-Bromomethyl-3-(4-chlorophenyl)-5,5-diethyl-3-pyrrolin-2-one, shown below, was prepared according to the methods described in Example 43. Yield: 480 mg, 99%; MS (IS): 342 [MH]$^+$.

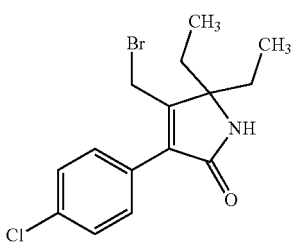

3-(4-Chlorophenyl)-5,5-diethyl-4-ethylaminomethyl-3-pyrrolin-2-one, shown below, was prepared according to the methods described in Example 43. Yield: 325 mg, 76%; MS (IS): 307 [MH]$^+$.

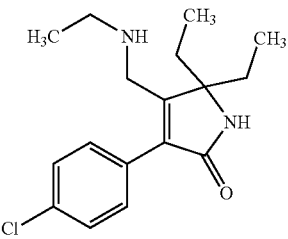

2-(R)-2-(2-(N-tert-Butoxycarbonylamino-2-methyl-propionylamino)-3-phenylmethoxypropionic acid N-(4-(4-chlorophenyl)-2,2-diethyl-5-oxo-3-pyrrolin-3-ylmethyl)-N-ethylamide was prepared according to the methods described in Example 1. Yield: 485 mg, 91%; MS (IS): 669 [MH]$^+$.

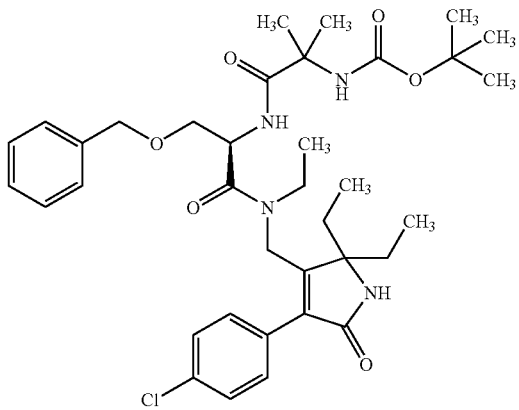

The title compound was prepared according to the methods described in Example 1. Yield: 335 mg, 69%; MS (IS): 569 [MH]$^+$; m.p. 140–145° C.

EXAMPLE 47

2-(R)-2-(2-Amino-2-methylpropionylamino)-3-phenylmethoxy-propionic acid N-(3-(4-chlorophenoxy)-2-oxo-1-azaspiro[4.5]dec-3-ene-4-ylmethyl)-N-ethylamide trifluoroacetate

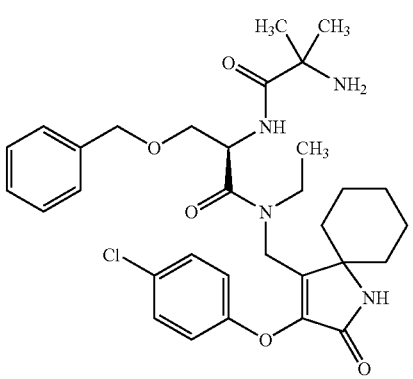

-continued

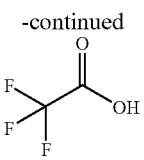

The title compound, shown above, was prepared as follows.

4-Bromomethyl-3-(4-chlorophenoxy)-1-azaspiro[4.5]dec-3-ene-2-one, shown below, was prepared from 4-chlorophenoxyacetic acid and 1-ethynyl-1-cyclohexylamine according to the methods described in Example 43. Yield: 0.9 g, 41%; MS (IS): 300 [MH]⁺.

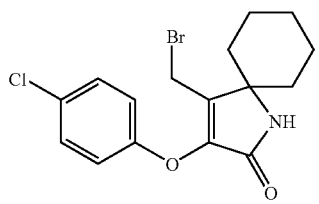

3-(4-Chlorophenoxy)-4-ethylaminomethyl-1-azaspiro[4.5]dec-3-ene-2-one, shown below, was prepared according to the methods described in Example 43. Yield: 200 mg, 25%; MS (IS): 335 [MH]⁺

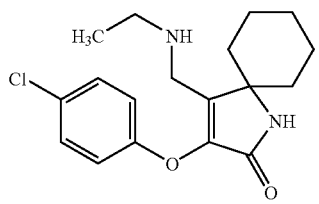

The title compound was prepared and deprotected according to the methods described in Example 1. Yield: 242 mg, 57%; MS (IS): 597 [MH]⁺; m.p. 118° C.

EXAMPLE 48

2-(R)-2-(2-Amino-2-methylpropionylamino)-3-phenylmethoxypropionic acid N-(3-(3-chloro-phenyl)-2-oxo-1-azaspiro[4.5]dec-3-ene-4-ylmethyl)-N-ethylamide trifluoroacetate

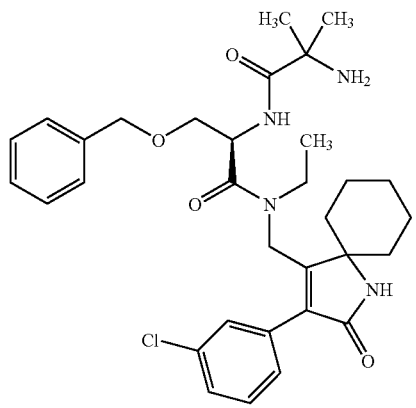

-continued

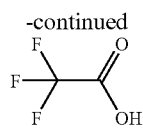

The title compound, shown above, was prepared as follows.

4-Bromomethyl-3-(3-chlorophenyl)-1-azaspiro[4.5]dec-3-ene-2-one, shown below, was prepared from 3-chlorophenylacetic acid and 1-ethynylcyclohexylamine according to the methods described in Example 43. Yield: 850 mg, 65%; MS (IS): 354 [MH]⁺.

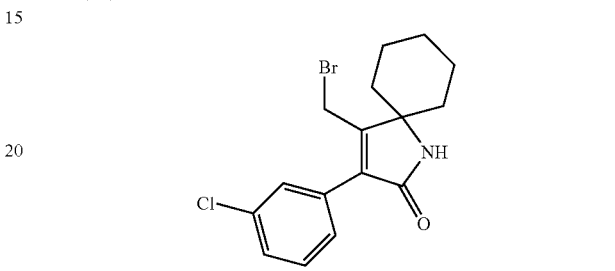

3-(3-Chlorophenyl)-4-ethylaminomethyl-1-azaspiro[4.5]dec-3-ene-2-one was prepared according to the methods described in Example 43. Yield: 120 mg, 94%; MS (IS): 319 [MH]⁺.

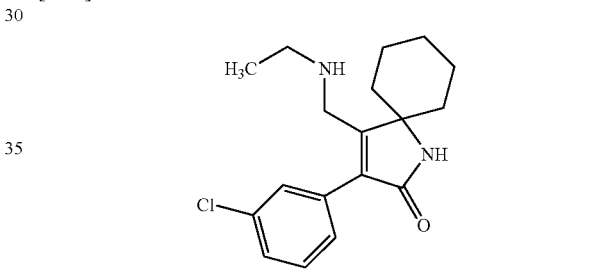

The title compound was prepared and deprotected according to the methods described in Example 1. Yield: 91 mg, 83%; MS (IS): 581 [MH]⁺; m.p. >90° C. (decomp.)

EXAMPLE 49

2-(R)-2-(2-Amino-2-methylpropionylamino)-3-phenylmethoxy-propionic acid N-(3-(2-chloro-phenyl)-2-oxo-1-azaspiro[4.5]dec-3-ene-4-ylmethyl)-N-ethylamide trifluoroacetate

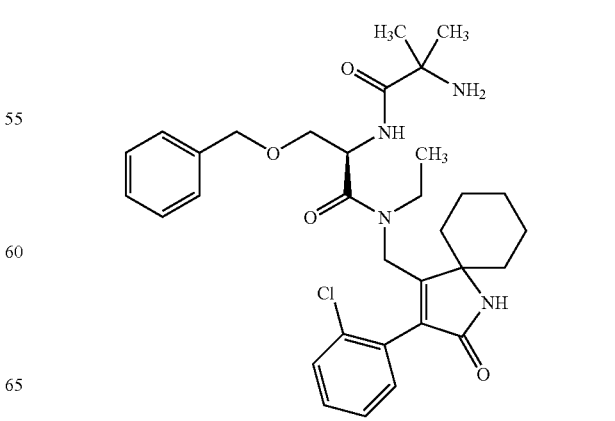

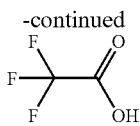

The title compound, as shown above, was prepared as follows.

3-(2-Chlorophenyl)-4-ethylaminomethyl-1-azaspiro[4.5]dec-3-ene-2-one, shown below, was prepared from 2-chlorophenylacetic acid and 1-ethynyl-1-cyclohexylamine according to the methods described in Example 43. Yield: 110 mg, 78%; MS (IS): 319 [MH]$^+$.

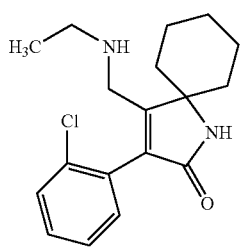

The title compound was prepared and deprotected according to the methods described in Example 1. Yield: 87 mg, 82%; MS (IS): 581 [MH]$^+$; m.p. 132–137° C.

EXAMPLE 50

2-(R)-2-(2-Amino-2-methylpropionylamino)-3-phenylmethoxy-propionic acid N-(3-(4-chlorophenyl)-2-oxo-1-azaspiro[4.5]dec-3-ene-4-ylmethyl)-N-ethylamide hydrochloride

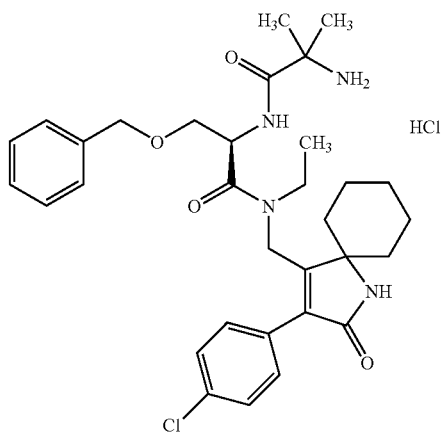

The title compound, as shown above, was prepared as follows.

3-(4-Chlorophenyl)-4-methyl-1-azaspiro[4.5]dec-3-ene-2-one, shown below, was prepared from 4-chlorophenylacetic acid and 1-ethynylcyclohexylamine according to the methods described in Example 43. Yield: 621 mg, 62%; MS (IS): 551 [M$_2$H]$^+$, 276 [MH]$^+$.

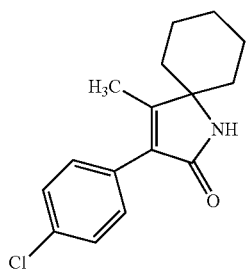

4-Bromomethyl-3-(4-chlorophenyl)-1-azaspiro[4.5]dec-3-ene-2-one was prepared according to the methods described in Example 43. Yield: 552 mg, 45%; MS (IS): 356 [MH]$^+$.

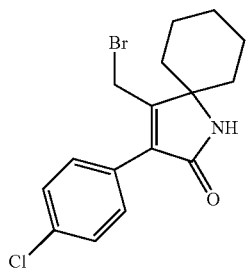

3-(4-Chlorophenyl)-4-ethylaminomethyl-1-azaspiro[4.5]dec-3-ene-2-one was prepared according to the methods described in Example 43. Yield: 444 mg, 89%; MS (IS): 319 [MH]$^+$.

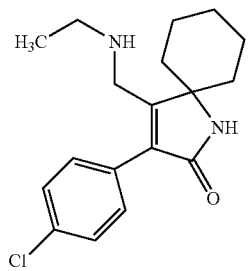

2-(R)-2-(2-(N-tert-Butoxycarbonylamino)-2-methyl-propionylamino)-3-phenyl-methoxypropionic acid N-(3-(4-chlorophenyl)-2-oxo-1-azaspiro[4.5]dec-3-ene-4-ylmethyl)-N-ethylamide, shown below, was prepared according to the methods described in Example 1. Yield: 900 mg, 95%; MS (IS): 703 [MNa]$^+$, 681 [MH]$^+$.

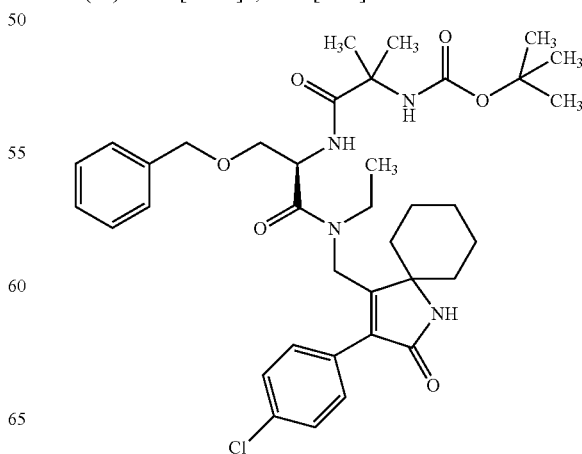

The title compound was prepared according to the methods described in Example 7. Yield: 521 mg, 64%; MS (IS): 581 [MH]+; m.p. >128° C. (decomp.)

EXAMPLE 51

2-(R)-2-(2-Amino-2-methylpropionylamino)-3-phenylmethoxy-propionic acid N-(3-(4-bromophenyl)-2-oxo-1-azaspiro[4.5]dec-3-ene-4-ylmethyl)-N-ethylamide trifluoroacetate

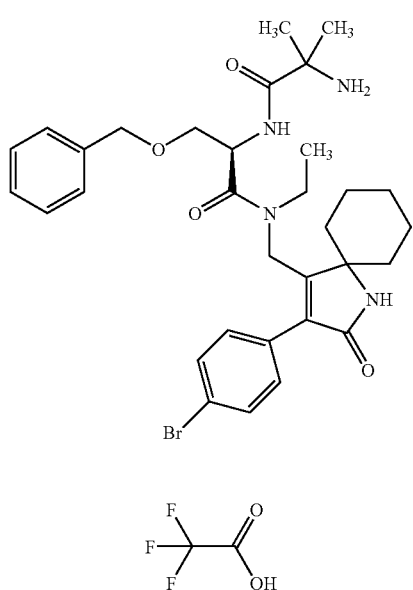

The title compound, as shown above, was prepared as follows.

4-Bromomethyl-3-(4-bromophenyl)-1-azaspiro[4.5]dec-3-ene-2-one, shown below, was prepared from 4-bromophenylacetic acid and 1-ethynylcyclohexylamine according to the methods described in Example 43. Yield: 580 mg, 63%; MS (IS): 398 [MH]+.

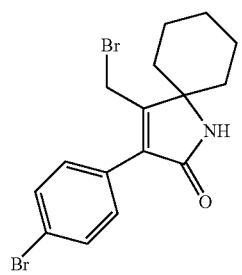

3-(4-Bromophenyl)-4-ethylaminomethyl-1-azaspiro[4.5]dec-3-ene-2-one, shown below, was prepared according to the methods described in Example 43. Yield: 145 mg, 99% MS (IS): 363 [MH]+.

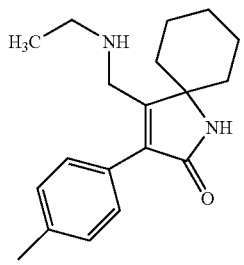

The title compound was prepared and deprotected according to the methods described in Example 1. Yield: 89 mg, 78%; MS (IS): 626 [MH]+; m.p. 132–137° C.

EXAMPLE 52

2-(R)-2-(2-Amino-2-methylpropionylamino)-3-phenylmethoxy-propionic acid N-ethyl-N-(3-(4-fluorophenyl)-2-oxo-1-azaspiro[4.5]dec-3-ene-4-ylmethyl)amide trifluoroacetate

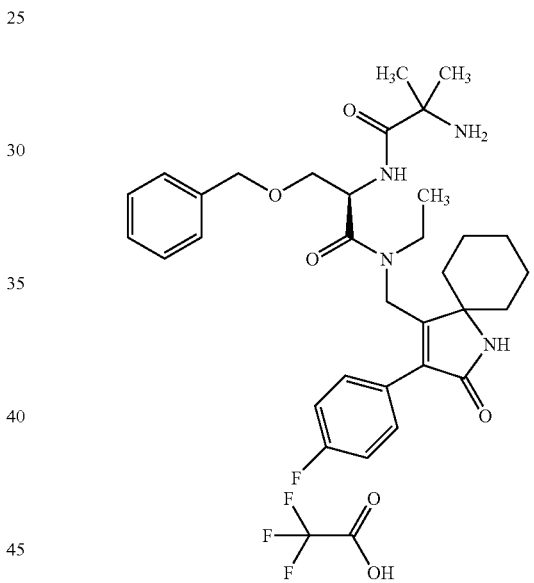

The title compound, shown above, was prepared as follows.

4-Bromomethyl-3-(4-fluorophenyl)-1-azaspiro[4.5]dec-3-ene-2-one, shown below, was prepared from 4-fluorophenylacetic acid and 1-ethynylcyclohexylamine according to the methods described in Example 43. Yield: 1.33 g, 49%; MS (IS): 338 [MH]+.

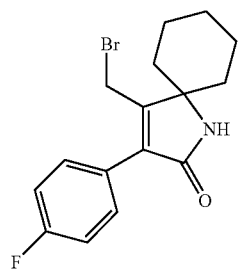

4-Ethylaminomethyl-3-(4-fluorophenyl)-1-azaspiro[4.5]dec-3-ene-2-one, shown below, was prepared according to the methods described in Example 43. Yield: 100 mg, 83%; MS (IS): 303 [MH]+.

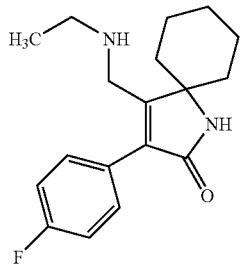

The title compound was prepared and deprotected according to the methods described in Example 1. Yield: 85 mg, 68%; MS (IS): 565 [MH]+; m.p. 140–150° C.

EXAMPLE 53

2-(R)-2-(2-Amino-2-methylpropionylamino)-3-phenylmethoxypropionic acid N-ethyl-N-(3-(4-methylphenyl)-2-oxo-1-azaspiro[4.5]dec-3-ene-4-ylmethyl)amide trifluoroacetate

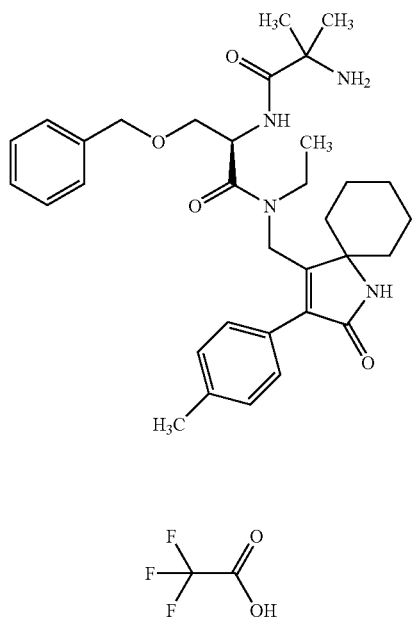

The title compound, as shown above, was prepared as follows.

4-Ethylaminomethyl-3-(4-methylphenyl)-1-azaspiro[4.5]dec-3-ene-2-one, shown below, was prepared from 4-methylphenylacetic acid and 1-ethynylcyclohexylamine according to the methods described in Example 43. The product was isolated after column chromatography (CH$_2$Cl$_2$/ethanol 95:5). Yield: 120 mg, 11%; MS (IS): 299 [MH]+.

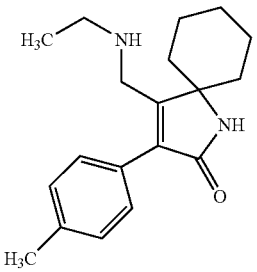

The title compound was prepared and deprotected according to the methods described in Example 1. Yield: 110 mg, 87%; MS (IS): 561 [MH]+; m.p. >135° C. (decomp.)

EXAMPLE 54

2-(R)-2-(2-Amino-2-methylpropionylamino)-3-phenylmethoxy-propionic acid N-(3-(4-biphenyl)-2-oxo-1-azaspiro[4.5]dec-3-ene-4-ylmethyl)-N-ethylamide hydrochloride

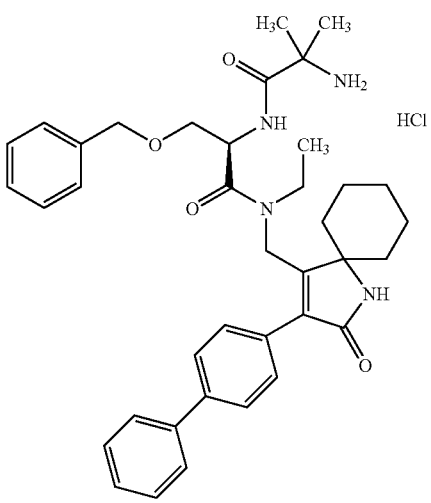

The title compound, shown above, was prepared as follows.

3-(4-Biphenyl)-4-bromomethyl-1-azaspiro[4.5]dec-3-ene-2-one, shown below, was prepared from 4-biphenylacetic acid and 1-ethynylcyclohexylamine according to the methods described in Example 43. Yield: 680 mg, 70%; MS (IS): 396 [MH]+.

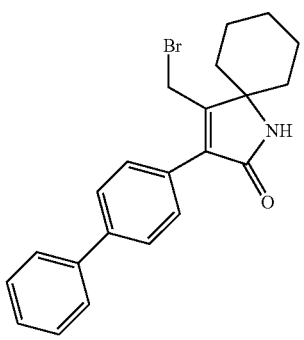

3-(4-Biphenyl)-4-ethylaminomethyl-1-azaspiro[4.5]dec-3-ene-2-one, shown below, was prepared according to the methods described in Example 43. Yield: 480 mg, 78%; MS (IS): 361 [MH]+.

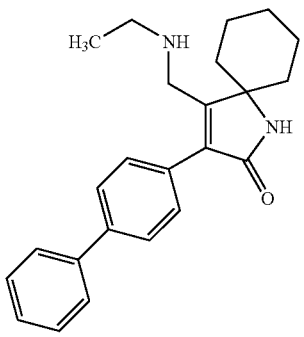

The title compound was prepared and deprotected according to the methods described in Examples 1 and 7. Yield: 383 mg, 52%; MS (IS): 623 [MH]+; m.p. 176° C.

EXAMPLE 55

2-(R)-2-(2-Amino-2-methylpropionylamino)-3-phenylmethoxy-propionic acid N-ethyl-N-(2-oxo-3-phenyl-1-azaspiro[4.5]dec-3-ene-4-ylmethyl) amide trifluoroacetate

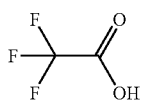
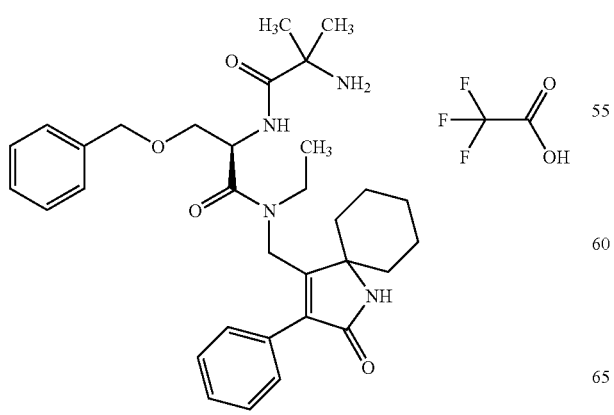

The title compound, shown above, was prepared as follows.

4-Methyl-3-phenyl-1-azaspiro[4.5]dec-3-ene-2-one, shown below, was prepared from phenylacetic acid and 1-ethynylcyclohexylamine according to the methods described in Example 43. Yield: 675 mg, 75%; MS (IS): 242 [MH]+.

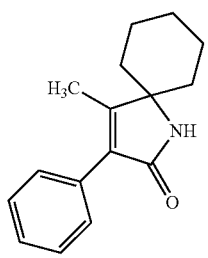

4-Bromomethyl-3-phenyl-1-azaspiro[4.5]dec-3-ene-2-one, shown below, was prepared according to the methods described in Example 43. Yield: 610 mg, 68%; MS (IS): 320 [MH]+.

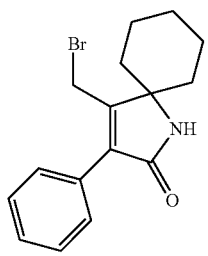

4-Ethylaminomethyl-3-phenyl-1-azaspiro[4.5]dec-3-ene-2-one, shown below, was prepared according to the methods described in Example 43. Yield: 360 mg, 67%; MS (IS): 285 [MH]+.

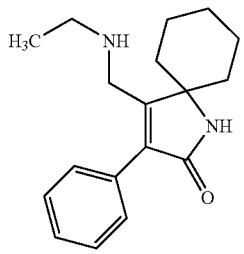

2-(R)-2-(2-(N-tert-Butoxycarbonylamino)-2-methyl-propionylamino)-3-phenylmethoxypropionic acid N-ethyl-N-(2-oxo-3-phenyl-1-azaspiro[4.5]dec-3-ene-4-ylmethyl) amide, shown below, was prepared according to the methods described in Example 1. Yield: 730 mg, 89%; MS (IS): 647 [MH]+.

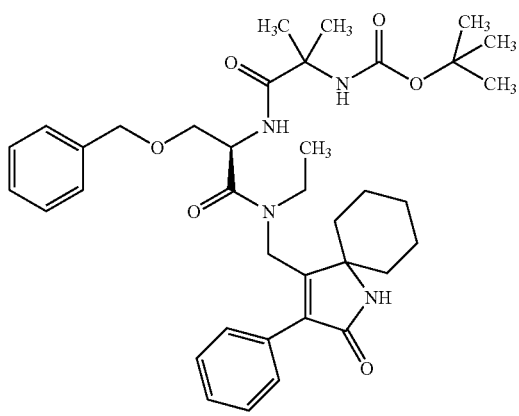

The title compound was prepared according to the methods described in Example 1. Yield: 640 mg, 86%; MS (IS): 547 [MH]+; m.p. 145° C.

EXAMPLE 56

2-(R)-2-(2-Amino-2-methylpropionylamino)-3-phenylmethoxypropionic acid N-ethyl-N-(2-oxo-3-(2-thienyl)-1-azaspiro[4.5]dec-3-ene-4-ylmethyl)amide trifluoroacetate

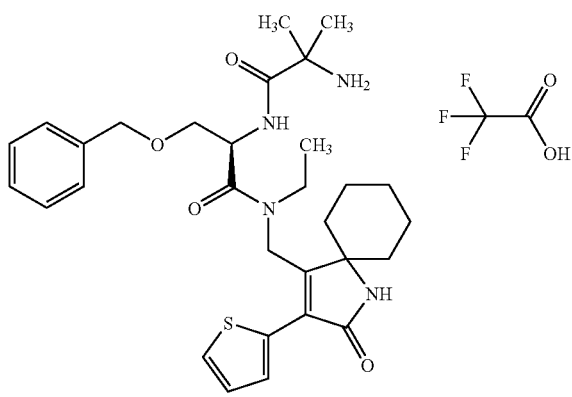

The title compound, as shown above, was prepared as follows.

N-(1-Acetylcyclohexyl)-(2-thienyl)acetamide, shown below, was prepared from 2-thienylacetic acid and 1-ethynyl-1-cyclohexylamine according to the methods described in Example 43. Yield: 2.37 g (64%); MS (IS): 266.

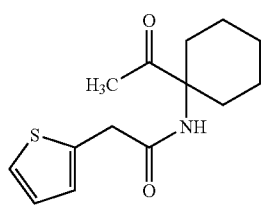

4-Methyl-3-(2-thienyl)-1-azaspiro[4.5]dec-3-ene-2-one, shown below, was prepared according to the methods described in Example 43. Yield: 1.6 g, 56%; MS (IS): 248 [MH]+.

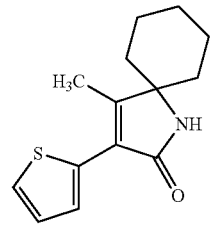

4-Ethylaminomethyl-3-(2-thienyl)-1-azaspiro[4.5]dec-3-ene-2-one, shown below, was prepared according to the methods described in Example 43 and isolated after column chromatography (CH2Cl2/ethanol 95:5). Yield: 70 mg, 5%; MS (IS): 291 [MH]+.

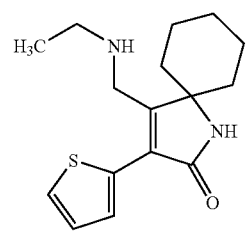

2-(R)-2-(2-(N-tert-Butoxycarbonylamino)-2-methyl-propionylamino)-3-phenyl-methoxypropionic acid N-ethyl-N-(2-oxo-3-(2-thienyl)-1-azaspiro[4.5]dec-3-ene-4-ylmethyl)amide, shown below, was prepared according to the methods described in Example 1. Yield: 150 mg, 96%; MS (IS): 653 [MH]+.

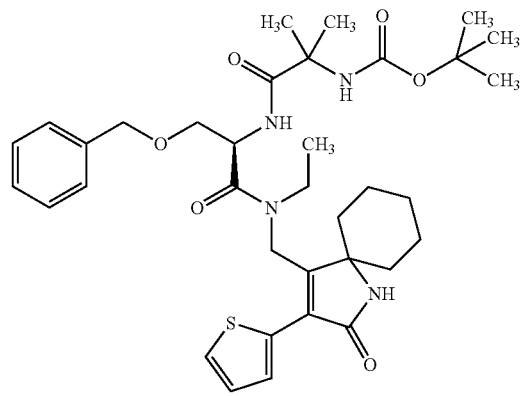

The title compound was prepared according to the methods described in Example 1. Yield: 120 mg, 78%; MS (IS): 553 [MH]+; m.p. 126–136° C.

EXAMPLE 57

2-(R)-2-(2-Amino-2-methylpropionylamino)-3-phenylmethoxy-propionic acid N-ethyl-N-(1-methyl-2-oxo-3-phenyl-1-azaspiro[4.5]dec-3-ene-4-ylmethyl)amide trifluoroacetate

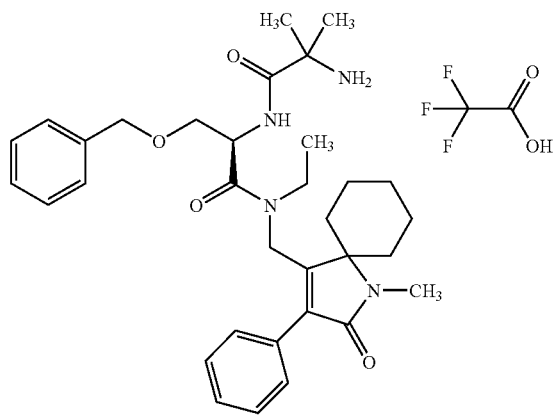

The title compound, shown above, was prepared as follows.

4-Bromomethyl-1-methyl-3-phenyl-1-azaspiro[4.5]dec-3-ene-2-one, shown below, was prepared from phenylacetic acid and 1-ethynylcyclohexylamine according to the methods described in Examples 43 and 44. Yield: 298 mg, 37%; MS (IS): 334 [MH]$^+$.

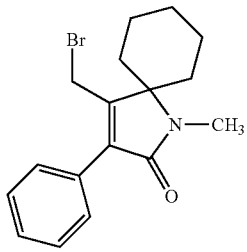

4-Ethylaminomethyl-1-methyl-3-phenyl-1-azaspiro[4.5]dec-3-ene-2-one, shown below, was prepared according to the methods described in Example 43. Yield: 235 mg, 91%; MS (IS): 299 [MH]$^+$.

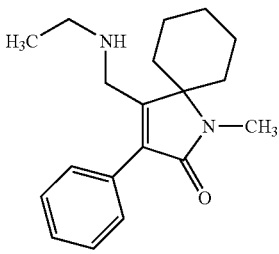

The title compound was prepared and deprotected according to the methods described in Example 1. Yield: 463 mg, 92%; MS (IS): 561 [MH]$^+$; m.p. >87° C. (decomp.)

EXAMPLE 58

2-(R)-2-(2-Amino-2-methylpropionylamino)-3-phenylmethoxy-propionic acid N-ethyl-N-(1-methyl-3-(3-trifluoromethyl-phenyl)-2-oxo-1-azaspiro[4.5]dec-3-ene-4-ylmethyl)amide trifluoroacetate

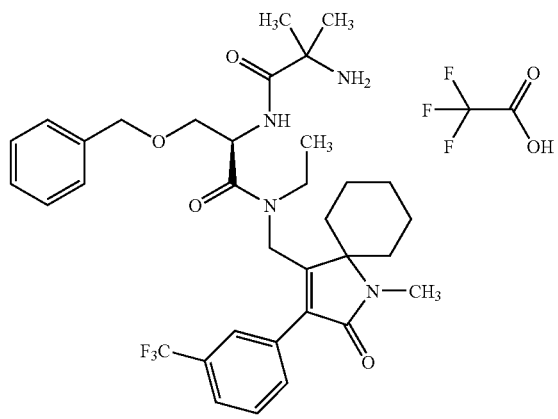

The title compound, as shown above, was prepared as follows.

4-Bromomethyl-1-methyl-3-(3-trifluoromethylphenyl)-1-azaspiro[4.5]dec-3-ene-2-one was prepared from 3-trifluoromethyl-phenylacetic acid and 1-ethynyl-cyclohexylamine according to the methods described in Examples 43 and 44. Yield: 71 mg, 54%; MS (IS): 402 [MH]$^+$.

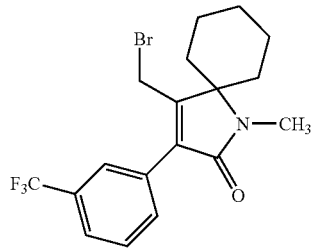

4-Ethylaminomethyl-1-methyl-3-(3-trifluoromethyl-phenyl)-1-azaspiro[4.5]dec-3-ene-2-one, shown below, was prepared according to the methods described in Example 43. Yield: 59 mg, 99%; MS (IS): 367 [MH].

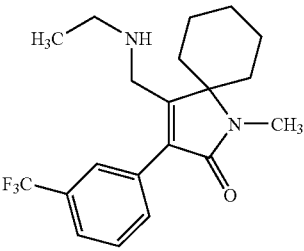

The title compound was prepared and deprotected according to the methods described in Example 1. Yield: 70 mg, 62%; MS (IS): 629 [MH]$^+$; m.p. 113–115° C.

EXAMPLE 59

2-(R)-2-(2-Amino-2-methylpropionylamino)-3-phenylmethoxy-propionic acid N-(3-(4-biphenyl)-1-methyl-2-oxo-1-azaspiro[4.5]dec-3-ene-4-ylmethyl)-N-ethylamide trifluoroacetate

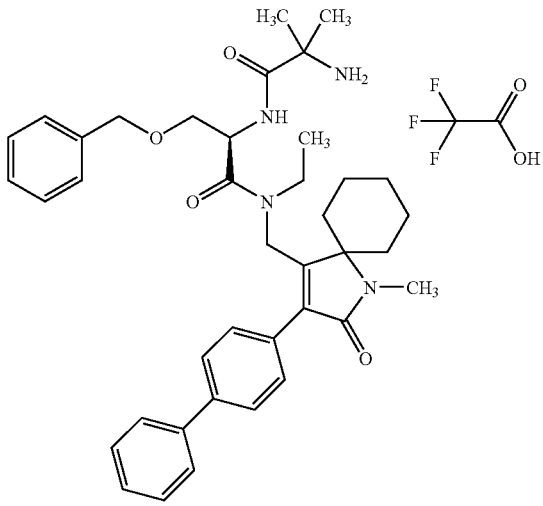

The title compound, as shown above, was prepared as follows.

3-(4-Biphenyl)-4-bromomethyl-1-methyl-1-azaspiro[4.5]dec-3-ene-2-one, shown below, was prepared from 4-biphenylacetic acid and 1-ethynylcyclohexylamine according to the methods described in Examples 43 and 44. Yield: 228 mg, 44%; MS (IS): 410 [MH]+.

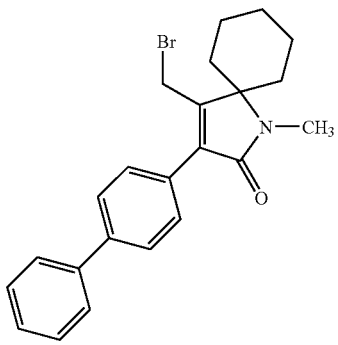

3-(4-Biphenyl)-4-ethylaminomethyl-1-methyl-1-azaspiro[4.5]dec-3-ene-2-one, shown below, was prepared according to the methods described in Example 43. Yield: 180 mg, 87%; MS (IS): 375 [MH]+.

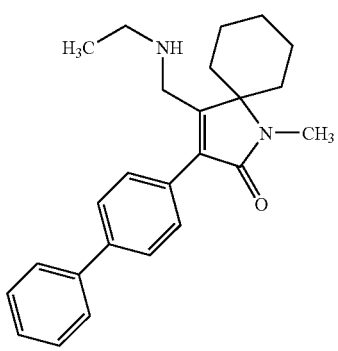

The title compound was prepared and deprotected according to the methods described in Example 1. Yield: 50 mg, 14%; MS (IS): 637 [MH]+; m.p. 114° C.

EXAMPLE 60

2-(R)-2-(2-Amino-2-methylpropionylamino)-3-phenylmethoxypropionic acid N-(3-(4-chlorophenyl)-1-methyl-2-oxo-1-azaspiro[4.5]dec-3-ene-4-ylmethyl)-N-ethylamide trifluoroacetate

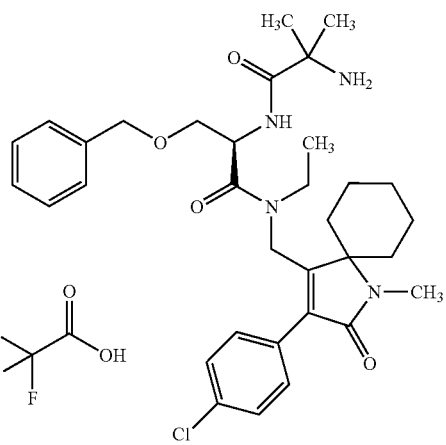

The title compound, as shown above, was prepared as follows.

3-(4-Chlorophenyl)-1,4-dimethyl-1-azaspiro[4.5]dec-3-ene-2-one, shown below, was prepared from 4-chlorophenylacetic acid and 1-ethynylcyclohexylamine according to the methods described in Examples 43 and 44. Yield: 1 g, 67%; MS (IS): 289 [MH]+.

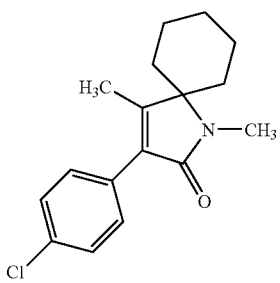

4-Bromomethyl-3-(4-chlorophenyl)-1-methyl-1-azaspiro[4.5]dec-3-ene-2-one, shown below, was prepared according to the methods described in Example 43. Yield: 1.3 g, 99%; MS (IS): 368 [MH]+.

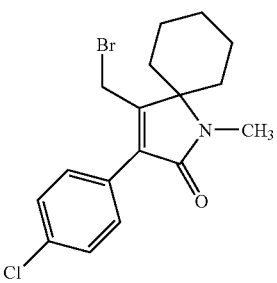

3-(4-Chlorophenyl)-4-ethylaminomethyl-1-methyl-1-azaspiro[4.5]dec-3-ene-2-one, shown below, was prepared according to the methods described in Example 43. Yield: 440 mg, 38%; MS (IS): 333 [MH]+.

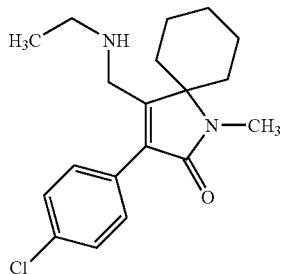

2-(R)-2-(2-(N-tert-Butoxycarbonylamino)-2-methyl-propionylamino)-3-phenyl-methoxypropionic acid N-(3-(4-chlorophenyl)-1-methyl-2-oxo-1-azaspiro[4.5]dec-3-ene-4-ylmethyl)-N-ethylamide, shown below, was prepared according to the methods described in Example 1. Yield: 600 mg, 86%; MS (IS): 695 [MH]+.

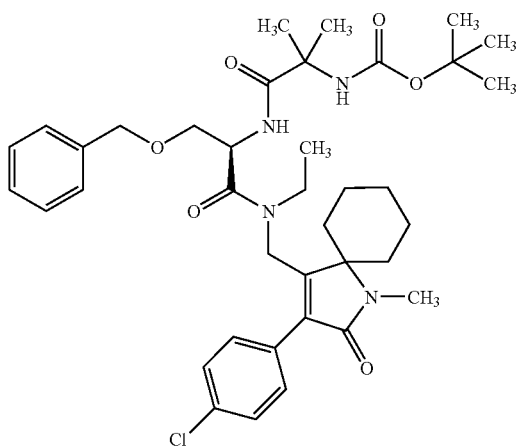

The title compound was prepared according to the methods described in Example 1. Yield: 450 mg, 75%; MS (IS): 595 [MH]+; m.p. 120–128° C.

EXAMPLE 61

2-(R)-2-(2-Amino-2-methylpropionylamino)-3-phenylmethoxy-propionic acid N-(4-(4-chlorophenyl)-2,2-dimethyl-5-oxo-3-pyrrolin-3-ylmethyl)-N-ethylamide hydrochloride

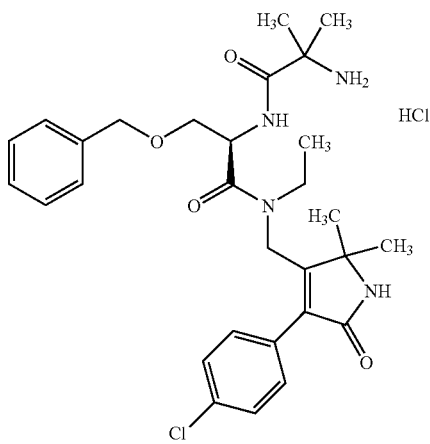

The title compound, shown above, was prepared as follows.

4-Bromomethyl-3-(4-chlorophenyl)-5,5-dimethyl-3-pyrrolin-2-one, shown below, was prepared from 4-chloroacetic acid and 1,1-dimethylpropargylamine according to the methods described in Example 43. Yield: 800 mg, 87%; MS (IS): 314 [MH]+.

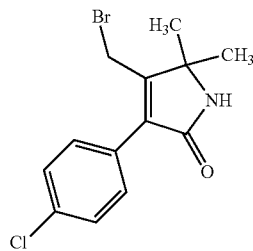

3-(4-Chlorophenyl)-4-ethylaminomethyl-5,5-dimethyl-3-pyrrolin-2-one, shown below, was prepared according to the methods described in Example 43. Yield: 590 mg, 84%; MS (IS): 279 [MH]+.

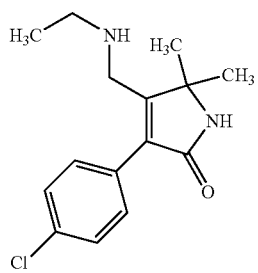

The title compound was prepared and deprotected according to the methods described in Examples 1 and 7. Yield: 209 mg, 17%; MS (IS): 541 [MH]+; m.p. 152° C.

EXAMPLE 62

2-(R)-2-(2-Amino-2-methylpropionylamino)-3-phenylmethoxy-propionic acid N-(4-(4-bromophenyl)-2,2-dimethyl-5-oxo-3-pyrrolin-3-ylmethyl)-N-ethylamide hydrochloride

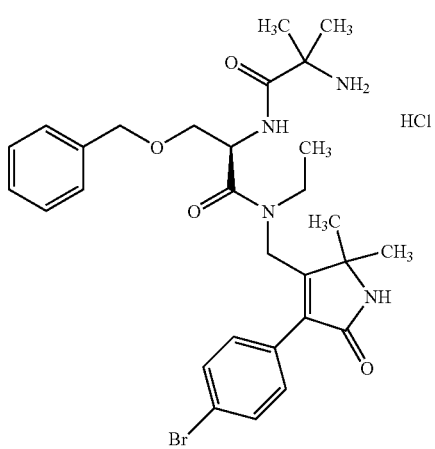

The title compound, shown above, was prepared as follows.

4-Bromomethyl-3-(4-bromophenyl)-5,5-dimethyl-3-pyrrolin-2-one, shown below, was prepared from 4-bromoacetic acid and 1,1-dimethylpropargylamine according to the methods described in Example 43. Yield: 1.39 g, 59%; MS (IS): 358 [MH]+.

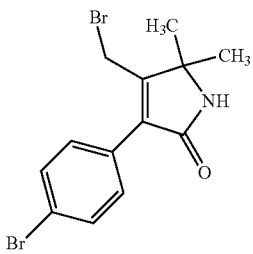

3-(4-Bromophenyl)-4-ethylaminomethyl-5,5-dimethyl-3-pyrrolin-2-one, shown below, was prepared according to the methods described in Example 43. Yield: 820 mg, 53%; MS (IS): 323 [MH]+.

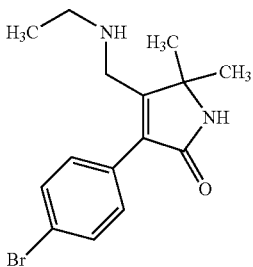

The title compound was prepared and deprotected according to the methods described in Examples 1 and 7. Yield: 605 mg, 41%; MS (IS): 585 [MH]+; m.p. 157° C.

EXAMPLE 63

2-(R)-2-(2-Amino-2-methylpropionylamino)-3-phenylmethoxy-propionic acid N-(2-oxo-3-phenoxy-1-azaspiro[4.5]dec-3-ene-4-ylmethyl)-N-ethylamide hydrochloride

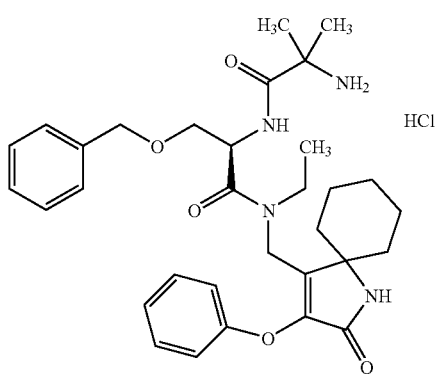

The title compound, as shown above, was prepared as follows.
4-Bromomethyl-3-phenoxy-1-azaspiro[4.5]dec-3-ene-2-one, shown below, was prepared from phenoxyacetic acid and 1-ethynyl-1-cyclohexylamine according to the methods described in Example 43. Yield: 0.7 g, 66%; MS (IS): 336 [MH]+.

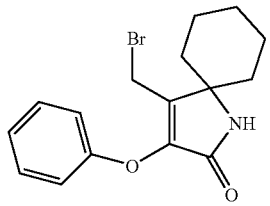

4-Ethylaminomethyl-3-phenoxy-1-azaspiro[4.5]dec-3-ene-2-one, shown below, was prepared according to the methods described in Example 43. Yield: 320 mg, 51%; MS (IS): 301 [MH]+.

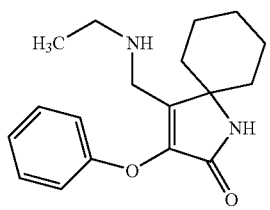

The title compound was prepared and deprotected according to the methods described in Examples 1 and 7. Yield: 143 mg, 23%; MS (IS): 563 [MH]+; m.p. 141° C.

EXAMPLE 64

2-(R)-2-(2-Amino-2-methylpropionylamino)-3-phenylmethoxy-propionic acid N-(3-(4-chlorophenoxy)-1-methyl-2-oxo-1-azaspiro[4.5]dec-3-ene-4-ylmethyl)-N-ethylamide hydrochloride

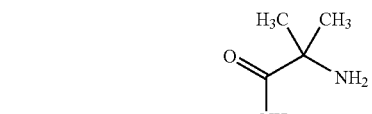

The title compound, shown above, was prepared as follows.
4-Bromomethyl-3-(4-chlorophenoxy)-1-methyl-1-azaspiro[4.5]dec-3-ene-2-one, shown below, was prepared from 4-chlorophenoxyacetic acid and 1-ethynyl-1-cyclo-hexylamine according to the methods described in Examples 43 and 44. Yield: 760 mg, 72%; MS (IS): 385 [MH]+.

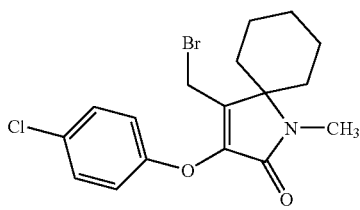

3-(4-Chlorophenoxy)-4-ethylaminomethyl-1-methyl-1-azaspiro[4.5]dec-3-ene-2-one, shown below, was prepared according to the methods described in Example 43. Yield: 560 mg, 81%; MS (IS): 350 [MH]⁺.

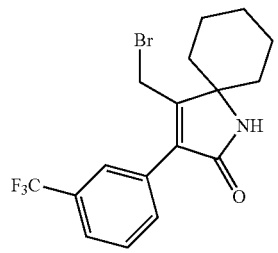

4-Ethylaminomethyl-3-(3-trifluoromethylphenyl)-1-azaspiro[4.5]dec-3-ene-2-one, shown below, was prepared according to the methods described in Example 43. Yield: 100 mg, 71%; MS (IS): 353 [MH]⁺.

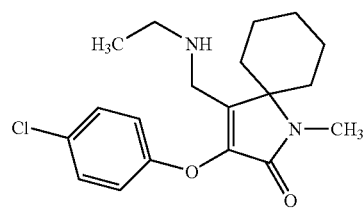

The title compound was prepared and deprotected according to the methods described in Examples 1 and 7. Yield: 161 mg, 16%; MS (IS): 612 [MH]⁺; m.p. 121° C.

EXAMPLE 65

2-(R)-2-(2-Amino-2-methylpropionylamino)-3-phenylmethoxy-propionic acid N-ethyl-N-(2-oxo-3-(3-trifluoromethyl-phenyl)-1-azaspiro[4.5]dec-3-ene-4-ylmethyl)amide trifluoroacetate

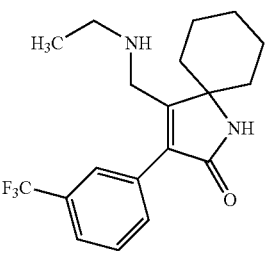

The title compound was prepared and deprotected according to the methods described in Example 1. Yield: 84 mg, 75%; MS (IS): 615 [MH]⁺; m.p. 140–150° C.

EXAMPLE 66

2-(R)-2-(2-Amino-2-methylpropionylamino)-3-phenylmethoxy-propionic acid N-(3-(3,4-dichlorophenyl)-2-oxo-1-azaspiro[4.5]dec-3-ene-4-ylmethyl)-N-ethylamide hydrochloride

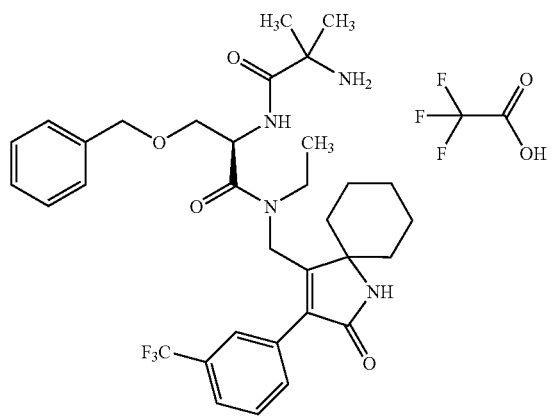

The title compound, shown above, was prepared as follows.

4-Bromomethyl-3-(3-trifluoromethylphenyl)-1-azaspiro[4.5]dec-3-ene-2-one, shown below, was prepared from 3-trifluoromethylphenyl-acetic acid and 1-ethynylcyclohexylamine according to the methods described in Example 43. Yield: 1.20 g, 39%; MS (IS): 388 [MH]⁺.

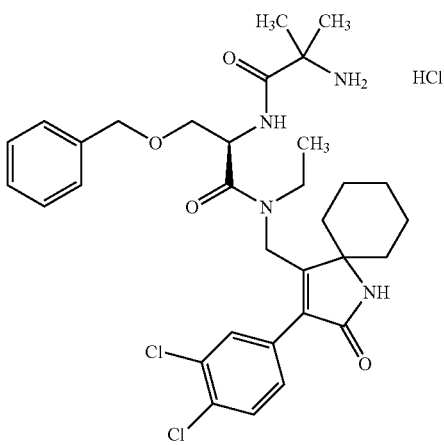

The title compound, shown above, was prepared as follows.

4-Bromomethyl-3-(3,4-dichlorophenyl)-1-azaspiro[4.5]dec-3-ene-2-one, shown below, was prepared from 3,4-dichloro-phenylacetic acid and 1-ethynylcyclohexylamine according to the methods described in Example 43. Yield: 2.45 g, 51%; MS (IS): 388 [MH]⁺.

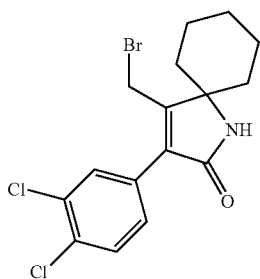

3-(3,4-Dichlorophenyl)-4-ethylaminomethyl-1-azaspiro[4.5]dec-3-ene-2-one was prepared according to the methods described in Example 43. Yield: 2.05 g, 92%; MS (IS): 353 [MH]⁺.

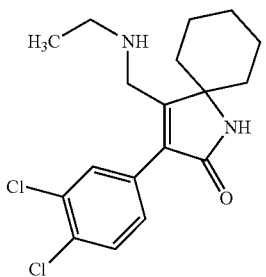

The title compound was prepared and deprotected according to the methods described in Examples 1 and 7. Yield: 762 mg, 21%; MS (IS): 615 [MH]⁺; m.p. 177° C.

EXAMPLE 67

2-(R)-2-(2-Amino-2-methylpropionylamino)-3-phenylmethoxypropionic acid N-(2-(3-(2-chlorophenyl)-2-oxo-1-azaspiro[4.5]dec-3-ene-4-yl)ethyl)-N-ethylamide hydrochloride

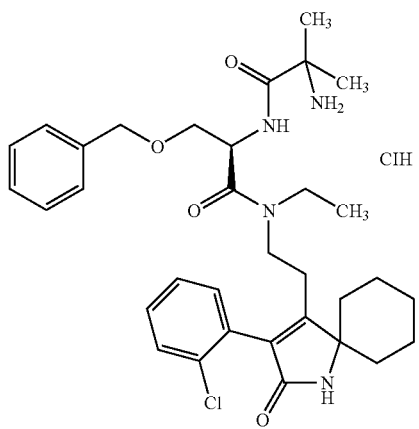

The title compound, shown above, was prepared as follows.

3-(2-Chlorophenyl)-4-(2-ethylamino)ethyl-1-azaspiro-[4.5]dec-3-ene-2-one, shown below, was prepared from 4-bromomethyl-3-(2-chlorophenyl)-1-azaspiro[4.5]dec-3-ene-2-one (Example 49) according to the methods described in Example 9. Yield: 340 mg, 46%, MS (IS): 333 [MH]⁺.

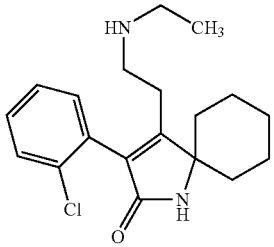

The title compound was prepared and deprotected according to the methods described in Examples 1 and 7. Yield: 520 mg, 99%, MS (IS): 595 [MH]⁺, m.p. 165–167° C.

EXAMPLE 68

2-(R)-2-(2-Amino-2-methylpropionylamino)-3-phenylmethoxy-propionic acid N-ethyl-N-(3-(1-naphthyl)-2,2-dioxo-2-thia-1-azaspiro[4.5]dec-3-ene-4-ylmethyl)amide trifluoroacetate

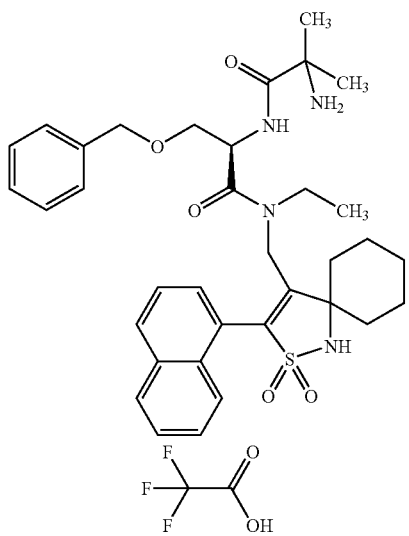

The title compound, shown above, was prepared as follows.

4-Ethylaminomethyl-3-(1-naphthyl)-2-thia-1-azaspiro[4.5]dec-3-ene 2,2-dioxide, shown below, was prepared from 1-naphthyl-methylchloride and 1-ethynylcyclohexylamine according to the methods described in Example 1. Yield: 40 mg, 16%; MS(IS): 371 [MH]⁺.

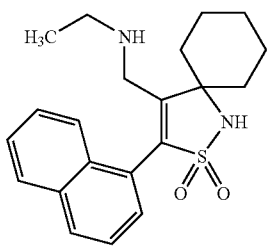

The title compound was prepared and deprotected according to the methods described in Example 1. Yield: 39 mg, 48%, MS (IS): 633 [MH]+, m.p. 144° C.

EXAMPLE 69

2-(R)-2-(2-Amino-2-methylpropionylamino)-3-phenylmethoxy-propionic acid N-ethyl-N-(3-(2-naphthyl)-2,2-dioxo-2-thia-1-azaspiro[4.5]dec-3-ene-4-ylmethyl)amide trifluoroacetate

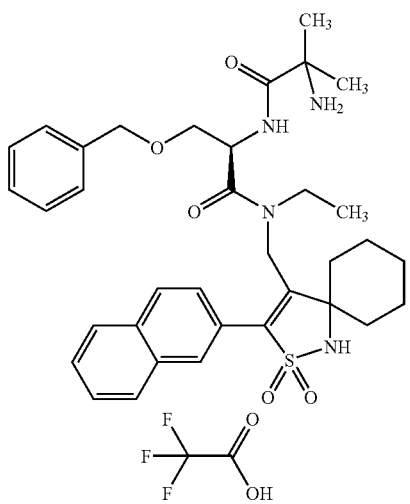

The title compound, as shown above, was prepared as follows.

4-Ethylaminomethyl-3-(2-naphthyl)-2-thia-1-azaspiro[4.5]dec-3-ene 2,2-dioxide, shown below, was prepared from 2-naphthyl-methylbromide and 1-ethynylcyclohexylamine according to the methods described in Example 1. Yield: 70 mg, 23%; MS(IS): 371 [MH]+.

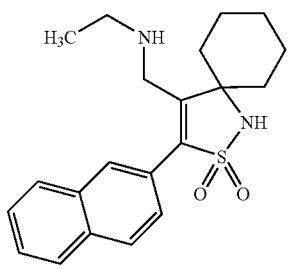

The title compound was prepared and deprotected according to the methods described in Example 1. Yield: 45 mg, 55%; MS (IS): 633 [MH]+, m.p. 122–126° C.

EXAMPLE 70

2-(R)-2-(2-Amino-2-methylpropionylamino)-3-phenylmethoxy-propionic acid N-ethyl-N-(3-(4-methylsulfonylphenyl)-2,2-dioxo-2-thia-1-azaspiro[4.5]dec-3-ene-4-ylmethyl)amide trifluoroacetate

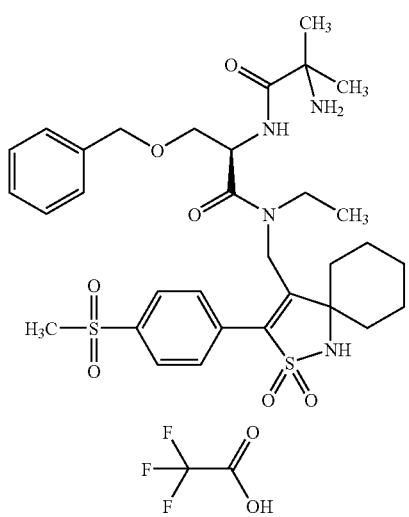

The title compound, as shown above, was prepared as follows.

4-Ethylaminomethyl-3-(4-methylsulfonylphenyl)-2-thia-1-azaspiro[4.5]dec-3-ene 2,2-dioxide, shown below, was prepared from 4-methylsulfonylbenzylbromide and 1-ethynylcyclohexylamine according to the methods described in Example 1. Yield: 121 mg, 38%; MS(IS): 339 [MH]+.

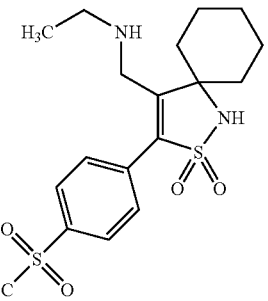

The title compound was prepared and deprotected according to the methods described in Example 1. Yield: 210 mg, 98%; MS(IS): 661 [MH]+, m.p. 160–165° C.

Additional compounds of the invention may also be synthesized by methods similar to the foregoing. These compounds include those disclosed in the following Tables:

TABLE I

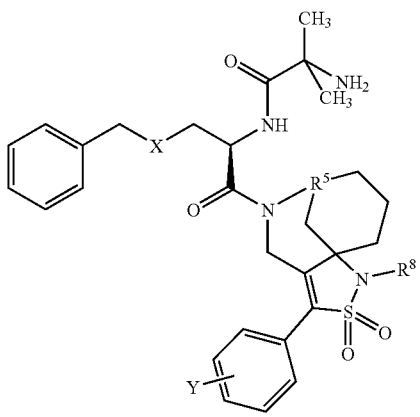

| X | Y | R⁵ | R⁸ |
|---|---|---|---|
| CH₂ | 4-Cl | H | H |
| CH₂ | 4-Cl | H | methyl |
| O | 4-Cl | H | methyl |
| CH₂ | 4-F | H | H |
| O | 4-F | H | H |
| CH₂ | 4-F | H | methyl |
| O | 4-F | H | methyl |
| CH₂ | H | H | H |
| O | H | H | H |
| CH₂ | H | H | methyl |
| O | H | H | methyl |
| CH₂ | 4-Cl | ethyl | ethyl |
| O | 4-Cl | ethyl | ethyl |
| CH₂ | 4-F | ethyl | ethyl |
| O | 4-F | ethyl | ethyl |
| CH₂ | H | ethyl | ethyl |
| CH₂ | 4-Cl | n-propyl | H |
| O | 4-Cl | n-propyl | methyl |
| CH₂ | 4-Cl | n-propyl | methyl |
| O | 4-Cl | i-propyl | H |
| CH₂ | 4-Cl | i-propyl | H |
| O | 4-Cl | i-propyl | methyl |
| CH₂ | 4-Cl | i-propyl | methyl |
| O | 4-F | n-propyl | H |
| CH₂ | 4-F | n-propyl | H |
| O | 4-F | n-propyl | methyl |
| CH₂ | 4-F | n-propyl | methyl |
| O | 4-F | i-propyl | H |
| CH₂ | 4-F | 1-propyl | H |
| O | 4-F | i-propyl | methyl |
| CH₂ | 4-F | 1-propyl | methyl |
| O | H | n-propyl | H |
| CH₂ | H | n-propyl | H |
| O | H | n-propyl | methyl |
| CH₂ | H | n-propyl | methyl |
| O | H | ethyl | n-propyl |
| CH₂ | H | ethyl | n-propyl |
| O | H | ethyl | n-butyl |
| CH₂ | H | ethyl | n-butyl |
| O | 4-F | ethyl | n-propyl |
| CH₂ | 4-F | ethyl | n-propyl |
| O | 4-F | ethyl | n-butyl |
| CH₂ | 4-F | ethyl | n-butyl |
| O | 4-Cl | ethyl | n-propyl |
| CH₂ | 4-Cl | ethyl | n-propyl |
| O | 4-Cl | ethyl | n-butyl |
| CH₂ | 4-Cl | ethyl | n-butyl |
| O | 4-F | ethyl | benzyl |
| CH₂ | 4-F | ethyl | Benzyl |

TABLE II

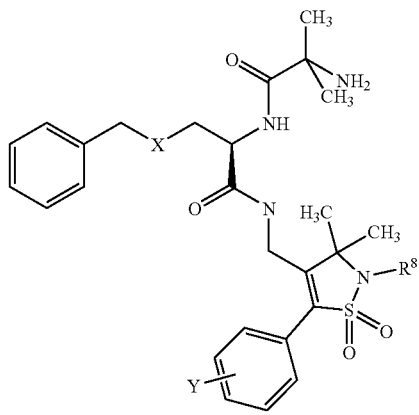

| X | Y | R⁸ |
|---|---|---|
| CH₂ | H | methyl |
| O | H | methyl |
| CH₂ | 4-Cl | methyl |
| O | 4-Cl | methyl |
| CH₂ | 3-Cl | H |
| O | 3-Cl | H |
| CH₂ | 3-Cl | methyl |
| O | 3-Cl | methyl |
| CH₂ | 2-Cl | H |
| O | 2-Cl | H |
| CH₂ | 2-Cl | methyl |
| O | 2-Cl | methyl |
| CH₂ | 4-F | H |
| O | 4-F | H |
| CH₂ | 4-F | methyl |
| O | 4-F | methyl |
| CH₂ | 3-F | H |
| O | 3-F | H |
| CH₂ | 3-F | methyl |
| O | 3-F | methyl |
| CH₂ | 2-F | H |
| O | 2-F | H |
| CH₂ | 2-F | methyl |
| O | 2-F | methyl |
| CH₂ | 3-Br | H |
| O | 3-Br | H |
| CH₂ | 3-Br | methyl |
| O | 3-Br | methyl |
| CH₂ | 4-Br | H |
| O | 4-Br | H |
| CH₂ | 4-Br | methyl |
| O | 4-Br | methyl |
| CH₂ | 4-CH₃ | H |
| O | 4-CH₃ | H |
| CH₂ | 4-CH₃ | methyl |
| O | 4-CH₃ | methyl |
| CH₂ | 3-CH₃ | H |
| O | 3-CH₃ | H |
| CH₂ | 3-CH₃ | methyl |
| O | 3-CH₃ | methyl |
| CH₂ | 4-CF₃ | H |
| O | 4-CF₃ | H |
| CH₂ | 4-CF₃ | methyl |
| O | 4-CF₃ | methyl |
| CH₂ | 3-CF₃ | H |
| O | 3-CF₃ | H |
| CH₂ | 3-CF₃ | methyl |
| O | 3-CF₃ | methyl |
| CH₂ | 4-OCH₃ | H |
| O | 4-OCH₃ | H |
| CH₂ | 4-OCH₃ | methyl |
| O | 4-OCH₃ | methyl |
| CH₂ | 3-OCH₃ | H |
| O | 3-OCH₃ | H |
| CH₂ | 3-OCH₃ | methyl |
| O | 3-OCH₃ | methyl |

TABLE II-continued

| X | Y | R⁸ |
|---|---|---|
| CH₂ | 4-C(CH₃)₃ | H |
| O | 4-C(CH₃)₃ | H |
| CH₂ | 4-C(CH₃)₃ | methyl |
| O | 4-C(CH₃)₃ | methyl |
| CH₂ | 4-CN | H |
| O | 4-CN | H |
| CH₂ | 4-CN | methyl |
| O | 4-CN | methyl |
| CH₂ | 3-CN | H |
| O | 3-CN | H |
| CH₂ | 3-CN | methyl |
| O | 3-CN | methyl |
| CH₂ | 4-SO₂CH₃ | H |
| O | 4-SO₂CH₃ | H |
| CH₂ | 4-SO₂CH₃ | methyl |
| O | 4-SO₂CH₃ | methyl |
| CH₂ | 3-SO₂CH₃ | H |
| O | 3-SO₂CH₃ | H |
| CH₂ | 3-SO₂CH₃ | methyl |
| O | 3-SO₂CH₃ | methyl |
| CH₂ | 3-phenoxy | H |
| O | 3-phenoxy | H |
| CH₂ | 3-phenoxy | methyl |
| O | 3-phenoxy | methyl |
| CH₂ | 4-phenoxy | H |
| O | 4-phenoxy | H |
| CH₂ | 4-phenoxy | methyl |
| O | 4-phenoxy | methyl |
| CH₂ | 2,4-F₂ | H |
| O | 2,4-F₂ | H |
| CH₂ | 2,4-F₂ | methyl |
| O | 2,4-F₂ | methyl |
| CH₂ | 3,4-F₂ | H |
| O | 3,4-F₂ | H |
| CH₂ | 3,4-F₂ | methyl |
| O | 3,4-F₂ | methyl |
| CH₂ | 3,5-F₂ | H |
| O | 3,5-F₂ | H |
| CH₂ | 3,5-F₂ | methyl |
| O | 3,5-F₂ | methyl |
| CH₂ | 2,3-F₂ | H |
| O | 2,3-F₂ | H |
| CH₂ | 2,3-F₂ | methyl |
| O | 2,3-F₂ | methyl |
| CH₂ | 2,6-F₂ | H |
| O | 2,6-F₂ | H |
| CH₂ | 2,6-F₂ | methyl |
| O | 2,6-F₂ | methyl |
| CH₂ | 2,5-F₂ | H |
| O | 2,5-F₂ | H |
| CH₂ | 2,5-F₂ | methyl |
| O | 2,5-F₂ | methyl |
| CH₂ | 2-F-3-Cl | H |
| O | 2-F-3-Cl | H |
| CH₂ | 2-F-3-Cl | methyl |
| O | 2-F-3-Cl | methyl |
| CH₂ | 3,4-Cl₂ | H |
| O | 3,4-Cl₂ | H |
| CH₂ | 3,4-Cl₂ | methyl |
| O | 3,4-Cl₂ | methyl |
| CH₂ | 3-phenyl | H |
| O | 3-phenyl | H |
| CH₂ | 3-phenyl | methyl |
| O | 3-phenyl | methyl |
| CH₂ | 4-phenyl | H |
| O | 4-phenyl | H |
| CH₂ | 4-phenyl | methyl |
| O | 4-phenyl | methyl |
| CH₂ | 3-(4-fluorophenyl) | H |
| O | 3-(4-fluorophenyl) | H |
| CH₂ | 3-(4-fluorophenyl) | methyl |
| O | 3-(4-fluorophenyl) | methyl |
| CH₂ | 4-(4-fluorophenyl) | H |
| O | 4-(4-fluorophenyl) | H |
| CH₂ | 4-(4-fluorophenyl) | methyl |
| O | 4-(4-fluorophenyl) | methyl |
| CH₂ | 3-(4-chlorophenyl) | H |
| O | 3-(4-chlorophenyl) | H |
| CH₂ | 3-(4-chlorophenyl) | methyl |
| O | 3-(4-chlorophenyl) | methyl |
| CH₂ | 4-(4-chlorophenyl) | H |
| O | 4-(4-chlorophenyl) | H |
| CH₂ | 4-(4-chlorophenyl) | methyl |
| O | 4-(4-chlorophenyl) | methyl |
| CH₂ | 3-(4-(CF₃)phenyl) | H |
| O | 3-(4-(CF₃)phenyl) | H |
| CH₂ | 3-(4-(CF₃)phenyl) | methyl |
| O | 3-(4-(CF₃)phenyl) | methyl |
| CH₂ | 4-(4-(CF₃)phenyl) | H |
| O | 4-(4-(CF₃)phenyl) | H |
| CH₂ | 4-(4-(CF₃)phenyl) | methyl |
| O | 4-(4-(CF₃)phenyl) | methyl |
| CH₂ | 3-(2-thienyl) | H |
| O | 3-(2-thienyl) | H |
| CH₂ | 3-(2-thienyl) | methyl |
| O | 3-(2-thienyl) | methyl |
| CH₂ | 4-(2-thienyl) | H |
| O | 4-(2-thienyl) | H |
| CH₂ | 4-(2-thienyl) | methyl |
| O | 4-(2-thienyl) | methyl |
| CH₂ | 3-(3-thienyl) | H |
| O | 3-(3-thienyl) | H |
| CH₂ | 3-(3-thienyl) | methyl |
| O | 3-(3-thienyl) | methyl |
| CH₂ | 4-(3-thienyl) | H |
| O | 4-(3-thienyl) | H |
| CH₂ | 4-(3-thienyl) | methyl |
| O | 4-(3-thienyl) | methyl |
| CH₂ | 3-(5-chloro-2-thienyl) | H |
| O | 3-(5-chloro-2-thienyl) | H |
| CH₂ | 3-(5-chloro-2-thienyl) | methyl |
| O | 3-(5-chloro-2-thienyl) | methyl |

TABLE II-continued

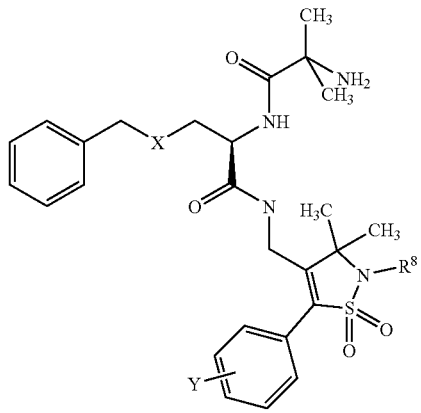

| X | Y | R⁸ |
|---|---|---|
| CH₂ | 4-(5-chloro-2-thienyl) | H |
| O | 4-(5-chloro-2-thienyl) | H |
| CH₂ | 4-(5-chloro-2-thienyl) | methyl |
| O | 4-(5-chloro-2-thienyl) | methyl |
| CH₂ | 4-(pyridin-2-yl) | H |
| O | 4-(pyridin-2-yl) | H |
| CH₂ | 4-(pyridin-2-yl) | methyl |
| O | 4-(pyridin-2-yl) | methyl |
| CH₂ | 4-(pyridin-3-yl) | H |
| O | 4-(pyridin-3-yl) | H |
| CH₂ | 4-(pyridin-3-yl) | methyl |
| O | 4-(pyridin-3-yl) | methyl |
| CH₂ | 3-(pyridin-4-yl) | H |
| O | 3-(pyridin-4-yl) | H |
| CH₂ | 3-(pyridin-4-yl) | methyl |
| O | 3-(pyridin-4-yl) | methyl |
| CH₂ | 4-(pyridin-4-yl) | H |
| O | 4-(pyridin-4-yl) | H |
| CH₂ | 4-(pyridin-4-yl) | methyl |
| O | 4-(pyridin-4-yl) | methyl |
| CH₂ | 3-(thiazol-2-yl) | H |
| O | 3-(thiazol-2-yl) | H |
| CH₂ | 3-(thiazol-2-yl) | methyl |
| O | 3-(thiazol-2-yl) | methyl |
| CH₂ | 4-(thiazol-2-yl) | H |
| O | 4-(thiazol-2-yl) | H |
| CH₂ | 4-(thiazol-2-yl) | methyl |
| O | 4-(thiazol-2-yl) | methyl |
| CH₂ | 3-(oxazol-2-yl) | H |
| O | 3-(oxazol-2-yl) | H |
| CH₂ | 3-(oxazol-2-yl) | methyl |
| O | 3-(oxazol-2-yl) | methyl |
| CH₂ | 4-(oxazol-2-yl) | H |
| O | 4-(oxazol-2-yl) | H |
| CH₂ | 4-(oxazol-2-yl) | methyl |
| O | 4-(oxazol-2-yl) | methyl |
| CH₂ | 3-NO₂ | H |
| O | 3-NO₂ | H |
| CH₂ | 3-NO₂ | methyl |
| O | 3-NO₂ | methyl |
| CH₂ | 4-NO₂ | H |
| O | 4-NO₂ | H |
| CH₂ | 4-NO₂ | methyl |
| O | 4-NO₂ | methyl |
| CH₂ | 4-C₂H₅ | H |
| O | 4-C₂H₅ | H |
| CH₂ | 4-C₂H₅ | methyl |
| O | 4-C₂H₅ | methyl |
| CH₂ | 4-OC₂H₅ | H |
| O | 4-OC₂H₅ | H |
| CH₂ | 4-OC₂H₅ | methyl |
| O | 4-OC₂H₅ | methyl |
| CH₂ | 4-CONH₂ | H |
| O | 4-CONH₂ | H |

TABLE II-continued

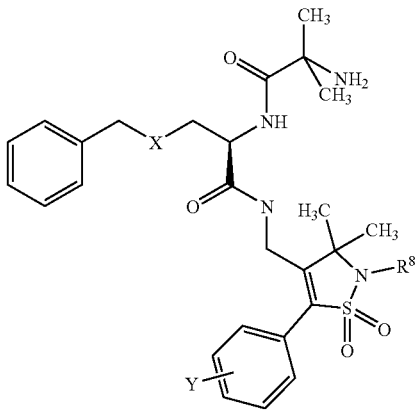

| X | Y | R⁸ |
|---|---|---|
| CH₂ | 4-CONH₂ | methyl |
| O | 4-CONH₂ | methyl |

TABLE III

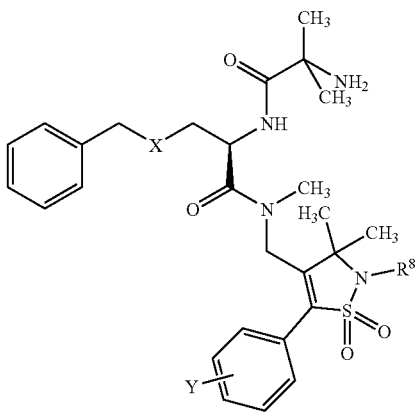

| X | Y | R⁸ |
|---|---|---|
| CH₂ | H | H |
| O | H | H |
| CH₂ | H | methyl |
| O | H | methyl |
| CH₂ | 4-Cl | H |
| O | 4-Cl | H |
| CH₂ | 4-Cl | methyl |
| O | 4-Cl | methyl |
| CH₂ | 3-Cl | H |
| O | 3-Cl | H |
| CH₂ | 3-Cl | methyl |
| O | 3-Cl | methyl |
| CH₂ | 2-Cl | H |
| O | 2-Cl | H |
| CH₂ | 2-Cl | methyl |
| O | 2-Cl | methyl |
| CH₂ | 4-F | H |
| O | 4-F | H |
| CH₂ | 4-F | methyl |
| O | 4-F | methyl |
| CH₂ | 3-F | H |
| O | 3-F | H |
| CH₂ | 3-F | methyl |
| O | 3-F | methyl |
| CH₂ | 2-F | H |
| O | 2-F | H |
| CH₂ | 2-F | methyl |

TABLE III-continued

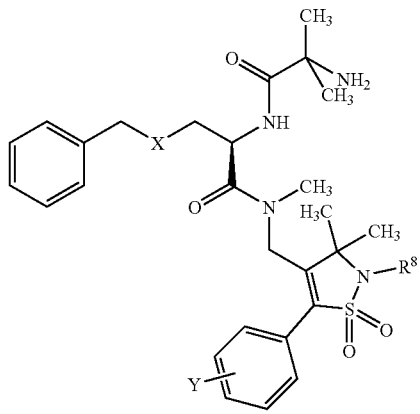

| X | Y | R⁸ |
|---|---|---|
| O | 2-F | methyl |
| CH₂ | 3-Br | H |
| O | 3-Br | H |
| CH₂ | 3-Br | methyl |
| O | 3-Br | methyl |
| CH₂ | 4-Br | H |
| O | 4-Br | H |
| CH₂ | 4-Br | methyl |
| O | 4-Br | methyl |
| CH₂ | 4-CH₃ | H |
| O | 4-CH₃ | H |
| CH₂ | 4-CH₃ | methyl |
| O | 4-CH₃ | methyl |
| CH₂ | 3-CH₃ | H |
| O | 3-CH₃ | H |
| CH₂ | 3-CH₃ | methyl |
| O | 3-CH₃ | methyl |
| CH₂ | 4-CF₃ | H |
| O | 4-CF₃ | H |
| CH₂ | 4-CF₃ | methyl |
| O | 4-CF₃ | methyl |
| CH₂ | 3-CF₃ | H |
| O | 3-CF₃ | H |
| CH₂ | 3-CF₃ | methyl |
| O | 3-CF₃ | methyl |
| CH₂ | 4-OCH₃ | H |
| O | 4-OCH₃ | H |
| CH₂ | 4-OCH₃ | methyl |
| O | 4-OCH₃ | methyl |
| CH₂ | 3-OCH₃ | H |
| O | 3-OCH₃ | H |
| CH₂ | 3-OCH₃ | methyl |
| O | 3-OCH₃ | methyl |
| CH₂ | 4-C(CH₃)₃ | H |
| O | 4-C(CH₃)₃ | H |
| CH₂ | 4-C(CH₃)₃ | methyl |
| O | 4-C(CH₃)₃ | methyl |
| CH₂ | 4-CN | H |
| O | 4-CN | H |
| CH₂ | 4-CN | methyl |
| O | 4-CN | methyl |
| CH₂ | 3-CN | H |
| O | 3-CN | H |
| CH₂ | 3-CN | methyl |
| O | 3-CN | methyl |
| CH₂ | 4-SO₂CH₃ | H |
| O | 4-SO₂CH₃ | H |
| CH₂ | 4-SO₂CH₃ | methyl |
| O | 4-SO₂CH₃ | methyl |
| CH₂ | 3-SO₂CH₃ | H |
| O | 3-SO₂CH₃ | H |
| CH₂ | 3-SO₂CH₃ | methyl |
| O | 3-SO₂CH₃ | methyl |

TABLE III-continued

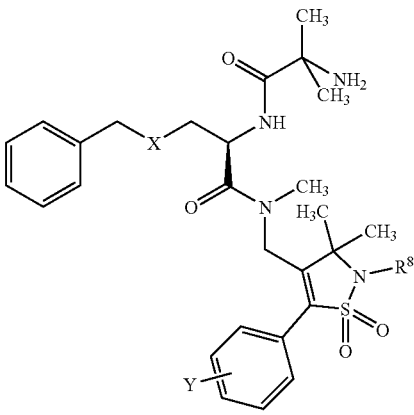

| X | Y | R⁸ |
|---|---|---|
| CH₂ | 3-phenoxy | H |
| O | 3-phenoxy | H |
| CH₂ | 3-phenoxy | methyl |
| O | 3-phenoxy | methyl |
| CH₂ | 4-phenoxy | H |
| O | 4-phenoxy | H |
| CH₂ | 4-phenoxy | methyl |
| O | 4-phenoxy | methyl |
| CH₂ | 2,4-F₂ | H |
| O | 2,4-F₂ | H |
| CH₂ | 2,4-F₂ | methyl |
| O | 2,4-F₂ | methyl |
| CH₂ | 3,4-F₂ | H |
| O | 3,4-F₂ | H |
| CH₂ | 3,4-F₂ | methyl |
| O | 3,4-F₂ | methyl |
| CH₂ | 3,5-F₂ | H |
| O | 3,5-F₂ | H |
| CH₂ | 3,5-F₂ | methyl |
| O | 3,5-F₂ | methyl |
| CH₂ | 2,3-F₂ | H |
| O | 2,3-F₂ | H |
| CH₂ | 2,3-F₂ | methyl |
| O | 2,3-F₂ | methyl |
| CH₂ | 2,6-F₂ | H |
| O | 2,6-F₂ | H |
| CH₂ | 2,6-F₂ | methyl |
| O | 2,6-F₂ | methyl |
| CH₂ | 2,5-F₂ | H |
| O | 2,5-F₂ | H |
| CH₂ | 2,5-F₂ | methyl |
| O | 2,5-F₂ | methyl |
| CH₂ | 2-F-3-Cl | H |
| O | 2-F-3-Cl | H |
| CH₂ | 2-F-3-Cl | methyl |
| O | 2-F-3-Cl | methyl |
| CH₂ | 3,4-Cl₂ | H |
| O | 3,4-Cl₂ | H |
| CH₂ | 3,4-Cl₂ | methyl |
| O | 3,4-Cl₂ | methyl |
| CH₂ | 3-phenyl | H |
| O | 3-phenyl | H |
| CH₂ | 3-phenyl | methyl |
| O | 3-phenyl | methyl |
| CH₂ | 4-phenyl | H |
| O | 4-phenyl | H |
| CH₂ | 4-phenyl | methyl |
| O | 4-phenyl | methyl |
| CH₂ | 3-(4-fluorophenyl) | H |
| O | 3-(4-fluorophenyl) | H |
| CH₂ | 3-(4-fluorophenyl) | methyl |
| O | 3-(4-fluorophenyl) | methyl |
| CH₂ | 4-(4-fluorophenyl) | H |

TABLE III-continued

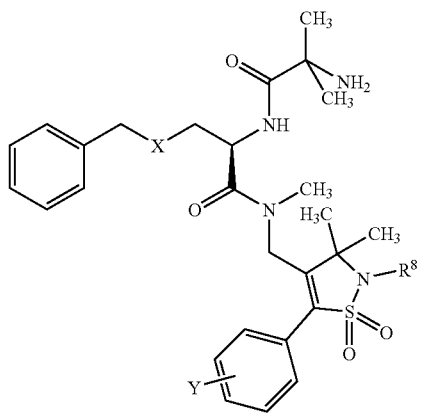

| X | Y | R[8] |
|---|---|---|
| O | 4-(4-fluorophenyl) | H |
| CH$_2$ | 4-(4-fluorophenyl) | methyl |
| O | 4-(4-fluorophenyl) | methyl |
| CH$_2$ | 3-(4-chlorophenyl) | H |
| O | 3-(4-chlorophenyl) | H |
| CH$_2$ | 3-(4-chlorophenyl) | methyl |
| O | 3-(4-chlorophenyl) | methyl |
| CH$_2$ | 4-(4-chlorophenyl) | H |
| O | 4-(4-chlorophenyl) | H |
| CH$_2$ | 4-(4-chlorophenyl) | methyl |
| O | 4-(4-chlorophenyl) | methyl |
| CH$_2$ | 3-(4-(CF$_3$)phenyl) | H |
| O | 3-(4-(CF$_3$)phenyl) | H |
| CH$_2$ | 3-(4-(CF$_3$)phenyl) | methyl |
| O | 3-(4-(CF$_3$)phenyl) | methyl |
| CH$_2$ | 4-(4-(CF$_3$)phenyl) | H |
| O | 4-(4-(CF$_3$)phenyl) | H |
| CH$_2$ | 4-(4-(CF$_3$)phenyl) | methyl |
| O | 4-(4-(CF$_3$)phenyl) | methyl |
| CH$_2$ | 3-(2-thienyl) | H |
| O | 3-(2-thienyl) | H |
| CH$_2$ | 3-(2-thienyl) | methyl |
| O | 3-(2-thienyl) | methyl |
| CH$_2$ | 4-(2-thienyl) | H |
| O | 4-(2-thienyl) | H |
| CH$_2$ | 4-(2-thienyl) | methyl |
| O | 4-(2-thienyl) | methyl |
| CH$_2$ | 3-(3-thienyl) | H |
| O | 3-(3-thienyl) | H |
| CH$_2$ | 3-(3-thienyl) | methyl |
| O | 3-(3-thienyl) | methyl |
| CH$_2$ | 4-(3-thienyl) | H |
| O | 4-(3-thienyl) | H |
| CH$_2$ | 4-(3-thienyl) | methyl |
| O | 4-(3-thienyl) | methyl |
| CH$_2$ | 3-(5-chloro-2-thienyl) | H |
| O | 3-(5-chloro-2-thienyl) | H |
| CH$_2$ | 3-(5-chloro-2-thienyl) | methyl |
| O | 3-(5-chloro-2-thienyl) | methyl |
| CH$_2$ | 4-(5-chloro-2-thienyl) | H |
| O | 4-(5-chloro-2-thienyl) | H |
| CH$_2$ | 4-(5-chloro-2-thienyl) | methyl |
| O | 4-(5-chloro-2-thienyl) | methyl |
| CH$_2$ | 4-(pyridin-2-yl) | H |
| O | 4-(pyridin-2-yl) | H |
| CH$_2$ | 4-(pyridin-2-yl) | methyl |
| O | 4-(pyridin-2-yl) | methyl |
| CH$_2$ | 4-(pyridin-3-yl) | H |
| O | 4-(pyridin-3-yl) | H |

TABLE III-continued

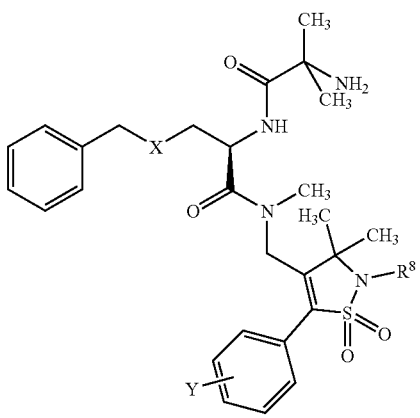

| X | Y | R[8] |
|---|---|---|
| CH$_2$ | 4-(pyridin-3-yl) | methyl |
| O | 4-(pyridin-3-yl) | methyl |
| CH$_2$ | 3-(pyridin-4-yl) | H |
| O | 3-(pyridin-4-yl) | H |
| CH$_2$ | 3-(pyridin-4-yl) | methyl |
| O | 3-(pyridin-4-yl) | methyl |
| CH$_2$ | 4-(pyridin-4-yl) | H |
| O | 4-(pyridin-4-yl) | H |
| CH$_2$ | 4-(pyridin-4-yl) | methyl |
| O | 4-(pyridin-4-yl) | methyl |
| CH$_2$ | 3-(thiazol-2-yl) | H |
| O | 3-(thiazol-2-yl) | H |
| CH$_2$ | 3-(thiazol-2-yl) | methyl |
| O | 3-(thiazol-2-yl) | methyl |
| CH$_2$ | 4-(thiazol-2-yl) | H |
| O | 4-(thiazol-2-yl) | H |
| CH$_2$ | 4-(thiazol-2-yl) | methyl |
| O | 4-(thiazol-2-yl) | methyl |
| CH$_2$ | 3-(oxazol-2-yl) | H |
| O | 3-(oxazol-2-yl) | H |
| CH$_2$ | 3-(oxazol-2-yl) | methyl |
| O | 3-(oxazol-2-yl) | methyl |
| CH$_2$ | 4-(oxazol-2-yl) | H |
| O | 4-(oxazol-2-yl) | H |
| CH$_2$ | 4-(oxazol-2-yl) | methyl |
| O | 4-(oxazol-2-yl) | methyl |
| CH$_2$ | 3-NO$_2$ | H |
| O | 3-NO$_2$ | H |
| CH$_2$ | 3-NO$_2$ | methyl |
| O | 3-NO$_2$ | methyl |
| CH$_2$ | 4-NO$_2$ | H |
| O | 4-NO$_2$ | H |
| CH$_2$ | 4-NO$_2$ | methyl |
| O | 4-NO$_2$ | methyl |
| CH$_2$ | 4-C$_2$H$_5$ | H |
| O | 4-C$_2$H$_5$ | H |
| CH$_2$ | 4-C$_2$H$_5$ | methyl |
| O | 4-C$_2$H$_5$ | methyl |
| CH$_2$ | 4-OC$_2$H$_5$ | H |
| O | 4-OC$_2$H$_5$ | H |
| CH$_2$ | 4-OC$_2$H$_5$ | methyl |
| O | 4-OC$_2$H$_5$ | methyl |
| CH$_2$ | 4-CONH$_2$ | H |
| O | 4-CONH$_2$ | H |
| CH$_2$ | 4-CONH$_2$ | methyl |
| O | 4-CONH$_2$ | methyl |

TABLE IV

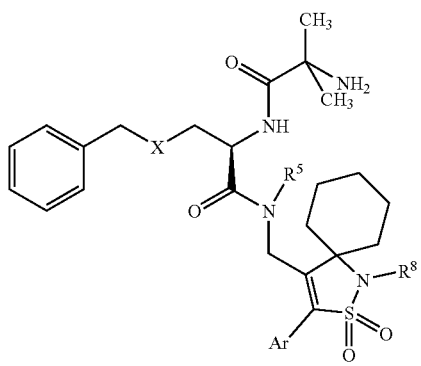

| X | Ar | R⁵ | R⁸ |
|---|---|---|---|
| CH₂ | 1-naphthyl | ethyl | H |
| CH₂ | 1-naphthyl | ethyl | methyl |
| O | 1-naphthyl | ethyl | methyl |
| CH₂ | 2-naphthyl | ethyl | H |
| CH₂ | 2-naphthyl | ethyl | methyl |
| O | 2-naphthyl | ethyl | methyl |
| CH₂ | pyridin-2-yl | ethyl | H |
| O | pyridin-2-yl | ethyl | H |
| CH₂ | pyridin-2-yl | ethyl | methyl |
| O | pyridin-2-yl | ethyl | methyl |
| CH₂ | pyridin-3-yl | ethyl | H |
| O | pyridin-3-yl | ethyl | H |
| CH₂ | pyridin-3-yl | ethyl | methyl |
| O | pyridin-3-yl | ethyl | methyl |
| CH₂ | pyridin-4-yl | ethyl | H |
| O | pyridin-4-yl | ethyl | H |
| CH₂ | pyridin-4-yl | ethyl | methyl |
| O | pyridin-4-yl | ethyl | methyl |
| CH₂ | 2-thienyl | ethyl | H |
| O | 2-thienyl | ethyl | H |
| CH₂ | 2-thienyl | ethyl | methyl |
| O | 2-thienyl | ethyl | methyl |
| CH₂ | 3-thienyl | ethyl | H |
| O | 3-thienyl | ethyl | H |
| CH₂ | 3-thienyl | ethyl | methyl |
| O | 3-thienyl | ethyl | methyl |
| CH₂ | thiazol-2-yl | ethyl | H |
| O | thiazol-2-yl | ethyl | H |
| CH₂ | thiazol-2-yl | ethyl | methyl |
| O | thiazol-2-yl | ethyl | methyl |
| CH₂ | oxazol-2-yl | ethyl | H |
| O | oxazol-2-yl | ethyl | H |
| CH₂ | oxazol-2-yl | ethyl | methyl |
| O | oxazol-2-yl | ethyl | methyl |
| CH₂ | 1-naphthyl | methyl | H |
| O | 1-naphthyl | methyl | H |
| CH₂ | 1-naphthyl | methyl | methyl |
| O | 1-naphthyl | methyl | methyl |
| CH₂ | 2-naphthyl | methyl | H |
| O | 2-naphthyl | methyl | H |
| CH₂ | 2-naphthyl | methyl | methyl |
| O | 2-naphthyl | methyl | methyl |
| CH₂ | pyridin-2-yl | methyl | H |
| O | pyridin-2-yl | methyl | H |
| CH₂ | pyridin-2-yl | methyl | methyl |
| O | pyridin-2-yl | methyl | methyl |
| CH₂ | pyridin-3-yl | methyl | H |
| O | pyridin-3-yl | methyl | H |
| CH₂ | pyridin-3-yl | methyl | methyl |

TABLE IV-continued

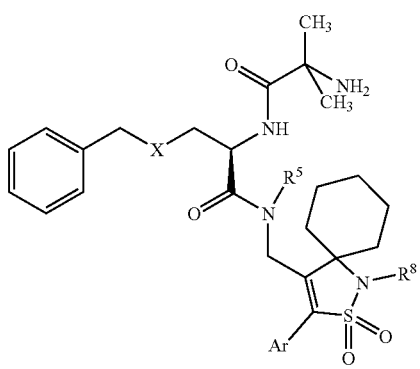

| X | Ar | R⁵ | R⁸ |
|---|---|---|---|
| O | pyridin-3-yl | methyl | methyl |
| CH₂ | pyridin-4-yl | methyl | H |
| O | pyridin-4-yl | methyl | H |
| CH₂ | pyridin-4-yl | methyl | methyl |
| O | pyridin-4-yl | methyl | methyl |
| CH₂ | 2-thienyl | methyl | H |
| O | 2-thienyl | methyl | H |
| CH₂ | 2-thienyl | methyl | methyl |
| O | 2-thienyl | methyl | methyl |
| CH₂ | 3-thienyl | methyl | H |
| O | 3-thienyl | methyl | H |
| CH₂ | 3-thienyl | methyl | methyl |
| O | 3-thienyl | methyl | methyl |
| CH₂ | thiazol-2-yl | methyl | H |
| O | thiazol-2-yl | methyl | H |
| CH₂ | thiazol-2-yl | methyl | methyl |
| O | thiazol-2-yl | methyl | methyl |
| CH₂ | oxazol-2-yl | methyl | H |
| O | oxazol-2-yl | methyl | H |
| CH₂ | oxazol-2-yl | methyl | methyl |
| O | oxazol-2-yl | methyl | methyl |
| CH₂ | cyano | ethyl | H |
| O | cyano | ethyl | H |
| CH₂ | cyano | ethyl | methyl |
| O | cyano | ethyl | methyl |
| CH₂ | cyano | methyl | H |
| O | cyano | methyl | H |
| CH₂ | cyano | methyl | methyl |
| O | cyano | methyl | methyl |
| CH₂ | cyclohexyl | ethyl | H |
| O | cyclohexyl | ethyl | H |
| CH₂ | cyclohexyl | ethyl | methyl |
| O | cyclohexyl | ethyl | methyl |
| CH₂ | cyclohexyl | methyl | H |
| O | cyclohexyl | methyl | H |
| CH₂ | cyclohexyl | methyl | methyl |
| O | cyclohexyl | methyl | methyl |
| CH₂ | isopropyl | ethyl | H |
| O | isopropyl | ethyl | H |
| CH₂ | isopropyl | ethyl | methyl |
| O | isopropyl | ethyl | methyl |
| CH₂ | isopropyl | methyl | H |
| O | isopropyl | methyl | H |
| CH₂ | isopropyl | methyl | methyl |
| O | isopropyl | methyl | methyl |

TABLE V

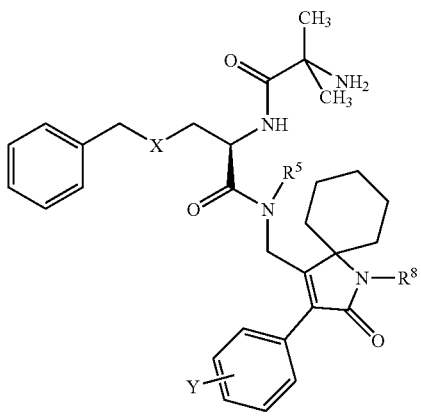

| X | Y | R⁵ | R⁸ |
|---|---|---|---|
| CH₂ | H | ethyl | H |
| CH₂ | H | ethyl | methyl |
| O | H | methyl | H |
| CH₂ | H | methyl | H |
| O | H | methyl | methyl |
| CH₂ | H | methyl | methyl |
| CH₂ | 2-Cl | ethyl | H |
| CH₂ | 3-Cl | ethyl | H |
| O | 3-Cl | ethyl | methyl |
| CH₂ | 3-Cl | ethyl | methyl |
| O | 3-Cl | methyl | H |
| CH₂ | 3-Cl | methyl | H |
| O | 3-Cl | methyl | methyl |
| CH₂ | 3-Cl | methyl | methyl |
| CH₂ | 4-Cl | ethyl | H |
| CH₂ | 4-Cl | ethyl | methyl |
| O | 4-Cl | methyl | H |
| CH₂ | 4-Cl | methyl | H |
| O | 4-Cl | methyl | methyl |
| CH₂ | 4-Cl | methyl | methyl |
| CH₂ | 3,4-Cl₂ | ethyl | H |
| CH₂ | 4-Br | ethyl | H |
| O | 4-Br | ethyl | methyl |
| CH₂ | 4-Br | ethyl | methyl |
| O | 4-Br | methyl | H |
| CH₂ | 4-Br | methyl | H |
| O | 4-Br | methyl | methyl |
| CH₂ | 4-Br | methyl | methyl |
| O | 3-Br | ethyl | H |
| CH₂ | 3-Br | ethyl | H |
| O | 3-Br | ethyl | methyl |
| CH₂ | 3-Br | ethyl | methyl |
| O | 3-Br | methyl | H |
| CH₂ | 3-Br | methyl | H |
| O | 3-Br | methyl | methyl |
| CH₂ | 3-Br | methyl | methyl |
| CH₂ | 4-F | ethyl | H |
| O | 4-F | ethyl | methyl |
| CH₂ | 4-F | ethyl | methyl |
| O | 4-F | methyl | H |
| CH₂ | 4-F | methyl | H |
| O | 4-F | methyl | methyl |
| CH₂ | 4-F | methyl | methyl |
| O | 3-F | ethyl | H |
| CH₂ | 3-F | ethyl | H |
| O | 3-F | ethyl | methyl |
| CH₂ | 3-F | ethyl | methyl |
| O | 3-F | methyl | H |
| CH₂ | 3-F | methyl | H |
| O | 3-F | methyl | methyl |
| CH₂ | 3-F | methyl | methyl |
| O | 2-F | ethyl | H |
| CH₂ | 2-F | ethyl | H |
| O | 2-F | ethyl | methyl |
| CH₂ | 2-F | ethyl | methyl |
| O | 2-F | methyl | H |

TABLE V-continued

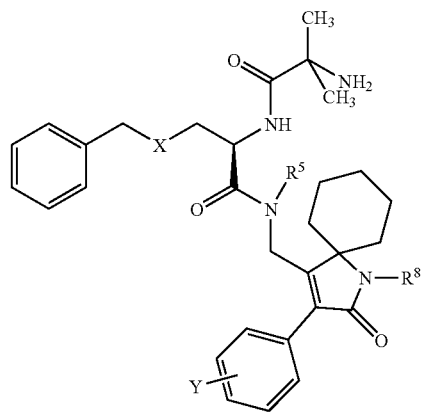

| X | Y | R⁵ | R⁸ |
|---|---|---|---|
| CH₂ | 2-F | methyl | H |
| O | 2-F | methyl | methyl |
| CH₂ | 2-F | methyl | methyl |
| CH₂ | 4-CH₃ | ethyl | H |
| O | 4-CH₃ | ethyl | methyl |
| CH₂ | 4-CH₃ | ethyl | methyl |
| CH₂ | 4-OCH₃ | H | H |
| CH₂ | 4-OCH₃ | ethyl | H |
| CH₂ | 4-OCH₃ | ethyl | methyl |
| CH₂ | 3-CF₃ | ethyl | H |
| CH₂ | 3-CF₃ | ethyl | methyl |
| O | 4-CF₃ | ethyl | H |
| CH₂ | 4-CF₃ | ethyl | H |
| O | 4-CF₃ | ethyl | methyl |
| CH₂ | 4-CF₃ | ethyl | methyl |
| CH₂ | 4-phenyl | ethyl | H |
| CH₂ | 4-phenyl | ethyl | methyl |
| O | 3-phenyl | ethyl | H |
| CH₂ | 3-phenyl | ethyl | H |
| O | 3-phenyl | ethyl | methyl |
| CH₂ | 3-phenyl | ethyl | methyl |
| O | 4-SO₂CH₃ | ethyl | H |
| CH₂ | 4-SO₂CH₃ | ethyl | H |
| O | 4-SO₂CH₃ | ethyl | methyl |
| CH₂ | 4-SO₂CH₃ | ethyl | methyl |
| O | 4-SO₂CH₃ | methyl | H |
| CH₂ | 4-SO₂CH₃ | methyl | H |
| O | 4-SO₂CH₃ | methyl | methyl |
| CH₂ | 4-SO₂CH₃ | methyl | methyl |
| O | 4-(4-fluorophenyl) | ethyl | H |
| CH₂ | 4-(4-fluorophenyl) | ethyl | H |
| O | 4-(4-fluorophenyl) | ethyl | methyl |
| CH₂ | 4-(4-fluorophenyl) | ethyl | methyl |
| O | 4-(4-chlorophenyl) | ethyl | H |
| CH₂ | 4-(4-chlorophenyl) | ethyl | H |
| O | 4-(4-chlorophenyl) | ethyl | methyl |
| CH₂ | 4-(4-chlorophenyl) | ethyl | methyl |
| O | 4-(pyridin-4-yl) | ethyl | H |
| CH₂ | 4-(pyridin-4-yl) | ethyl | H |
| O | 4-(pyridin-4-yl) | ethyl | methyl |
| CH₂ | 4-(pyridin-4-yl) | ethyl | methyl |
| O | 4-(2-thienyl) | ethyl | H |
| CH₂ | 4-(2-thienyl) | ethyl | H |
| O | 4-(2-thienyl) | ethyl | methyl |
| CH₂ | 4-(2-thienyl) | ethyl | methyl |
| O | 4-(3-thienyl) | ethyl | H |
| CH₂ | 4-(3-thienyl) | ethyl | H |
| O | 4-(3-thienyl) | ethyl | methyl |
| CH₂ | 4-(3-thienyl) | ethyl | methyl |
| O | 4-(4-(CF₃)phenyl) | ethyl | H |
| CH₂ | 4-(4-(CF₃)phenyl) | ethyl | H |
| O | 4-(4-(CF₃)phenyl) | ethyl | methyl |
| CH₂ | 4-(4-(CF₃)phenyl) | ethyl | methyl |

TABLE VI

| X | Y | R⁸ |
|---|---|---|
| CH₂ | H | H |
| O | H | methyl |
| CH₂ | H | methyl |
| CH₂ | 4-Cl | H |
| CH₂ | 4-Cl | methyl |
| O | 4-F | H |
| CH₂ | 4-F | H |
| O | 4-F | Methyl |
| CH₂ | 4-F | Methyl |
| O | 4-SO₂CH₃ | H |
| CH₂ | 4-SO₂CH₃ | H |
| O | 4-SO₂CH₃ | Methyl |
| CH₂ | 4-SO₂CH₃ | Methyl |

TABLE VII

| X | Y | A | R |
|---|---|---|---|
| CH₂ | 4-Cl | O | H |
| O | 4-Cl | O | H |
| CH₂ | 4-Cl | O | methyl |
| O | 4-Cl | O | methyl |
| CH₂ | 4-F | O | H |
| O | 4-F | O | H |
| CH₂ | 4-F | O | methyl |
| O | 4-F | O | methyl |
| CH₂ | H | O | H |
| O | H | O | H |
| CH₂ | H | O | methyl |
| O | H | O | methyl |

TABLE VII

| X | Y | R⁸ |
|---|---|---|
| CH₂ | H | methyl |
| CH₂ | 4-Cl | methyl |
| CH₂ | 3-Cl | H |
| O | 3-Cl | H |
| CH₂ | 3-Cl | methyl |
| CH₂ | 2-Cl | H |
| CH₂ | 2-Cl | methyl |
| CH₂ | 4-F | methyl |
| O | 4-F | methyl |
| CH₂ | 3-F | H |
| O | 3-F | H |
| CH₂ | 3-F | methyl |
| O | 3-F | methyl |
| CH₂ | 2-F | H |
| O | 2-F | H |
| CH₂ | 2-F | methyl |
| O | 2-F | methyl |
| CH₂ | 2-Br | methyl |
| O | 2-Br | methyl |
| CH₂ | 3-Br | H |
| CH₂ | 3-Br | methyl |
| O | 3-Br | methyl |
| CH₂ | 4-Br | H |
| CH₂ | 4-Br | methyl |
| O | 4-Br | methyl |
| CH₂ | 4-CH₃ | H |
| CH₂ | 4-CH₃ | methyl |
| O | 4-CH₃ | methyl |
| CH₂ | 3-CH₃ | H |
| O | 3-CH₃ | H |
| CH₂ | 3-CH₃ | methyl |
| O | 3-CH₃ | methyl |
| CH₂ | 4-CF₃ | H |
| O | 4-CF₃ | H |
| CH₂ | 4-CF₃ | methyl |
| CH₂ | 3-CF₃ | H |
| CH₂ | 3-CF₃ | methyl |
| O | 3-CF₃ | methyl |
| CH₂ | 4-OCH₃ | H |
| O | 4-OCH₃ | H |
| CH₂ | 4-OCH₃ | methyl |
| O | 4-OCH₃ | methyl |
| CH₂ | 3-OCH₃ | H |
| O | 3-OCH₃ | H |
| CH₂ | 3-OCH₃ | methyl |
| O | 3-OCH₃ | methyl |
| CH₂ | 4-C(CH₃)₃ | H |
| CH₂ | 4-C(CH₃)₃ | methyl |
| O | 4-C(CH₃)₃ | methyl |
| CH₂ | 4-CN | H |
| CH₂ | 4-CN | methyl |
| O | 4-CN | methyl |
| CH₂ | 3-CN | H |
| O | 3-CN | H |
| CH₂ | 3-CN | methyl |
| O | 3-CN | methyl |
| CH₂ | 4-SO₂CH₃ | H |
| CH₂ | 4-SO₂CH₃ | methyl |
| O | 4-SO₂CH₃ | methyl |

TABLE VII-continued

| X | Y | R⁸ |
|---|---|---|
| CH₂ | 3-SO₂CH₃ | H |
| O | 3-SO₂CH₃ | H |
| CH₂ | 3-SO₂CH₃ | methyl |
| O | 3-SO₂CH₃ | methyl |
| CH₂ | 3-phenoxy | H |
| O | 3-phenoxy | H |
| CH₂ | 3-phenoxy | methyl |
| O | 3-phenoxy | methyl |
| CH₂ | 4-phenoxy | H |
| O | 4-phenoxy | H |
| CH₂ | 4-phenoxy | methyl |
| O | 4-phenoxy | methyl |
| CH₂ | 2,4-F₂ | H |
| O | 2,4-F₂ | H |
| CH₂ | 2,4-F₂ | methyl |
| O | 2,4-F₂ | methyl |
| CH₂ | 3,4-F₂ | H |
| O | 3,4-F₂ | H |
| CH₂ | 3,4-F₂ | methyl |
| O | 3,4-F₂ | methyl |
| CH₂ | 3,5-F₂ | H |
| O | 3,5-F₂ | H |
| CH₂ | 3,5-F₂ | methyl |
| O | 3,5-F₂ | methyl |
| CH₂ | 2,3-F₂ | H |
| O | 2,3-F₂ | H |
| CH₂ | 2,3-F₂ | methyl |
| O | 2,3-F₂ | methyl |
| CH₂ | 2,6-F₂ | H |
| O | 2,6-F₂ | H |
| CH₂ | 2,6-F₂ | methyl |
| O | 2,6-F₂ | methyl |
| CH₂ | 2,5-F₂ | H |
| O | 2,5-F₂ | H |
| CH₂ | 2,5-F₂ | methyl |
| O | 2,5-F₂ | methyl |
| CH₂ | 2-F-3-Cl | H |
| O | 2-F-3-Cl | H |
| CH₂ | 2-F-3-Cl | methyl |
| O | 2-F-3-Cl | methyl |
| CH₂ | 3,4-Cl₂ | H |
| O | 3,4-Cl₂ | H |
| CH₂ | 3,4-Cl₂ | methyl |
| O | 3,4-Cl₂ | methyl |
| CH₂ | 3-phenyl | H |
| O | 3-phenyl | H |
| CH₂ | 3-phenyl | methyl |
| O | 3-phenyl | methyl |
| CH₂ | 4-phenyl | H |
| CH₂ | 4-phenyl | methyl |
| O | 4-phenyl | methyl |
| CH₂ | 3-(4-fluorophenyl) | H |
| O | 3-(4-fluorophenyl) | H |
| CH₂ | 3-(4-fluorophenyl) | methyl |
| O | 3-(4-fluorophenyl) | methyl |
| CH₂ | 4-(4-fluorophenyl) | H |
| O | 4-(4-fluorophenyl) | H |
| CH₂ | 4-(4-fluorophenyl) | methyl |
| O | 4-(4-fluorophenyl) | methyl |
| CH₂ | 3-(4-chlorophenyl) | H |
| O | 3-(4-chlorophenyl) | H |
| CH₂ | 3-(4-chlorophenyl) | methyl |
| O | 3-(4-chlorophenyl) | methyl |
| CH₂ | 4-(4-chlorophenyl) | H |
| O | 4-(4-chlorophenyl) | H |
| CH₂ | 4-(4-chlorophenyl) | methyl |
| O | 4-(4-chlorophenyl) | methyl |
| CH₂ | 3-(4-(CF₃)phenyl) | H |
| O | 3-(4-(CF₃)phenyl) | H |
| CH₂ | 3-(4-(CF₃)phenyl) | methyl |
| O | 3-(4-(CF₃)phenyl) | methyl |
| CH₂ | 4-(4-(CF₃)phenyl) | H |
| O | 4-(4-(CF₃)phenyl) | H |
| CH₂ | 4-(4-(CF₃)phenyl) | methyl |
| O | 4-(4-(CF₃)phenyl) | methyl |
| CH₂ | 3-(2-thienyl) | H |
| O | 3-(2-thienyl) | H |
| CH₂ | 3-(2-thienyl) | methyl |
| O | 3-(2-thienyl) | methyl |
| CH₂ | 4-(2-thienyl) | H |
| O | 4-(2-thienyl) | H |
| CH₂ | 4-(2-thienyl) | methyl |
| O | 4-(2-thienyl) | methyl |
| CH₂ | 3-(3-thienyl) | H |
| O | 3-(3-thienyl) | H |
| CH₂ | 3-(3-thienyl) | methyl |
| O | 3-(3-thienyl) | methyl |
| CH₂ | 4-(3-thienyl) | H |
| O | 4-(3-thienyl) | H |
| CH₂ | 4-(3-thienyl) | methyl |
| O | 4-(3-thienyl) | methyl |
| CH₂ | 3-(5-chloro-2-thienyl) | H |
| O | 3-(5-chloro-2-thienyl) | H |
| CH₂ | 3-(5-chloro-2-thienyl) | methyl |
| O | 3-(5-chloro-2-thienyl) | methyl |
| CH₂ | 4-(5-chloro-2-thienyl) | H |
| O | 4-(5-chloro-2-thienyl) | H |
| CH₂ | 4-(5-chloro-2-thienyl) | methyl |
| O | 4-(5-chloro-2-thienyl) | methyl |
| CH₂ | 4-(3,4-(methylenedioxy)phenyl) | H |
| O | 4-(3,4-(methylenedioxy)phenyl) | H |
| CH₂ | 4-(3,4-(methylenedioxy)phenyl) | methyl |
| O | 4-(3,4-(methylenedioxy)phenyl) | methyl |
| CH₂ | 4-(furan-2-yl) | H |
| O | 4-(furan-2-yl) | H |
| CH₂ | 4-(furan-2-yl) | methyl |
| O | 4-(furan-2-yl) | methyl |
| CH₂ | 4-(benzothiophen-2-yl) | H |
| O | 4-(benzothiophen-2-yl) | H |
| CH₂ | 4-(benzothiophen-2-yl) | methyl |
| O | 4-(benzothiophen-2-yl) | methyl |
| CH₂ | 4-(benzofuran-2-yl) | H |
| O | 4-(benzofuran-2-yl) | H |
| CH₂ | 4-(benzofuran-2-yl) | methyl |
| O | 4-(benzofuran-2-yl) | methyl |
| CH₂ | 4-(pyridin-2-yl) | H |
| O | 4-(pyridin-2-yl) | H |
| CH₂ | 4-(pyridin-2-yl) | methyl |
| O | 4-(pyridin-2-yl) | methyl |

TABLE VII-continued

| X | Y | R8 |
|---|---|---|
| CH2 | 4-(pyridin-3-yl) | H |
| O | 4-(pyridin-3-yl) | H |
| CH2 | 4-(pyridin-3-yl) | methyl |
| O | 4-(pyridin-3-yl) | methyl |
| CH2 | 3-(pyridin-4-yl) | H |
| O | 3-(pyridin-4-yl) | H |
| CH2 | 3-(pyridin-4-yl) | methyl |
| O | 3-(pyridin-4-yl) | methyl |
| CH2 | 4-(pyridin-4-yl) | H |
| O | 4-(pyridin-4-yl) | H |
| CH2 | 4-(pyridin-4-yl) | methyl |
| O | 4-(pyridin-4-yl) | methyl |
| CH2 | 3-(thiazol-2-yl) | H |
| O | 3-(thiazol-2-yl) | H |
| CH2 | 3-(thiazol-2-yl) | methyl |
| O | 3-(thiazol-2-yl) | methyl |
| CH2 | 4-(thiazol-2-yl) | H |
| O | 4-(thiazol-2-yl) | H |
| CH2 | 4-(thiazol-2-yl) | methyl |
| O | 4-(thiazol-2-yl) | methyl |
| CH2 | 3-(oxazol-2-yl) | H |
| O | 3-(oxazol-2-yl) | H |
| CH2 | 3-(oxazol-2-yl) | methyl |
| O | 3-(oxazol-2-yl) | methyl |
| CH2 | 4-(oxazol-2-yl) | H |
| O | 4-(oxazol-2-yl) | H |
| CH2 | 4-(oxazol-2-yl) | methyl |
| O | 4-(oxazol-2-yl) | methyl |
| CH2 | 3-NO2 | H |
| O | 3-NO2 | H |
| CH2 | 3-NO2 | methyl |
| O | 3-NO2 | methyl |
| CH2 | 4-NO2 | H |
| O | 4-NO2 | H |
| CH2 | 4-NO2 | methyl |
| CH2 | 4-C2H5 | H |
| O | 4-C2H5 | H |
| CH2 | 4-C2H5 | methyl |
| O | 4-C2H5 | methyl |
| CH2 | 4-OC2H5 | H |
| O | 4-OC2H5 | H |
| CH2 | 4-OC2H5 | methyl |
| O | 4-OC2H5 | methyl |
| CH2 | 4-CONH2 | H |
| CH2 | 4-CONH2 | methyl |
| O | 4-CONH2 | methyl |

TABLE IX

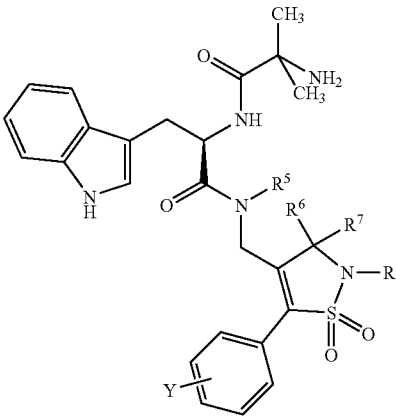

| Y | R5 | R6,R7 | R8 |
|---|---|---|---|
| H | ethyl | dimethyl | H |
| H | ethyl | dimethyl | methyl |
| H | ethyl | tetramethylene | H |
| H | ethyl | tetramethylene | methyl |
| H | ethyl | pentamethylene | H |
| H | ethyl | pentamethylene | methyl |
| H | methyl | dimethyl | H |
| H | methyl | dimethyl | methyl |
| H | methyl | tetramethylene | H |
| H | methyl | tetramethylene | methyl |
| H | methyl | pentamethylene | H |
| H | methyl | pentamethylene | methyl |
| 4-Cl | ethyl | dimethyl | methyl |
| 4-Cl | ethyl | tetramethylene | H |
| 4-Cl | ethyl | tetramethylene | methyl |
| 4-Cl | ethyl | pentamethylene | H |
| 4-Cl | ethyl | pentamethylene | methyl |
| 4-Cl | methyl | dimethyl | H |
| 4-Cl | methyl | dimethyl | methyl |
| 4-Cl | methyl | tetramethylene | H |
| 4-Cl | methyl | tetramethylene | methyl |
| 4-Cl | methyl | pentamethylene | H |
| 4-Cl | methyl | pentamethylene | methyl |
| 4-F | ethyl | dimethyl | H |
| 4-F | ethyl | dimethyl | methyl |
| 4-F | ethyl | tetramethylene | H |
| 4-F | ethyl | tetramethylene | methyl |
| 4-F | ethyl | pentamethylene | H |
| 4-F | ethyl | pentamethylene | methyl |
| 4-F | methyl | dimethyl | H |
| 4-F | methyl | dimethyl | methyl |
| 4-F | methyl | tetramethylene | H |
| 4-F | methyl | tetramethylene | methyl |
| 4-F | methyl | pentamethylene | H |
| 4-F | methyl | pentamethylene | methyl |
| 4-C(CH3)3 | ethyl | pentamethylene | H |
| 4-C(CH3)3 | ethyl | pentamethylene | methyl |
| 4-SO2CH3 | ethyl | dimethyl | H |
| 4-SO2CH3 | ethyl | dimethyl | methyl |
| 4-SO2CH3 | ethyl | tetramethylene | H |
| 4-SO2CH3 | ethyl | tetramethylene | methyl |
| 4-SO2CH3 | ethyl | pentamethylene | H |
| 4-SO2CH3 | ethyl | pentamethylene | methyl |
| 4-SO2CH3 | methyl | dimethyl | H |
| 4-SO2CH3 | methyl | dimethyl | methyl |
| 4-SO2CH3 | methyl | tetramethylene | H |
| 4-SO2CH3 | methyl | tetramethylene | methyl |
| 4-SO2CH3 | methyl | pentamethylene | H |
| 4-SO2CH3 | methyl | pentamethylene | methyl |

TABLE X

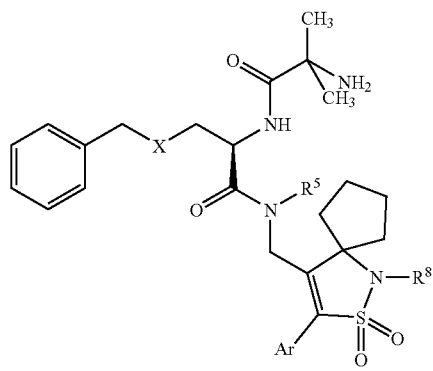

| X | Ar | R⁵ | R⁸ |
|---|---|---|---|
| CH₂ | 1-naphthyl | ethyl | H |
| O | 1-naphthyl | ethyl | H |
| CH₂ | 1-naphthyl | ethyl | methyl |
| O | 1-naphthyl | ethyl | methyl |
| CH₂ | 2-naphthyl | ethyl | H |
| O | 2-naphthyl | ethyl | H |
| CH₂ | 2-naphthyl | ethyl | methyl |
| O | 2-naphthyl | ethyl | methyl |
| CH₂ | pyridin-2-yl | ethyl | H |
| O | pyridin-2-yl | ethyl | H |
| CH₂ | pyridin-2-yl | ethyl | methyl |
| O | pyridin-2-yl | ethyl | methyl |
| CH₂ | pyridin-3-yl | ethyl | H |
| O | pyridin-3-yl | ethyl | H |
| CH₂ | pyridin-3-yl | ethyl | methyl |
| O | pyridin-3-yl | ethyl | methyl |
| CH₂ | pyridin-4-yl | ethyl | H |
| O | pyridin-4-yl | ethyl | H |
| CH₂ | pyridin-4-yl | ethyl | methyl |
| O | pyridin-4-yl | ethyl | methyl |
| CH₂ | 2-thienyl | ethyl | H |
| O | 2-thienyl | ethyl | H |
| CH₂ | 2-thienyl | ethyl | methyl |
| O | 2-thienyl | ethyl | methyl |
| CH₂ | 3-thienyl | ethyl | H |
| O | 3-thienyl | ethyl | H |
| CH₂ | 3-thienyl | ethyl | methyl |
| O | 3-thienyl | ethyl | methyl |
| CH₂ | thiazol-2-yl | ethyl | H |
| O | thiazol-2-yl | ethyl | H |
| CH₂ | thiazol-2-yl | ethyl | methyl |
| O | thiazol-2-yl | ethyl | methyl |
| CH₂ | oxazol-2-yl | ethyl | H |
| O | oxazol-2-yl | ethyl | H |
| CH₂ | oxazol-2-yl | ethyl | methyl |
| O | oxazol-2-yl | ethyl | methyl |
| CH₂ | 1-naphthyl | methyl | H |
| O | 1-naphthyl | methyl | H |
| CH₂ | 1-naphthyl | methyl | methyl |
| O | 1-naphthyl | methyl | methyl |
| CH₂ | 2-naphthyl | methyl | H |
| O | 2-naphthyl | methyl | H |
| CH₂ | 2-naphthyl | methyl | methyl |
| O | 2-naphthyl | methyl | methyl |
| CH₂ | pyridin-2-yl | methyl | H |
| O | pyridin-2-yl | methyl | H |
| CH₂ | pyridin-2-yl | methyl | methyl |
| O | pyridin-2-yl | methyl | methyl |
| CH₂ | pyridin-3-yl | methyl | H |
| O | pyridin-3-yl | methyl | H |
| CH₂ | pyridin-3-yl | methyl | methyl |
| O | pyridin-3-yl | methyl | methyl |
| CH₂ | pyridin-4-yl | methyl | H |
| O | pyridin-4-yl | methyl | H |
| CH₂ | pyridin-4-yl | methyl | methyl |
| O | pyridin-4-yl | methyl | methyl |
| CH₂ | 2-thienyl | methyl | H |
| O | 2-thienyl | methyl | H |

TABLE X-continued

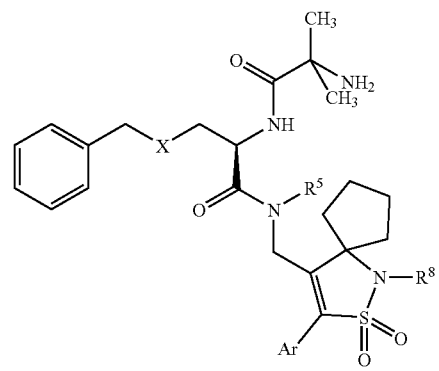

| X | Ar | R⁵ | R⁸ |
|---|---|---|---|
| CH₂ | 2-thienyl | methyl | methyl |
| O | 2-thienyl | methyl | methyl |
| CH₂ | 3-thienyl | methyl | H |
| O | 3-thienyl | methyl | H |
| CH₂ | 3-thienyl | methyl | methyl |
| O | 3-thienyl | methyl | methyl |
| CH₂ | thiazol-2-yl | methyl | H |
| O | thiazol-2-yl | methyl | H |
| CH₂ | thiazol-2-yl | methyl | methyl |
| O | thiazol-2-yl | methyl | methyl |
| CH₂ | oxazol-2-yl | methyl | H |
| O | oxazol-2-yl | methyl | H |
| CH₂ | oxazol-2-yl | methyl | methyl |
| O | oxazol-2-yl | methyl | methyl |
| CH₂ | cyclohexyl | ethyl | H |
| O | cyclohexyl | ethyl | H |
| CH₂ | cyclohexyl | ethyl | methyl |
| O | cyclohexyl | ethyl | methyl |
| CH₂ | isopropyl | ethyl | H |
| O | isopropyl | ethyl | H |
| CH₂ | isopropyl | ethyl | methyl |
| O | isopropyl | ethyl | methyl |
| CH₂ | cyclohexyl | methyl | H |
| O | cyclohexyl | methyl | H |
| CH₂ | cyclohexyl | methyl | Thethyl |
| O | cyclohexyl | methyl | methyl |
| CH₂ | isopropyl | methyl | H |
| O | isopropyl | methyl | H |
| CH₂ | isopropyl | methyl | methyl |
| O | isopropyl | methyl | methyl |

TABLE XI

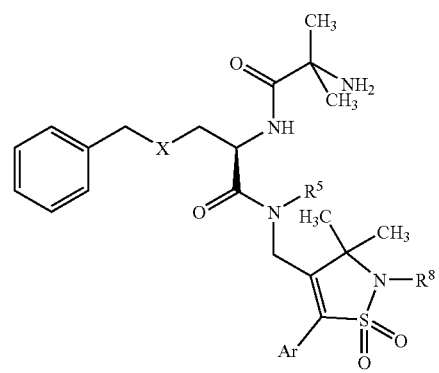

| X | Ar | R⁵ | R⁸ |
|---|---|---|---|
| CH₂ | 1-naphthyl | ethyl | H |
| O | 1-naphthyl | ethyl | H |
| CH₂ | 1-naphthyl | ethyl | methyl |

TABLE XI-continued

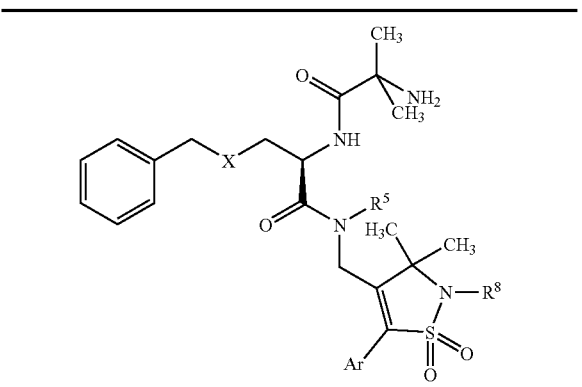

| X | Ar | R⁵ | R⁸ |
|---|---|---|---|
| O | 1-naphthyl | ethyl | methyl |
| CH₂ | 2-naphthyl | ethyl | H |
| O | 2-naphthyl | ethyl | H |
| CH₂ | 2-naphthyl | ethyl | methyl |
| O | 2-naphthyl | ethyl | methyl |
| CH₂ | pyridin-2-yl | ethyl | H |
| O | pyridin-2-yl | ethyl | H |
| CH₂ | pyridin-2-yl | ethyl | methyl |
| O | pyridin-2-yl | ethyl | methyl |
| CH₂ | pyridin-3-yl | ethyl | H |
| O | pyridin-3-yl | ethyl | H |
| CH₂ | pyridin-3-yl | ethyl | methyl |
| O | pyridin-3-yl | ethyl | methyl |
| CH₂ | pyridin-4-yl | ethyl | H |
| O | pyridin-4-yl | ethyl | H |
| CH₂ | pyridin-4-yl | ethyl | methyl |
| O | pyridin-4-yl | ethyl | methyl |
| CH₂ | 2-thienyl | ethyl | H |
| O | 2-thienyl | ethyl | H |
| CH₂ | 2-thienyl | ethyl | methyl |
| O | 2-thienyl | ethyl | methyl |
| CH₂ | 3-thienyl | ethyl | H |
| O | 3-thienyl | ethyl | H |
| CH₂ | 3-thienyl | ethyl | methyl |
| O | 3-thienyl | ethyl | methyl |
| CH₂ | thiazol-2-yl | ethyl | H |
| O | thiazol-2-yl | ethyl | H |
| CH₂ | thiazol-2-yl | ethyl | methyl |
| O | thiazol-2-yl | ethyl | methyl |
| CH₂ | oxazol-2-yl | ethyl | H |
| O | oxazol-2-yl | ethyl | H |
| CH₂ | oxazol-2-yl | ethyl | methyl |
| O | oxazol-2-yl | ethyl | methyl |
| CH₂ | 1-naphthyl | methyl | H |
| O | 1-naphthyl | methyl | H |
| CH₂ | 1-naphthyl | methyl | methyl |
| O | 1-naphthyl | methyl | methyl |
| CH₂ | 2-naphthyl | methyl | H |
| O | 2-naphthyl | methyl | H |
| CH₂ | 2-naphthyl | methyl | methyl |
| O | 2-naphthyl | methyl | methyl |
| CH₂ | pyridin-2-yl | methyl | H |
| O | pyridin-2-yl | methyl | H |
| CH₂ | pyridin-2-yl | methyl | methyl |
| O | pyridin-2-yl | methyl | methyl |
| CH₂ | pyridin-3-yl | methyl | H |
| O | pyridin-3-yl | methyl | H |
| CH₂ | pyridin-3-yl | methyl | methyl |
| O | pyridin-3-yl | methyl | methyl |
| CH₂ | pyridin-4-yl | methyl | H |
| O | pyridin-4-yl | methyl | H |
| CH₂ | pyridin-4-yl | methyl | methyl |
| O | pyridin-4-yl | methyl | methyl |
| CH₂ | 2-thienyl | methyl | H |
| O | 2-thienyl | methyl | H |
| CH₂ | 2-thienyl | methyl | methyl |
| O | 2-thienyl | methyl | methyl |
| CH₂ | 3-thienyl | methyl | H |

TABLE XI-continued

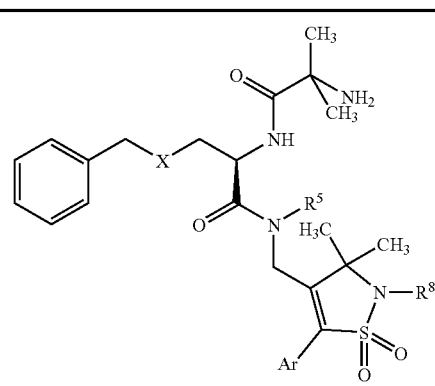

| X | Ar | R⁵ | R⁸ |
|---|---|---|---|
| O | 3-thienyl | methyl | H |
| CH₂ | 3-thienyl | methyl | methyl |
| O | 3-thienyl | methyl | methyl |
| CH₂ | thiazol-2-yl | methyl | H |
| O | thiazol-2-yl | methyl | H |
| CH₂ | thiazol-2-yl | methyl | methyl |
| O | thiazol-2-yl | methyl | methyl |
| CH₂ | oxazol-2-yl | methyl | H |
| O | oxazol-2-yl | methyl | H |
| CH₂ | oxazol-2-yl | methyl | methyl |
| O | oxazol-2-yl | methyl | methyl |

TABLE XII

| X | Y | R⁶ |
|---|---|---|
| CH₂ | H | H |
| O | H | H |
| CH₂ | H | methyl |
| O | H | methyl |
| CH₂ | 4-Cl | methyl |
| O | 4-Cl | methyl |
| CH₂ | 3-Cl | H |
| O | 3-Cl | H |
| CH₂ | 3-Cl | methyl |
| O | 3-Cl | methyl |
| CH₂ | 2-Cl | H |
| O | 2-Cl | H |
| CH₂ | 2-Cl | methyl |
| O | 2-Cl | methyl |
| CH₂ | 4-F | H |
| O | 4-F | H |
| CH₂ | 4-F | methyl |
| O | 4-F | methyl |
| CH₂ | 3-F | H |
| O | 3-F | H |

TABLE XII-continued

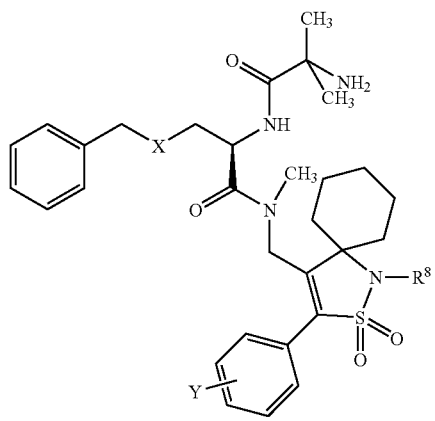

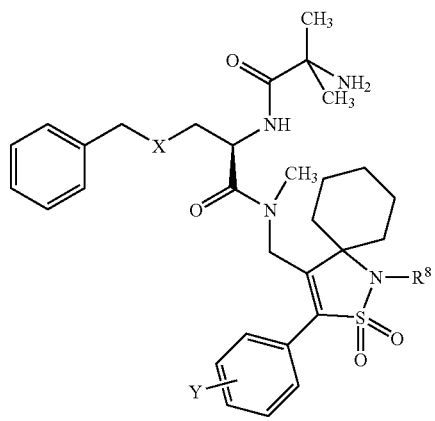

| X | Y | R6 |
|---|---|---|
| CH2 | 3-F | methyl |
| O | 3-F | methyl |
| CH2 | 2-F | H |
| O | 2-F | H |
| CH2 | 2-F | methyl |
| O | 2-F | methyl |
| CH2 | 3-Br | H |
| O | 3-Br | H |
| CH2 | 3-Br | methyl |
| O | 3-Br | methyl |
| CH2 | 4-Br | H |
| O | 4-Br | H |
| CH2 | 4-Br | methyl |
| O | 4-Br | methyl |
| CH2 | 4-CH3 | H |
| O | 4-CH3 | H |
| CH2 | 4-CH3 | methyl |
| O | 4-CH3 | methyl |
| CH2 | 3-CH3 | H |
| O | 3-CH3 | H |
| CH2 | 3-CH3 | methyl |
| O | 3-CH3 | methyl |
| CH2 | 4-CF3 | H |
| O | 4-CF3 | H |
| CH2 | 4-CF3 | methyl |
| O | 4-CF3 | methyl |
| CH2 | 3-CF3 | H |
| O | 3-CF3 | H |
| CH2 | 3-CF3 | methyl |
| O | 3-CF3 | methyl |
| CH2 | 4-OCH3 | H |
| O | 4-OCH3 | H |
| CH2 | 4-OCH3 | methyl |
| O | 4-OCH3 | methyl |
| CH2 | 3-OCH3 | H |
| O | 3-OCH3 | H |
| CH2 | 3-OCH3 | methyl |
| O | 3-OCH3 | methyl |
| CH2 | 4-C(CH3)3 | H |
| O | 4-C(CH3)3 | H |
| CH2 | 4-C(CH3)3 | methyl |
| O | 4-C(CH3)3 | methyl |
| CH2 | 4-CN | H |
| O | 4-CN | H |
| CH2 | 4-CN | methyl |
| O | 4-CN | methyl |
| CH2 | 3-CN | H |
| O | 3-CN | H |
| CH2 | 3-CN | methyl |
| O | 3-CN | methyl |
| CH2 | 4-SO2CH3 | H |
| O | 4-SO2CH3 | H |
| CH2 | 4-SO2CH3 | methyl |
| O | 4-SO2CH3 | methyl |
| CH2 | 3-SO2CH3 | H |
| O | 3-SO2CH3 | H |
| CH2 | 3-SO2CH3 | methyl |
| O | 3-SO2CH3 | methyl |
| CH2 | 3-phenoxy | H |
| O | 3-phenoxy | H |
| CH2 | 3-phenoxy | methyl |
| O | 3-phenoxy | methyl |
| CH2 | 4-phenoxy | H |
| O | 4-phenoxy | H |
| CH2 | 4-phenoxy | methyl |
| O | 4-phenoxy | methyl |
| CH2 | 2,4-F2 | H |
| O | 2,4-F2 | H |
| CH2 | 2,4-F2 | methyl |
| O | 2,4-F2 | methyl |
| CH2 | 3,4-F2 | H |
| O | 3,4-F2 | H |
| CH2 | 3,4-F2 | methyl |
| O | 3,4-F2 | methyl |
| CH2 | 3,5-F2 | H |
| O | 3,5-F2 | H |
| CH2 | 3,5-F2 | methyl |
| O | 3,5-F2 | methyl |
| CH2 | 2,3-F2 | H |
| O | 2,3-F2 | H |
| CH2 | 2,3-F2 | methyl |
| O | 2,3-F2 | methyl |
| CH2 | 2,6-F2 | H |
| O | 2,6-F2 | H |
| CH2 | 2,6-F2 | methyl |
| O | 2,6-F2 | methyl |
| CH2 | 2,5-F2 | H |
| O | 2,5-F2 | H |
| CH2 | 2,5-F2 | methyl |
| O | 2,5-F2 | methyl |
| CH2 | 2-F-3-Cl | H |
| O | 2-F-3-Cl | H |
| CH2 | 2-F-3-Cl | methyl |
| O | 2-F-3-Cl | methyl |
| CH2 | 3,4-F2 | H |
| O | 3,4-F2 | H |
| CH2 | 3,4-Cl2 | methyl |
| O | 3,4-Cl2 | methyl |
| CH2 | 3-phenyl | H |
| O | 3-phenyl | H |
| CH2 | 3-phenyl | methyl |
| O | 3-phenyl | methyl |
| CH2 | 4-phenyl | H |
| O | 4-phenyl | H |
| CH2 | 4-phenyl | methyl |
| O | 4-phenyl | methyl |
| CH2 | 3-(4-fluorophenyl) | H |
| O | 3-(4-fluorophenyl) | H |
| CH2 | 3-(4-fluorophenyl) | methyl |
| O | 3-(4-fluorophenyl) | methyl |
| CH2 | 4-(4-fluorophenyl) | H |
| O | 4-(4-fluorophenyl) | H |

TABLE XII-continued

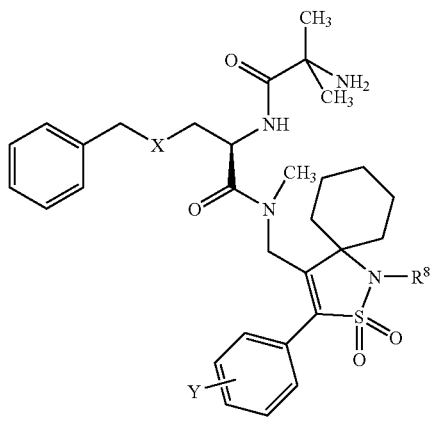

| X | Y | R⁶ |
|---|---|---|
| CH₂ | 4-(4-fluorophenyl) | methyl |
| O | 4-(4-fluorophenyl) | methyl |
| CH₂ | 3-(4-chlorophenyl) | H |
| O | 3-(4-chlorophenyl) | H |
| CH₂ | 3-(4-chlorophenyl) | methyl |
| O | 3-(4-chlorophenyl) | methyl |
| CH₂ | 4-(4-chlorophenyl) | H |
| O | 4-(4-chlorophenyl) | H |
| CH₂ | 4-(4-chlorophenyl) | methyl |
| O | 4-(4-chlorophenyl) | methyl |
| CH₂ | 3-(4-(CF₃)phenyl) | H |
| O | 3-(4-(CF₃)phenyl) | H |
| CH₂ | 3-(4-(CF₃)phenyl) | methyl |
| O | 3-(4-(CF₃)phenyl) | methyl |
| CH₂ | 4-(4-(CF₃)phenyl) | H |
| O | 4-(4-(CF₃)phenyl) | H |
| CH₂ | 4-(4-(CF₃)phenyl) | methyl |
| O | 4-(4-(CF₃)phenyl) | methyl |
| CH₂ | 3-(2-thienyl) | H |
| O | 3-(2-thienyl) | H |
| CH₂ | 3-(2-thienyl) | methyl |
| O | 3-(2-thienyl) | methyl |
| CH₂ | 4-(2-thienyl) | H |
| O | 4-(2-thienyl) | H |
| CH₂ | 4-(2-thienyl) | methyl |
| O | 4-(2-thienyl) | methyl |
| CH₂ | 3-(3-thienyl) | H |
| O | 3-(3-thienyl) | H |
| CH₂ | 3-(3-thienyl) | methyl |
| O | 3-(3-thienyl) | methyl |
| CH₂ | 4-(3-thienyl) | H |
| O | 4-(3-thienyl) | H |
| CH₂ | 4-(3-thienyl) | methyl |
| O | 4-(3-thienyl) | methyl |
| CH₂ | 3-(5-chloro-2-thienyl) | H |
| O | 3-(5-chloro-2-thienyl) | H |
| CH₂ | 3-(5-chloro-2-thienyl) | methyl |
| O | 3-(5-chloro-2-thienyl) | methyl |
| CH₂ | 4-(5-chloro-2-thienyl) | H |
| O | 4-(5-chloro-2-thienyl) | H |
| CH₂ | 4-(5-chloro-2-thienyl) | methyl |
| O | 4-(5-chloro-2-thienyl) | methyl |
| CH₂ | 4-(pyridin-2-yl) | H |
| O | 4-(pyridin-2-yl) | H |
| CH₂ | 4-(pyridin-2-yl) | methyl |
| O | 4-(pyridin-2-yl) | methyl |
| CH₂ | 4-(pyridin-3-yl) | H |
| O | 4-(pyridin-3-yl) | H |
| CH₂ | 4-(pyridin-3-yl) | methyl |

TABLE XII-continued

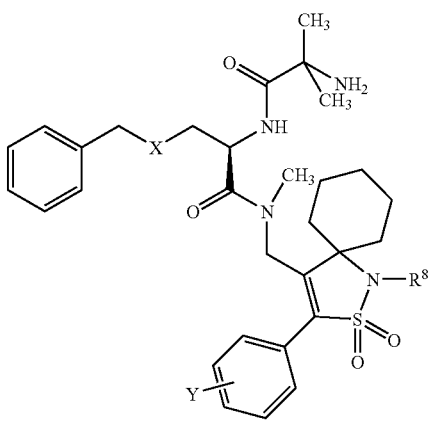

| X | Y | R⁶ |
|---|---|---|
| O | 4-(pyridin-3-yl) | methyl |
| CH₂ | 3-(pyridin-4-yl) | H |
| O | 3-(pyridin-4-yl) | H |
| CH₂ | 3-(pyridin-4-yl) | methyl |
| O | 3-(pyridin-4-yl) | methyl |
| CH₂ | 4-(pyridin-4-yl) | H |
| O | 4-(pyridin-4-yl) | H |
| CH₂ | 4-(pyridin-4-yl) | methyl |
| O | 4-(pyridin-4-yl) | methyl |
| CH₂ | 3-(thiazol-2-yl) | H |
| O | 3-(thiazol-2-yl) | H |
| CH₂ | 3-(thiazol-2-yl) | methyl |
| O | 3-(thiazol-2-yl) | methyl |
| CH₂ | 4-(thiazol-2-yl) | H |
| O | 4-(thiazol-2-yl) | H |
| CH₂ | 4-(thiazol-2-yl) | methyl |
| O | 4-(thiazol-2-yl) | methyl |
| CH₂ | 3-(oxazol-2-yl) | H |
| O | 3-(oxazol-2-yl) | H |
| CH₂ | 3-(oxazol-2-yl) | methyl |
| O | 3-(oxazol-2-yl) | methyl |
| CH₂ | 4-(oxazol-2-yl) | H |
| O | 4-(oxazol-2-yl) | H |
| CH₂ | 4-(oxazol-2-yl) | methyl |
| O | 4-(oxazol-2-yl) | methyl |
| CH₂ | 3-NO₂ | H |
| O | 3-NO₂ | H |
| CH₂ | 3-NO₂ | methyl |
| O | 3-NO₂ | methyl |
| CH₂ | 4-NO₂ | H |
| O | 4-NO₂ | H |
| CH₂ | 4-NO₂ | methyl |
| O | 4-NO₂ | methyl |
| CH₂ | 4-C₂H₅ | H |
| O | 4-C₂H₅ | H |
| CH₂ | 4-C₂H₅ | methyl |
| O | 4-C₂H₅ | methyl |
| CH₂ | 4-OC₂H₅ | H |
| O | 4-OC₂H₅ | H |
| CH₂ | 4-OC₂H₅ | methyl |
| O | 4-OC₂H₅ | methyl |
| CH₂ | 4-CONH₂ | H |
| O | 4-CONH₂ | H |
| CH₂ | 4-CONH₂ | methyl |
| O | 4-CONH₂ | methyl |

TABLE XIII

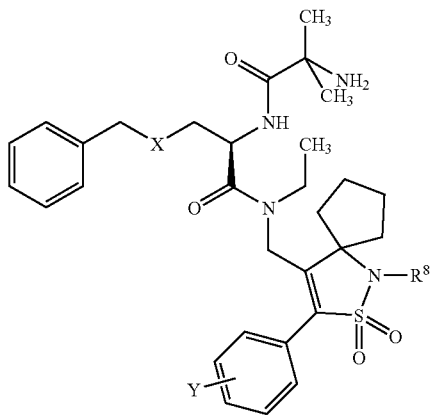

| X | Y | R⁸ |
|---|---|---|
| CH₂ | H | methyl |
| O | H | methyl |
| CH₂ | 4-Cl | H |
| CH₂ | 4-Cl | methyl |
| O | 4-Cl | methyl |
| CH₂ | 3-Cl | H |
| O | 3-Cl | H |
| CH₂ | 3-Cl | methyl |
| O | 3-Cl | methyl |
| CH₂ | 2-Cl | H |
| O | 2-Cl | H |
| CH₂ | 2-Cl | methyl |
| O | 2-Cl | methyl |
| CH₂ | 4-F | H |
| O | 4-F | H |
| CH₂ | 4-F | methyl |
| O | 4-F | methyl |
| CH₂ | 3-F | H |
| O | 3-F | H |
| CH₂ | 3-F | methyl |
| O | 3-F | methyl |
| CH₂ | 2-F | H |
| O | 2-F | H |
| CH₂ | 2-F | methyl |
| O | 2-F | methyl |
| CH₂ | 3-Br | H |
| O | 3-Br | H |
| CH₂ | 3-Br | methyl |
| O | 3-Br | methyl |
| CH₂ | 4-Br | H |
| O | 4-Br | H |
| CH₂ | 4-Br | methyl |
| O | 4-Br | methyl |
| CH₂ | 4-CH₃ | H |
| O | 4-CH₃ | H |
| CH₂ | 4-CH₃ | methyl |
| O | 4-CH₃ | methyl |
| CH₂ | 3-CH₃ | H |
| O | 3-CH₃ | H |
| CH₂ | 3-CH₃ | methyl |
| O | 3-CH₃ | methyl |
| CH₂ | 4-CF₃ | H |
| O | 4-CF₃ | H |
| CH₂ | 4-CF₃ | methyl |
| O | 4-CF₃ | methyl |
| CH₂ | 3-CF₃ | H |
| O | 3-CF₃ | H |
| CH₂ | 3-CF₃ | methyl |
| O | 3-CF₃ | methyl |
| CH₂ | 4-OCH₃ | H |
| O | 4-OCH₃ | H |
| CH₂ | 4-OCH₃ | methyl |
| O | 4-OCH₃ | methyl |
| CH₂ | 3-OCH₃ | H |
| O | 3-OCH₃ | H |
| CH₂ | 3-OCH₃ | methyl |

TABLE XIII-continued

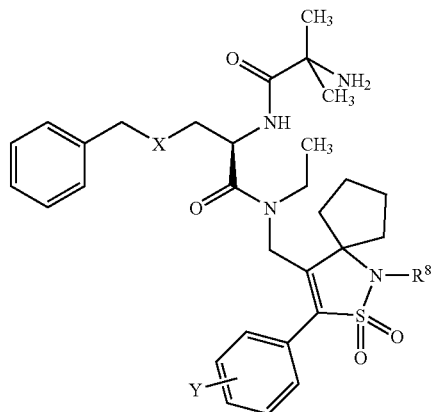

| X | Y | R⁸ |
|---|---|---|
| O | 3-OCH₃ | methyl |
| CH₂ | 4-C(CH₃)₃ | H |
| O | 4-C(CH₃)₃ | H |
| CH₂ | 4-C(CH₃)₃ | methyl |
| O | 4-C(CH₃)₃ | methyl |
| CH₂ | 4-CN | H |
| O | 4-CN | H |
| CH₂ | 4-CN | methyl |
| O | 4-CN | methyl |
| CH₂ | 3-CN | H |
| O | 3-CN | H |
| CH₂ | 3-CN | methyl |
| O | 3-CN | methyl |
| CH₂ | 4-SO₂CH₃ | H |
| O | 4-SO₂CH₃ | H |
| CH₂ | 4-SO₂CH₃ | methyl |
| O | 4-SO₂CH₃ | methyl |
| CH₂ | 3-SO₂CH₃ | H |
| O | 3-SO₂CH₃ | H |
| CH₂ | 3-SO₂CH₃ | methyl |
| O | 3-SO₂CH₃ | methyl |
| CH₂ | 3-phenoxy | H |
| O | 3-phenoxy | H |
| CH₂ | 3-phenoxy | methyl |
| O | 3-phenoxy | methyl |
| CH₂ | 4-phenoxy | H |
| O | 4-phenoxy | H |
| CH₂ | 4-phenoxy | methyl |
| O | 4-phenoxy | methyl |
| CH₂ | 2,4-F₂ | H |
| O | 2,4-F₂ | H |
| CH₂ | 2,4-F₂ | methyl |
| O | 2,4-F₂ | methyl |
| CH₂ | 3,4-F₂ | H |
| O | 3,4-F₂ | H |
| CH₂ | 3,4-F₂ | methyl |
| O | 3,4-F₂ | methyl |
| CH₂ | 3,5-F₂ | H |
| O | 3,5-F₂ | H |
| CH₂ | 3,5-F₂ | methyl |
| O | 3,5-F₂ | methyl |
| CH₂ | 2,3-F₂ | H |
| O | 2,3-F₂ | H |
| CH₂ | 2,3-F₂ | methyl |
| O | 2,3-F₂ | methyl |
| CH₂ | 2,6-F₂ | H |
| O | 2,6-F₂ | H |
| CH₂ | 2,6-F₂ | methyl |
| O | 2,6-F₂ | methyl |
| CH₂ | 2,5-F₂ | H |
| O | 2,5-F₂ | H |
| CH₂ | 2,5-F₂ | methyl |
| O | 2,5-F₂ | methyl |
| CH₂ | 2-F-3-Cl | H |
| O | 2-F-3-Cl | H |
| CH₂ | 2-F-3-Cl | methyl |

TABLE XIII-continued

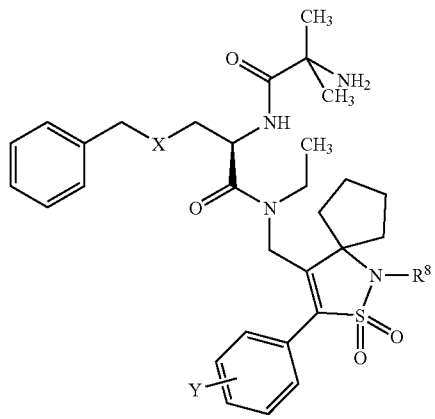

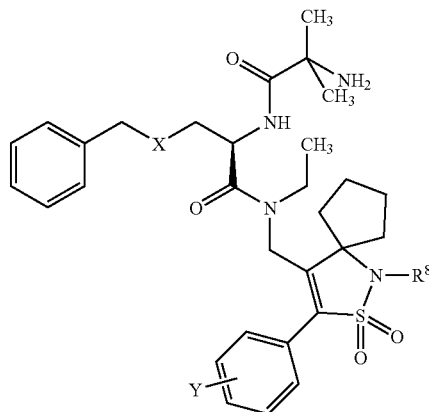

| X | Y | R8 |
|---|---|---|
| O | 2-F-3-Cl | methyl |
| CH2 | 3,4-Cl2 | H |
| O | 3,4-Cl2 | H |
| CH2 | 3,4-Cl2 | methyl |
| O | 3,4-Cl2 | methyl |
| CH2 | 3-phenyl | H |
| O | 3-phenyl | H |
| CH2 | 3-phenyl | methyl |
| O | 3-phenyl | methyl |
| CH2 | 4-phenyl | H |
| O | 4-phenyl | H |
| CH2 | 4-phenyl | methyl |
| O | 4-phenyl | methyl |
| CH2 | 3-(4-fluorophenyl) | H |
| O | 3-(4-fluorophenyl) | H |
| CH2 | 3-(4-fluorophenyl) | methyl |
| O | 3-(4-fluorophenyl) | methyl |
| CH2 | 4-(4-fluorophenyl) | H |
| O | 4-(4-fluorophenyl) | H |
| CH2 | 4-(4-fluorophenyl) | methyl |
| O | 4-(4-fluorophenyl) | methyl |
| CH2 | 3-(4-chlorophenyl) | H |
| O | 3-(4-chlorophenyl) | H |
| CH2 | 3-(4-chlorophenyl) | methyl |
| O | 3-(4-chlorophenyl) | methyl |
| CH2 | 4-(4-chlorophenyl) | H |
| O | 4-(4-chlorophenyl) | H |
| CH2 | 4-(4-chlorophenyl) | methyl |
| O | 4-(4-chlorophenyl) | methyl |
| CH2 | 3-(4-(CF3)phenyl) | H |
| O | 3-(4-(CF3)phenyl) | H |
| CH2 | 3-(4-(CF3)phenyl) | methyl |
| O | 3-(4-(CF3)phenyl) | methyl |
| CH2 | 4-(4-(CF3)phenyl) | H |
| O | 4-(4-(CF3)phenyl) | H |
| CH2 | 4-(4-(CF3)phenyl) | methyl |
| O | 4-(4-(CF3)phenyl) | methyl |
| CH2 | 3-(2-thienyl) | H |
| O | 3-(2-thienyl) | H |
| CH2 | 3-(2-thienyl) | methyl |
| O | 3-(2-thienyl) | methyl |
| CH2 | 4-(2-thienyl) | H |
| O | 4-(2-thienyl) | H |
| CH2 | 4-(2-thienyl) | methyl |
| O | 4-(2-thienyl) | methyl |
| CH2 | 3-(3-thienyl) | H |
| O | 3-(3-thienyl) | H |
| CH2 | 3-(3-thienyl) | methyl |
| O | 3-(3-thienyl) | methyl |
| CH2 | 4-(3-thienyl) | H |
| O | 4-(3-thienyl) | H |
| CH2 | 4-(3-thienyl) | methyl |
| O | 4-(3-thienyl) | methyl |
| CH2 | 3-(5-chloro-2-thienyl) | H |
| O | 3-(5-chloro-2-thienyl) | H |
| CH2 | 3-(5-chloro-2-thienyl) | methyl |
| O | 3-(5-chloro-2-thienyl) | methyl |
| CH2 | 4-(5-chloro-2-thienyl) | H |
| O | 4-(5-chloro-2-thienyl) | H |
| CH2 | 4-(5-chloro-2-thienyl) | methyl |
| O | 4-(5-chloro-2-thienyl) | methyl |
| CH2 | 4-(pyridin-2-yl) | H |
| O | 4-(pyridin-2-yl) | H |
| CH2 | 4-(pyridin-2-yl) | methyl |
| O | 4-(pyridin-2-yl) | methyl |
| CH2 | 4-(pyridin-3-yl) | H |
| O | 4-(pyridin-3-yl) | H |
| CH2 | 4-(pyridin-3-yl) | methyl |
| O | 4-(pyridin-3-yl) | methyl |
| CH2 | 3-(pyridin-4-yl) | H |
| O | 3-(pyridin-4-yl) | H |
| CH2 | 3-(pyridin-4-yl) | methyl |
| O | 3-(pyridin-4-yl) | methyl |
| CH2 | 4-(pyridin-4-yl) | H |
| O | 4-(pyridin-4-yl) | H |
| CH2 | 4-(pyridin-4-yl) | methyl |
| O | 4-(pyridin-4-yl) | methyl |
| CH2 | 3-(thiazol-2-yl) | H |
| O | 3-(thiazol-2-yl) | H |
| CH2 | 3-(thiazol-2-yl) | methyl |
| O | 3-(thiazol-2-yl) | methyl |
| CH2 | 4-(thiazol-2-yl) | H |
| O | 4-(thiazol-2-yl) | H |
| CH2 | 4-(thiazol-2-yl) | methyl |
| O | 4-(thiazol-2-yl) | methyl |
| CH2 | 3-(oxazol-2-yl) | H |
| O | 3-(oxazol-2-yl) | H |
| CH2 | 3-(oxazol-2-yl) | methyl |
| O | 3-(oxazol-2-yl) | methyl |
| CH2 | 4-(oxazol-2-yl) | H |
| O | 4-(oxazol-2-yl) | H |
| CH2 | 4-(oxazol-2-yl) | methyl |
| O | 4-(oxazol-2-yl) | methyl |
| CH2 | 3-NO2 | H |
| O | 3-NO2 | H |
| CH2 | 3-NO2 | methyl |
| O | 3-NO2 | methyl |
| CH2 | 4-NO2 | H |
| O | 4-NO2 | H |
| CH2 | 4-NO2 | methyl |
| O | 4-NO2 | methyl |
| CH2 | 4-C2H5 | H |
| O | 4-C2H5 | H |
| CH2 | 4-C2H5 | methyl |
| O | 4-C2H5 | methyl |
| CH2 | 4-OC2H5 | H |
| O | 4-OC2H5 | H |
| CH2 | 4-OC2H5 | methyl |
| O | 4-OC2H5 | methyl |
| CH2 | 4-CONH2 | H |
| O | 4-CONH2 | H |

TABLE XIII-continued

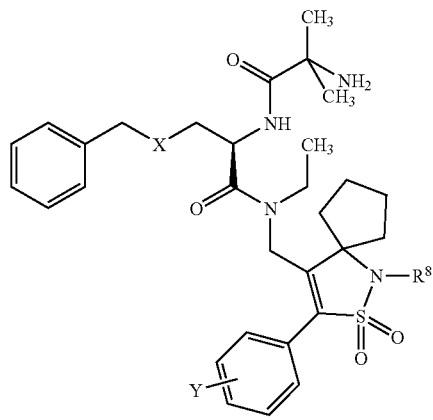

| X | Y | R[8] |
|---|---|---|
| CH$_2$ | 4-CONH$_2$ | methyl |
| O | 4-CONH$_2$ | methyl |

TABLE XIV

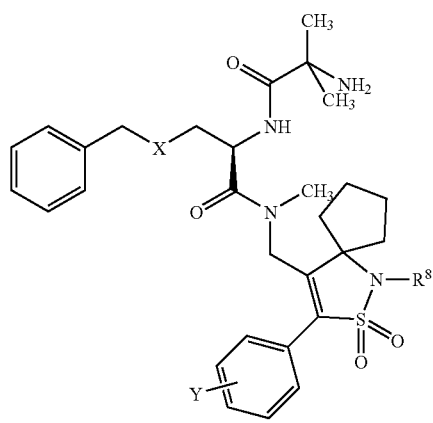

| X | Y | R[8] |
|---|---|---|
| CH$_2$ | H | H |
| O | H | H |
| CH$_2$ | H | methyl |
| O | H | methyl |
| CH$_2$ | 4-Cl | H |
| O | 4-Cl | H |
| CH$_2$ | 4-Cl | methyl |
| O | 4-Cl | methyl |
| CH$_2$ | 3-Cl | H |
| O | 3-Cl | H |
| CH$_2$ | 3-Cl | methyl |
| O | 3-Cl | methyl |
| CH$_2$ | 2-Cl | H |
| O | 2-Cl | H |
| CH$_2$ | 2-Cl | methyl |
| O | 2-Cl | methyl |
| CH$_2$ | 4-F | H |
| O | 4-F | H |
| CH$_2$ | 4-F | methyl |
| O | 4-F | methyl |
| CH$_2$ | 3-F | H |
| O | 3-F | H |
| CH$_2$ | 3-F | methyl |
| O | 3-F | methyl |
| CH$_2$ | 2-F | H |
| O | 2-F | H |

TABLE XIV-continued

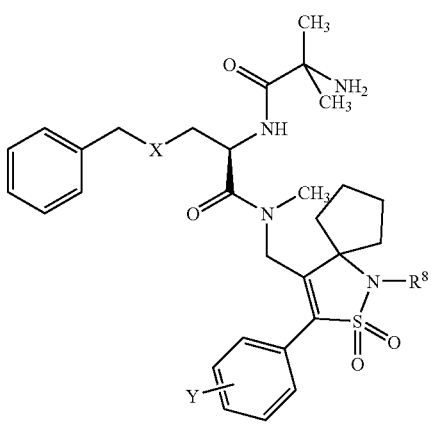

| X | Y | R[8] |
|---|---|---|
| CH$_2$ | 2-F | methyl |
| O | 2-F | methyl |
| CH$_2$ | 3-Br | H |
| O | 3-Br | H |
| CH$_2$ | 3-Br | methyl |
| O | 3-Br | methyl |
| CH$_2$ | 4-Br | H |
| O | 4-Br | H |
| CH$_2$ | 4-Br | methyl |
| O | 4-Br | methyl |
| CH$_2$ | 4-CH$_3$ | H |
| O | 4-CH$_3$ | H |
| CH$_2$ | 4-CH$_3$ | methyl |
| O | 4-CH$_3$ | methyl |
| CH$_2$ | 3-CH$_3$ | H |
| O | 3-CH$_3$ | H |
| CH$_2$ | 3-CH$_3$ | methyl |
| O | 3-CH$_3$ | methyl |
| CH$_2$ | 4-CF$_3$ | H |
| O | 4-CF$_3$ | H |
| CH$_2$ | 4-CF$_3$ | methyl |
| O | 4-CF$_3$ | methyl |
| CH$_2$ | 3-CF$_3$ | H |
| O | 3-CF$_3$ | H |
| CH$_2$ | 3-CF$_3$ | methyl |
| O | 3-CF$_3$ | methyl |
| CH$_2$ | 4-OCH$_3$ | H |
| O | 4-OCH$_3$ | H |
| CH$_2$ | 4-OCH$_3$ | methyl |
| O | 4-OCH$_3$ | methyl |
| CH$_2$ | 3-OCH$_3$ | H |
| O | 3-OCH$_3$ | H |
| CH$_2$ | 3-OCH$_3$ | methyl |
| O | 3-OCH$_3$ | methyl |
| CH$_2$ | 4-C(CH$_3$)$_3$ | H |
| O | 4-C(CH$_3$)$_3$ | H |
| CH$_2$ | 4-C(CH$_3$)$_3$ | methyl |
| O | 4-C(CH$_3$)$_3$ | methyl |
| CH$_2$ | 4-CN | H |
| O | 4-CN | H |
| CH$_2$ | 4-CN | methyl |
| O | 4-CN | methyl |
| CH$_2$ | 3-CN | H |
| O | 3-CN | H |
| CH$_2$ | 3-CN | methyl |
| O | 3-CN | methyl |

TABLE XIV-continued

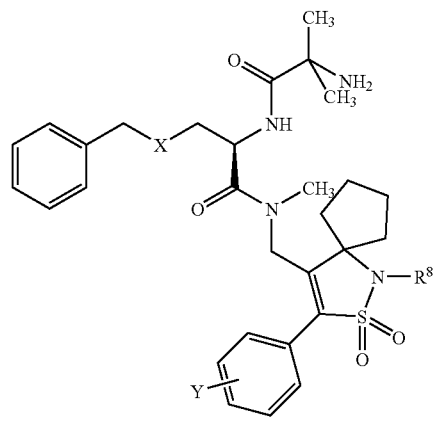

| X | Y | R⁸ |
|---|---|---|
| CH₂ | 4-SO₂CH₃ | H |
| O | 4-SO₂CH₃ | H |
| CH₂ | 4-SO₂CH₃ | methyl |
| O | 4-SO₂CH₃ | methyl |
| CH₂ | 3-SO₂CH₃ | H |
| O | 3-SO₂CH₃ | H |
| CH₂ | 3-SO₂CH₃ | methyl |
| O | 3-SO₂CH₃ | methyl |
| CH₂ | 3-phenoxy | H |
| O | 3-phenoxy | H |
| CH₂ | 3-phenoxy | methyl |
| O | 3-phenoxy | methyl |
| CH₂ | 4-phenoxy | H |
| O | 4-phenoxy | H |
| CH₂ | 4-phenoxy | methyl |
| O | 4-phenoxy | methyl |
| CH₂ | 2,4-F₂ | H |
| O | 2,4-F₂ | H |
| CH₂ | 2,4-F₂ | methyl |
| O | 2,4-F₂ | methyl |
| Ol[]l2 | 3,4-F₂ | H |
| O | 3,4-F₂ | H |
| CH₂ | 3,4-F₂ | methyl |
| O | 3,4-F₂ | methyl |
| CH₂ | 3,5-F₂ | H |
| O | 3,5-F₂ | H |
| CH₂ | 3,5-F₂ | methyl |
| O | 3,5-F₂ | methyl |
| CH₂ | 2,3-F₂ | CH₂ |
| O | 2,3-F₂ | O |
| CH₂ | 2,3-F₂ | CH₂ |
| O | 2,3-F₂ | O |
| CH₂ | 2,6-F₂ | CH₂ |
| O | 2,6-F₂ | O |
| CH₂ | 2,6-F₂ | CH₂ |
| O | 2,6-F₂ | O |
| CH₂ | 2,5-F₂ | CH₂ |
| O | 2,5-F₂ | O |
| CH₂ | 2,5-F₂ | CH₂ |
| O | 2,5-F₂ | O |
| CH₂ | 2-F-3-Cl | CH₂ |
| O | 2-F-3-Cl | O |
| CH₂ | 2-F-3-Cl | CH₂ |
| O | 2-F-3-Cl | O |
| CH₂ | 3,4-Cl₂ | H |
| O | 3,4-Cl₂ | H |
| CH₂ | 3,4-Cl₂ | methyl |
| O | 3,4-Cl₂ | methyl |

TABLE XIV-continued

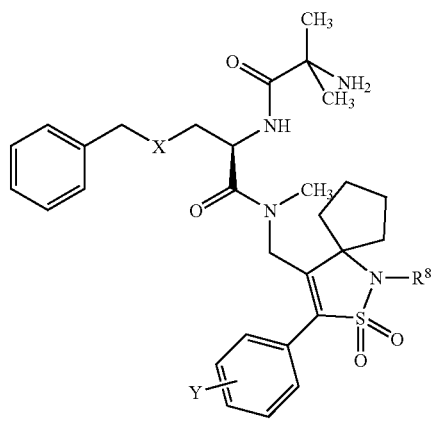

| X | Y | R⁸ |
|---|---|---|
| CH₂ | 3-phenyl | H |
| O | 3-phenyl | H |
| CH₂ | 3-phenyl | methyl |
| O | 3-phenyl | methyl |
| CH₂ | 4-phenyl | H |
| O | 4-phenyl | H |
| CH₂ | 4-phenyl | methyl |
| O | 4-phenyl | methyl |
| CH₂ | 3-(4-fluorophenyl) | H |
| O | 3-(4-fluorophenyl) | H |
| CH₂ | 3-(4-fluorophenyl) | methyl |
| O | 3-(4-fluorophenyl) | methyl |
| CH₂ | 4-(4-fluorophenyl) | H |
| O | 4-(4-fluorophenyl) | H |
| CH₂ | 4-(4-fluorophenyl) | methyl |
| O | 4-(4-fluorophenyl) | methyl |
| CH₂ | 3-(4-chlorophenyl) | H |
| O | 3-(4-chlorophenyl) | H |
| CH₂ | 3-(4-chlorophenyl) | methyl |
| O | 3-(4-chlorophenyl) | methyl |
| CH₂ | 4-(4-chlorophenyl) | H |
| O | 4-(4-chlorophenyl) | H |
| CH₂ | 4-(4-chlorophenyl) | methyl |
| O | 4-(4-chlorophenyl) | methyl |
| CH₂ | 3-(4-(CF₃)phenyl) | H |
| O | 3-(4-(CF₃)phenyl) | H |
| CH₂ | 3-(4-(CF₃)phenyl) | methyl |
| O | 3-(4-(CF₃)phenyl) | methyl |
| CH₂ | 4-(4-(CF₃)phenyl) | H |
| O | 4-(4-(CF₃)phenyl) | H |
| CH₂ | 4-(4-(CF₃)phenyl) | methyl |
| O | 4-(4-(CF₃)phenyl) | methyl |
| CH₂ | 3-(2-thienyl) | H |
| O | 3-(2-thienyl) | H |
| CH₂ | 3-(2-thienyl) | methyl |
| O | 3-(2-thienyl) | methyl |
| CH₂ | 4-(2-thienyl) | H |
| O | 4-(2-thienyl) | H |
| CH₂ | 4-(2-thienyl) | methyl |
| O | 4-(2-thienyl) | methyl |
| CH₂ | 3-(3-thienyl) | H |
| O | 3-(3-thienyl) | H |
| CH₂ | 3-(3-thienyl) | methyl |
| O | 3-(3-thienyl) | methyl |
| CH₂ | 4-(3-thienyl) | H |
| O | 4-(3-thienyl) | H |
| CH₂ | 4-(3-thienyl) | methyl |
| O | 4-(3-thienyl) | methyl |
| CH₂ | 3-(5-chloro-2-thienyl) | H |
| O | 3-(5-chloro-2-thienyl) | H |

TABLE XIV-continued

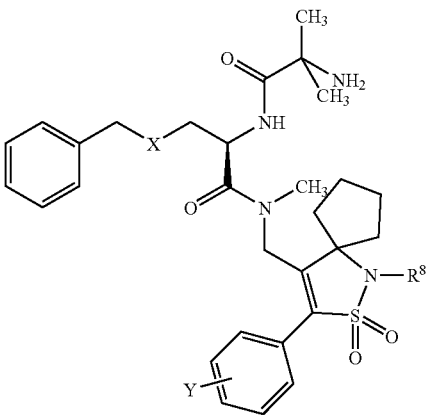

| X | Y | R8 |
|---|---|---|
| CH2 | 3-(5-chloro-2-thienyl) | methyl |
| O | 3-(5-chloro-2-thienyl) | methyl |
| CH2 | 4-(5-chloro-2-thienyl) | H |
| O | 4-(5-chloro-2-thienyl) | H |
| CH2 | 4-(5-chloro-2-thienyl) | methyl |
| O | 4-(5-chloro-2-thienyl) | methyl |
| CH2 | 4-(pyridin-2-yl) | H |
| O | 4-(pyridin-2-yl) | H |
| CH2 | 4-(pyridin-2-yl) | methyl |
| O | 4-(pyridin-2-yl) | methyl |
| CH2 | 4-(pyridin-3-yl) | H |
| O | 4-(pyridin-3-yl) | H |
| CH2 | 4-(pyridin-3-yl) | methyl |
| O | 4-(pyridin-3-yl) | methyl |
| CH2 | 3-(pyridin-4-yl) | H |
| O | 3-(pyridin-4-yl) | H |
| CH2 | 3-(pyridin-4-yl) | methyl |
| O | 3-(pyridin-4-yl) | methyl |
| CH2 | 4-(pyridin-4-yl) | H |
| O | 4-(pyridin-4-yl) | H |
| CH2 | 4-(pyridin-4-yl) | methyl |
| O | 4-(pyridin-4-yl) | methyl |
| CH2 | 3-(thiazol-2-yl) | H |
| O | 3-(thiazol-2-yl) | H |
| CH2 | 3-(thiazol-2-yl) | methyl |
| O | 3-(thiazol-2-yl) | methyl |
| CH2 | 4-(thiazol-2-yl) | H |
| O | 4-(thiazol-2-yl) | H |
| CH2 | 4-(thiazol-2-yl) | methyl |
| O | 4-(thiazol-2-yl) | methyl |
| CH2 | 3-(oxazol-2-yl) | H |
| O | 3-(oxazol-2-yl) | H |
| CH2 | 3-(oxazal-2-yl) | methyl |
| O | 3-(oxazol-2-yl) | methyl |
| CH2 | 4-(oxazol-2-yl) | H |
| O | 4-(oxazol-2-yl) | H |
| CH2 | 4-(oxazol-2-yl) | methyl |
| O | 4-(oxazol-2-yl) | methyl |
| CH2 | 3-NO2 | H |
| O | 3-NO2 | H |
| CH2 | 3-NO2 | methyl |
| O | 3-NO2 | methyl |
| CH2 | 4-NO2 | H |
| O | 4-NO2 | H |
| CH2 | 4-NO2 | methyl |
| O | 4-NO2 | methyl |
| CH2 | 4-C2H5 | H |
| O | 4-C2H5 | H |
| CH2 | 4-C2H5 | methyl |
| O | 4-C2H5 | methyl |
| CH2 | 4-OC2H5 | H |
| O | 4-OC2H5 | H |
| CH2 | 4-OC2H5 | methyl |
| O | 4-OC2H5 | methyl |
| CH2 | 4-CONH2 | H |
| O | 4-CONH2 | H |

TABLE XIV-continued

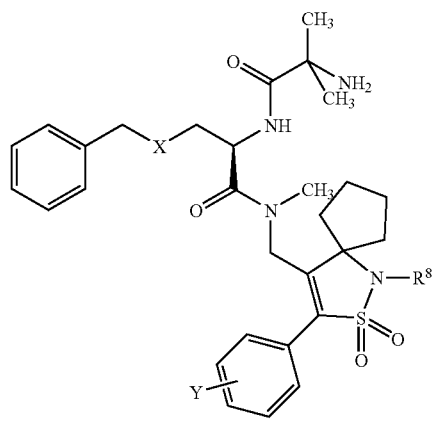

| X | Y | R8 |
|---|---|---|
| CH2 | 4-CONH2 | methyl |
| O | 4-CONH2 | methyl |

TABLE XV

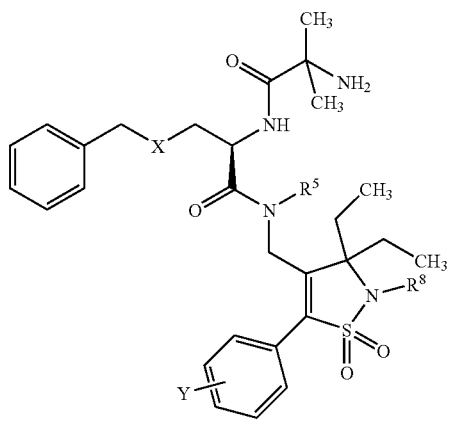

| X | Y | R5 | R8 |
|---|---|---|---|
| CH2 | 4-Cl | ethyl | H |
| O | 4-Cl | ethyl | H |
| CH2 | 4-Cl | ethyl | methyl |
| CH2 | 4-Cl | methyl | H |
| O | 4-Cl | methyl | H |
| CH2 | 4-Cl | methyl | methyl |
| O | 4-Cl | methyl | methyl |
| CH2 | H | ethyl | H |
| O | H | ethyl | H |
| CH2 | H | ethyl | methyl |
| O | H | ethyl | methyl |
| CH2 | H | methyl | H |
| O | H | methyl | H |
| CH2 | H | methyl | methyl |
| O | H | methyl | methyl |
| CH2 | 4-F | ethyl | H |
| O | 4-F | ethyl | H |
| CH2 | 4-F | ethyl | methyl |
| O | 4-F | ethyl | methyl |
| CH2 | 4-F | methyl | H |
| O | 4-F | methyl | H |
| CH2 | 4-F | methyl | methyl |
| O | 4-F | methyl | methyl |
| CH2 | 4-SO2CH3 | ethyl | H |
| O | 4-SO2CH3 | ethyl | H |
| CH2 | 4-SO2CH3 | ethyl | methyl |

TABLE XV-continued

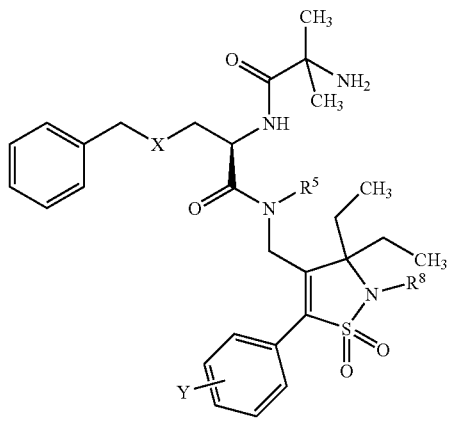

| X | Y | R⁵ | R⁸ |
|---|---|---|---|
| O | 4-SO₂CH₃ | ethyl | methyl |
| CH₂ | 4-SO₂CH₃ | methyl | H |
| O | 4-SO₂CH₃ | methyl | H |
| CH₂ | 4-SO₂CH₃ | methyl | methyl |
| O | 4-SO₂CH₃ | methyl | methyl |

TABLE XVI

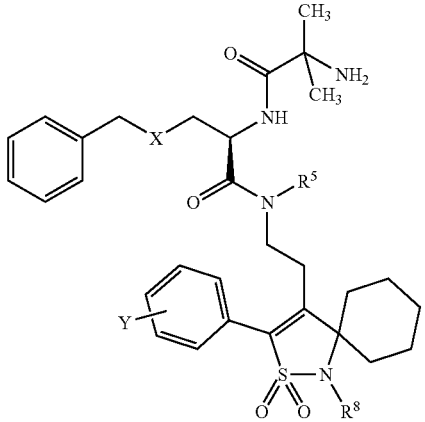

| X | Y | R⁵ | R⁸ |
|---|---|---|---|
| CH₂ | 4-Cl | ethyl | H |
| CH₂ | 4-Cl | ethyl | methyl |
| O | 4-Cl | ethyl | methyl |
| CH₂ | 4-F | ethyl | H |
| O | 4-F | ethyl | H |
| CH₂ | 4-F | ethyl | methyl |
| O | 4-F | ethyl | methyl |
| CH₂ | 4-Cl | methyl | H |
| O | 4-Cl | methyl | H |
| CH₂ | 4-Cl | methyl | methyl |
| O | 4-Cl | methyl | methyl |
| CH₂ | 4-F | methyl | H |
| O | 4-F | methyl | H |
| CH₂ | 4-F | methyl | methyl |
| O | 4-F | methyl | methyl |
| CH₂ | H | ethyl | H |
| O | H | ethyl | H |
| CH₂ | H | ethyl | methyl |
| O | H | ethyl | methyl |
| CH₂ | H | methyl | H |
| O | H | methyl | H |

TABLE XVI-continued

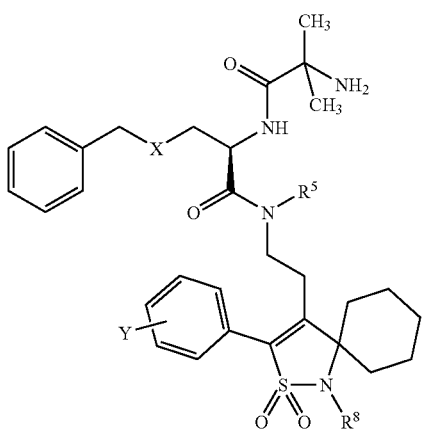

| X | Y | R⁵ | R⁸ |
|---|---|---|---|
| CH₂ | H | methyl | methyl |
| O | H | methyl | methyl |

TABLE XVII

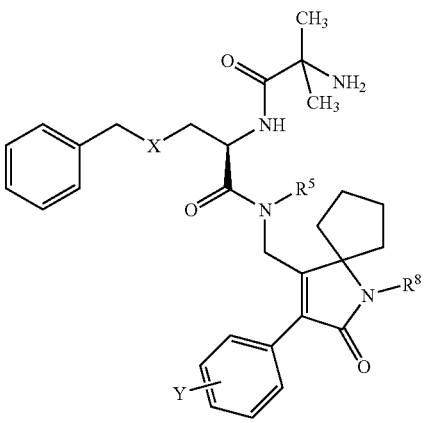

| X | Y | R⁵ | R⁸ |
|---|---|---|---|
| O | H | ethyl | H |
| CH₂ | H | ethyl | H |
| O | H | ethyl | methyl |
| CH₂ | H | ethyl | methyl |
| O | H | methyl | H |
| CH₂ | H | methyl | H |
| O | H | methyl | methyl |
| CH₂ | H | methyl | methyl |
| O | 3-Cl | ethyl | H |
| CH₂ | 3-Cl | ethyl | H |
| O | 3-Cl | ethyl | methyl |
| CH₂ | 3-Cl | ethyl | methyl |
| O | 3-Cl | methyl | H |
| CH₂ | 3-Cl | methyl | H |
| O | 3-Cl | methyl | methyl |
| CH₂ | 3-Cl | methyl | methyl |
| O | 4-Cl | ethyl | H |
| CH₂ | 4-Cl | ethyl | H |
| O | 4-Cl | ethyl | methyl |
| CH₂ | 4-Cl | ethyl | methyl |
| O | 4-Cl | methyl | H |
| CH₂ | 4-Cl | methyl | H |
| O | 4-Cl | methyl | methyl |
| CH₂ | 4-Cl | methyl | methyl |
| O | 4-Br | ethyl | H |
| CH₂ | 4-Br | ethyl | H |

TABLE XVII-continued

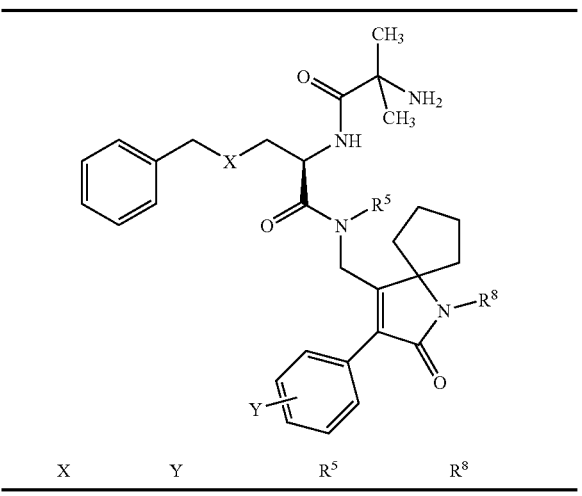

| X | Y | R⁵ | R⁸ |
|---|---|---|---|
| O | 4-Br | ethyl | methyl |
| CH₂ | 4-Br | ethyl | methyl |
| O | 4-Br | methyl | H |
| CH₂ | 4-Br | methyl | H |
| O | 4-Br | methyl | methyl |
| CH₂ | 4-Br | methyl | methyl |
| O | 3-Br | ethyl | H |
| CH₂ | 3-Br | ethyl | H |
| O | 3-Br | ethyl | methyl |
| CH₂ | 3-Br | ethyl | methyl |
| O | 3-Br | methyl | H |
| CH₂ | 3-Br | methyl | H |
| O | 3-Br | methyl | methyl |
| CH₂ | 3-Br | methyl | methyl |
| O | 4-F | ethyl | H |
| CH₂ | 4-F | ethyl | H |
| O | 4-F | ethyl | methyl |
| CH₂ | 4-F | ethyl | methyl |
| O | 4-F | methyl | H |
| CH₂ | 4-F | methyl | H |
| O | 4-F | methyl | methyl |
| CH₂ | 4-F | methyl | methyl |
| O | 3-F | ethyl | H |
| CH₂ | 3-F | ethyl | H |
| O | 3-F | ethyl | methyl |
| CH₂ | 3-F | ethyl | methyl |
| O | 3-F | methyl | H |
| CH₂ | 3-F | methyl | H |
| O | 3-F | methyl | methyl |
| CH₂ | 3-F | methyl | methyl |
| O | 2-F | ethyl | H |
| CH₂ | 2-F | ethyl | H |
| O | 2-F | ethyl | methyl |
| CH₂ | 2-F | ethyl | methyl |
| O | 2-F | methyl | H |
| CH₂ | 2-F | methyl | H |
| O | 2-F | methyl | methyl |
| CH₂ | 2-F | methyl | methyl |
| O | 4-OCH₃ | ethyl | H |
| CH₂ | 4-OCH₃ | ethyl | H |
| O | 4-OCH₃ | ethyl | methyl |
| CH₂ | 4-OCH₃ | ethyl | methyl |
| O | 3-CF₃ | ethyl | H |
| CH₂ | 3-CF₃ | ethyl | H |
| O | 3-CF₃ | ethyl | methyl |
| CH₂ | 3-CF₃ | ethyl | methyl |
| O | 4-CF₃ | ethyl | H |
| CH₂ | 4-CF₃ | ethyl | H |
| O | 4-CF₃ | ethyl | methyl |
| CH₂ | 4-CF₃ | ethyl | methyl |
| O | 4-SO₂CH₃ | ethyl | H |
| CH₂ | 4-SO₂CH₃ | ethyl | H |
| O | 4-SO₂CH₃ | ethyl | methyl |
| CH₂ | 4-SO₂CH₃ | ethyl | methyl |
| O | 4-SO₂CH₃ | methyl | H |
| CH₂ | 4-SO₂CH₃ | methyl | H |

TABLE XVII-continued

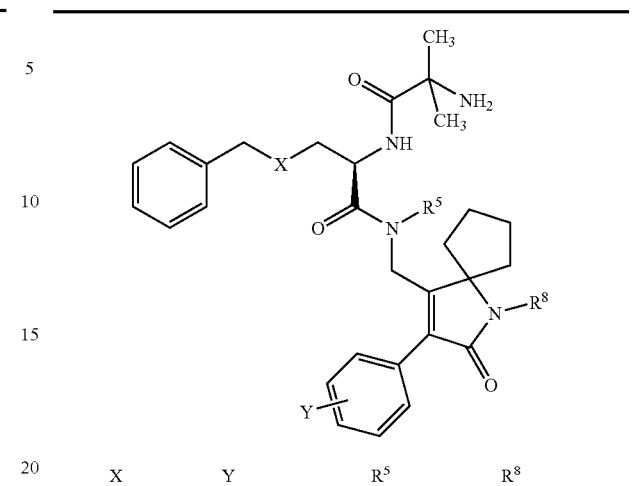

| X | Y | R⁵ | R⁸ |
|---|---|---|---|
| O | 4-SO₂CH₃ | methyl | methyl |
| CH₂ | 4-SO₂CH₃ | methyl | methyl |

TABLE XVIII

| X | Y | R⁵ | R⁶ and R⁷ | R |
|---|---|---|---|---|
| O | H | ethyl | methyl | H |
| CH₂ | H | ethyl | methyl | H |
| O | H | ethyl | methyl | methyl |
| CH₂ | H | ethyl | methyl | methyl |
| O | H | methyl | methyl | H |
| CH₂ | H | methyl | methyl | H |
| O | H | methyl | methyl | methyl |
| CH₂ | H | methyl | methyl | methyl |
| O | 3-Cl | ethyl | methyl | H |
| CH₂ | 3-Cl | ethyl | methyl | H |
| O | 3-Cl | ethyl | methyl | methyl |
| CH₂ | 3-Cl | ethyl | methyl | methyl |
| O | 4-Cl | ethyl | methyl | H |
| CH₂ | 4-Cl | ethyl | methyl | H |
| O | 4-Cl | ethyl | methyl | methyl |
| CH₂ | 4-Cl | ethyl | methyl | methyl |
| O | 4-Cl | methyl | methyl | H |
| CH₂ | 4-Cl | methyl | methyl | H |
| O | 4-Cl | methyl | methyl | methyl |
| CH₂ | 4-Cl | methyl | methyl | methyl |
| CH₂ | 4-Br | ethyl | methyl | H |
| O | 4-Br | ethyl | methyl | methyl |
| CH₂ | 4-Br | ethyl | methyl | methyl |
| O | 4-Br | methyl | methyl | H |
| CH₂ | 4-Br | methyl | methyl | H |
| O | 4-Br | methyl | methyl | methyl |
| CH₂ | 4-Br | methyl | methyl | methyl |

TABLE XVIII-continued

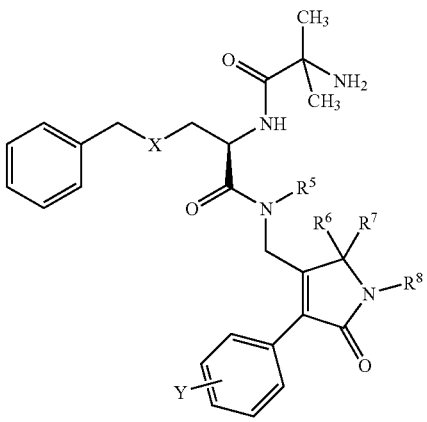

| X | Y | R⁵ | R⁶ and R⁷ | R |
|---|---|---|---|---|
| O | 3-Br | ethyl | methyl | H |
| CH₂ | 3-Br | ethyl | methyl | H |
| O | 3-Br | ethyl | methyl | methyl |
| CH₂ | 3-Br | ethyl | methyl | methyl |
| O | 4-F | ethyl | methyl | H |
| CH₂ | 4-F | ethyl | methyl | H |
| O | 4-F | ethyl | methyl | methyl |
| CH₂ | 4-F | ethyl | methyl | methyl |
| O | 4-F | methyl | methyl | H |
| CH₂ | 4-F | methyl | methyl | H |
| O | 4-F | methyl | methyl | methyl |
| CH₂ | 4-F | methyl | methyl | methyl |
| O | 3-F | ethyl | methyl | H |
| CH₂ | 3-F | ethyl | methyl | H |
| O | 3-F | ethyl | methyl | methyl |
| CH₂ | 3-F | ethyl | methyl | methyl |
| O | 3-F | methyl | methyl | H |
| CH₂ | 3-F | methyl | methyl | H |
| O | 3-F | methyl | methyl | methyl |
| CH₂ | 3-F | methyl | methyl | methyl |
| O | 2-F | ethyl | methyl | H |
| CH₂ | 2-F | ethyl | methyl | H |
| O | 2-F | ethyl | methyl | methyl |
| CH₂ | 2-F | ethyl | methyl | methyl |
| O | 2-F | methyl | methyl | H |
| CH₂ | 2-F | methyl | methyl | H |
| O | 2-F | methyl | methyl | methyl |
| CH₂ | 2-F | methyl | methyl | methyl |
| O | 4-OCH₃ | ethyl | methyl | H |
| CH₂ | 4-OCH₃ | ethyl | methyl | H |
| O | 4-OCH₃ | ethyl | methyl | methyl |
| CH₂ | 4-OCH₃ | ethyl | methyl | methyl |
| O | 3-CF₃ | ethyl | methyl | H |
| CH₂ | 3-CF₃ | ethyl | methyl | H |
| O | 3-CF₃ | ethyl | methyl | methyl |
| CH₂ | 3-CF₃ | ethyl | methyl | methyl |
| O | 4-CF₃ | ethyl | methyl | H |
| CH₂ | 4-CF₃ | ethyl | methyl | H |
| O | 4-CF₃ | ethyl | methyl | methyl |
| CH₂ | 4-CF₃ | ethyl | methyl | methyl |
| O | H | ethyl | ethyl | H |
| CH₂ | H | ethyl | ethyl | H |
| O | H | ethyl | ethyl | methyl |
| CH₂ | H | ethyl | ethyl | methyl |
| O | H | methyl | ethyl | H |
| CH₂ | H | methyl | ethyl | H |
| O | H | methyl | ethyl | methyl |
| CH₂ | H | methyl | ethyl | methyl |
| O | 3-Cl | ethyl | ethyl | H |
| CH₂ | 3-Cl | ethyl | ethyl | H |
| O | 3-Cl | ethyl | ethyl | methyl |
| CH₂ | 3-Cl | ethyl | ethyl | methyl |
| O | 4-Cl | ethyl | ethyl | H |
| CH₂ | 4-Cl | ethyl | ethyl | H |
| O | 4-Cl | ethyl | ethyl | methyl |
| CH₂ | 4-Cl | ethyl | ethyl | methyl |
| O | 4-Cl | methyl | ethyl | H |

TABLE XVIII-continued

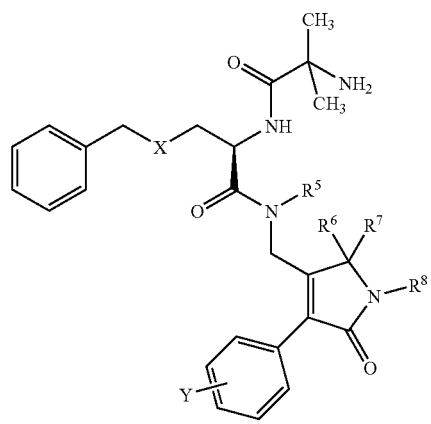

| X | Y | R⁵ | R⁶ and R⁷ | R |
|---|---|---|---|---|
| CH₂ | 4-Cl | methyl | ethyl | H |
| O | 4-Cl | methyl | ethyl | methyl |
| CH₂ | 4-Cl | methyl | ethyl | methyl |
| O | 4-Br | ethyl | ethyl | H |
| CH₂ | 4-Br | ethyl | ethyl | H |
| O | 4-Br | ethyl | ethyl | methyl |
| CH₂ | 4-Br | ethyl | ethyl | methyl |
| O | 4-Br | methyl | ethyl | H |
| CH₂ | 4-Br | methyl | ethyl | H |
| O | 4-Br | methyl | ethyl | methyl |
| CH₂ | 4-Br | methyl | ethyl | methyl |
| O | 4-F | ethyl | ethyl | H |
| CH₂ | 4-F | ethyl | ethyl | H |
| O | 4-F | ethyl | ethyl | methyl |
| CH₂ | 4-F | ethyl | ethyl | methyl |
| O | 4-F | methyl | ethyl | H |
| CH₂ | 4-F | methyl | ethyl | H |
| O | 4-F | methyl | ethyl | methyl |
| CH₂ | 4-F | methyl | ethyl | methyl |
| O | 3-F | ethyl | ethyl | H |
| CH₂ | 3-F | ethyl | ethyl | H |
| O | 3-F | ethyl | ethyl | methyl |
| CH₂ | 3-F | ethyl | ethyl | methyl |
| O | 3-F | methyl | ethyl | H |
| CH₂ | 3-F | methyl | ethyl | H |
| O | 3-F | methyl | ethyl | methyl |
| CH₂ | 3-F | methyl | ethyl | methyl |
| O | 2-F | ethyl | ethyl | H |
| CH₂ | 2-F | ethyl | ethyl | H |
| O | 2-F | ethyl | ethyl | methyl |
| CH₂ | 2-F | ethyl | ethyl | methyl |
| O | 2-F | methyl | ethyl | H |
| CH₂ | 2-F | methyl | ethyl | H |
| O | 2-F | methyl | ethyl | methyl |
| CH₂ | 2-F | methyl | ethyl | methyl |
| O | 4-SO₂CH₃ | ethyl | ethyl | H |
| CH₂ | 4-SO₂CH₃ | ethyl | ethyl | H |
| O | 4-SO₂CH₃ | ethyl | ethyl | methyl |
| CH₂ | 4-SO₂CH₃ | ethyl | ethyl | methyl |
| O | 4-SO₂CH₃ | methyl | ethyl | H |
| CH₂ | 4-SO₂CH₃ | methyl | ethyl | H |
| O | 4-SO₂CH₃ | methyl | ethyl | methyl |
| CH₂ | 4-SO₂CH₃ | methyl | ethyl | methyl |
| O | 4-SO₂CH₃ | ethyl | methyl | H |
| CH₂ | 4-SO₂CH₃ | ethyl | methyl | H |
| O | 4-SO₂CH₃ | ethyl | methyl | methyl |
| CH₂ | 4-SO₂CH₃ | ethyl | methyl | methyl |
| O | 4-SO₂CH₃ | methyl | methyl | H |
| CH₂ | 4-SO₂CH₃ | methyl | methyl | H |
| O | 4-SO₂CH₃ | methyl | methyl | methyl |
| CH₂ | 4-SO₂CH₃ | methyl | methyl | methyl |

TABLE XIX

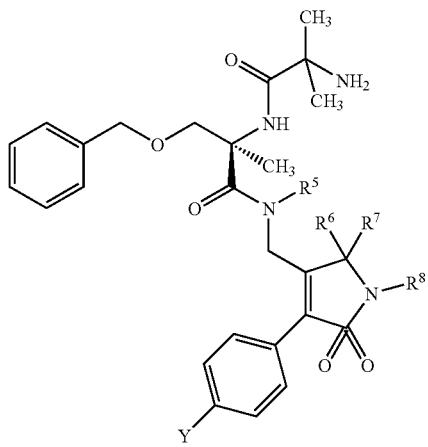

| V | R | R6, R7 | R8 |
|---|---|---|---|
| H | ethyl | tetramethylene | H |
| H | methyl | tetramethylerte | H |
| H | ethyl | tetramethylene | methyl |
| H | methyl | tetramethylene | methyl |
| H | ethyl | pentamethylene | H |
| H | methyl | pentamethylene | H |
| H | ethyl | pentamethylene | methyl |
| H | methyl | pentamethylene | methyl |
| Cl | ethyl | tetramethylene | H |
| Cl | methyl | tetramethylene | H |
| Cl | ethyl | tetramethylene | methyl |
| Cl | methyl | tetramethylene | methyl |
| Cl | ethyl | pentamethylene | H |
| Cl | methyl | pentamethylene | H |
| Cl | ethyl | pentamethylene | methyl |
| Cl | methyl | pentamethylene | methyl |
| F | ethyl | tetramethylene | H |
| F | methyl | tetramethylene | H |
| F | ethyl | tetramethylene | methyl |
| F | methyl | tetramethylene | methyl |
| F | ethyl | pentamethylene | H |
| F | methyl | pentamethylene | H |
| F | ethyl | pentamethylene | methyl |
| F | methyl | pentamethylene | methyl |
| 4-SO2CH3 | ethyl | tetramethylene | H |
| 4-SO2CH3 | methyl | tetramethylene | H |
| 4-SO2CH3 | ethyl | tetramethylene | methyl |
| 4-SO2CH3 | methyl | tetramethylene | methyl |
| 4-SO2CH3 | ethyl | pentamethylene | H |
| 4-SO2CH3 | methyl | pentamethylene | H |
| 4-SO2CH3 | ethyl | pentamethylene | methyl |
| 4-SO2CH3 | methyl | pentamethylene | methyl |

Pituitary Cell Culture Assay for Growth Hormone (GH) Secretion

Fifteen 250 g male Sprague-Dawley rats are used for each assay. The animals are killed by decapitation and anterior pituitaries are removed and placed into ice cold culture medium. The pituitaries are sectioned in small pieces and enzymatically digested using trypsin (Difco) to weaken connective tissue. Pituitary cells are dispersed by mechanical agitation, collected, pooled and then seeded into 96-well plates (50,000 cells/well). After 5 days of culture, the cells formed as monolayer (70–80% confluent). Cells are then washed with medium (without phenol red) and incubated for 90 min at 37° C. Afterwards the cells are challenged to secrete GH by the addition of GH secretagogues to the medium. After 45 min at room temperature, the medium is removed, filtered and stored frozen until radioimmunoassays for rat GH were performed. Doses of secretagogue are added in triplicates. Compounds disclosed herein are active in the assay as described. The compounds cause a stimulation of GH secretion resulting in at least 20% increase of the basal level of GH with and EC50<500 nM. Preferred compounds caused a 50% increase with an EC50<50 nM, and more preferred compounds a 50% increase with an EC50<10 nM. Both EC50 and efficacy values were calculated by the 4-parameter logistic equation. Such values were pooled and represented as mean +/− standard error, when appropriate.

We claim:

1. A compound of the Formula I

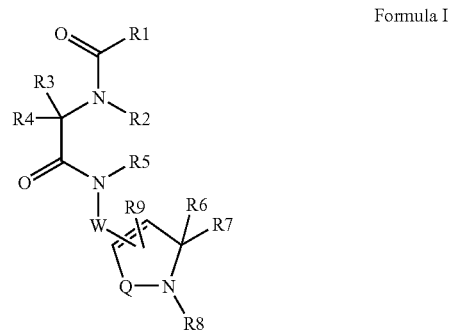

Formula I wherein:

R1 is NHR10 or $C_1$–$C_6$alkylNHR10;

R10 selected from the group consisting of hydrogen, $C_1$–$C_6$alkyl, $C_1$–$C_6$alkyl(OH), $C_1$–$C_6$alkylidenyl(OH) R11, and an amino protecting group;

R11 is selected from the group consisting of $C_1$–$C_6$alkyl, $C_2$–$C_6$alkenyl, $C_1$–$C_6$alkyl(O)$C_1$–$C_6$alkyl, C(O)O—$C_1$–$C_6$alkyl, aryl, and $C_1$–$C_6$alkylaryl;

R2 is selected from hydrogen, $C_1$–$C_6$alkyl, aryl, and $C_1$–$C_6$alkylaryl;

R3 is selected from the group consisting of optionally substituted aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl)$C_3$–$C_8$ cycloalkyl, indolyl, indolinyl, ($C_1$–$C_6$ alkyl) indolyl;

R4 is hydrogen, $C_1$–$C_6$alkyl, aryl, $C_1$–$C_6$alkylaryl, $C_2$–$C_6$alkenyl;

R5 is selected from hydrogen, $C_1$–$C_6$alkyl, aryl, and $C_1$–$C_6$alkylaryl;

W is —$CH_2C_6H_4$— or —$(CH_2)_m$, where m is a number selected from 1 to 4;

R6 and R7 are independently selected from the group consisting of hydrogen, $C_1$–$C_6$alkyl, $C_2$–$C_6$alkenyl, or R6 and R7 together with the carbon atom to which they are attached may form a carbocyclic ring of up to 8 atoms which is optionally partly unsaturated;

R8 is selected from the group consisting of hydrogen, $C_1$–$C_6$alkyl, aryl, and $C_1$–$C_6$alkylaryl;

R9 is selected from the group consisting of hydrogen, $C_1$–$C_6$alkyl, $C_2$–$C_6$alkenyl, $C_2$–$C_6$alkynyl, $C_3$–$C_8$cycloalkyl, $C_3$–$C_8$cycloalkenyl, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), —S-aryl-aryl(K1)(K2), —O—$C_1$–$C_6$alkyl, and $C_1$–$C_6$alkylaryl, wherein K1 is halo or —$CF_3$ and K2 is hydrogen, halo or —$CF_3$; and Q is —$S(O)_2$— or —C(O)—;

or a pharmaceutically acceptable salt thereof.

2. A compound as claimed by claim 1 wherein R3 is selected from the group consisting of aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl) $C_3$–$C_8$ cycloalkyl, indolyl, indolinyl, ($C_1$–$C_6$ alkyl) indolyl; and R9 is selected from the group consisting of hydrogen, $C_1$–$C_6$alkyl, $C_2$–$C_6$alkenyl, $C_2$–$C_6$alkynyl, $C_3$–$C_8$cycloalkyl, $C_3$–$C_8$cycloalkenyl, optionally substituted aryl, optionally substituted —O-aryl, optionally substituted —N-aryl, optionally substituted —S-aryl, —O—$C_1$–$C_6$alkyl, and $C_1$–$C_6$alkylaryl; or a pharmaceutically acceptable salt thereof.

3. A compound as claimed by claim 2 wherein Q is $SO_2$.

4. A compound as claimed by claim 3 wherein R3 is

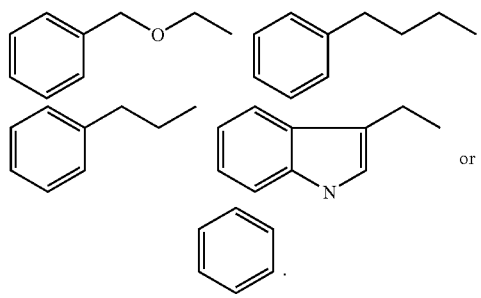

or

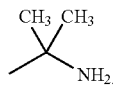

5. A compound as claimed by claim 4 wherein $R_1$ is

6. A compound as claimed by claim 5 wherein R6 and R7 form a carbocyclic ring.

7. A compound as claimed by claim 5 wherein R6 and R7 are each C1–3 alkyl.

8. A compound as claimed by claim 5 wherein R6 and R7 are each independently selected from the group consisting of hydrogen, $C_{1-6}$ alkyl, and $C_{2-6}$ alkenyl.

9. A compound as claimed by claim 8 wherein W is $(CH_2)_m$ and R2 is hydrogen.

10. A compound as claimed by claim 9 wherein R4 is hydrogen.

11. A compound as claimed by claim 10 wherein R5 is hydrogen, methyl or ethyl.

12. A compound as claimed by claim 11 wherein R9 is selected from the group consisting of optionally substituted thienyl, naphthyl, O-phenyl and phenyl; wherein the substituents are each independently selected from the group consisting of $C_1$–$C_6$ alkyl, —$C_1$–$C_6$ alkoxy, halo($C_1$–$C_6$ alkyl), halo($C_1$–$C_6$ alkoxy), O-aryl, $CONH_2$, $CONH(C_1$–$C_6$ alkyl), $NHCO(C_1$–$C_6$ alkyl), $SO_2NH_2$, $SO_2NH(C_1$–$C_6$ alkyl), $NHSO_2(C_1$–$C_6$ alkyl), COOH, $COO(C_1$–$C_6$ alkyl), hydroxy, nitro, halo, $SO_2(C_{1-6}$ alkyl), and cyano.

13. A compound as claimed by claim 12 wherein R8 is hydrogen, methyl or ethyl.

14. A compound as claimed by claim 13 wherein W is $(CH_2)_m$ and m is 1 or 2.

15. A compound as claimed by claim 14 wherein R9 is a carbocyclic aryl.

16. A compound as claimed by claim 2 wherein Q is —C(O)—.

17. A compound as claimed by claim 16 wherein R3 is

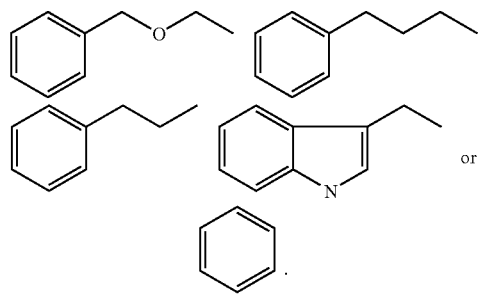

or

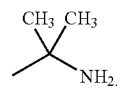

18. A compound as claimed by claim 17 wherein $R_1$ is

19. A compound as claimed by claim 18 wherein R6 and R7 form a carbocyclic ring.

20. A compound as claimed by claim 18 wherein R6 and R7 are each $C_1$–$C_3$ alkyl.

21. A compound as claimed by claim 18 wherein R6 and R7 are each independently selected from the group consisting of hydrogen, C1–6 alkyl, and $C_2$–$C_6$ alkenyl.

22. A compound as claimed by claim 21 wherein W is $(CH_2)_m$ and R2 is hydrogen.

23. A compound as claimed by any one of claim 22 wherein R4 is hydrogen.

24. A compound as claimed by any one of claim 23 wherein R5 is hydrogen, methyl or ethyl.

25. A compound as claimed by claim 24 wherein R9 is selected from the group consisting of optionally substituted thienyl, naphthyl, O-phenyl and phenyl; wherein the substituents are each independently selected from the group consisting of $C_1$–$C_6$ alkyl, —$C_1$–$C_6$ alkoxy, halo($C_1$–$C_6$ alkyl), halo($C_1$–$C_6$ alkoxy), O-aryl, $CONH_2$, $CONH(C_1$–$C_6$ alkyl), $NHCO(C_1$–$C_6$ alkyl), $SO_2NH_2$, $SO_2NH(C_1$–$C_6$ alkyl), $NHSO_2(C_1$–$C_6$ alkyl), COOH, $COO(C_1$–$C_6$ alkyl), hydroxy, nitro, halo, $SO_2(C_{1-6}$ alkyl), and cyano.

26. A compound as claimed by claim 25 wherein R8 is hydrogen, methyl or ethyl.

27. A compound as claimed by claim 26 wherein W is $(CH_2)_m$ and m is 1 or 2.

28. A compound as claimed by claim 27 wherein R9 is a carbocyclic aryl.

29. A pharmaceutical formulation comprising one or more compounds according to claim 1 together with one or more pharmaceutically acceptable diluents or carriers therefor.

30. A pharmaceutical formulation of claim 29 wherein the formulation comprises a compound according to claim 1 and one or more growth hormone secretagogue compounds and/or a bone-antiresorptive agent.

31. A method for treatment of a physiological condition which may be modulated by an increase in endogenous growth hormone, which method comprises administering to an animal in need of said treatment an effective amount of a compound of claim 1.

32. A process for preparing a compound of Formula I

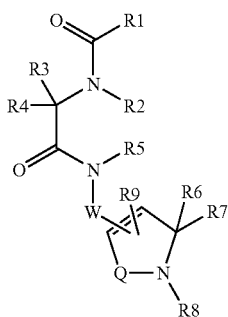

Formula I wherein:
R1 is NHR10 or $C_1$–$C_6$alkylNHR10;
R10 selected from the group consisting of hydrogen, $C_1$–$C_6$alkyl, $C_1$–$C_6$alkyl(OH), $C_1$–$C_6$alkylidenyl(OH) R11, and an amino protecting group;
R11 is selected from the group consisting of $C_1$–$C_6$alkyl, $C_2$–$C_6$alkenyl, $C_1$–$C_6$alkyl(O)$C_1$–$C_6$alkyl, C(O)O—$C_1$–$C_6$alkyl, aryl, and $C_1$–$C_6$alkylaryl;
R2 is selected from hydrogen, $C_1$–$C_6$alkyl, aryl, and $C_1$–$C_6$alkylaryl;
R3 is selected from the group consisting of optionally substituted aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl) $C_3$–$C_8$ cycloalkyl, indolyl, indolinyl, ($C_1$–$C_6$ alkyl) indolyl;
R4 is hydrogen, $C_1$–$C_6$alkyl, aryl, $C_1$–$C_6$alkylaryl, $C_2$–$C_6$alkenyl;
R5 is selected from hydrogen, $C_1$–$C_6$alkyl, aryl, and $C_1$–$C_6$alkylaryl;
W is —$CH_2C_6H_4$— or —$(CH_2)_m$, where m is a number selected from 1 to 4;
R6 and R7 are independently selected from the group consisting of hydrogen, $C_1$–$C_6$alkyl, $C_2$–$C_6$alkenyl, or R6 and R7 together with the carbon atom to which they are attached may form a carbocyclic ring of up to 8 atoms which is optionally partly unsaturated;
R8 is selected from the group consisting of hydrogen, $C_1$–$C_6$alkyl, aryl, and $C_1$–$C_6$alkylaryl;
R9 is selected from the group consisting of hydrogen, $C_1$–$C_6$alkyl, $C_1$–$C_6$alkenyl, $C_2$–$C_6$alkynyl, $C_2$–$C_6$alkynyl, $C_3$–$C_8$cycloalkyl, $C_3$–$C_8$cycloalkenyl, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), —S-aryl-aryl(K1)(K2), —O—$C_1$–$C_6$alkyl, and $C_1$–$C_6$alkylaryl, wherein K1 is halo or —$CF_3$ and K2 is hydrogen, halo or —$CF_3$; and
Q is —$S(O)_2$— or —$C(O)$—;
comprising coupling a compound of Formula IX'

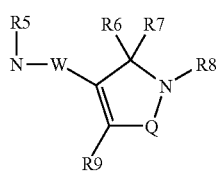

IX' with a compound of Formula XI'

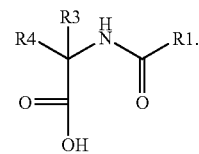

XI'

33. A process for preparing a compound of Formula I

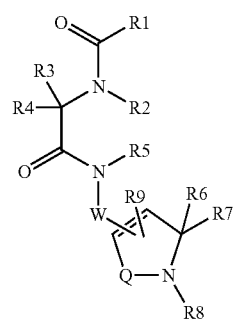

Formula I wherein:
R1 is NHR10 or $C_1$–$C_6$alkylNHR10;
R10 selected from the group consisting of hydrogen, $C_1$–$C_6$alkyl, $C_1$–$C_6$alkyl(OH), $C_1$–$C_6$alkylidenyl(OH) R11, and an amino protecting group;
R11 is selected from the group consisting of $C_1$–$C_6$alkyl, $C_2$–$C_6$alkenyl, $C_1$–$C_6$alkyl(O)$C_1$–$C_6$alkyl, C(O)O—$C_1$–$C_6$alkyl, aryl, and $C_1$–$C_6$alkylaryl;
R2 is selected from hydrogen, $C_1$–$C_6$alkyl, aryl, and $C_1$–$C_6$alkylaryl;
R3 is selected from the group consisting of optionally substituted aryl, $C_1$–$C_6$alkylaryl, $C_1$–$C_6$alkyl(O)—$C_1$–$C_6$alkylaryl, $C_3$–$C_8$ cycloalkyl, ($C_1$–$C_6$ alkyl) $C_3$–$C_8$ cycloalkyl, indolyl, indolinyl, ($C_1$–$C_6$ alkyl) indolyl;
R4 is hydrogen, $C_1$–$C_6$alkyl, aryl, $C_1$–$C_6$alkylaryl, $C_2$–$C_6$alkenyl;
R5 is selected from hydrogen, $C_1$–$C_6$alkyl, aryl, and $C_1$–$C_6$alkylaryl;
W is —$CH_2C_6H_4$— or —$(CH_2)_m$, where m is a number selected from 1 to 4;
R6 and R7 are independently selected from the group consisting of hydrogen, $C_1$–$C_6$alkyl, $C_2$–$C_6$alkenyl, or R6 and R7 together with the carbon atom to which they are attached may form a carbocyclic ring of up to 8 atoms which is optionally partly unsaturated;
R8 is selected from the group consisting of hydrogen, $C_1$–$C_6$alkyl, aryl, and $C_1$–$C_6$alkylaryl;
R9 is selected from the group consisting of hydrogen, $C_1$–$C_6$alkyl, $C_2$–$C_6$alkenyl, —$C_2$–$C_6$alkynyl, $C_3$–$C_8$cycloalkyl, $C_3$–$C_8$cycloalkenyl, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), —S-aryl-aryl(K1)(K2), —O—$C_1$–$C_6$alkyl, and $C_1$–$C_6$alkylaryl, wherein K1 is halo or —$CF_3$ and K2 is hydrogen, halo or —$CF_3$; and
Q is —$S(O)_2$— or —$C(O)$—;

comprising deprotecting a group of the formula Ia'

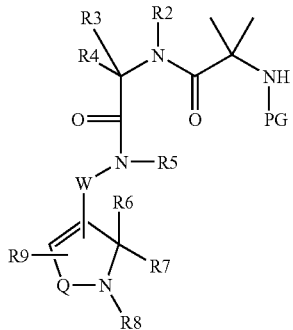

Ia'; wherein PG is an amino-protecting group.

34. A compound of claim 1 of the formula

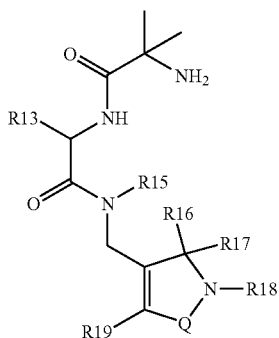

Formula III or a pharmaceutically acceptable salt thereof, wherein:
R13 is 3-phenylpropyl, phenylmethoxymethyl, 3-indolylmethyl, or cyclohexylmethyl;
R15 is hydrogen, methyl, ethyl, or n-propyl;
R16 and R17 both are methyl or ethyl, or together with the carbon atom to which they are attached form a cyclopentane or cyclohexane ring;
R18 is selected from hydrogen, methyl or ethyl;
R19 is thienyl, naphthyl, thiazolyl, oxazolyl, pyridinyl, O-phenyl, or phenyl, which is optionally substituted with one or more substituents independently selected from the group consisting of $C_1$–$C_6$ alkyl, $C_1$–$C_6$ alkoxy, $CONH_2$, $CONH(C_1$–$C_6$ alkyl), $NHCO(C_1$–$C_6$ alkyl), $SO_2NH_2$, $SO_2NH(C_1$–$C_6$ alkyl), $NHSO_2(C_1$–$C_6$ alkyl), COOH, $COO(C_1$–$C_6$ alkyl), hydroxy, nitro, halo, $SO_2(C_{1-6}$ alkyl), and cyano; and
Q is —S(O)$_2$— or —C(O)—.

35. A compound of claim 34 wherein Q is —S(O)$_2$—.
36. A compound of claim 34 wherein Q is —C(O)—.
37. A compound as claimed by claim 35 wherein R16 and R17 together with the carbon atom to which they are attached form a cyclopentane or cyclohexane ring.
38. A compound as claimed by claim 35 wherein R16 and R17 both are methyl or ethyl.
39. A compound of claim 1 selected from the group consisting of 2-(R)-2-(2-Amino-2-methylpropionylamino)-3-phenylmethoxy propionic acid N-(3-(4-chlorophenyl)-2,2-dioxo-1-methyl-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-chlorophenyl)-2,2-dioxo-2-thia-1-azaspiro[4.5]dec-3-ene-4-ylmethyl)-N-methylamide, 2-(R)-2-(2-Amino-2-methylpropionylamino)-3-(3-indolyl) propionic acid N-(3-(4-chlorophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-(3-(4-chlorophenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-tert-butylphenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(4-chloro-phenyl)-2,2-dioxo-2-thia-1-azaspiro[4.5]dec-3-ene-4-ylmethyl)-N-propylamide, 2-(R)-2-(2-Amino-2-methylpropionylamino)-5-phenyl-pentanoic acid N-(3-(4-chlorophenyl)-2,2-dioxo-2-thia-1-azaspiro[4.5]dec-3-ene-4-ylmethyl)-N-methylamide, 2-(R)-2-(2-Amino-2-methylpropionylamino)-3-phenylmethoxy-propionic acid N-ethyl-N-(1-methyl-2,2-dioxo-3-phenyl-2-thia-1-azaspiro[4.5]dec-3-ene-4-ylmethyl)amide, 2-(R)-2-(2-Amino-2-methylpropionylamino)-3-phenylmethoxy-propionic acid N-(3-(3-chlorophenyl)-1-methyl-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-(3-(2-chlorophenyl)-1-methyl-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxypropionic acid N-ethyl-N-1-methyl-2,2-dioxo-3-(4-trifluoromethylphenyl)-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(1-methyl-3-(4-nitrophenyl)-2,2-dioxo-2-thia-1-azaspiro[4.5]dec-3-ene-4-ylmethyl)amide, 2-(R)-2-(2-Amino-2-methylpropionylamino)-3-phenylmethoxy-propionic acid N-(3-(4-bromophenyl)-2,2-dioxo-2-thia-1-azaspiro[4.5]dec-3-ene-4-ylmethyl)-N-ethylamide, 2-(R)-2-(2-Amino-2-methylpropionylamino)-3-phenylmethoxy-propionic acid N-ethyl-N-(2,2-dioxo-3-(4-methylphenyl)-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(1-ethyl-2,2-dioxo-3-phenyl-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(2,2-dioxo-3-(3-phenoxyphenyl)-2-thia-1-azaspiro[4.5]dec-3-ene-4-ylmethyl)-N-ethylamide, 2-(R)-2-(2-Amino-2-methylpropionylamino)-3-phenyl-methoxy-propionic acid N-(3-(3-bromophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-ethyl-N-(2,2-dioxo-3-phenyl-2-thia-1-azaspiro[4.5]dec-3-ene-4-ylmethyl)amide, 2-(R)-2-(2-Amino-2-methylpropionylamino)-3-phenylmethoxy-propionic acid N-ethyl-N-(3-(4-fluorophenyl)-2,2-dioxo-2-thia-1-azaspiro[4.5]dec-3-ene-4-ylmethyl)amide, 2-(R)-2-(2-Amino-2-methylpropionylamino)-5-phenyl-pentanoic acid N-ethyl-N-(3-(4-fluorophenyl)-2,2-dioxo-2-thia-1-azaspiro[4.5]dec-3-ene-4-ylmethyl)amide, 2-(R)-2-(2-Amino-2-methylpropionylamino)-3-phenylmethoxy-propionic acid N-(3-(2-bromophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-(3-(2-bromophenyl)-2,2-dioxo-2-thia-1-azaspiro[4.5]dec-3-ene-4-ylmethyl)-N-ethylamide, 2-(R)-2-(2-Amino-2-methylpropionylamino)-5-phenyl-pentanoic acid N-(3-(2-bromophenyl)-2,2-dioxo-2-thia-1-azaspiro[4.5]dec-3-ene- 4-ylmethyl)-N-ethylamide, 2-Amino-N-{2-benzyloxy-1-[(3,3-dimethyl-1,1-dioxo-5-phenyl-2,3-dihydro-1H-1$\gamma^6$-isothiazol-4-yl-methyl)-ethyl-carbamoyl]-ethyl}-2-methyl-propionamide, 2-(2-Amino-2-methyl-propionylamino)-5-phenyl-pentanoic acid (3,3-dimethyl-1,1-dioxo-5-phenyl-2,3-dihydro-1H-1$\gamma^6$-isothiazol-4-ylmethyl)-ethyl-amide, 2-Amino-N-{2-benzyloxy-1-[2,2-dioxo-3-phenyl-2$\lambda^6$-thia-1-aza-spiro[4.4]non-3-en-4-ylmethyl)-ethyl-carbamoyl]-ethyl}-2-methyl-propionamide, 2-(2-Amino-2-methyl-propionylamino)-5-phenyl-pentanoic acid [5-(4-chloro-phenyl)-3,3-dimethyl-1,1-dioxo-2,3-dihydro-1H-1$\gamma^6$-isothiazol-4-ylmethyl]-ethylamide, 2-(2-Amino-2-methyl-propionylamino)-5-phenyl-pentanoic acid (2,2-dioxo-3-phenyl-2$\lambda^6$-thia-1-aza-spiro[4.4]non-3-en-4-ylmethyl)-ethylamide, 2-Amino-N-(2-benzyloxy-1-{[3-(4-chloro-phenyl)-2,2-dioxo-2$\lambda^6$-thia-1-aza-spiro[4.4]non-3-en-4-yl methyl]-ethyl-carbamoyl}-ethyl)-2-methyl-propionamide, and 2-(R)-2-(2-Amino-2-methylpropionylamino)-3-phenyl-methoxypropionic acid N-ethyl-N-(2,2-dioxo-3-phenyl-2-thia-1-azaspiro[4.5]dec-3-ene-4-ylmethyl)amide; or a pharmaceutically acceptable salt thereof.

40. A compound of claim 1 wherein said compound is 2-(R)-2-(2-amino-2-methylpropionylamino)-3-phenyl-methoxy-propionic acid N-ethyl-N-(1-methyl-2,2-dioxo-3-phenyl-2-thia-1-azaspiro[4.5]dec-3-ene-4-ylmethyl)amide; or a pharmaceutically acceptable salt thereof.

41. A compound of claim 40 wherein said pharmaceutically acceptable salt is the hydrochloride salt.

42. A compound of claim 36 wherein R16 and R17 together with the carbon atom to which they are attached form a cyclopentane or cyclohexane ring.

43. A compound of claim 36 wherein R16 and R17 both are methyl or ethyl.

44. A compound of claim 1 selected from the group consisting of 2-(R)-2-(2-Amino-2-methylpropionylamino)-3-phenylmethoxy propionic acid N-(5-(4-chlorophenyl)-3,3-dimethyl-1,1-dioxo-2,3-dihydroisothiiazol-4-ylmethyl)-N-ethylamide, or a pharmaceutically acceptable salt thereof.

* * * * *